US008574857B2

(12) United States Patent
Vandeghinste et al.

(10) Patent No.: US 8,574,857 B2
(45) Date of Patent: Nov. 5, 2013

(54) METHOD AND MEANS FOR TREATMENT OF OSTEOARTHRITIS

(75) Inventors: Nick Vandeghinste, Duffel (BE); Peter Herwig Maria Tomme, Gent (BE); Frits Michiels, Leiderdorp (NL); Libin Ma, Oegstgeest (NL); Blandine Mille-Baker, Oegstgeest (NL); Helmuth G. G. van Es, Haarlem (NL)

(73) Assignee: Galapagos N.V., Mechelen (BE)

( * ) Notice: Subject to any disclaimer, the term of this patent is extended or adjusted under 35 U.S.C. 154(b) by 0 days.

(21) Appl. No.: 13/360,393

(22) Filed: Jan. 27, 2012

(65) Prior Publication Data

US 2012/0190727 A1 Jul. 26, 2012

Related U.S. Application Data

(62) Division of application No. 12/575,220, filed on Oct. 7, 2009, now abandoned, which is a division of application No. 11/158,252, filed on Jun. 21, 2005, now abandoned.

(60) Provisional application No. 60/581,568, filed on Jun. 21, 2004.

(51) Int. Cl.
*G01N 33/53* (2006.01)
*C12Q 1/68* (2006.01)

(52) U.S. Cl.
USPC ................ 435/7.21; 435/7.2; 435/7.1; 435/4; 530/356; 530/355; 530/350

(58) Field of Classification Search
USPC ........ 435/7.21, 7.2, 7.1, 4; 530/356, 355, 350
See application file for complete search history.

(56) References Cited

U.S. PATENT DOCUMENTS

| | | | |
|---|---|---|---|
| 6,706,267 B1 | 3/2004 | Adalsteinsson et al. | |
| 7,259,137 B2 | 8/2007 | Min et al. | |
| 7,671,020 B2 | 3/2010 | Deisher et al. | |
| 2005/0202421 A1 | 9/2005 | Hirsch et al. | |
| 2006/0046249 A1 | 3/2006 | Huang et al. | |
| 2007/0004658 A1 | 1/2007 | Vandeghinste et al. | |
| 2007/0031940 A1 | 2/2007 | Van Rompaey et al. | |
| 2007/0155662 A1* | 7/2007 | Golz et al. ..................... | 514/12 |

OTHER PUBLICATIONS

Arts et al. "Adenoviral Vectors Expressing siRNAs for Discovery and Validation of Gene Function." Genome Research, vol. 13, 2003, pp. 2325-2332.
Chubinskaya et al. "Regulation of Osteogenic Proteins by Chondrocytes." The International Journal of Biochemistry & Call Biology, vol. 35, 2003, pp. 1323-1340.
Cortez-Retamozo et al. "Efficient Cancer Therapy with Nanobody Based Conjugate." Cancer Research, vol. 64, Apr. 15, 2004, pp. 2853-2857.
Dorsett et al. siRNAs: Applications in Functional Genomics and Potential as Therapeutics, 2004 Nature Publishing Group, vol. 3, Apr. 2004, pp. 318-329.
Haroborth et al. "Sequence, Chemical and Structural Variation of Small Interfering RNAs and Short Hairpin RNAs and the Effect on Mammalian Gene Silencing." Antisense and Nucleic Acid Drug Development, vol. 13, 2003, pp. 83-105.
Khvorova et al. "Functional siRNAs and miRNAs Exhibit Strand Bias." Cell, vol. 115, Oct. 17, 2003, pp. 209-216.
Legendre et al. "JAK/STAT but Not ERK1/ERK2 Pathway Mediates Interleukin (IL)-6/Soluble IL-6R Down-regulation of Type II Collagen, Aggrecan Core, and Link Protein Transcription in Articular Chondrocytes." The Journal of Biological Chemistry, vol. 278(5), Jan. 31, 2003, pp. 2903-2912.
Li et al. "Oncostatin M-induced Matrix Metalloproteinase and Tissue Inhibitor of Metalloproteinase-3 Genes Expression in Chondrocytes Requires Janus Kinase/STAT Signaling Pathway." The Joutnal of Immunology, vol. 166, 2001, pp. 3491-3498.
Lipinski et al. "Experimental and computational approaches to estimate solubility and permeability in drug discovery and development settings." Advanced Drug Delivery Reviews, vol. 46, 2001, pp. 3-26.
Moeller et al. "Carbopxypeptidase Z (CPZ) mopdulates Wnt signaling and regulates the development of skeletal elements in the chicken." Development, vol. 130(21), 2003, pp. 5103-5111.
Novikova et al. "Purification and Characterization of Human Metallocarboxypeptidase Z." Biochemical and Biophysical Research Comms, vol. 256(3), 1999, pp. 546-568.
Novikova et al. "Carboxypeptidase Z is present in the regulated secretory pathway and extracellular matrix in cultured cells and in human tissue." The Journal of Biological Chemistry, vol. 275(7), 2000, pp. 4865-4870.
Osaki et al. The TATA-containing core promoter of the type II collagen gene (COL2A1) is the target of interferon-y-mediated inhibition in human chondrocytes: Requirements for Stat1, Jak1 and Jak2. Journal of Biochemistry, vol. 269, 2003, pp. 103-115.
Otero et al. "Signalling pathway involved in nitric oxide synthase type II activation in chondrocytes: Synergistic effect of leplin with interleukin-1." Arthritis Research & Therapy, vol. 7, 2005, pp. R581-R591.
Reynolds et al. "Rational siRNA design for RNA interference." Nature Biotechnology, vol. 22(3), Mar. 2004, pp. 326-330.
Reznik et al. "Carboxypeptidases from A to Z: implications in embryonic development and Wnt binding." Cell Mol Life Sci. vol. 58, 2001, pp. 1790-1804.
Rodig et al. "Disruption of the Jak 1 Gene Demonstrates Obligatory and Nonredundant Roles of the Jakes in Cytokine-Induced Biological Responses." Cell. vol. 93, 1998, pp. 373-383.
Song et al. "Cloning and Expression of Human Carboxypeptidase Z, a novel metallocarboxypeptidase." Journal of Biological Chemistry, vol. 272(16), 1997, pp. 10543-10550.

(Continued)

*Primary Examiner* — Teresa D. Wessendorf
(74) *Attorney, Agent, or Firm* — Martin Savitzky, Esq.

(57) ABSTRACT

The present invention relates to in vivo and in vitro methods, agents and compound screening assays for inducing anabolic stimulation of chondrocytes, including cartilage formation enhancing pharmaceutical compositions, and the use thereof in treating and/or preventing a disease involving a systemic or local decrease in mean cartilage thickness in a subject.

14 Claims, 46 Drawing Sheets

(56) References Cited

OTHER PUBLICATIONS

Tuschl "Expanding small RNA interference." Nature Biotechnology, vol. 20, May 2002, pp. 446-448.
Ui-Tei et al. "Guidelines for the selection of highly effective siRNA sequences for a mammalian and chick RNA interference." Nucleic Acids Research, vol. 32(3), 2004, pp. 936-948.
Wang et al. "A web-based design center for vector-based siRNA and siRNA cassette." Bioinformatics Applications Note, vol. 20(11), 2004, pp. 1818-1820.
Wang et al. "Carboxypeptidase Z (CPZ) links thyroid hormone and Wnt signaling pathways in growth plate chondrocytes." Journal of Bone and Mineral Research, vol. 24(3), 2009, pp. 265-273.

* cited by examiner

METHOD AND MEANS FOR TREATMENT OF OSTEOARTHRITIS

CROSS-REFERENCE TO RELATED APPLICATIONS

This application is a Divisional of U.S. application Ser. No. 12/075,220 filed Oct. 7, 2009, which is a Divisional of U.S. application Ser. No. 11/158,252, filed Jun. 21, 2005, which claims the benefit of priority of U.S. Provisional Application No. 60/581,568, filed Jun. 21, 2004, each of which are hereby incorporated by reference in their entirety.

FIELD OF THE INVENTION

The invention relates to the field of medicinal research, cartilage physiology and diseases involving the degeneration of cartilage tissue. More specifically, the invention relates to methods and means for identifying compounds that stimulate anabolic processes in chondrocytes and that typically induce the synthesis of cartilage. The invention also relates to the compounds that are useful in the treatment of osteoarthritis.

Cartilage is an avascular tissue made up largely of cartilage-specific cells, the chondrocytes, proteoglycans and collagen proteins, which are structural proteins that provide structural strength to connective tissue, such as skin, bone and cartilage. Collagen II, together with the protein collagen IX, forms a "biological alloy", which is molded into a fibril-like structure and is arranged in a precise network, providing cartilage with great mechanical strength. The chondrocytes in normal articular cartilage occupy approximately 5% of the tissue volume, while the extra-cellular matrix makes up the remaining 95% of the tissue. The chondrocytes secrete the components of the matrix, which in turn supplies the chondrocytes with an environment suitable for their survival under mechanical stress.

Breakdown of articular cartilage, which is part of joints and which cushions the ends of the bones, causes the bones to rub against each other leading to pain and loss of movement. Cartilage degradation may also be the result of an imbalance in cartilage synthesizing (anabolic) and cartilage degrading (catabolic) processes. Unlike most tissues, cartilage does not self-repair following injury. The inability of cartilage to self-repair after injury, disease, or surgery is a major limiting factor in rehabilitation of degrading joint surfaces and injury to meniscal cartilage.

There are many diseases involving the degeneration of cartilage. Rheumatoid arthritis and osteoarthritis are among the most prominent. Osteoarthritis (also referred to as OA, or as wear-and-tear arthritis) is the most common form of arthritis and is characterized by loss of articular cartilage, often associated with hypertrophy of the bone. The disease mainly affects hands and weight-bearing joints such as knees, hips and spines. This process thins the cartilage through a phenomenon called apoptosis, or programmed cell death. When the surface area has disappeared due to the thinning, there is a grade I osteoarthritis; when the tangential surface area has disappeared, there is a grade two osteoarthritis. There are other levels of degeneration and destruction, which affect the deep and the calcified layers that border with the subchondral bone.

The clinical manifestations of the development of the osteoarthritis condition are: increased volume of the joint, pain, crepitation and functional disability that, gradually and steadily, first hinders the performance of lengthy walks and forced flexion and extension movements, depending on the affected joint, and then pain and limitation of minimum efforts emerge as well as pain at rest which interrupts sleeping. If the condition persists without correction and/or therapy, the joint is destroyed, leading the patient to major replacement surgery with total prosthesis, or to disability.

Therapeutic methods for the correction of the articular cartilage lesions that appear during the osteoarthritic disease have been developed, but so far none of them have been able to achieve the regeneration of articular cartilage in situ and in vivo.

REPORTED DEVELOPMENTS

Osteoarthritis is difficult to treat. At present, no cure is available and treatment focuses on relieving pain and preventing the affected joint from becoming deformed. Common treatments include the use of non-steroidal anti-inflammatory drugs (NSAID's), which are often used to relieve pain, while specific COX-2 inhibitors are used to relieve severe pain. Medicines such as chondroitin and glucosamine are thought to improve the cartilage itself. These treatments may be relatively successful, but not a substantive amount of research data is available.

In severe cases, joint replacement may be necessary. This is especially true for hips and knees. If a joint is extremely painful and cannot be replaced, it may be fused. This procedure stops the pain, but results in the permanent loss of joint function, making walking and bending difficult.

The treatment that has 74% to 90% effectiveness and produces excellent results is the transplantation of cultured autologous chondrocytes, by taking chondral cellular material from the patient, sending it to a laboratory where it is seeded in a proper medium for its proliferation, and, once enough volume is achieved after a variable period that may last from weeks to months, transporting it in a special container and implanting it in the damaged tissues to cover the tissue's defects.

Another treatment includes the intraarticular instillation of Hylan G-F 20 (Synvisc, Hyalgan, Artz etc.), a substance that improves temporarily the rheology of the synovial fluid, producing an almost immediate sensation of free movement and a marked reduction of pain. The residual effects of this substance act on the synovial receptors causing a pain reduction that lasts several weeks and even months. However, this isolated effect is counterproductive for the course of the disease and for the viability of the cartilage because, as it masks the symptoms, the joint is used with more intensity and its destruction is accelerated as the original problem is not corrected and the damaged articular cartilage is not restored.

Other reported methods include application of tendinous, periosteal, fascial, muscular or perichondral grafts; implantation of fibrin or cultured chondrocytes; implantation of synthetic matrices, such as collagen, carbon fiber; administration of electromagnetic fields. All of these have reported minimal and incomplete results with formation of repair, but not regenerative tissue, resulting in a poor quality tissue that can neither support the weighted load nor allow the restoration of an articular function with normal movement.

Stimulation of the anabolic processes, blocking catabolic processes, or a combination of these two, may result in stabilization of the cartilage, and perhaps even reversion of the damage, and therefore prevent further progression of the disease. Various triggers may stimulate anabolic stimulation of chondrocytes. Insulin-like growth factor-I (IGF-I) is the predominant anabolic growth factor in synovial fluid and stimulates the synthesis of both proteoglycans and collagen. It has also been shown that members of the bone morphogenetic protein (BMP) family, notably BMP2, BMP4, BMP6, and BMP7, and members of the human transforming growth factor-b (TGF-b) family can induce chondrocyte anabolic stimulation (Chubinskaya and Kuettner, 2003). A compound has recently been identified that induces anabolic stimulation of chondrocytes (U.S. Pat. No. 6,500,854; EP 1.391211). However, most of these compounds show severe side effects and, consequently, there is a strong need for compounds that stimulate chondrocyte differentiation without severe side effects.

The present invention relates to the relationship between the function of selected proteins identified by the present inventors (hereinafter referred to as "TARGETS") and anabolic stimulation of chondrocytes.

SUMMARY OF THE INVENTION

The present invention relates to a method for identifying compounds that induce cartilage-synthesizing processes, which lead to anabolic stimulation of chondrocytes, comprising contacting the compound with a polypeptide comprising an amino acid sequence selected from the group consisting of SEQ ID NO: 55-82 and 198-391 or a functional fragment or derivative thereof, under conditions that allow said polypeptide to bind to the compound, and measuring a compound-polypeptide property related to the anabolic stimulation of chondrocytes.

The present invention also relates to expression inhibitory agents, pharmaceutical compositions comprising the same, methods for the in vitro production of cartilage tissue, and host cells expressing said agents.

Aspects of the present method include the in vitro assay of compounds using polypeptide of a TARGET, and cellular assays wherein TARGET inhibition is followed by observing indicators of efficacy, including collagen type II, alpha-1 (col2α1) and aggrecan levels.

Another aspect of the invention is a method of treatment or prevention of a condition involving de-differentiation of chondrocytes and/or loss of cartilage thickness, in a subject suffering or susceptible thereto, by administering a pharmaceutical composition comprising an effective cartilage formation-enhancing amount of a TARGET inhibitor.

A further aspect of the present invention is a pharmaceutical composition for use in said method wherein said inhibitor comprises a polynucleotide selected from the group of an antisense polynucleotide, a ribozyme, and a small interfering RNA (siRNA), wherein said inhibitor comprises a nucleic acid sequence complementary to, or engineered from, a naturally occurring polynucleotide sequence encoding a polypeptide, comprising an amino acid sequence selected from the group consisting of SEQ ID NO: 55-82 and 198-391 or a fragment thereof.

Another further aspect of the present invention is a pharmaceutical composition comprising a therapeutically effective cartilage formation-enhancing amount of a TARGET inhibitor or its pharmaceutically acceptable salt, hydrate, solvate, or prodrug thereof in admixture with a pharmaceutically acceptable carrier. The present polynucleotides and TARGET inhibitor compounds are also useful for the manufacturing of a medicament for the treatment of conditions involving de-differentiation of chondrocytes and/or cartilage thickness loss.

Furthermore, the invention relates also to diagnostic methods.

DETAILED DESCRIPTION

Figure 1:
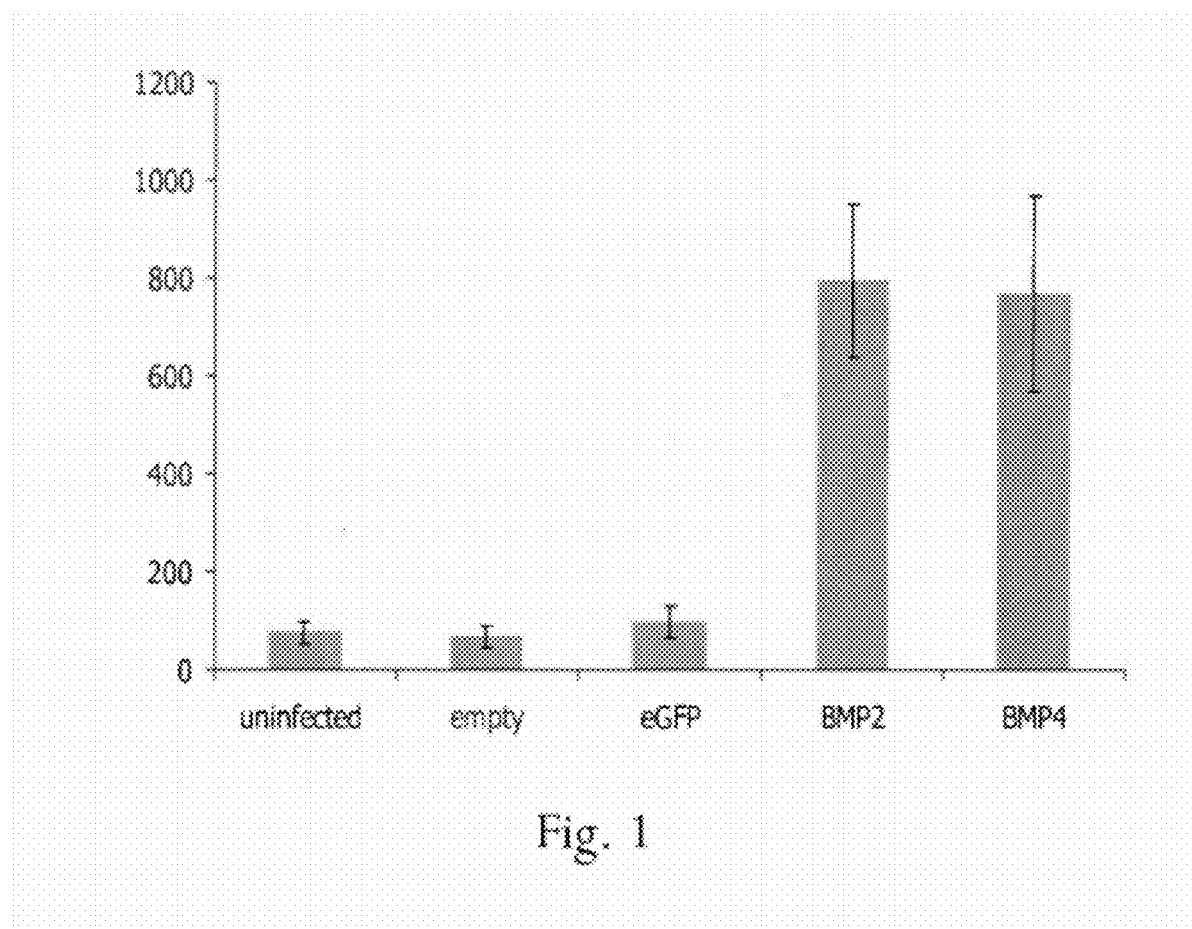
FIG. 1. Quantification of Col2α1 expression in primary human chondrocytes 12 days post infection with the indicated viruses.

The following terms are used herein in accordance with the following definitions:

The term "agent" means any molecule, including polypeptides, polynucleotides and small molecules.

The term "anabolic stimulation of chondrocytes" should be understood as inducing chondrogenesis or as inducing or enhancing the anabolic activity of chondrocytes. Anabolic stimulation takes place for instance by stimulating the synthesis of cartilage components, or inducing synthesis of components that are required for cartilage synthesis. "Anabolic stimulation of chondrocytes" may also be understood as a process in which the expression of the matrix Gla protein (MGP) is induced. Anabolic stimulation of chondrocytes may furthermore be understood as inducing the expression of cartilage derived retinoic acid sensitive protein (CD-RAP), as inducing the expression of cartilage oligomeric matrix protein (COMP), as inducing the expression of aggrecan 1 (agc1, also termed chondroitin sulfate proteoglycan core protein 1, or CSPG1), or as inducing synthesis of collagen II, also known as collagen, type II, alpha-1 (col2α1), collagen of cartilage, chondrocalcin, and collagen, type xi, alpha-3 (col11α3).

The term 'antisense nucleic acid' refers to an oligonucleotide that has a nucleotide sequence that interacts through base pairing with a specific complementary nucleic acid sequence involved in the expression of the target such that the expression of the gene is reduced. Preferably, the specific nucleic acid sequence involved in the expression of the gene is a genomic DNA molecule or mRNA molecule that encodes (a part of) the gene. This genomic DNA molecule can comprise regulatory regions of the gene, or the coding sequence for the mature gene.

The term "assay" means any process used to measure a specific property of a compound. A "screening assay" means a process used to characterize or select compounds based upon their activity from a collection of compounds.

The term "binding affinity" is a property that describes how strongly two or more compounds associate with each other in a non-covalent relationship. Binding affinities can be characterized qualitatively, (such as "strong", "weak", "high", or "low") or quantitatively (such as measuring the $K_D$).

The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "complex" means the entity created when two or more compounds bind to each other.

The term "compound" is used herein in the context of a "test compound" or a "drug candidate compound" described in connection with the assays of the present invention. As such, these compounds comprise organic or inorganic compounds, derived synthetically or from natural sources. The compounds include inorganic or organic compounds such as polynucleotides, lipids or hormone analogs that are characterized by relatively low molecular weights. Other biopolymeric organic test compounds include peptides comprising from about 2 to about 40 amino acids and larger polypeptides comprising from about 40 to about 500 amino acids, such as antibodies or antibody conjugates.

The term 'complementary to a nucleotide sequence' in the context of antisense oligonucleotides and methods should be understood as sufficiently complementary to such a sequence as to allow hybridization to that sequence in a cell, i.e., under physiological conditions.

The term "condition" or "disease" means the overt presentation of symptoms (i.e., illness) or the manifestation of abnormal clinical indicators (e.g., biochemical indicators). Alternatively, the term "disease" refers to a genetic or environmental risk of or propensity for developing such symptoms or abnormal clinical indicators.

The term "contact" or "contacting" means bringing at least two moieties together, whether in an in vitro system or an in vivo system.

The term "de-differentiation" refers to a general process wherein chondrocytes differentiate away from a cell phenotype that synthesizes cartilage components. Such components include, but are not limited to, collagen II, aggrecan 1, versican, link protein, perlecan, SZP/lubricin, biglycan (DS-PGI), decorin (DS-PGII), epiphycan (DS-PGIII), fibromodulin, lumican, CILP, C-type lectin, fibronectin, PRELP, COMP (thrombospondin-5), thrombospondin-1 and -3, CMP (matrilin-1), matrilin-3, C-type lectin, fibronectin, condroadherin, tenascin-C, fibrillin, elastin, gp-39/YKL-40, matrix Gla protein/MGP, pleiotrophin, chondromodulin-I/SCGP, chondromodulin-II, CD-RAP, chondrocalcin, PARP, lysozyme, and phospholipase A2.

The term "effective amount" or "therapeutically effective amount" means that amount of a compound or agent that will elicit the biological or medical response of a subject that is being sought by a medical doctor or other clinician. In particular, with regard to inducing anabolic stimulation of chondrocytes, the term "effective amount" is intended to mean an effective differentiation-promoting amount of a compound or agent that will bring about a biologically meaningful increase in the levels of chondrocyte markers, representative for the process of an increase in chondrocyte anabolism.

The term "expressible nucleic acid" means a nucleic acid coding for a proteinaceous molecule, an RNA molecule, or a DNA molecule.

The term "endogenous" shall mean a material that a mammal naturally produces. Endogenous in reference to the term "protease", "kinase", or G-Protein Coupled Receptor ("GPCR") shall mean that which is naturally produced by a mammal (for example, and not limitation, a human). In contrast, the term non-endogenous in this context shall mean that which is not naturally produced by a mammal (for example, and not limitation, a human). Both terms can be utilized to describe both "in vivo" and "in vitro" systems. For example, and not a limitation, in a screening approach, the endogenous or non-endogenous TARGET may be in reference to an in vitro screening system. As a further example and not limitation, where the genome of a mammal has been manipulated to include a non-endogenous TARGET, screening of a candidate compound by means of an in vivo system is viable.

The term "expression" comprises both endogenous expression and overexpression by transduction.

The term "expression inhibitory agent" means a polynucleotide designed to interfere selectively with the transcription, translation and/or expression of a specific polypeptide or protein normally expressed within a cell. More particularly, "expression inhibitory agent" comprises a DNA or RNA molecule that contains a nucleotide sequence identical to or complementary to at least about 17 sequential nucleotides within the polyribonucleotide sequence coding for a specific polypeptide or protein. Exemplary expression inhibitory molecules include ribozymes, double stranded siRNA molecules, self-complementary single-stranded siRNA molecules, genetic antisense constructs, and synthetic RNA antisense molecules with modified stabilized backbones.

The term "expressible nucleic acid" means a nucleic acid coding for a proteinaceous molecule, an RNA molecule, or a DNA molecule.

The term 'genetic antisense' as used herein refers to the incorporation of antisense constructs complementary to sequences of genes into the genome of a cell. Such incorporation allows for the continued synthesis of the antisense molecule.

The term "hybridization" means any process by which a strand of nucleic acid binds with a complementary strand through base pairing. The term "hybridization complex" refers to a complex formed between two nucleic acid sequences by virtue of the formation of hydrogen bonds between complementary bases. A hybridization complex may be formed in solution (e.g., $C_{0t}$ or $R_{0t}$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, e.g., formamide, temperature, and other conditions well known in the art. In particular, reducing the concentration of salt, increasing the concentration of formamide, or raising the hybridization temperature can increase stringency.

The term "inhibit" or "inhibiting", in relationship to the term "response" means that a response is decreased or prevented in the presence of a compound as opposed to in the absence of the compound.

The term "inhibition" refers to the reduction, down regulation of a process or the elimination of a stimulus for a process that results in the absence or minimization of the expression of a protein or polypeptide.

The term "induction" refers to the inducing, up-regulation, or stimulation of a process that results in the expression of a protein or polypeptide, and that may also result in a phenotypical cellular change.

The term "ligand" means an endogenous, naturally occurring molecule specific for an endogenous, naturally occurring receptor.

The term "pharmaceutically acceptable salts" refers to the non-toxic, inorganic and organic acid addition salts, and base addition salts, of compounds of the present invention. These salts can be prepared in situ during the final isolation and purification of compounds useful in the present invention.

The term "polynucleotide" means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more preferably 70 percent of its base pairs are in common, most preferably 90 percent, and in a special embodiment 100 percent of its base pairs. The polynucleotides include polyribonucleic acids, polydeoxyribonucleic acids, and synthetic analogues thereof. The polynucleotides are described by sequences that vary in length, that range from about 10 to about 5000 bases, preferably about 100 to about 4000 bases, more preferably about 250 to about 2500 bases. A preferred polynucleotide embodiment comprises from about 10 to about 30 bases in length. A special embodiment of polynucleotide is the polyribonucleotide of from about 10 to about 22 nucleotides, more commonly described as small interfering RNAs (siRNAs). Another special embodiment are nucleic acids with modified backcartilages such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term "polypeptide" relates to proteins (such as TARGETS), proteinaceous molecules, fractions of proteins peptides and oligopeptides.

The term 'ribozymes' as used herein relates to catalytic RNA molecules capable of cleaving other RNA molecules at phosphodiester bonds in a manner specific to the sequence.

The term "solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "subject" includes humans and other mammals.

The term "treating" means an intervention performed with the intention of preventing the development or altering the pathology of, and thereby alleviating a disorder, disease or condition, including one or more symptoms of such disorder or condition. Accordingly, "treating" refers to both therapeutic treatment and prophylactic or preventative measures. Those in need of treating include those already with the disorder as well as those in which the disorder is to be prevented. The related term "treatment," as used herein, refers to the act of treating a disorder, symptom, disease or condition, as the term "treating" is defined above.

The term 'vectors' also relates to plasmids as well as to viral vectors, such as recombinant viruses, or the nucleic acid encoding the recombinant virus.

The term "vertebrate cells" means cells derived from animals having vertera structure, including fish, avian, reptilian, amphibian, marsupial, and mammalian species. Preferred cells are derived from mammalian species, and most preferred cells are human cells. Mammalian cells include feline, canine, bovine, equine, caprine, ovine, porcine murine, such as mice and rats, and rabbits.

Applicants' Invention Based on TARGET Relationship to Anabolic Stimulation of Chondrocytes As noted above, the present invention is based on the present inventors' discovery that TARGETS are factors in the up-regulation and/or induction of anabolic processes of chondrocytes. The term "TARGET" or "TARGETS" means the proteins identified in accordance with the assay described below to be involved in the induction of the anabolic stimulation of chondrocytes. The present inventors have identified such TARGETS by screening recombinant adenoviruses mediating the expression of a library of shRNAs, referred to herein as "Ad-siRNAs." The collection used herein is further referred to as "adenoviral siRNA library" or SILENCESELECT® collection. These libraries contain recombinant adenoviruses, further referred to as knock-down (KD) viruses or Ad-siRNAs, that mediate the expression in cells of shRNAs which reduce the expression levels of targeted genes by a RNA interference (RNAi)-based mechanism (WO03/020931).

The preferred TARGETS are identified as SEQ ID NOS. 55-82 and 198-391 in Table 1A. Table 1A lists the polypeptides, polynucleotides and knock-down target sequences of the present invention. Table 1B lists exemplary fragments of the TARGETS, SEQ ID NOS. 198-391. Table 1C lists exemplary KD target sequences useful in the practice of the present expression-inhibitory agent invention.

TABLE 1A

| Hit ID | KD Target Sequence | Target Gene Symbol | GenBank Accession | Name | Class | DNA or mRNA | Protein | KD SEQ NO. |
|---|---|---|---|---|---|---|---|---|
| H33-025 | CCTGAATGTGACTGTGGAC (SEQ ID NO: 91) | DGKB-INCENP | NM_020238 NM_004080 NM_145695 | diacylglycerol kinase, beta 90 kDa/inner centromere protein antigens 135/155 kDa | Kinase | 1 2 3 | 55 56 57 | 84-91 |
| H33-032 | GACTGACTGGCCTGAAGGC (SEQ ID NO: 92) | ICK | NM_016513 NM_014920 | intestinal cell (MAK-like) kinase | Kinase | 4 5 | 58 59 | 92-99 |
| H33-034 | GATCTACACCACCTTCATC (SEQ ID NO: 101) | GPR103 | AF411117 NM_198179 | G protein-coupled receptor 103 | GPCR | 6 7 | 60 61 | 100-107 |
| H33-041 | GGTGTATGGGCTCATGTAC (SEQ ID NO: 108) | FZD1 | NM_003505 | frizzled homolog 1 (*Drosophila*) | GPCR | 8 | 62 | 108-114 |
| H33-056 | AGAACTGGGTGATGACAGC (SEQ ID NO: 116) | ELA1 | NM_001971 | elastase 1, pancreatic | Protease | 9 | 63 | 115-122 |
| H33-061 | ATGAACTCTGTGATCCAGC (SEQ ID NO: 123) | USP9Y | NM_004654 | ubiquitin specific protease 9, Y-linked (fat facets-like, *Drosophila*) | Protease | 10 | 64 | 123-130 |
| H33-082 | TTGGAATTCCAGTGTACCC (SEQ ID NO: 132) | DUSP11 | NM_003584 | dual specificity phosphatase 11 (RNA/RNP complex 1-interacting) | Phosphatase | 11 | 65 | 131-138 |
| H33-083 | GCTAGTTATCGCCTACCTC (SEQ ID NO: 139) | DUSP3 | NM_004090 | dual specificity phosphatase 3 (vaccinia virus phosphatase VH1-related) | Phosphatase | 12 | 66 | 139-145 |
| H33-096 | AGATTCCAGATGCAACCCC (SEQ ID NO: 148) | JAK1 | SK185-NM_002227 | Janus kinase 1 (a protein tyrosine kinase) | Kinase | 13 14 | 67 68 | 146-154 |
| H33-107 | CTGAACTACTGGTACAGCC (SEQ ID NO: 157) | ABCG1 | NM_016818 NM_004915 NM_207174 NM_207627 NM_207628 NM_207629 NM_207630 | ATP-binding cassette, sub-family G (WHITE), member 1 | Transporter | 15 16 17 18 19 20 21 | 69 70 71 72 73 74 75 | 155-162 |
| H33-130 | GCGAATTCCACCAGCATTC (SEQ ID NO: 165) | SLC26A8 | NM_052961 | solute carrier family 26, member 8 | Transporter | 22 | 76 | 163-175 |
| H33-192 | ACATTGACCAGGAAGTGAC (SEQ ID NO: 178) | GGTLA4 | NM_178312 NM_178311 NM_080920 | gamma-glutamyl-transferase-like activity 4 | Enzyme | 23 24 25 | 77 78 79 | 176-182 |
| H33-217 | GAAGCTGAATTAGGGCTTC (SEQ ID NO: 184) | PDE1A | NM_005019 NM_00100-3683 | phosphodiesterase 1A, calmodulin-dependent | PDE | 26 27 | 80 81 | 183-190 |
| H33-279 | GAAGCCATCTCCGACAATC (SEQ ID NO: 192) | SLC15A2 | NM_021082 | solute carrier family 15 (H+/peptide transporter), member 2 | Transporter | 28 | 82 | 191-197 |

TABLE 1B

| Accession | Name | Protein Segment | Seq ID protein segment |
|---|---|---|---|
| AF411117 | GPR103 | Extracellular domain | 198 |
| AF411117 | GPR103 | Transmembrane domain | 199 |
| AF411117 | GPR103 | Intracellular domain | 200 |
| AF411117 | GPR103 | Transmembrane domain | 201 |
| AF411117 | GPR103 | Extracellular domain | 202 |
| AF411117 | GPR103 | Transmembrane domain | 203 |
| AF411117 | GPR103 | Intracellular domain | 204 |
| AF411117 | GPR103 | Transmembrane domain | 205 |
| AF411117 | GPR103 | Extracellular domain | 206 |
| AF411117 | GPR103 | Transmembrane domain | 207 |
| AF411117 | GPR103 | Intracellular domain | 208 |
| AF411117 | GPR103 | Transmembrane domain | 209 |
| AF411117 | GPR103 | Extracellular domain | 210 |
| NM_198179 | GPR103 | Extracellular domain | 211 |
| NM_198179 | GPR103 | Transmembrane domain | 212 |
| NM_198179 | GPR103 | Intracellular domain | 213 |
| NM_198179 | GPR103 | Transmembrane domain | 214 |
| NM_198179 | GPR103 | Extracellular domain | 215 |
| NM_198179 | GPR103 | Transmembrane domain | 216 |
| NM_198179 | GPR103 | Intracellular domain | 217 |
| NM_198179 | GPR103 | Transmembrane domain | 218 |
| NM_198179 | GPR103 | Extracellular domain | 219 |
| NM_198179 | GPR103 | Transmembrane domain | 220 |
| NM_198179 | GPR103 | Intracellular domain | 221 |
| NM_198179 | GPR103 | Transmembrane domain | 222 |
| NM_198179 | GPR103 | Extracellular domain | 223 |
| NM_198179 | GPR103 | Transmembrane domain | 224 |
| NM_198179 | GPR103 | Intracellular domain | 225 |
| NM_003505 | FZD1 | Extracellular domain | 226 |
| NM_003505 | FZD1 | Transmembrane domain | 227 |
| NM_003505 | FZD1 | Intracellular domain | 228 |
| NM_003505 | FZD1 | Transmembrane domain | 229 |
| NM_003505 | FZD1 | Extracellular domain | 230 |
| NM_003505 | FZD1 | Transmembrane domain | 231 |
| NM_003505 | FZD1 | Intracellular domain | 232 |
| NM_003505 | FZD1 | Transmembrane domain | 233 |
| NM_003505 | FZD1 | Extracellular domain | 234 |
| NM_003505 | FZD1 | Transmembrane domain | 235 |
| NM_003505 | FZD1 | Intracellular domain | 236 |
| NM_003505 | FZD1 | Transmembrane domain | 237 |
| NM_003505 | FZD1 | Extracellular domain | 238 |
| NM_003505 | FZD1 | Transmembrane domain | 239 |
| NM_003505 | FZD1 | Intracellular domain | 240 |
| NM_016818 | ABCG1 | Extracellular domain | 241 |
| NM_016818 | ABCG1 | Transmembrane domain | 242 |
| NM_016818 | ABCG1 | Intracellular domain | 243 |
| NM_016818 | ABCG1 | Transmembrane domain | 244 |
| NM_016818 | ABCG1 | Extracellular domain | 245 |
| NM_016818 | ABCG1 | Transmembrane domain | 246 |
| NM_016818 | ABCG1 | Intracellular domain | 247 |
| NM_016818 | ABCG1 | Transmembrane domain | 248 |
| NM_016818 | ABCG1 | Extracellular domain | 249 |
| NM_016818 | ABCG1 | Transmembrane domain | 250 |
| NM_016818 | ABCG1 | Intracellular domain | 251 |
| NM_016818 | ABCG1 | Transmembrane domain | 252 |
| NM_016818 | ABCG1 | Extracellular domain | 253 |
| NM_016818 | ABCG1 | Transmembrane domain | 254 |
| NM_016818 | ABCG1 | Intracellular domain | 255 |
| NM_004915 | ABCG1 | Extracellular domain | 256 |
| NM_004915 | ABCG1 | Transmembrane domain | 257 |
| NM_004915 | ABCG1 | Intracellular domain | 258 |
| NM_004915 | ABCG1 | Transmembrane domain | 259 |
| NM_004915 | ABCG1 | Extracellular domain | 260 |
| NM_004915 | ABCG1 | Transmembrane domain | 261 |
| NM_004915 | ABCG1 | Intracellular domain | 262 |
| NM_004915 | ABCG1 | Transmembrane domain | 263 |
| NM_004915 | ABCG1 | Extracellular domain | 264 |
| NM_004915 | ABCG1 | Transmembrane domain | 265 |
| NM_004915 | ABCG1 | Intracellular domain | 266 |
| NM_004915 | ABCG1 | Transmembrane domain | 267 |
| NM_004915 | ABCG1 | Extracellular domain | 268 |
| NM_004915 | ABCG1 | Transmembrane domain | 269 |
| NM_004915 | ABCG1 | Intracellular domain | 270 |
| NM_207174 | ABCG1 | Extracellular domain | 271 |
| NM_207174 | ABCG1 | Transmembrane domain | 272 |
| NM_207174 | ABCG1 | Intracellular domain | 273 |
| NM_207174 | ABCG1 | Transmembrane domain | 274 |
| NM_207174 | ABCG1 | Extracellular domain | 275 |
| NM_207174 | ABCG1 | Transmembrane domain | 276 |
| NM_207174 | ABCG1 | Intracellular domain | 277 |
| NM_207174 | ABCG1 | Transmembrane domain | 278 |
| NM_207174 | ABCG1 | Extracellular domain | 279 |
| NM_207174 | ABCG1 | Transmembrane domain | 280 |
| NM_207174 | ABCG1 | Intracellular domain | 281 |
| NM_207174 | ABCG1 | Transmembrane domain | 282 |
| NM_207174 | ABCG1 | Extracellular domain | 283 |
| NM_207174 | ABCG1 | Transmembrane domain | 284 |
| NM_207174 | ABCG1 | Intracellular domain | 285 |
| NM_207627 | ABCG1 | Extracellular domain | 286 |
| NM_207627 | ABCG1 | Transmembrane domain | 287 |
| NM_207627 | ABCG1 | Intracellular domain | 288 |
| NM_207627 | ABCG1 | Transmembrane domain | 289 |
| NM_207627 | ABCG1 | Extracellular domain | 290 |
| NM_207627 | ABCG1 | Transmembrane domain | 291 |
| NM_207627 | ABCG1 | Intracellular domain | 292 |
| NM_207627 | ABCG1 | Transmembrane domain | 293 |
| NM_207627 | ABCG1 | Extracellular domain | 294 |
| NM_207627 | ABCG1 | Transmembrane domain | 295 |
| NM_207627 | ABCG1 | Intracellular domain | 296 |
| NM_207627 | ABCG1 | Transmembrane domain | 297 |
| NM_207627 | ABCG1 | Extracellular domain | 298 |
| NM_207627 | ABCG1 | Transmembrane domain | 299 |
| NM_207627 | ABCG1 | Intracellular domain | 300 |
| NM_207628 | ABCG1 | Extracellular domain | 301 |
| NM_207628 | ABCG1 | Transmembrane domain | 302 |
| NM_207628 | ABCG1 | Intracellular domain | 303 |
| NM_207628 | ABCG1 | Transmembrane domain | 304 |
| NM_207628 | ABCG1 | Extracellular domain | 305 |
| NM_207628 | ABCG1 | Transmembrane domain | 306 |
| NM_207628 | ABCG1 | Intracellular domain | 307 |
| NM_207628 | ABCG1 | Transmembrane domain | 308 |
| NM_207628 | ABCG1 | Extracellular domain | 309 |
| NM_207628 | ABCG1 | Transmembrane domain | 310 |
| NM_207628 | ABCG1 | Intracellular domain | 311 |
| NM_207628 | ABCG1 | Transmembrane domain | 312 |
| NM_207628 | ABCG1 | Extracellular domain | 313 |
| NM_207628 | ABCG1 | Transmembrane domain | 314 |
| NM_207628 | ABCG1 | Intracellular domain | 315 |
| NM_207629 | ABCG1 | Extracellular domain | 316 |
| NM_207629 | ABCG1 | Transmembrane domain | 317 |
| NM_207629 | ABCG1 | Intracellular domain | 318 |
| NM_207629 | ABCG1 | Transmembrane domain | 319 |
| NM_207629 | ABCG1 | Extracellular domain | 320 |
| NM_207629 | ABCG1 | Transmembrane domain | 321 |
| NM_207629 | ABCG1 | Intracellular domain | 322 |
| NM_207629 | ABCG1 | Transmembrane domain | 323 |
| NM_207629 | ABCG1 | Extracellular domain | 324 |
| NM_207629 | ABCG1 | Transmembrane domain | 325 |
| NM_207629 | ABCG1 | Intracellular domain | 326 |
| NM_207629 | ABCG1 | Transmembrane domain | 327 |
| NM_207629 | ABCG1 | Extracellular domain | 328 |
| NM_207629 | ABCG1 | Transmembrane domain | 329 |
| NM_207629 | ABCG1 | Intracellular domain | 330 |
| NM_207630 | ABCG1 | Extracellular domain | 331 |
| NM_207630 | ABCG1 | Transmembrane domain | 332 |
| NM_207630 | ABCG1 | Intracellular domain | 333 |
| NM_207630 | ABCG1 | Transmembrane domain | 334 |
| NM_207630 | ABCG1 | Extracellular domain | 335 |
| NM_207630 | ABCG1 | Transmembrane domain | 336 |
| NM_207630 | ABCG1 | Intracellular domain | 337 |
| NM_207630 | ABCG1 | Transmembrane domain | 338 |
| NM_207630 | ABCG1 | Extracellular domain | 339 |
| NM_207630 | ABCG1 | Transmembrane domain | 340 |
| NM_207630 | ABCG1 | Intracellular domain | 341 |
| NM_207630 | ABCG1 | Transmembrane domain | 342 |
| NM_207630 | ABCG1 | Extracellular domain | 343 |
| NM_207630 | ABCG1 | Transmembrane domain | 344 |
| NM_207630 | ABCG1 | Intracellular domain | 345 |
| NM_052961 | SLC26A8 | Intracellular domain | 346 |
| NM_052961 | SLC26A8 | Transmembrane domain | 347 |
| NM_052961 | SLC26A8 | Extracellular domain | 348 |
| NM_052961 | SLC26A8 | Transmembrane domain | 349 |
| NM_052961 | SLC26A8 | Intracellular domain | 350 |
| NM_052961 | SLC26A8 | Transmembrane domain | 351 |

TABLE 1B-continued

| Accession | Name | Protein Segment | Seq ID protein segment |
|---|---|---|---|
| NM_052961 | SLC26A8 | Extracellular domain | 352 |
| NM_052961 | SLC26A8 | Transmembrane domain | 353 |
| NM_052961 | SLC26A8 | Intracellular domain | 354 |
| NM_052961 | SLC26A8 | Transmembrane domain | 355 |
| NM_052961 | SLC26A8 | Extracellular domain | 356 |
| NM_052961 | SLC26A8 | Transmembrane domain | 357 |
| NM_052961 | SLC26A8 | Intracellular domain | 358 |
| NM_052961 | SLC26A8 | Transmembrane domain | 359 |
| NM_052961 | SLC26A8 | Extracellular domain | 360 |
| NM_052961 | SLC26A8 | Transmembrane domain | 361 |
| NM_052961 | SLC26A8 | Intracellular domain | 362 |
| NM_052961 | SLC26A8 | Transmembrane domain | 363 |
| NM_052961 | SLC26A8 | Extracellular domain | 364 |
| NM_052961 | SLC26A8 | Transmembrane domain | 365 |
| NM_052961 | SLC26A8 | Intracellular domain | 366 |
| NM_052961 | SLC26A8 | Transmembrane domain | 367 |
| NM_052961 | SLC26A8 | Extracellular domain | 368 |
| NM_021082 | SLC15A2 | Intracellular domain | 369 |
| NM_021082 | SLC15A2 | Transmembrane domain | 370 |
| NM_021082 | SLC15A2 | Extracellular domain | 371 |
| NM_021082 | SLC15A2 | Transmembrane domain | 372 |
| NM_021082 | SLC15A2 | Intracellular domain | 373 |
| NM_021082 | SLC15A2 | Transmembrane domain | 374 |
| NM_021082 | SLC15A2 | Extracellular domain | 375 |
| NM_021082 | SLC15A2 | Transmembrane domain | 376 |
| NM_021082 | SLC15A2 | Intracellular domain | 377 |
| NM_021082 | SLC15A2 | Transmembrane domain | 378 |
| NM_021082 | SLC15A2 | Extracellular domain | 379 |
| NM_021082 | SLC15A2 | Transmembrane domain | 380 |
| NM_021082 | SLC15A2 | Intracellular domain | 381 |
| NM_021082 | SLC15A2 | Transmembrane domain | 382 |
| NM_021082 | SLC15A2 | Extracellular domain | 383 |
| NM_021082 | SLC15A2 | Transmembrane domain | 384 |
| NM_021082 | SLC15A2 | Intracellular domain | 385 |
| NM_021082 | SLC15A2 | Transmembrane domain | 386 |
| NM_021082 | SLC15A2 | Extracellular domain | 387 |
| NM_021082 | SLC15A2 | Transmembrane domain | 388 |
| NM_021082 | SLC15A2 | Intracellular domain | 389 |
| NM_021082 | SLC15A2 | Transmembrane domain | 390 |
| NM_021082 | SLC15A2 | Extracellular domain | 391 |

TABLE 1C

| TARGET | Name | siRNA_Name | KD Target Sequence | SEQ ID NO. |
|---|---|---|---|---|
| ABCG1 | A150100-ABCG1_v5 | NM_004915_idx1797 | AGTGGATGTCCTACATCTC | 155 |
| | A150100-ABCG1_v6 | NM_004915_idx500 | ATCATGCAGGATGACATGC | 156 |
| | A150100-ABCG1_v7 | NM_004915_idx1481 | CTGAACTACTGGTACAGCC | 157 |
| | A150100-ABCG1_v10 | NM_004915_idx872 | CAGCTTTACGTCCTGAGTC | 158 |
| | A150100-ABCG1_v11 | NM_004915_idx1067 | TCAGACCACAAGAGAGACC | 159 |
| | A150100-ABCG1_v12 | NM_004915_idx1789 | GTACCTACAGTGGATGTCC | 160 |
| | A150100-ABCG1_v8 | NM_016818_idx603 | TGGTCAAGGAGATACTGAC | 161 |
| | A150100-ABCG1_v9 | NM_016818_idx718 | CCCTCCAGTCATGTTCTTC | 162 |
| DGKB | A150100-DGKB_v1 | NM_004080_idx104 | TTCCATGGTAATGGTGTGC | 84 |
| | A150100-DGKB_v2 | NM_004080_idx1064 | CCTGAATGTGACTGTGGAC | 91 |
| | A150100-DGKB_v3 | NM_004080_idx2398 | CCGAAGCAAGGAATAATCC | 85 |
| | A150100-DGKB_v10 | NM_145695_idx466 | TATGTTTCGCCTTTATGAC | 86 |
| | A150100-DGKB_v11 | NM_145695_idx654 | GGATTCAAGGAGGAATGAC | 87 |
| | A150100-DGKB_v12 | NM_145695_idx870 | CTCCCTCTTGCATCAAGAC | 88 |
| | A150100-DGKB_v13 | NM_145695_idx1387 | AAATCCTCGTCAGGTTTAC | 89 |
| | A150100-DGKB_v14 | NM_145695_idx1729 | AGTGCCTTACAGTATCATC | 90 |
| DUSP11 | A150100-DUSP11_v1 | NM_003584_idx427 | CAGAGGATTTGCCAGAAAC | 131 |
| | A150100-DUSP11_v2 | NM_003584_idx743 | TTGGAATTCCAGTGTACCC | 132 |
| | A150100-DUSP11_v3 | NM_003584_idx945 | CAGAGACACCATCTCCCTC | 133 |
| | A150100-DUSP11_v4 | NM_003584_idx885 | ACCCAGACCCAAAGTTTGC | 134 |
| | A150100-DUSP11_v5 | NM_003584_idx221 | AAGGTGGAAAGACTATCTC | 135 |
| | A150100-DUSP11_v6 | NM_003584_idx420 | TATAAACCAGAGGATTTGC | 136 |
| | A150100-DUSP11_v7 | NM_003584_idx836 | GTATAATCTACATCAGATC | 137 |
| | A150100-DUSP11_v8 | NM_003584_idx933 | CCACATGTTTACCAGAGAC | 138 |

TABLE 1C-continued

| TARGET | Name | siRNA_Name | KD Target Sequence | SEQ ID NO. |
|---|---|---|---|---|
| DUSP3 | A150100-DUSP3_v1 | NM_004090_idx425 | GCTAGTTATCGCCTACCTC | 139 |
| | A150100-DUSP3_v2 | NM_004090_idx300 | GACACACAGGAGTTCAACC | 140 |
| | A150100-DUSP3_v3 | NM_004090_idx176 | GCTGCAGAAACTAGGCATC | 141 |
| | A150100-DUSP3_v4 | NM_004090_idx248 | TGCCAACTTCTACAAGGAC | 142 |
| | A150100-DUSP3_v5 | NM_004090_idx299 | CGACACACAGGAGTTCAAC | 143 |
| | A150100-DUSP3_v6 | NM_004090_idx458 | GATGGACGTCAAGTCTGCC | 144 |
| | A150100-DUSP3_v7 | NM_004090_idx4305 | ACAGGAGTTCAACCTCAGC | 145 |
| ELA1 | A150100-ELA1_v1 | NM_001971_idx754 | TAATGTCATCGCCTCCAAC | 115 |
| | A150100-ELA1_v2 | NM_001971_idx162 | AGAACTGGGTGATGACAGC | 116 |
| | A150100-ELA1_v3 | NM_001971_idx421 | CAACAGTCCCTGCTACATC | 117 |
| | A150100-ELA1_v4 | NM_001971_idx280 | GATCGTGGTGCATCCATAC | 118 |
| | A150100-ELA1_v5 | NM_001971_idx230 | GCGTGGATTACCAGAAGAC | 119 |
| | A150100-ELA1_v6 | NM_001971_idx459 | TAACAACAGTCCCTGCTAC | 120 |
| | A150100-ELA1_v7 | NM_001971_idx669 | CCATTGCTTGGTGAATGGC | 121 |
| | A150100-ELA1_v8 | NM_001971_idx692 | ATTCTCTCCATGGAGTGAC | 122 |
| FZD1 | A150100-FZD1_v10 | NM_003505_idx1323 | GGTGTATGGGCTCATGTAC | 108 |
| | A150100-FZD1_v11 | NM_003505_idx2058 | CATCGTCATCGCCTGCTAC | 109 |
| | A150100-FZD1_v9 | NM_003505_idx2007 | GCTCATGGTGCGCATTGGC | 110 |
| | A150100-FZD1_v12 | NM_003505_idx2229 | GTACCTTATGACGCTGATC | 111 |
| | A150100-FZD1_v13 | NM_003505_idx3317 | ACCTGGTATGGGTTTGGCC | 112 |
| | A150100-FZD1_v14 | NM_003505_idx3883 | ATGTGTGCAGGTCTACTGC | 113 |
| | A150100-FZD1_v15 | NM_003505_idx2704 | TTATTTAGGGCGGTTTAAC | 114 |
| GGTLA4 | A150100-GGT1_v8 | NM_080839_idx451 | ACTGGCCATCATCTACAAC | 176 |
| | A150100-GGTLA4_v5 | NM_080920_idx292 | TGCTCACCTGTCTGTGGTC | 177 |
| | A150100-GGTLA4_v6 | NM_080920_idx702 | ACATTGACCAGGAAGTGAC | 178 |
| | A150100-GGTLA4_v7 | NM_080920_idx411 | TGGATGACTTCAGCTCTAC | 179 |
| | A150100-GGT1_v10 | NM_178311_idx629 | CTACAACCTCTGGTTCGGC | 180 |
| | A150100-GGT1_v11 | NM_178311_idx707 | CACGACAGTGGAGAGAAAC | 181 |
| | A150100-GGTLA4_v8 | NM_178311_idx287 | GTTCTACATGCCGGATGAC | 182 |
| GPR103 | A150100-GPR103_v5 | AF411117_idx611 | AGGCACCAGGGACTTGTGC | 100 |
| | A150100-GPR103_v6 | AF411117_idx820 | GATCTACACCACCTTCATC | 101 |
| | A150100-GPR103_v7 | XM_172359_idx288 | TGGTGTTCTACGTGGTGAC | 102 |
| | A150100-GPR103_v8 | AF411117_idx136 | TGTTAGGCGCCTGCATTGC | 103 |
| | A150100-GPR103_v10 | AF411117_idx424 | CAACATCTTTATCTGCTCC | 104 |
| | A150100-GPR103_v11 | AF411117_idx662 | CGAAGGGCTTTCACAATGC | 105 |
| | A150100-GPR103_v12 | AF411117_idx106 | GTACTACGTTGTAGCCCAC | 106 |
| | A150100-GPR103_v9 | AF411117_idx186 | TGCAGGCGCTTAACATTAC | 107 |

TABLE 1C-continued

| TARGET | Name | siRNA_Name | KD Target Sequence | SEQ ID NO. |
|---|---|---|---|---|
| ICK | A150100-ICK_v1 | NM_016513_idx870 | GACTGACTGGCCTGAAGGC | 92 |
|  | A150100-ICK_v2 | NM_016513_idx1665 | GCAGCACTATTTGAAGCAC | 93 |
|  | A150100-ICK_v3 | NM_016513_idx588 | GCCTGAGAACCTCCTCTGC | 94 |
|  | A150100-ICK_v10 | NM_016513_idx1027 | ACAGCTAGTCAGGCACTTC | 95 |
|  | A150100-ICK_v11 | NM_016513_idx1707 | TATAAGAAATGGCATACTC | 96 |
|  | A150100-ICK_v12 | NM_016513_idx1754 | CTAATCCATGGTCTAGTTC | 97 |
|  | A150100-ICK_v8 | NM-016513_idx504 | GTCTGCTATAAGGAATATC | 98 |
|  | A150100-ICK_v9 | NM_016513_idx713 | AAGTACTCCTGAGGTCTAC | 99 |
| JAK1 | A150100-JAK1_v1 | oKD271 | TTGGCATGGAACCAACGAC | 146 |
|  | A150100-JAK1_v2 | oKD270 | CCTCTTTGCCCTGTATGAC | 147 |
|  | A150100-JAK1_v7 | oKD272 | AGATTCCAGATGCAACCCC | 148 |
|  | A150100-JAK1_v8 | SK185_idx1743 | CATGAGCCAGCTGAGTTTC | 149 |
|  | A150100-JAK1_v9 | SK185_idx142 | GTGGAAGTGATCTTCTATC | 150 |
|  | A150100-JAK1_v12 | NM_002227_idx1351 | TGGCTGTCATGGTCCAATC | 151 |
|  | A150100-JAK1_v13 | NM_002227_idx2512 | CCGCTGCATGAACTATGAC | 152 |
|  | A150100-JAK1_v14 | NM_002227_idx3093 | TTGGAGACTTCGGTTTAAC | 153 |
|  | A150100-JAK1_v15 | NM_002227_idx3269 | TGTGATTCAGATTCTAGTC | 154 |
| PDE1A | A150100-PDE1A_v5 | NM_005019_idx913 | AGGTATCATGCACTGGCTC | 183 |
|  | A150100-PDE1A_v6 | NM_005019_idx1382 | GAAGCTGAATTAGGGCTTC | 184 |
|  | A150100-PDE1A_v7 | NM_005019_idx1709 | CTGGTGGACATCATTCAGC | 185 |
|  | A150100-PDE1A_v10 | NM_005019_idx1413 | TTTGTGATCGGAAGTCAAC | 186 |
|  | A150100-PDE1A_v11 | NM_005019_idx1601 | ATTGCTGATGCACTAAGAC | 187 |
|  | A150100-PDE1A_v12 | NM_005019_idx754 | CAGATATGATCTTATCAAC | 188 |
|  | A150100-PDE1A_v13 | NM_005019_idx887 | ACTGTGCATTACATAATGC | 189 |
|  | A150100-PDE1A_v9 | NM_005019_idx1073 | CACGTGAGTGCAGCTTATC | 190 |
| SLC15A2 | A150100-SLC15A2_v1 | NM_021082_idx457 | AGTCCTATCATTGATCGGC | 191 |
|  | A150100-SLC15A2_v2 | NM_021082_idx_121 | GAAGCCATCTCCGACAATC | 192 |
|  | A150100-SLC15A2_v3 | NM_021082_idx_1166 | ATGGCTGTTGGTATGATCC | 193 |
|  | A150100-SLC15A2_v4 | NM_021082_idx_1575 | CCGTGAGGTTTGTTAACAC | 194 |
|  | A150100-SLC15A2_v5 | NM_021082_idx_423 | TTGGGTGCCTTACCAATAC | 195 |
|  | A150100-SLC15A2_v6 | NM_021082_idx_1136 | CTCCAAGTGTGGAATTAAC | 196 |
|  | A150100-SLC15A2_v7 | NM_021082_idx_1534 | GCATGATGGTAAAGGATAC | 197 |
| SLC26A8 | A150100-SLC26A8_v10 | NM_052961_idx1925 | TTCTGCAACTGTGATGATC | 163 |
|  | A150100-SLC26A8_v11 | NM_052961_idx2288 | GTACACTACGTGGATTCAC | 164 |
|  | A150100-SLC26A8_v2 | NM_052961_idx923 | GCGAATTCCACCAGCATTC | 165 |
|  | A150100-SLC26A8_v3 | NM_052961_idx1761 | TCTTCCAGTGCTGCAGCTC | 166 |
|  | A150100-SLC26A8_v4 | NM_052961_idx2693 | TCAGAACAAGAGGCTGGGC | 167 |

TABLE 1C-continued

| TARGET | Name | siRNA_Name | KD Target Sequence | SEQ ID NO. |
|---|---|---|---|---|
| | A150100-SLC26A8_v5 | NM_052961_idx1228 | GAAGATTGCCAGTCTTCAC | 168 |
| | A150100-SLC26A8_v6 | NM_052961_idx457 | GATTCCTCCTCTCAACATC | 169 |
| | A150100-SLC26A8_v7 | NM_052961_idx936 | GCATTCTAGTATTTCTAAC | 170 |
| | A150100-SLC26A8_v8 | NM_052961_idx1249 | TTACAGTGTCAATTCCAAC | 171 |
| | A150100-SLC26A8_v9 | NM_052961_idx1723 | TGATTATCGGGAGATCATC | 172 |
| | A150100-SLC26A8_v12 | NM_052961_idx338 | GAATGGATGTGTATGTATC | 173 |
| | A150100-SLC26A8_v13 | NM_052961_idx1105 | TGACATGATTCCTTATAGC | 174 |
| | A150100-SLC26A8_v14 | NM_052961_idx1446 | TCTACACACTGCCAAATGC | 175 |
| USP9Y | A150100-USP9Y_v1 | NM_004654_idx5651 | ATGAACTCTGTGATCCAGC | 123 |
| | A150100-USP9Y_v2 | NM_004654_idx1600 | AGGTTGGCTAGTGGATCTC | 124 |
| | A150100-USP9Y_v3 | NM_004654_idx2636 | AAGTGGGTAATTCCTGCTC | 125 |
| | A150100-USP9X_v4 | NM_021906_idx1189 | CGAATGGCAGAATGGATAC | 126 |
| | A150100-USP9X_v5 | NM_004654_idx7911 | TCTGGCAGGTTGCATATTC | 127 |
| | A150100-USP9Y_v4 | NM_004654_idx1489 | CTGCAAGTTTCATATCTAC | 128 |
| | A150100-USP9Y_v5 | NM_004654_idx2820 | ATAGCATCAGATTGTATGC | 129 |
| | A150100-USP9Y_v6 | NM_004654_idx5731 | TTTACACGATGATATGTTC | 130 |

The present invention relates to a method for assaying for compounds that induce anabolic stimulation of chondrocytes, comprising contacting the compound with a polypeptide comprising an amino acid sequence of the polypeptides of SEQ ID NO: 55-82 ("TARGETS") or a functional fragment thereof under conditions that allow said polypeptide to bind to the compound, and detecting the formation of a complex between the polypeptide and the compound. One preferred means of measuring the complex formation is to determine the binding affinity of said compound to said polypeptide.

More particularly, the invention relates to a method for identifying an agent that induces anabolic stimulation of chondrocytes, the method comprising further:
(a) contacting a population of chondrocyte cells with one or more of said compound that exhibits binding affinity for said TARGETS, and
(b) measuring a compound-polypeptide property related to the anabolic stimulation of chondrocytes.

The compound-polypeptide property referred to above is related to the anabolic stimulation of chondrocytes, and is a measurable phenomenon chosen by the person of ordinary skill in the art. The measurable property may e.g. be the binding affinity for a peptide domain of the polypeptide TARGET or the level of any one of a number of biochemical marker levels of increased chondrocyte anabolism. Anabolic stimulation of chondrocytes can e.g. be measured by measuring the level of proteins and other molecules that are induced during the differentiation process, such as key components of normal cartilage. In particular, the induction of the major protein component of cartilage, collagen II, is measured.

In addition, compound-polypeptide properties related to the anabolic stimulation of chondrocytes are measured in C20/A4; T/C-28a2; T/C-28a4; C-28/12; Ch-4,8, N; Ch-8-OA; TC6; MCT; MC615; IRC; RCS2; Hig82; and D1 ORL UVA (D1) cells. However, such properties are also measured in non-chondrocyte cell systems. For example, in situ binding assays that determine the affinity of compounds to bind to polypeptides of the invention are performed using any cell type that expresses the polypeptide. Expression of the polypeptide is exogenous or endogenous. Furthermore, when the compound-polypeptide property is activation of a biological pathway, any cell that contains the pathway cellular components is used to measure the compound-polypeptide property. For example, induction of col2α1 or aggrecan in chondrocytes is indicative of anabolic stimulation of chondrocytes. Specifically, non-chondrocyte cells can be engineered to contain a reporter molecule activated by the col2α1 or aggrecan promoters. In this way a non-chondrocyte can be used to measure a property indicative of anabolic stimulation of chondrocytes.

The invention relates to a method for identifying a compound that induces and/or increases anabolic stimulation of chondrocytes, said method comprising the steps of: culturing a population of cells expressing a polypeptide of any one of those listed in Table 1A, or a functional fragment or derivative thereof; determining a first level of chondrogenic differentiation in said population of cells; exposing said population of cells to a compound, or a mixture of compounds; determining the level of chondrogenic differentiation in said population of cells during or after exposure of said population of cells to the compound, or the mixture of compounds; and identifying the compound that induces and/or increases chondrogenic differentiation.

The invention also relates to a method for identifying a compound that decreases the expression and/or activity of any one of the polypeptides listed in Table 1A, said method comprising the steps of: culturing a population of cells expressing said polypeptide, or a fragment, or a derivative thereof; determining a first level of expression and/or activity of said polypeptide; exposing said population of cells to a compound, or a mixture of compounds; determining the level of expression and/or activity of said polypeptide during or after exposure of said population of cells to the compound, or the mixture of compounds; and identifying the compound that decreases the expression and/or activity of said polypeptide. If the polypeptide activity is not readily measurable, the identification of the compound may benefit from an extra step comprising exposing said population of cells to an agonist of said polypeptide. Furthermore, the methods of the present invention may comprise the step of introducing a gene encoding any one of the polypeptides listed in Table 1A, in said population of cells. For high-throughput purposes it may be beneficial to have the gene stably integrated in the genome of said cells.

In a preferred embodiment, the level of chondrocyte (re-) differentiation is determined by measuring the expression level of a marker gene, wherein a preferred marker gene encodes collagen type II, alpha-1 (col2α1) or aggrecan. For proper anabolic stimulation it is preferred that the expression and/or activity of col2α1 or aggrecan is increased.

The present invention provides in one particular embodiment methods for identifying novel compounds, wherein the polypeptide is a GPCR. If so, the expression and/or activity of said GPCR is preferably determined by measuring the level of a second messenger. Preferred second messengers are cyclic AMP, $Ca^{2+}$ or both. Typically, the level of the second messenger is determined with a reporter gene under the control of a promoter that is responsive to the second messenger, wherein it is preferred that the promoter is a cyclic AMP-responsive promoter, an NF-KB responsive promoter, or a NF-AT responsive promoter, and wherein the reporter gene is selected from the group consisting of: alkaline phosphatase, GFP, eGFP, dGFP, luciferase and β-α galactosidase.

In another particular embodiment, the invention provides methods for identifying novel compounds, wherein the polypeptide is a kinase or a phosphatase. Preferably, the activity of said kinase or phosphatase is determined by measuring the level of phosphorylation of a substrate of said kinase or phosphatase.

In yet another particular embodiment, the invention provides methods for identifying novel compounds, wherein the polypeptide is a protease. Preferably, the activity of said protease is measured by determining the level of cleavage of a substrate of said protease.

Methods for determining second messenger levels, use of the reporter genes and second-messenger responsive promoters as well as phosphatase assays and protease assays are well known in the art and not further elaborated upon herein.

In a preferred embodiment, the compound that inhibits the polypeptide exhibits a binding affinity to the polypeptide of at most 10 micromolar.

In a preferred embodiment of the invention, the polypeptide TARGET comprises an amino acid sequence selected from the group consisting of SEQ ID NO: 55-82 and 198-391 (Tables 1A and 1B). In an especially preferred embodiment of the invention, the polypeptide TARGET comprises an amino acid sequence selected from the group consisting of SEQ ID NO: 55-82 (Table 1A).

Depending on the choice of the skilled artisan, the present assay method may be designed to function as a series of measurements, each of which is designed to determine whether the drug candidate compound is indeed acting on the polypeptide to thereby induce the anabolic stimulation of chondrocytes. For example, an assay designed to determine the binding affinity of a compound to the polypeptide, or fragment thereof, may be necessary, but not sufficient, to ascertain whether the test compound would be useful for increasing mean cartilage thickness when administered to a subject. Nonetheless, such binding information would be useful in identifying a set of test compounds for use in an assay that would measure a different property, further up the biochemical pathway, such as cartilage component synthesis, assayed by measuring the amount of collagen II. Such second assay may be designed to confirm that the test compound, having binding affinity for the polypeptide, actually induces the anabolic stimulation of chondrocytes. Suitable controls should always be in place to insure against false positive readings.

The order of taking these measurements is not believed to be critical to the practice of the present invention, which may be practiced in any order. For example, one may first perform a screening assay of a set of compounds for which no information is known respecting the compounds' binding affinity for the polypeptide. Alternatively, one may screen a set of compounds identified as having binding affinity for a polypeptide domain, or a class of compounds identified as being an inhibitor of the polypeptide. However, for the present assay to be meaningful to the ultimate use of the drug candidate compounds, a measurement of collagen II levels or aggrecan is necessary. Validation studies including controls, and measurements of binding affinity to the polypeptides of the invention are nonetheless useful in identifying a compound useful in any therapeutic or diagnostic application.

The binding affinity of the compound with the polypeptide TARGET can be measured by methods known in the art, such as using surface plasmon resonance biosensors (Biacore), by saturation binding analysis with a labeled compound (e.g. Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as IC50 or EC50. The IC50 represents the concentration of a compound that is required for 50% inhibition of binding of another ligand to the polypeptide. The EC50 represents the concentration required for obtaining 50% of the maximum effect in any assay that measures TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, IC50 and EC50 values, i.e. in the range of 100 nM to 1 pM; a moderate to low affinity binding relates to a high Kd, IC50 and EC50 values, i.e. in the micromolar range.

The present assay method may also be practiced in a cellular assay, A host cell expressing TARGET can be a cell with endogenous expression or a cell over-expressing the TARGET e.g. by transduction. When the endogenous expression of the polypeptide is not sufficient to determine a baseline that can easily be measured, one may use using host cells that over-express TARGET. Over-expression has the advantage that the level of the TARGET substrate end products is higher than the activity level by endogenous expression. Accordingly, measuring such levels using presently available techniques is easier. In such cellular assay, the biological activity of TARGET may be measured by following the production of cartilage component synthesis.

The present invention further relates to a method for identifying a compound that induces anabolic stimulation of chondrocytes, comprising:
(a) contacting a compound with a polypeptide comprising an amino acid sequence selected from the group consisting of SEQ ID NO: 55-82 and 198-391;
(b) determining the binding affinity of the compound to the polypeptide;
(c) contacting a population of mammalian cells expressing said polypeptide with the compound that exhibits a binding affinity of at least 10 micromolar; and
(d) identifying the compound that induces the synthesis of proteins that are a constituent of normal cartilage and/or that are required for the formation of cartilage.

For high-throughput purposes, libraries of compounds may be used such as antibody fragment libraries, peptide phage display libraries, peptide libraries (e.g. LOPAP™, Sigma Aldrich), lipid libraries (BioMol), synthetic compound libraries (e.g. LOPAC™, Sigma Aldrich) or natural compound libraries (Specs, TimTec).

Preferred drug candidate compounds are low molecular weight compounds. Low molecular weight compounds, i.e. with a molecular weight of 500 Dalton or less, are likely to have good absorption and permeation in biological systems and are consequently more likely to be successful drug candidates than compounds with a molecular weight above 500 Dalton (Lipinski et al. (1997)). Peptides comprise another preferred class of drug candidate compounds. Peptides may be excellent drug candidates and there are multiple examples of commercially valuable peptides such as fertility hormones and platelet aggregation inhibitors. Natural compounds are another preferred class of drug candidate compound. Such compounds are found in and extracted from natural sources, and which may thereafter be synthesized. The lipids are another preferred class of drug candidate compound.

Another preferred class of drug candidate compounds is an antibody. The present invention also provides antibodies directed against a TARGET. These antibodies may be endogenously produced to bind to the TARGET within the cell, or added to the tissue to bind to TARGET polypeptide present outside the cell. These antibodies may be monoclonal antibodies or polyclonal antibodies. The present invention includes chimeric, single chain, and humanized antibodies, as well as FAb fragments and the products of a FAb expression library, and Fv fragments and the products of an Fv expression library.

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact TARGET protein or polypeptide, or against a fragment, derivatives including conjugates, or other epitope of the TARGET protein or polypeptide, such as the TARGET embedded in a cellular membrane, or a library of antibody variable regions, such as a phage display library.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991). J. Mol. Biol. 222:581-97). The techniques of Cole, et al. and Boerner, et al. are also available for the preparation of human monoclonal antibodies (Cole, et al. (1985) Monoclonal Antibodies and Cancer Therapy, Alan R. Liss, p. 77; Boerner, et al (1991). J. Immunol., 147(1):86-95).

Techniques known in the art for the production of single chain antibodies can be adapted to produce single chain antibodies to the TARGET polypeptides and proteins of the present invention. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively; the relevant cysteine residues are substituted with another amino acid residue or are deleted so as to prevent cross-linking.

Bispecific antibodies are monoclonal, preferably human or humanized, antibodies that have binding specificities for at least two different antigens and preferably for a cell-surface protein or receptor or receptor subunit. In the present case, one of the binding specificities is for one domain of the TARGET; the other one is for another domain of the same or different TARGET.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

According to another preferred embodiment, the assay method uses a drug candidate compound identified as having a binding affinity for a TARGET, and/or has already been identified as having down-regulating activity such as antagonist activity vis-à-vis one or more TARGET.

The present invention further relates to a method for inducing anabolic stimulation of chondrocytes comprising contacting said cells with an expression inhibitory agent comprising a polynucleotide sequence that complements at least about 17 nucleotides of the polyribonucleotide comprising a nucleotide sequence selected from the group consisting of SEQ ID NO: 1-28. In a preferred embodiment the expression-inhibitory agent comprises a polynucleotide sequence that complements a nucleotide sequence selected from the group consisting of SEQ ID NO: 84-197 and 410.

Another aspect of the present invention relates to a method for inducing the anabolic stimulation of chondrocytes, comprising by contacting said cell with an expression-inhibiting agent that inhibits the translation in the cell of a polyribonucleotide encoding a TARGET polypeptide. A particular embodiment relates to a composition comprising a polynucleotide including at least one antisense strand that functions to pair the agent with the TARGET TARGET mRNA, and thereby down-regulate or block the expression of TARGET polypeptide. The inhibitory agent preferably comprises antisense polynucleotide, a ribozyme, and a small interfering RNA (siRNA), wherein said agent comprises a nucleic acid sequence complementary to, or engineered from, a naturally-occurring polynucleotide sequence encoding a portion of a polypeptide comprising an amino acid sequence selected from the group consisting of SEQ ID NO: 55-82. In a preferred embodiment the expression-inhibiting agent is complementary to a polynucleotide sequence selected from the group consisting of SEQ ID NO: 1-28. In an especially preferred embodiment the expression-inhibiting agent is complementary to a polynucleotide sequence selected from the group consisting of SEQ ID NO: 84-197 and 410.

An embodiment of the present invention relates to a method wherein the expression-inhibiting agent is selected from the group consisting of antisense RNA, antisense oligodeoxynucleotide (ODN), a ribozyme that cleaves the polyribonucleotide coding for SEQ ID NO: 55-82, a small interfering RNA (siRNA, preferably shRNA,) that is sufficiently complementary to a portion of the polyribonucleotide coding for SEQ ID NO: 55-82, such that the siRNA, preferably shRNA, interferes with the translation of the TARGET polyribonucleotide to the TARGET polypeptide. Preferably the expression-inhibiting agent is an antisense RNA, ribozyme, antisense oligodeoxynucleotide, or siRNA, preferably shRNA, complementary to a nucleotide sequence selected from the group consisting of SEQ ID NO: 1-28. In an especially preferred embodiment the expression-inhibiting agent is complementary to a polynucleotide sequence selected from the group consisting of SEQ ID NO: 84-197 and 410.

A special embodiment of the present invention relates to a method wherein the expression-inhibiting agent is a nucleic acid expressing the antisense RNA, antisense oligodeoxynucleotide (ODN), a ribozyme that cleaves the polyribonucleotide coding for SEQ ID NO: 55-82, a small interfering RNA (siRNA, preferably shRNA,) that is sufficiently complementary to a portion of the polyribonucleotide coding for SEQ ID NO: 55-82, such that the siRNA, preferably shRNA, interferes with the translation of the TARGET polyribonucleotide to the TARGET polypeptide. Preferably the nucleotide sequence is complementary to a polynucleotide selected from the group consisting of SEQ ID NO: 1-28. In an especially preferred embodiment nucleotide sequence is complementary to a polynucleotide selected from the group consisting of SEQ ID NO: 84-197 and 410.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding a TARGET polypeptide or the corresponding messenger RNA. In addition, antisense nucleic acids may be designed which decrease expression of the nucleic acid sequence capable of encoding a TARGET polypeptide by inhibiting splicing of its primary transcript. Any length of antisense sequence is suitable for practice of the invention so long as it is capable of down-regulating or blocking expression of a nucleic acid coding for a TARGET. Preferably, the antisense sequence is at least about 17 nucleotides in length. The preparation and use of antisense nucleic acids, DNA encoding antisense RNAs and the use of oligo and genetic antisense is known in the art.

One embodiment of expression-inhibitory agent is a nucleic acid that is antisense to a nucleic acid comprising SEQ ID NO: 1-28. For example, an antisense nucleic acid (e.g. DNA) may be introduced into cells in vitro, or administered to a subject in vivo, as gene therapy to inhibit cellular expression of nucleic acids comprising SEQ ID NO: 1-28. Antisense oligonucleotides preferably comprise a sequence containing from about 17 to about 100 nucleotides and more preferably the antisense oligonucleotides comprise from about 18 to about 30 nucleotides. Antisense nucleic acids may be prepared from about 10 to about 30 contiguous nucleotides complementary to a nucleic acid sequence selected from the sequences of SEQ ID NO: 1-28.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its TARGET site, the RN202-315NA duplex activates the endogenous enzyme ribonuclease (RNase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its TARGET site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that reduces the levels of TARGETS is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its TARGET sequence. The catalytic portion cleaves the TARGET RNA at a specific site. The substrate domain of a ribozyme can be engineered to direct it to a specified mRNA sequence. The ribozyme recognizes and then binds a TARGET mRNA through complementary base pairing. Once it is bound to the correct TARGET site, the ribozyme acts enzymatically to cut the TARGET mRNA. Cleavage of the mRNA by a ribozyme destroys its ability to direct synthesis of the corresponding polypeptide. Once the ribozyme has cleaved its TARGET sequence, it is released and can repeatedly bind and cleave at other mRNAs.

Ribozyme forms include a hammerhead motif, a hairpin motif, a hepatitis delta virus, group I intron or RNaseP RNA (in association with an RNA guide sequence) motif or Neurospora VS RNA motif Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the TARGET mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

A particularly preferred inhibitory agent is a small interfering RNA (siRNA, preferably shRNA). siRNA, preferably shRNA, mediate the post-transcriptional process of gene silencing by double stranded RNA (dsRNA) that is homologous in sequence to the silenced RNA. siRNA according to the present invention comprises a sense strand of 17-25 nucleotides complementary or homologous to a contiguous 17-25 nucleotide sequence selected from the group of sequences described in SEQ ID NO: 1-28, preferably from the group of sequences described in SEQ ID No: 84-197 or 410, and an antisense strand of 17-23 nucleotides complementary to the sense strand. Exemplary sequences are described as sequences complementary to SEQ ID NO: 84-197 or 410. The most preferred siRNA comprises sense and anti-sense strands that are 100 percent complementary to each other and the TARGET polynucleotide sequence. Preferably the siRNA further comprises a loop region linking the sense and the antisense strand.

A self-complementing single stranded siRNA molecule polynucleotide according to the present invention comprises a sense portion and an antisense portion connected by a loop region linker. Preferably, the loop region sequence is 4-30 nucleotides long, more preferably 5-15 nucleotides long and most preferably 8 nucleotides long. In a most preferred embodiment the linker sequence is UUGCUAUA (SEQ ID NO: 83). Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates. The nucleotide sequences are selected according to siRNA designing rules that give an improved reduction of the TARGET sequences compared to nucleotide sequences that do not comply with these siRNA designing rules (For a discussion of these rules and examples of the preparation of siRNA, WO2004094636, published Nov. 4, 2004, and UA20030198627, are hereby incorporated by reference).

The present invention also relates to compositions, and methods using said compositions, comprising a DNA expression vector capable of expressing a polynucleotide capable of inducing anabolic stimulation of chondrocytes and described hereinabove as an expression inhibition agent.

A special aspect of these compositions and methods relates to the down-regulation or blocking of the expression of a TARGET polypeptide by the induced expression of a polynucleotide encoding an intracellular binding protein that is capable of selectively interacting with the TARGET polypeptide. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of the TARGET polypeptide of SEQ ID NO: 55-82, 198-391. More preferably, the intracellular binding protein is a single chain antibody.

A special embodiment of this composition comprises the expression-inhibiting agent selected from the group consisting of antisense RNA, antisense oligodeoxynucleotide (ODN), a ribozyme that cleaves the polyribonucleotide coding for SEQ ID NO: 55-82, and a small interfering RNA (siRNA) that is sufficiently homologous to a portion of the polyribonucleotide coding for SEQ ID NO: 55-82, such that the siRNA interferes with the translation of the TARGET polyribonucleotide to the TARGET polypeptide.

The polynucleotide expressing the expression-inhibiting agent is preferably included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaviral vector systems, and all may be used to introduce and express polynucleotide sequence for the expression-inhibiting agents in TARGET cells.

Preferably, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from an adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the TARGET cell population that an adenoviral capsid of the invention can enter in a preferred embodiment, the vehicle includes adenoviral fiber proteins from at least two adenoviruses. Preferred adenoviral fiber protein sequences are serotype 17, 45 and 51. Techniques or construction and expression of these chimeric vectors are disclosed in US Published Patent Applications 20030180258 and 20040071660, hereby incorporated by reference.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to TARGET the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda $P_r$, $P_1$, and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift, et al. (1984) Cell 38:639-46; Ornitz, et al. (1986) Cold Spring Harbor Symp. Quant. Biol. 50:399-409; MacDonald, (1987) Hepatology 7:425-515); insulin gene control region which is active in pancreatic beta cells (Hanahan, (1985) Nature 315:115-22), immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), albumin gene control region which is active in liver (Pinkert, et al. (1987) Genes and Devel. 1:268-76), alpha-fetoprotein gene control region which is active in liver (Krumlauf, et al. (1985) Mol. Cell. Biol., 5:1639-48; Hammer, et al. (1987) Science 235:53-8), alpha 1-antitrypsin gene control region which is active in the liver (Kelsey, et al. (1987) Genes and Devel., 1: 161-71), beta-globin gene control region which is active in myeloid cells (Mogram, et al. (1985) Nature 315: 338-40; Kollias, et al. (1986) Cell 46:89-94), myelin basic protein gene control region which is active in oligodendrocyte cells in the brain (Readhead, et al. (1987) Cell 48:703-12), myosin light chain-2 gene control region which is active in skeletal muscle (Sani, (1985) Nature 314.283-6), and gonadotropic releasing hormone gene control region which is active in the hypothalamus (Mason, et al. (1986) Science 234:1372-8).

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Felgner, et. al. (1987) Proc. Natl. Acad Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Felgner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589,466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263: 14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

The present invention also provides biologically compatible, cartilage formation-enhancing compositions comprising an effective amount of one or more compounds identified as TARGET inhibitors, and/or the expression-inhibiting agents as described hereinabove.

A biologically compatible composition is a composition, that may be solid, liquid, gel, or other form, in which the compound, polynucleotide, vector, and antibody of the invention is maintained in an active form, e.g., in a form able to effect a biological activity. For example, a compound of the invention would have inverse agonist or antagonist activity on the TARGET; a nucleic acid would be able to replicate, translate a message, or hybridize to a complementary mRNA of a TARGET; a vector would be able to transfect a TARGET cell and expression the antisense, antibody, ribozyme or siRNA as described hereinabove; an antibody would bind a TARGET polypeptide domain.

A preferred biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particularly preferred embodiment of the present composition invention is a cartilage formation-enhancing pharmaceutical composition comprising a therapeutically effective amount of an expression-inhibiting agent as described hereinabove, in admixture with a pharmaceutically acceptable carrier. Another preferred embodiment is a pharmaceutical composition for the treatment or prevention of a condition a systemic or local decrease in mean cartilage thickness, or a susceptibility to the condition, comprising an effective cartilage formation-enhancing amount of a TARGET antagonist or inverse agonist, its pharmaceutically acceptable salts, hydrates, solvates, or prodrugs thereof in admixture with a pharmaceutically acceptable carrier.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the polynucleotide inhibitory agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to TARGET tissues, complexed with cationic lipids, packaged within liposomes, or delivered to TARGET cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

The present invention also provides methods of enhancing cartilage formation, which comprise the administration to said subject a therapeutically effective amount of an expression-inhibiting agent of the invention. A further aspect of the invention relates to a method of treating or preventing a disease involving chondrocyte anabolic stimulation, comprising administering to said subject a cartilage formation-enhancing pharmaceutical composition as described herein.

Examples of diseases involving anabolic stimulation of chondrocytes that are treatable using the means and methods of the present invention include, but are not limited to osteoarthritis, rheumatoid arthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease, and Handigodu disease; degeneration resulting from fibromyalgia, systemic lupus erythematosus, scleroderma, and ankylosing spondylitis. Furthermore, people suffering from congenital cartilage malformations, including hereditary chondrolysis, chondrodysplasias and pseudoachondrodysplasias, are likely to benefit from programs that result in anabolic stimulation of chondrocytes, and these diseases therefore may also be treated by using the methods and means of the present invention. Non-limiting examples of congenital cartilage malformation related diseases are microtia, anotia, and metaphyseal chondrodysplasia.

The polypeptides or the polynucleotides employed in the methods of the present invention may be free in solution, affixed to a solid support, borne on a cell surface, or located intracellularly. To perform the methods it is feasible to immobilize either the polypeptide of the present invention or the compound to facilitate separation of complexes from uncomplexed forms of the polypeptide, as well as to accommodate automation of the assay. Interaction (e.g., binding of) of the polypeptide of the present invention with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the polypeptide of the present invention can be "His" tagged, and subsequently adsorbed onto Ni-NTA microtitre plates, or ProtA fusions with the polypeptides of the present invention can be adsorbed to IgG, which are then combined with the cell lysates (e.g., ($^{35}$S-labelled) and the candidate compound, and the mixture incubated under conditions favorable for complex formation (e.g., at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the protein of the present invention quantitated from the gel using standard electrophoretic techniques.

Other techniques for immobilizing protein on matrices can also be used in the method of identifying compounds. For example, either the polypeptide of the present invention or the compound can be immobilized utilizing conjugation of biotin and streptavidin. Biotinylated protein molecules of the present invention can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptides of the present invention but which do not interfere with binding of the polypeptide to the compound can be derivatized to the wells of the plate, and the polypeptide of the present invention can be trapped in the wells by antibody conjugation. As described above, preparations of a labeled candidate compound are incubated in the wells of the plate presenting the polypeptide of the present invention, and the amount of complex trapped in the well can be quantitated.

Another embodiment of the present invention relates to a method for in vitro production of cartilage tissue, comprising the steps of contacting chondrocyte cells with a polynucleotide sequence comprising a sequence selected from the group consisting of sequences complementary to SEQ ID No: 1-28, preferably selected from the group consisting of sequences complementary to SEQ ID NO: 84-197 for a time sufficient to re-differentiate the chondrocytes thereby producing a cartilaginous matrix.

In a preferred embodiment, the method comprises the steps of:
(a) applying chondrocyte cells on a substrate to form a cellular substrate,
(b) introducing a polynucleotide comprising a nucleotide sequence selected from the group consisting of sequences complementary to SEQ ID No: 1-28, preferably selected from the group consisting of sequences complementary to SEQ ID NO: 84-197, for a time sufficient to re-differentiate the chondrocyte cells, thereby producing a cartilaginous matrix.

The invention thus provides a method for producing a substrate with a matrix grown thereon, which matrix may be used for the provision of load-bearing implants, including joint prostheses, such as artificial knee joints and finger joints, and maxillofacial implants. It can also be used for special surgery devices, such as spacers, or cartilage fillers, and for use in augmentation, obliteration or reconstitution of cartilage defects and damaged or lost cartilage.

The present invention also relates to a combination of a load-bearing implant (preferably coated with a matrix as described above) with a cartilage filler comprising a matrix as described.

The method of the invention is also very suitable in relation to revision surgery, i.e., when previous surgical devices require replacement.

Suitable cells are stem cells cells, including mesenchymal stem cells cells and in particular chondrosyte precursor cells. The mesenchymal stem cells, and especially the chondrosyte precursor cells are found to be very effective in the cartilage producing process when taken from their original environment. In addition, cells derived from cartilage biopsies of a subject may be cultured and utilized with the present invention.

The mesenchymal stem cells can be directly applied on the substrate or they can advantageously be multiplied in the absence of the substrate before being applied on the substrate. In the latter mode, the cells are still largely multipotent after multiplication and, for the purpose of the invention, they are still referred to as undifferentiated. Subsequently, the cells are allowed to differentiate. Differentiation can be induced or enhanced by the presence of suitable inductors, such as bone morphogenic proteins (BMP2; BM4; BMP7), transforming growth factor beta (TGFbeta), CDMP1 and CDMP2. Especially suitable inductors of differentiation are the expression inhibitory agents of the present invention.

The use of mesenchymal stem cells provides several advantages. Firstly, their lower differentiation implies a higher proliferation rate and allows the eventual functionality to be better directed and controlled. Moreover, culturing these cells not only produces the required cartilage matrix containing organic and inorganic components, but also results in the presence, in the culture medium and in the matrix, of several factors which are essential for growth of the tissue and for adaptation to existing living tissue. Also, the culture medium can be a source of active factors such as growth factors, to be used in connection with the implanting process. Furthermore, such undifferentiated cells are often available in large quantities and more conveniently than e.g., mature cartilage cells, and exhibit a lower morbidity during recovery. Moreover, the undifferentiated cells can be obtained from the patient for whom the implant is intended. The cartilage resulting from these cells is autologous to the patient and thus no immune response will be induced. Matrices as thick as 100 μm can be produced as a result of the use of undifferentiated cells.

The substrate on which the undifferentiated cells can be applied and cultured can be a metal, such as titanium, cobalt/chromium alloy or stainless steel, a bioactive surface such as a calcium phosphate, polymer surfaces such as polyethylene, and the like. Although less preferred, siliceous material such as glass ceramics, can also be used as a substrate. Most preferred are metals, such as titanium, and calcium phosphates, even though calcium phosphate is not an indispensable component of the substrate. The substrate may be porous or non-porous. The cells can be applied at a rate of e.g., $10^3$-$10^6$ per $cm^2$, in particular $10^4$-$2\times10^5$ cells per $cm^2$.

The culture medium to be used in the method according to the invention can be a commonly known culture medium such as MEM (minimum essential medium). Advantageously, the medium can be a conditioned medium. In this context, a conditioned medium is understood to be a medium wherein similar cells have previously been incubated, causing the medium to contain factors such as polypeptides, secreted by the cells which are important for cell growth and cell differentiation.

The cells are cultured for a time sufficient to produce a matrix layer, e.g., a matrix layer having a thickness of at least 0.5 μm, in particular from 1 up to 100 μm, more in particular of 10-50 μm. The cells may be contacted with the culture medium for e.g. 2-15 weeks, in particular 4-10 weeks.

The production of the matrix, when applied on a substrate, results in a continuous or quasi-continuous coating covering the substrate for at least 50%, in particular at least 80% of its surface area.

In yet another aspect of the invention, the invention provides a method for diagnosing a pathological condition involving chondrocyte de-differentiation, said method comprising the steps of: determining the nucleic acid sequence of any one of the genes encoding the polypeptides listed in Table 1A in a genomic DNA sample; comparing the sequence from step (a) with the nucleic acid sequence of a healthy subject; and identifying any difference(s) related to the pathological condition. Such differences may be further checked in in vitro assays applying similar marker genes as disclosed herein. Such assays will reveal the role of the gene or its encoded polypeptide in anabolic stimulation processes of chondrocytes. If such mutations are identified this knowledge can be further exploited in test-kits for diagnosis of similar diseases.

Still another aspect or the invention relates to a method for diagnosing a pathological condition involving chondrocyte anabolic stimulation or a susceptibility to the condition in a subject, comprising determining the amount of polypeptide comprising an amino acid sequence selected from the group consisting of SEQ ID NO: 55-82, 198-391 in a biological sample, and comparing the amount with the amount of the polypeptide in a healthy subject, wherein an increase of the amount of polypeptide compared to the healthy subject is indicative of the presence of the pathological condition. Clearly, the activity and/or expression levels of the target genes as disclosed herein may have an effect on anabolic stimulation of chondrocytes. It remains to be determined to what level the activity should be elevated to diagnose for the disease. However, by comparing levels found in patients, individuals without symptoms and clearly healthy individuals the skilled person may easily determine these relevant levels. Since the skilled person is now aware which polypeptides should be monitored, the present invention provides novel tools for test assays for such diagnostics. A prominent disease that may be controlled, checked and diagnosed by using the knowledge provided by the present invention is osteoarthritis.

The rate of chondrocyte anabolic stimulation can typically be measured by determining the deposition of cartilage, or cartilage components, or cartilage-containing extra-cellular matrix produced by the chondrocytes, in the medium. A cell-based ELISA, enzymatic assays, or other general techniques known in the art can be used to measure cartilage components, like the ones described in Walsh G., Proteins: Biotechnology and Biochemistry. John Wiley and Sons, 2001.

The invention is further illustrated in the following figures and examples.

EXAMPLES

Example 1

Development of a High-Throughput Screening Method for the Detection of Endogenous Collagen Type II, Alpha-1 (col2α1)

Principle of the Assay:
Normal human articular chondrocytes (NHAC's) that are grown in two-dimensional cultures become dedifferentiated and gradually cease to synthesize cartilage. They can be re-differentiated into anabolic, active chondrocytes in the presence of appropriate factors (e.g. BMP2). An assay to screen for such factors was developed by monitoring the levels of collagen type ii, alpha-1 (col2α1), a major constituent of normal cartilage. NHAC's are seeded in 384 well plates and 1 day after plating infected with individual siRNA adenoviruses (Ad-siRNA) from the SILENCESELECT® collection (see WO03/020931). Col2α1 deposition is determined at 14 days after the start of the infection (14 dpi.
Control Viruses
Ad-BMP2; described in WO 03/018799
BMP4; Ad5 dE1/E2A adenoviruses that mediate the expression of full length bone morphogenetic protein 4 pre-protein (see NP_570912).
Ad-LacZ; referred to as pIPspAdApt6-lacZ in WO 02/070744
Ad-eGFP; referred to as pIPspAdApt6-eGFP in WO 02/070744
Ad-Empty; described in WO 02/070744
Development of the Assay NHAC's were isolated from donors who died from unrelated causes, and were obtained after informed consent (Cambrex, Verviers, Belgium).

In a series of experiments, carried out in 384-well plates, several parameters are optimized: cell seeding density, multiplicities of infection (MOI) of control viruses (Ad-BMP2 or Ad-eGFP), duration of infection, toxicity, infection efficiency (using Ad-eGFP) and the day of readout.

Using Ad-BMP2 (BMP2 over-expression) as a positive control for assay development, the following protocol resulted in the highest dynamic range for the assay with the lowest standard deviation on the background signal:

NHAC's are seeded on day 0 at 1500 cells/well of a 384-well plate in 60 μl of DMEM/F12 (InVitrogen), containing 10% heat-inactivated fetal calf serum (FBS-HI) and Pen/Strep) and infected the next day with 2.5 μl of Ad-control-virus (Ad-BMP2 or Ad-eGFP; this corresponds to an assumed MOI of 2000). After 7 days, 10 μl of a 50 μg/ml 2-Phospho-L-ascorbic acid in assay culture medium is added to each well. Up-regulation of Col2α1 is read at 10 dpi: The medium is removed with a VacuSafe; 50 μl ice-cold MeOH is added with a multidrop and removed immediately with a VacuSafe; 80 µl of ice-cold MeOH is added with a multidrop to fixate the cells, and plates are incubated for 20 min at −20° C.; MeOH is removed with a VacuSafe; plates are air-dried for 20 min, followed by 2× washing with 80 µl of phosphate buffered saline (PBS); 75 µl of blocking buffer (0.1% casein in PBS) is added and plates are incubated for at least 2 h at room temperature (RT); blocking buffer is removed; cells are washed with 25 µl of EC buffer (20 mM sodium phosphate, 2 mM EDTA, 400 mM NaCl, 0.2% BSA, 0.05% CHAPS, 0.4% casein, 0.05% NaN3, pH 7) and 35 µl of the primary antibody (Collagen II Ab-2 Neomarkers. Catalogus number MS-235-P) diluted 1/450, 1/225 in buffer C (20 mM sodium phosphate, 2 mM EDTA, 400 mM NaCl, 1% BSA, pH 7)) is added with a multichannel pipette; plates are incubated overnight at 4° C.; primary antibody is removed; cells are washed twice with 80 µl of PBST (0.5% Tween 20 in PBS) and once with 80 µl PBS; 35 µl of the secondary antibody (Goat-anti-mouse Immunoglobulins/HRP. DAKO. Catalogus number P0477; diluted 1/2000 in buffer C) is added with multichannel pipette; plates are incubated at RT for 1 h; secondary antibody is removed and cells are washed twice with 80 µl PBST and once with 80 µl PBS; 50 µl of luminol substrate is added and after 5 minutes read-out is determined on a luminometer.

After optimization of the assay (see FIG. 1), a 384 well control plate is prepared that contains positive control viruses (BMP2 and BMP4) and neutral viruses (eGFP; lacZ and empty, see FIG. 1). Aliquots of the control plate are prepared and frozen at −20° C. A control plate is thawed and taken along in every screening batch.

Example 2

Screening of 9216 Adenoviral siRNA Vectors in the Chondrogenesis Assay

Figure 2:
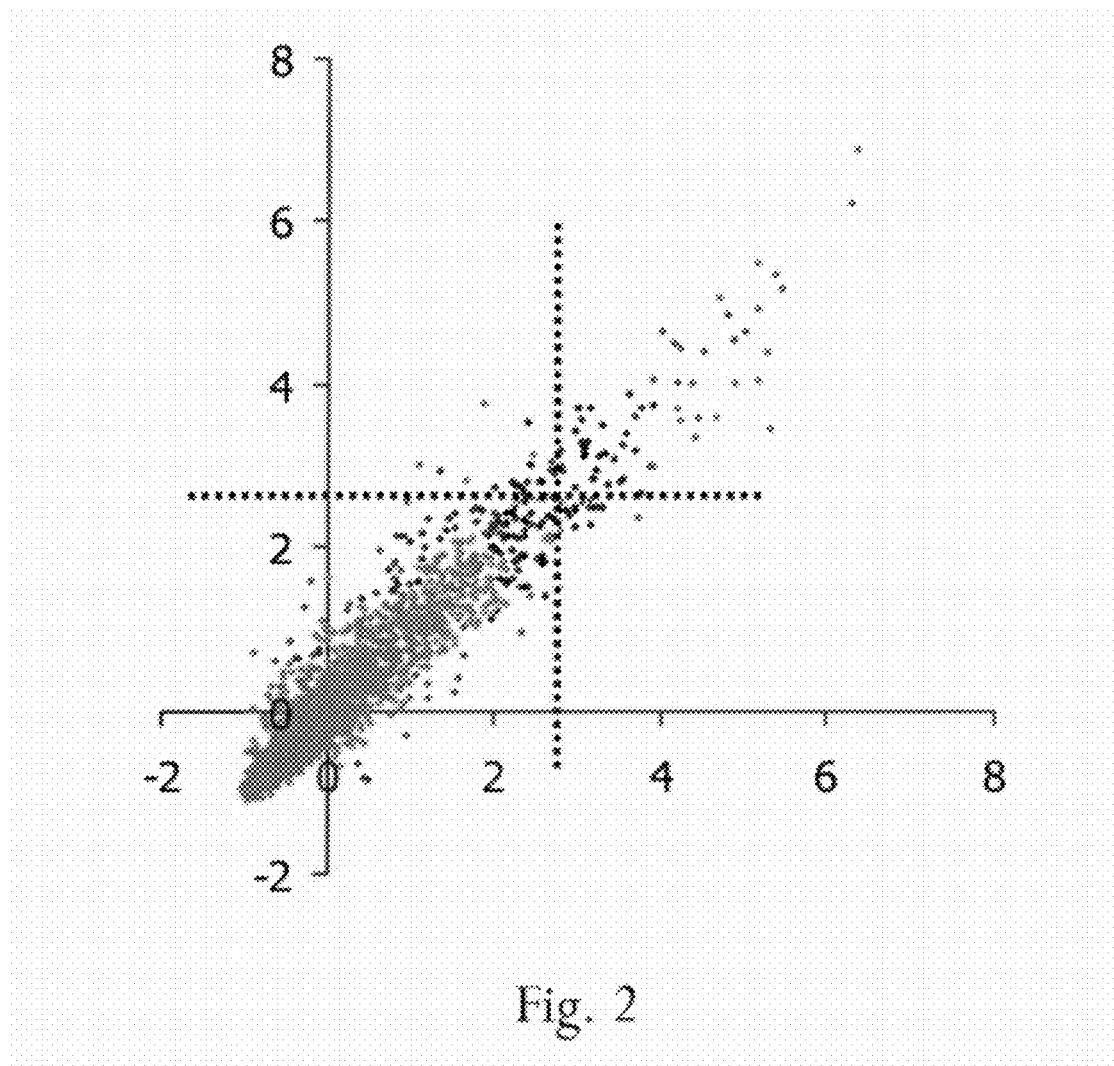
FIG. 2. Example of duplicate screening results for Col2α1 expression of part of the SILENCESELECT® library.
Figure 3A:
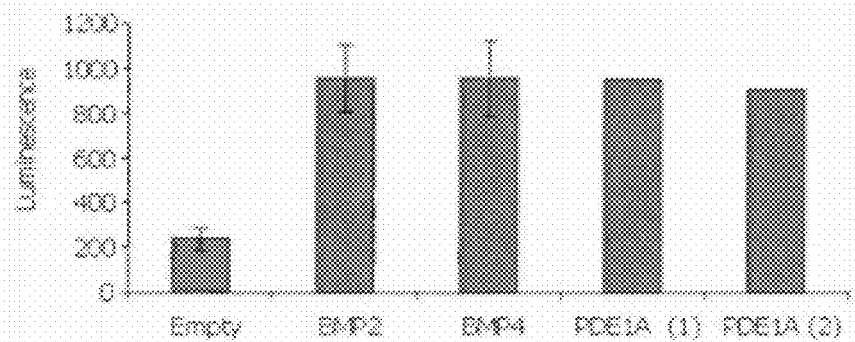
FIG. 3 (A-N): Quantification of Col2α1 expression in primary human chondrocytes 12 days post infection with the indicated viruses.
Figure 3B:
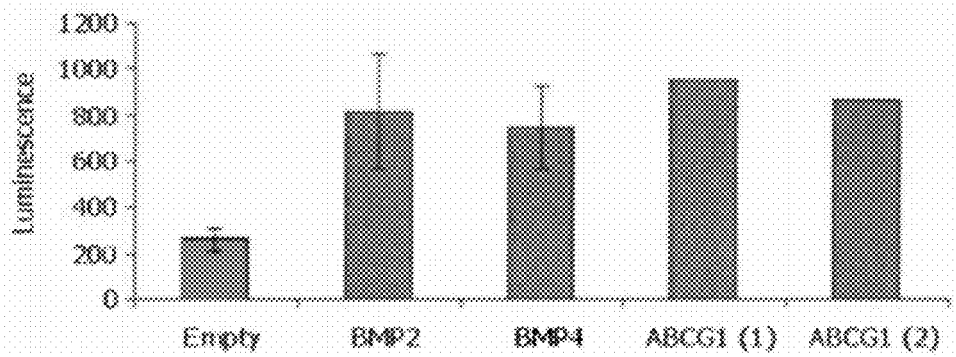
Figure 3C:
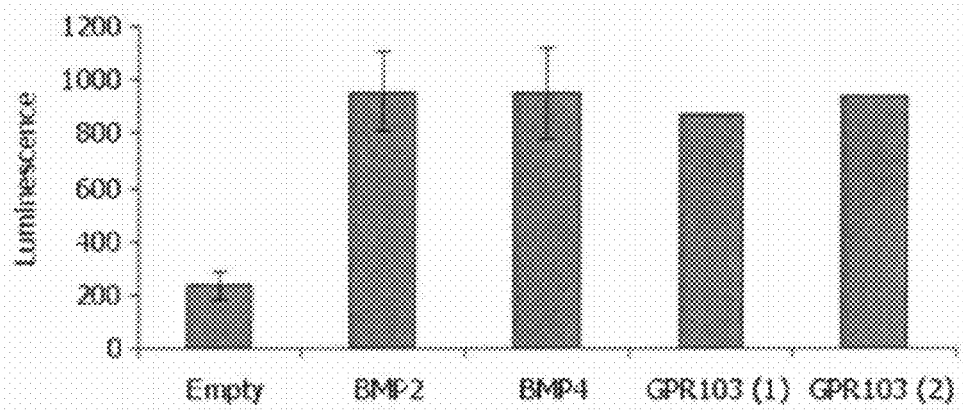
Figure 3D:
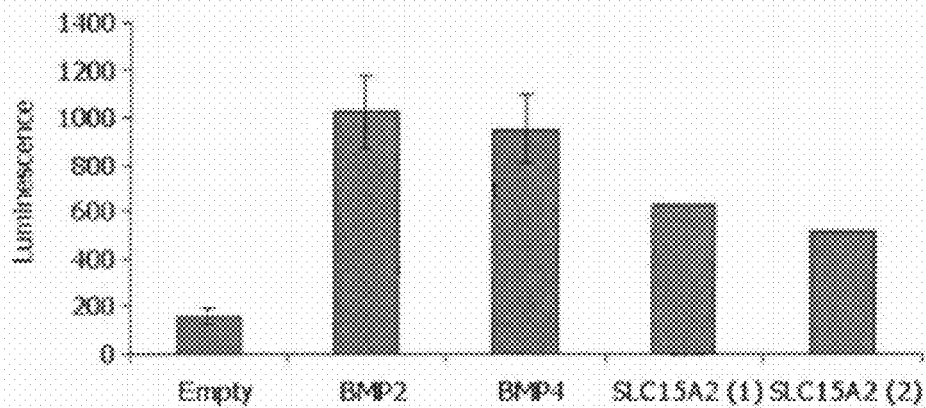
Figure 3E:
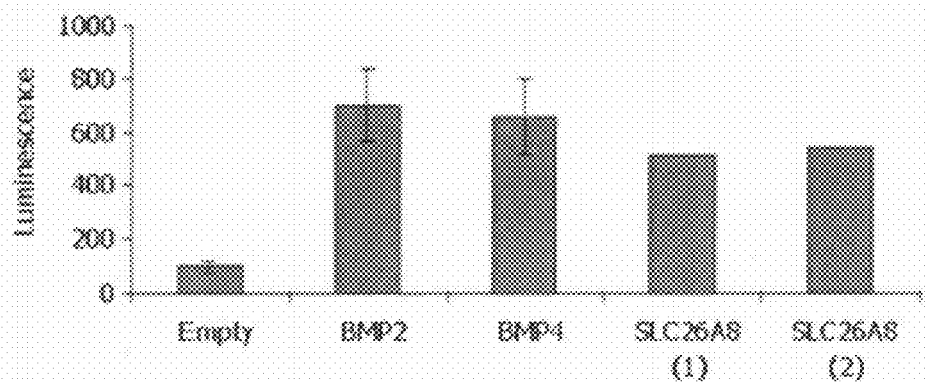
Figure 3F:
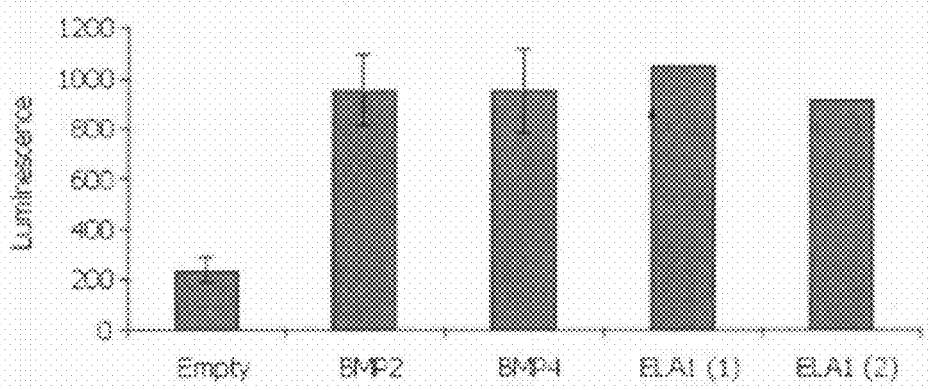
Figure 3G:
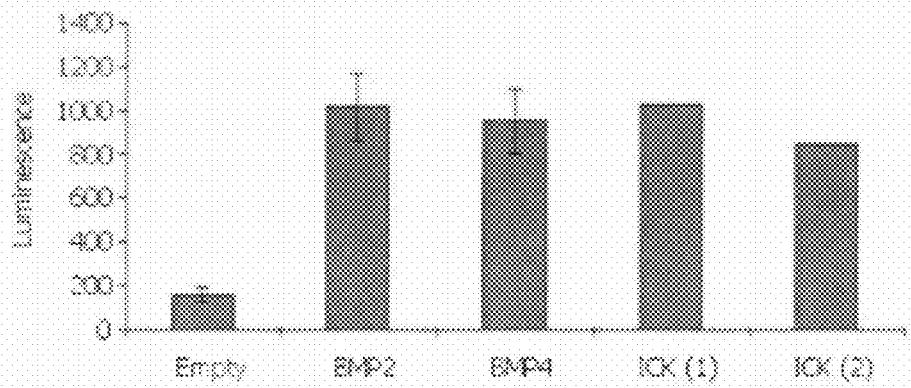
Figure 3H:
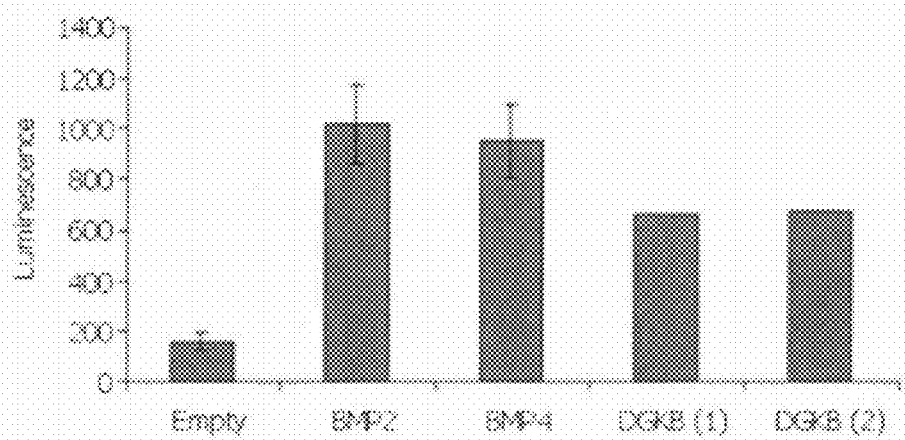
Figure 3I:
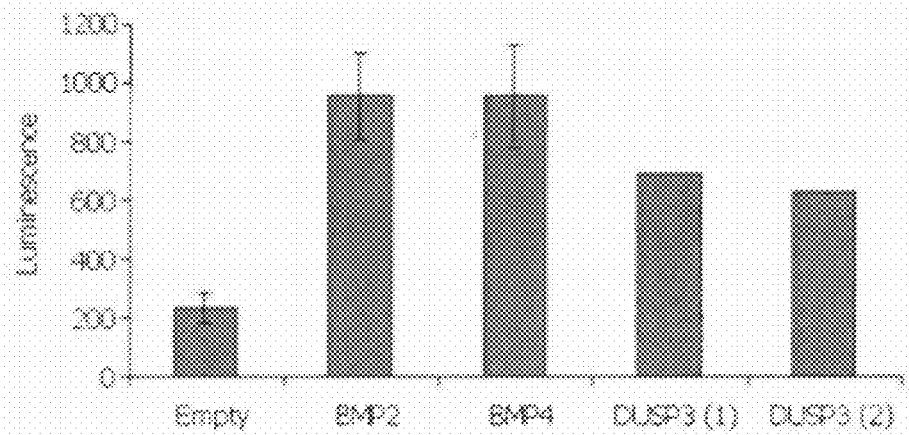
Figure 3J:
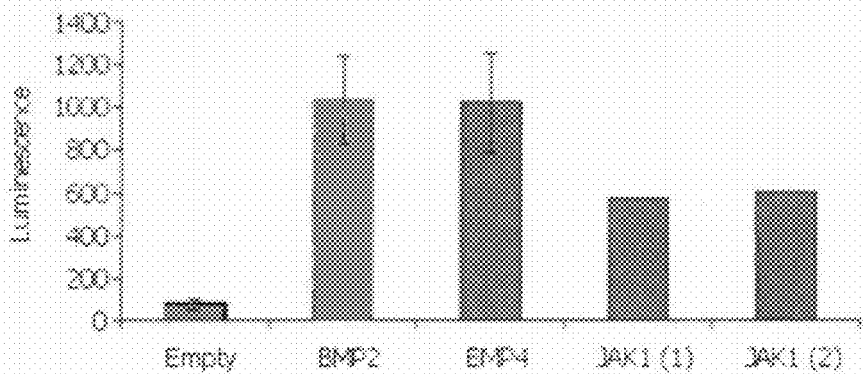
Figure 3K:
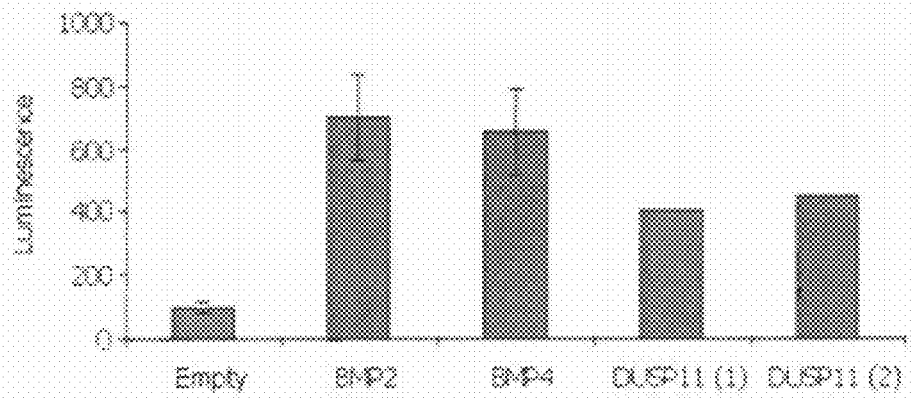
Figure 3L:
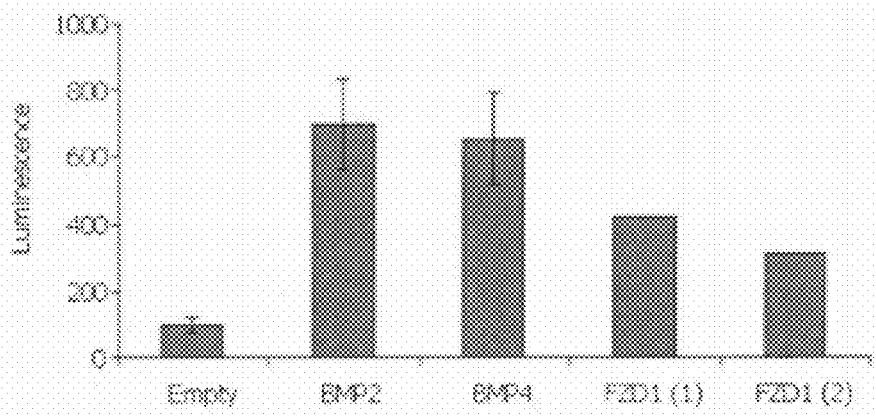
Figure 3M:
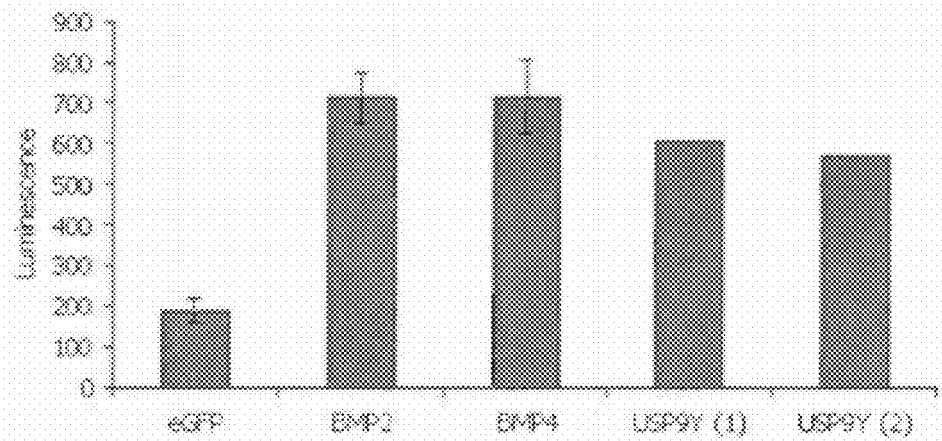
Figure 3N:
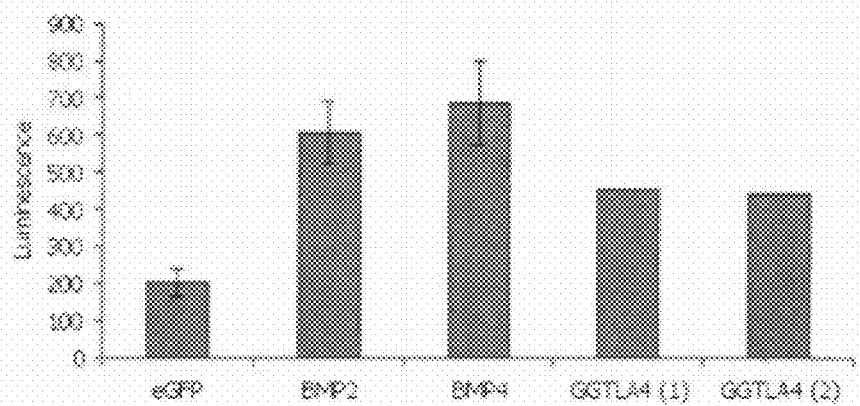

The optimized protocol for screening the SILENCES-ELECT® library runs as follows: on day 0, propagated human primary chondrocytes are seeded in Greiner white, flat bottom, TC-treated 384 well plates with clear bottom (Catalogue number 781080) in 60 µl medium at a density of 1500 cells per well. One day later, 2.5 µl Ad-siRNA virus from each well of the SILENCESELECT® collection (WO 03/020931), stored in 384 well plates (estimated titer of $1 \times 10^9$ viral particles per ml) is transferred with the aid of a 96/384 channel dispenser (Tecan Freedom 200 equipped with TeMO96, TeMO384 and RoMa, Tecan AG, Switzerland) to individual wells of the 384 well plates containing chondrocytes. The control plate is run under the same conditions as the aliquot plates from the SILENCESELECT® collection. All Ad-siRNA viruses are screened in duplicate on independent assay plates. After infection, plates are incubated at 37° C. Seven days post infection the medium containing the adenoviruses is replaced by fresh medium. Thirteen days post infection, the amounts of col2α1 depositions per well is determined with the cELISA method. A typical result of a 384 well screening plate is depicted in FIG. 2.

The duplicate screen is repeated once. Ad-siRNA viruses are nominated as hits if at least 2 data points of the four tested (two times screened in duplicate) score above threshold. Threshold is set at average plus 2.5 times standard deviation of all data points per plate.

A total of 282 hits are isolated that scored above the threshold, representing 274 independent genes. A representative example is provided in FIG. 2, in which the "times standard deviation" of duplicate data points are indicated on the X-axis and Y-axis. The threshold (2.5 times standard deviation) is indicated by dotted lines. Negative values indicate data points that scored below average.

The results for some of the genes are shown in FIG. 3. A clear induction of the collagen II levels is observed upon infection of the Ad-siRNA targeting the indicated gene. The data are represented as relative light units (rlu) correlating to collagen II levels.

Example 3

Propagation of Hits

The 282 Ad-siRNA hits are subjected to further analysis to establish their therapeutic potential to induce chondrocyte anabolic stimulation. A first step entails a quality control on the Ad-siRNA selected for further analysis (this example). Next steps are the screening of the targets in other assays to validate their role in chondrocyte anabolic stimulation such as the induction of aggrecan, another main constituent of cartilage besides collagen II (Example 4), the ability to induce chondrocyte anabolic stimulation in chondrocytes from other donors (Example 5), the induction of a correct marker profile in three-dimensional chondrocyte cultures (example 11), the presence of posttranslational modifications on aggrecan (example 9) and collagen II (example 10) in three-dimensional chondrocyte cultures, the development of additional Ad-siRNAs targeting the identified transcripts (example 7), and confirmation that the corresponding genes are indeed expressed in residing chondrocytes (example 12).

To propagate the 282 hits of the chondrogenesis assay, $2.25 \times 10^4$ PerC6.E2A cells are seeded in 200 µl of DMEM containing 10% non-heat inactivated FCS into each well of a 96 well plate and incubated overnight at 39° C. in a humidified incubator at 10% $CO_2$. Subsequently, 1 µl of crude lysate from the siRNA adenovirus stocks in matrix tubes is added and incubation proceeds at 34° C. in a humidified incubator at 10% $CO_2$ for 7 days. All hits are propagated in duplicate on two independent plates. The two lysates are pooled and aliquots are frozen at −20° C.

The propagated Ad-siRNAs are re-screened at three MOI's in the chondrogenesis assay in duplicate (see Example 1). The Ad-siRNAs have to score at least once above threshold (average+2.5 times standard deviation) to pass this quality control step.

Example 4

Aggrecan Induction

A second assay to screen for chondrocyte anabolic factors is developed by monitoring the levels of aggrecan, another major constituent of cartilage. In this assay, glycosaminoglycans on aggrecan are stained by Alcian blue. NHACs are seeded in 384 well plates and 1 day after plating infected with individual Ad-siRNA from the SILENCESELECT® collection. Aggrecan deposition is determined at 14 days post infection. Using Ad-BMP2 as a positive control, we confirm in a series of experiments that several parameters optimized for the ColII cELISA assay are also applicable for the Alcian blue stain assay for aggrecan. These parameters include cell seeding density, MOIs of control viruses, duration of infection, and the day of readout.

NHAC's are seeded on day 0 at 1500 cells/well of a 384 well black-plate with clear bottom in 60 µl of DMEM/F12, containing 10% FBS-HI and Pen/Strep and infected the next day with 2.5 µl of Ad-BMP2 or Ad-eGFP; at an MOI of 2000.

Figure 4:
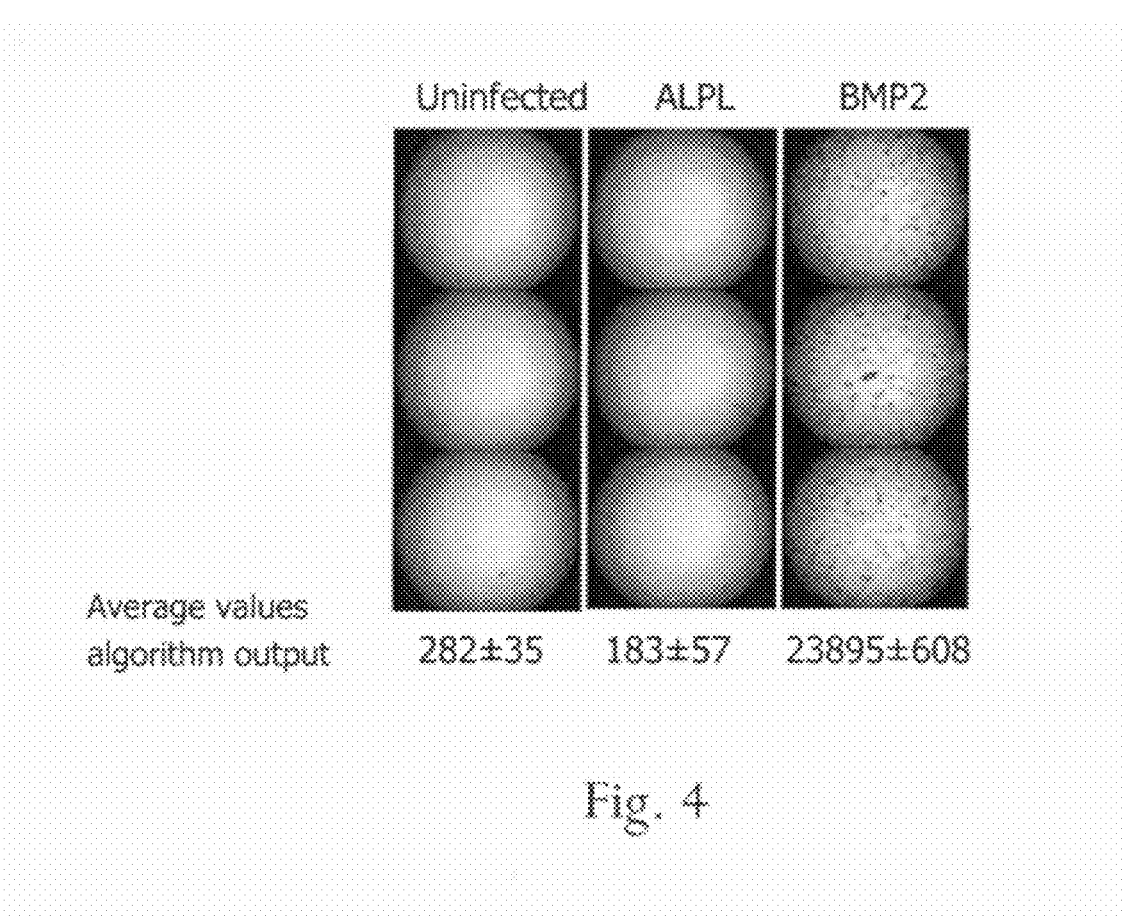
FIG. 4. Quantification of alcian blue staining on human primary chondrocytes, 12 days after infection with the indicated viruses, compared to uninfected cells.
Figure 5A:
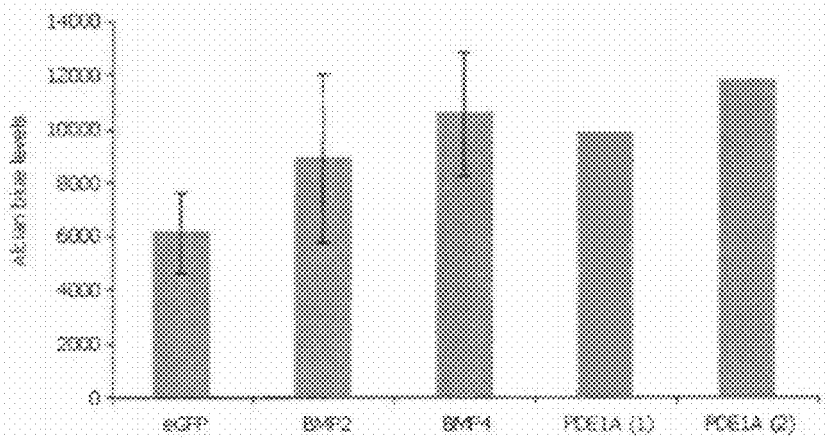
FIG. 5 (A-N): Quantification of aggrecan expression in primary human chondrocytes 12 days post infection with the indicated viruses.
Figure 5B:
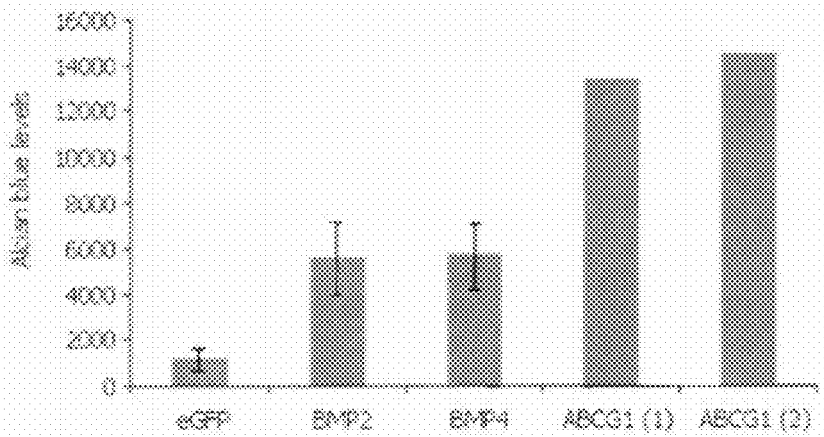
Figure 5C:
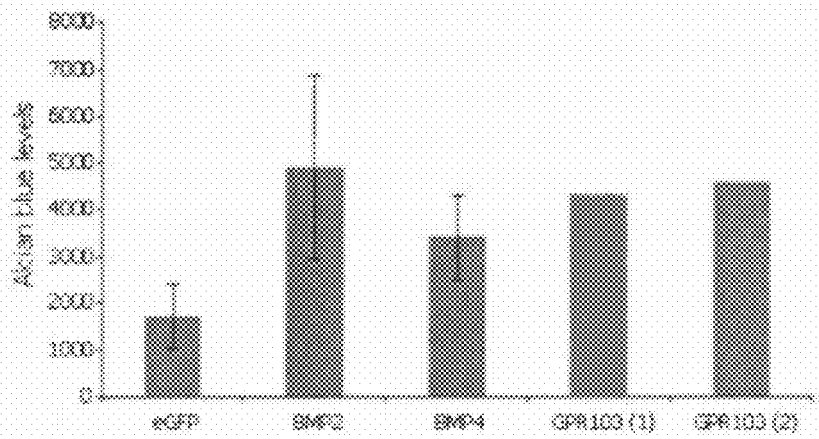
Figure 5D:
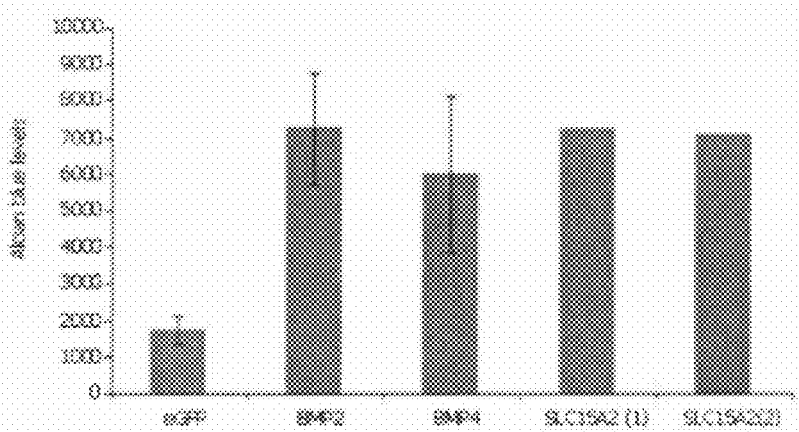
Figure 5E:
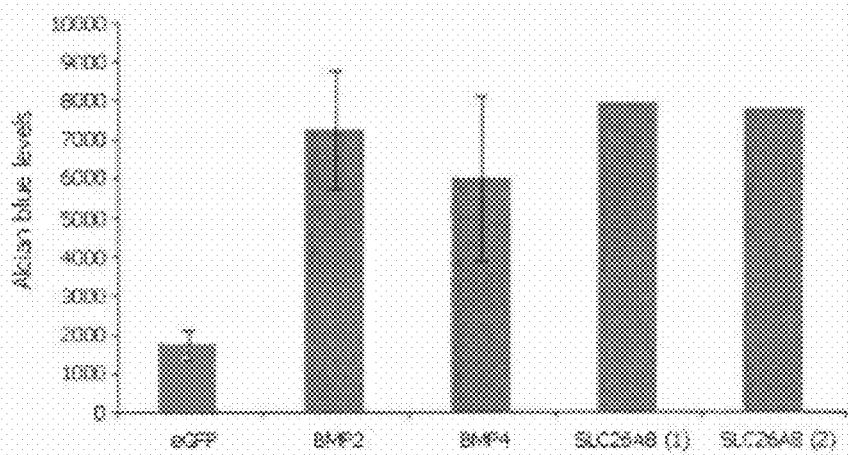
Figure 5F:
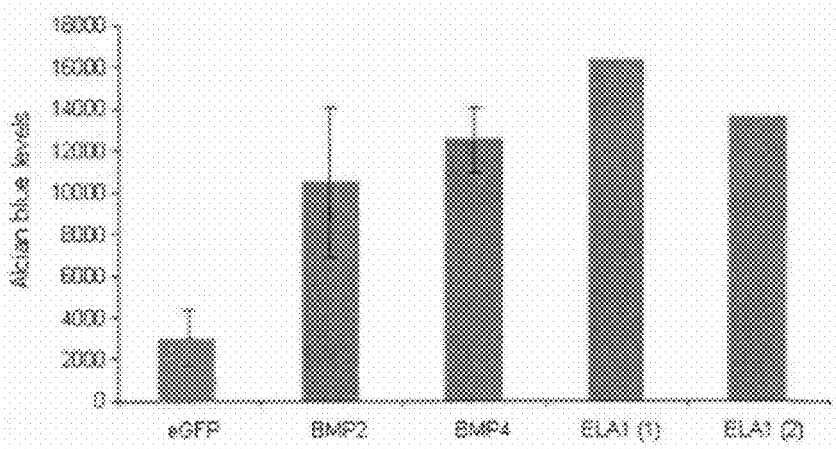
Figure 5G:
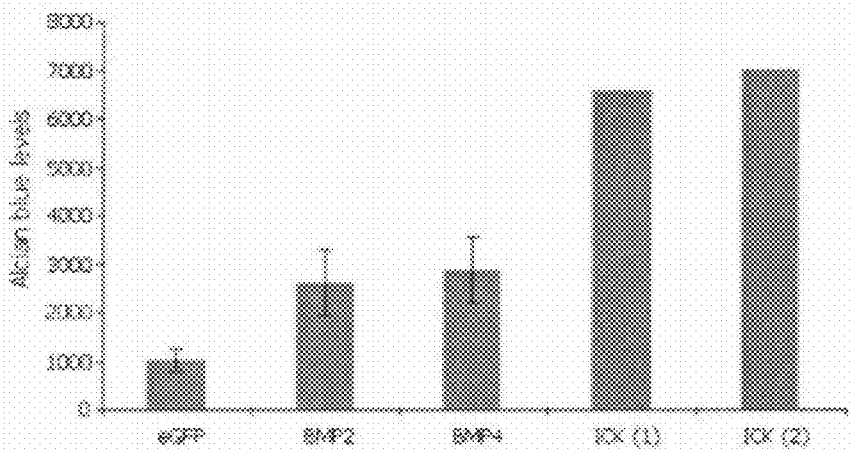
Figure 5H:
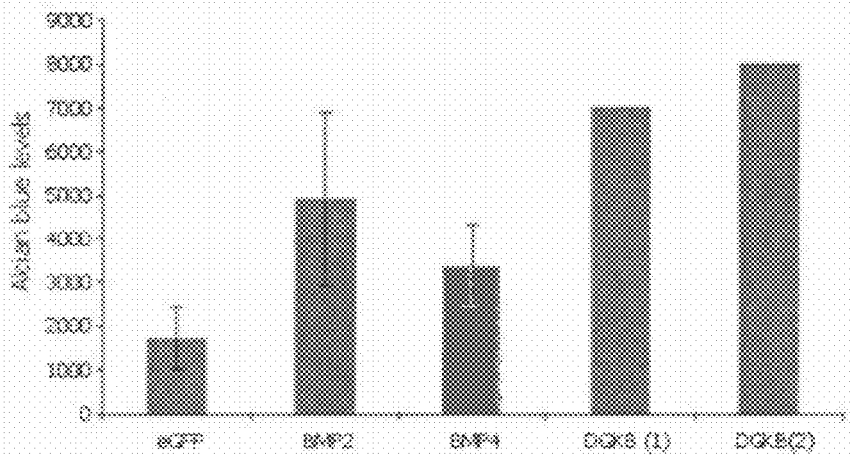
Figure 5I:
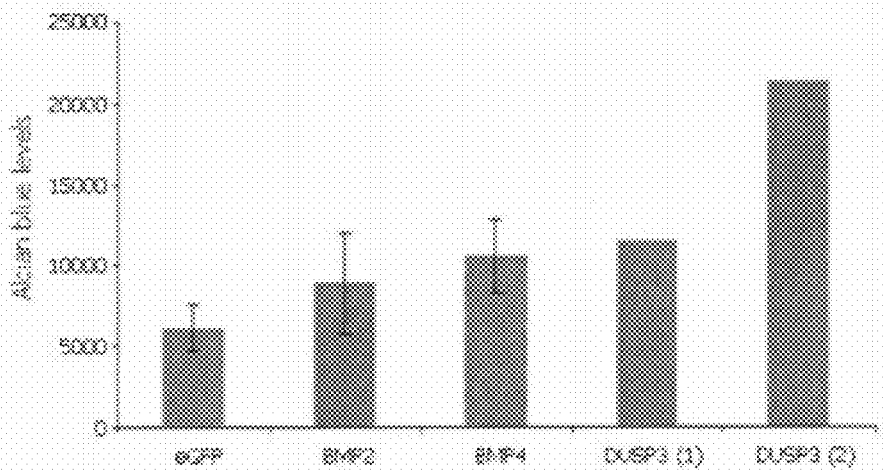
Figure 5J:
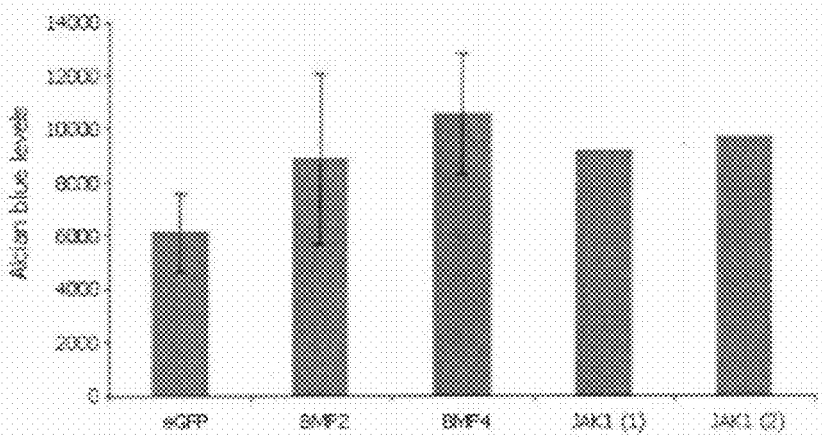
Figure 5K:
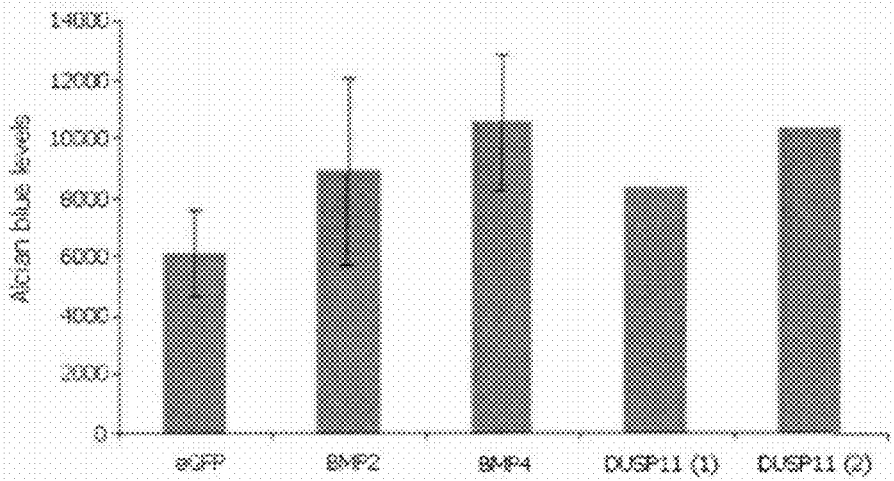
Figure 5L:
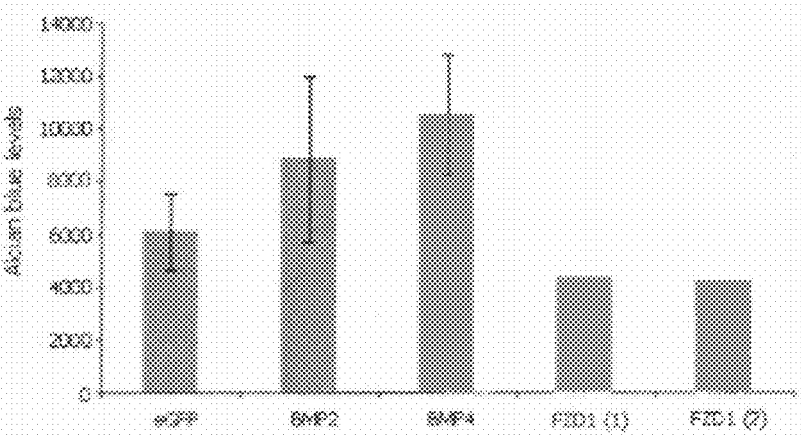
Figure 5M:
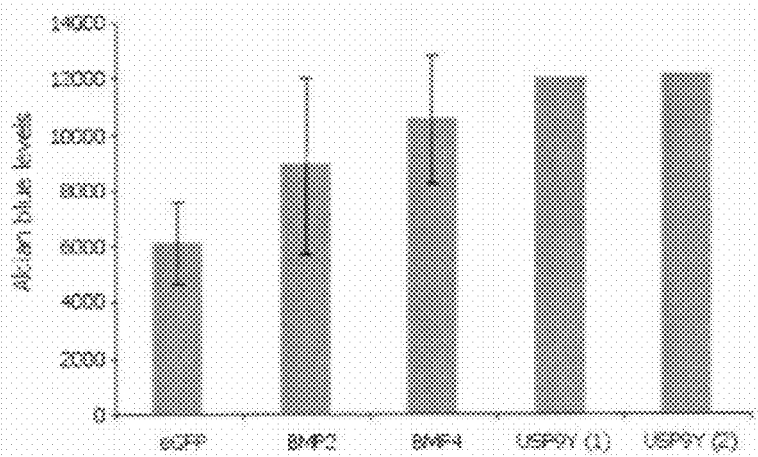
Figure 5N:
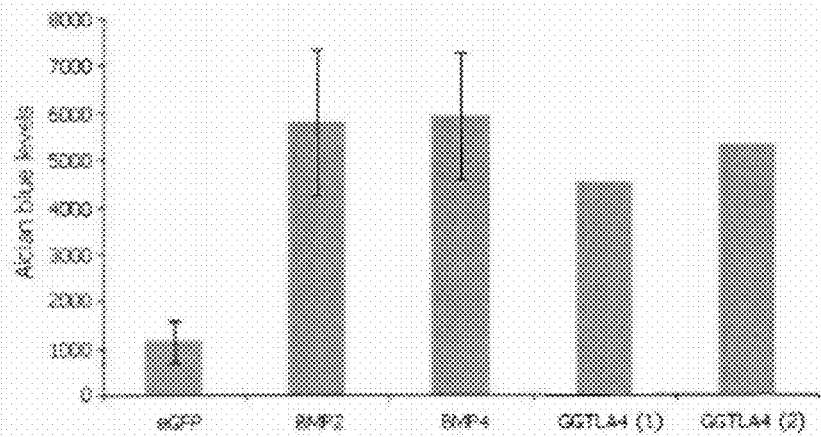
Figure 6A:
FIG. 6 (A-K): On target analysis with different constructs targeting the indicated genes. The on target analysis is assessed through detection of the Col2α1 expression in primary human chondrocytes 12 days post infection with the indicated viruses. Data are represented as luminescence units. The different thresholds corresponding to the different infection volumes are indicated as a line. Increasing the infection volumes leads to an increased threshold.
Figure 6B:
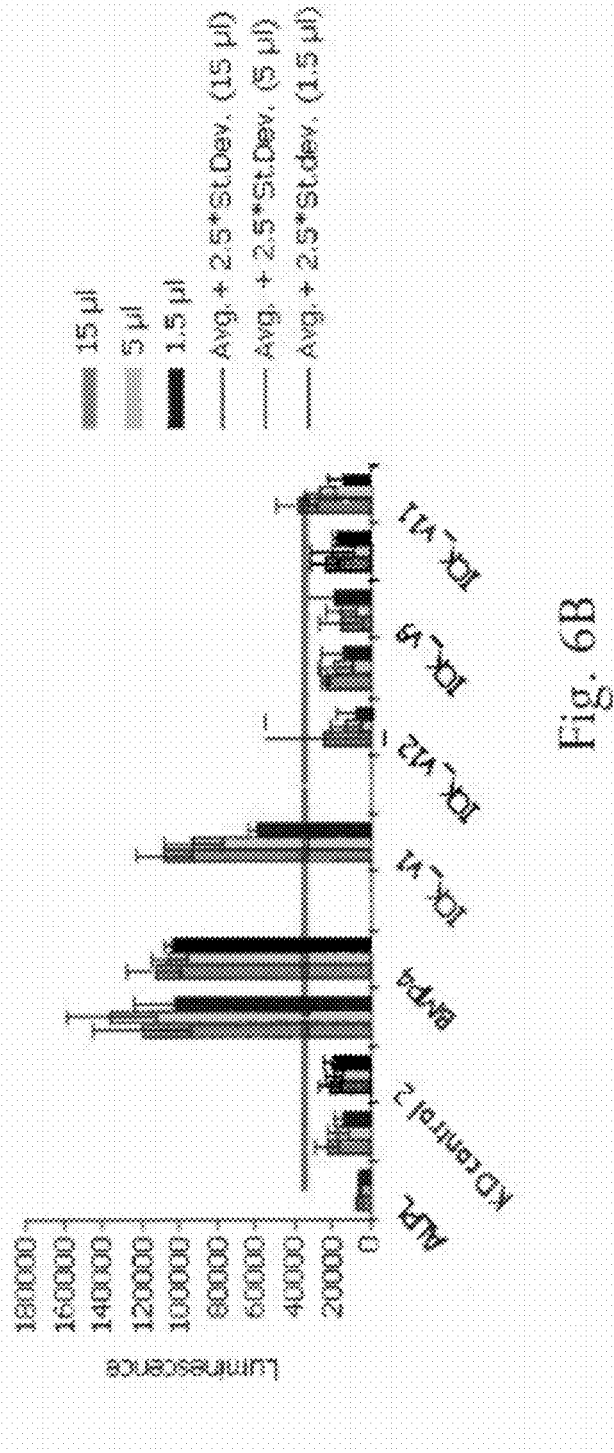
Figure 6C:
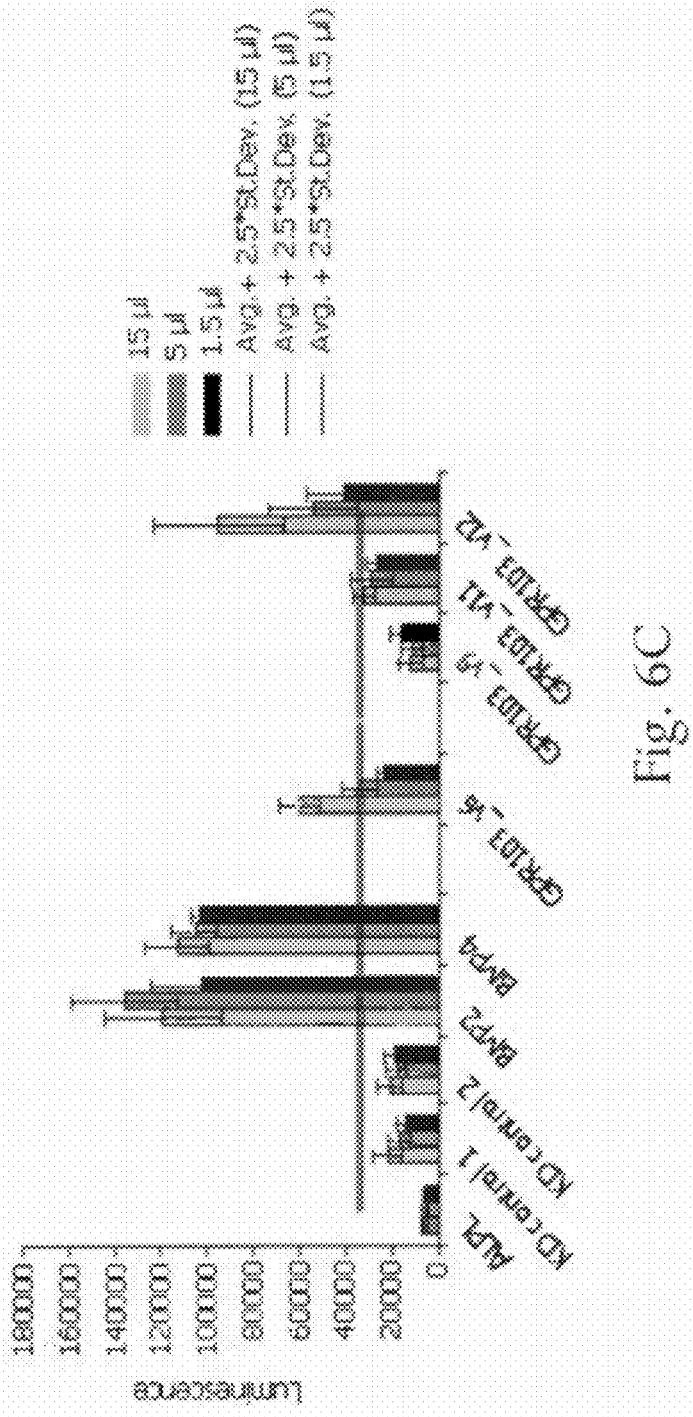
Figure 6D:
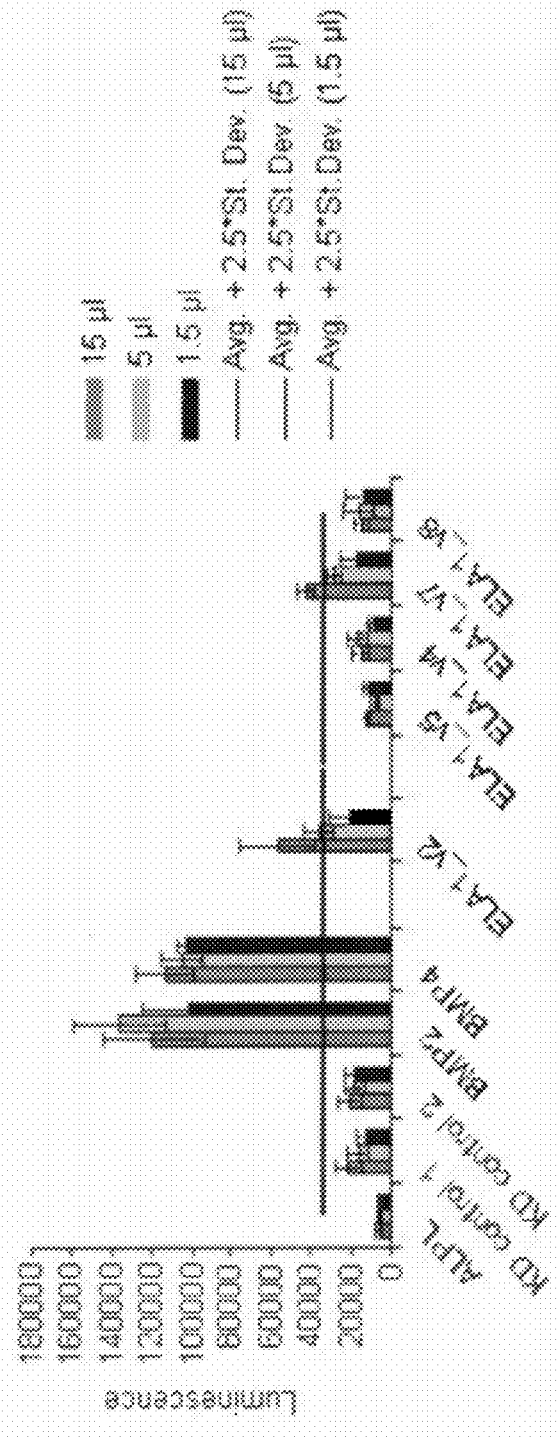
Figure 6E:
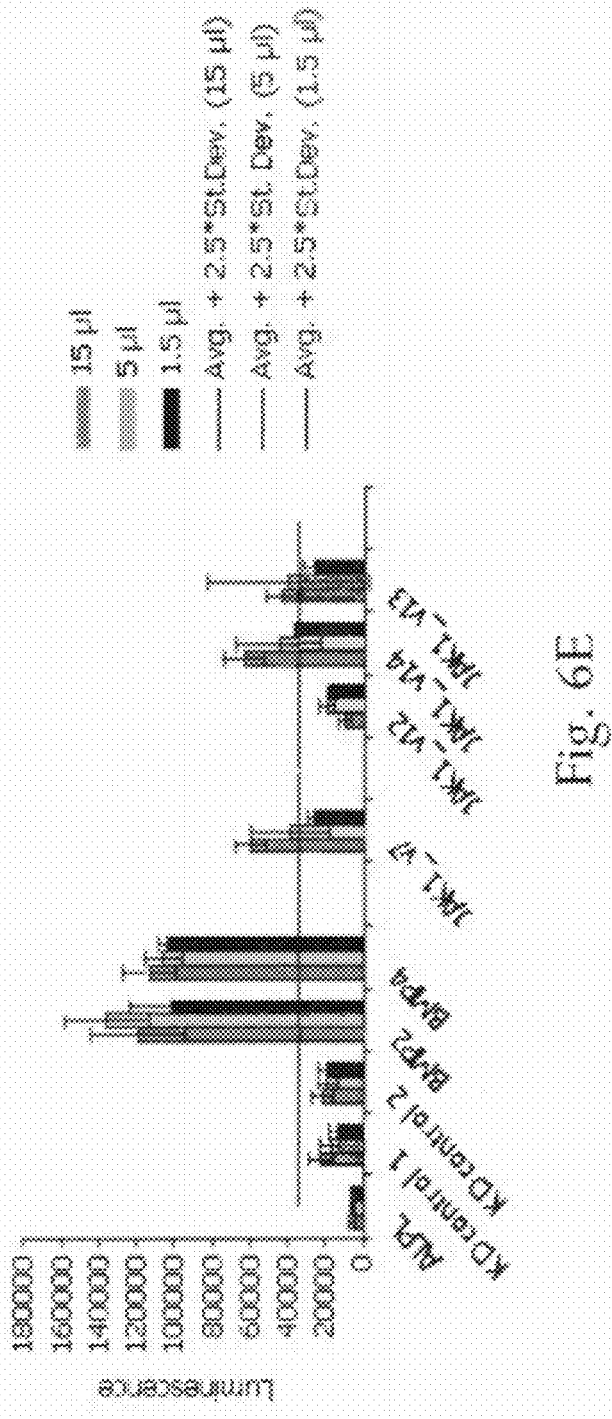
Figure 6F:
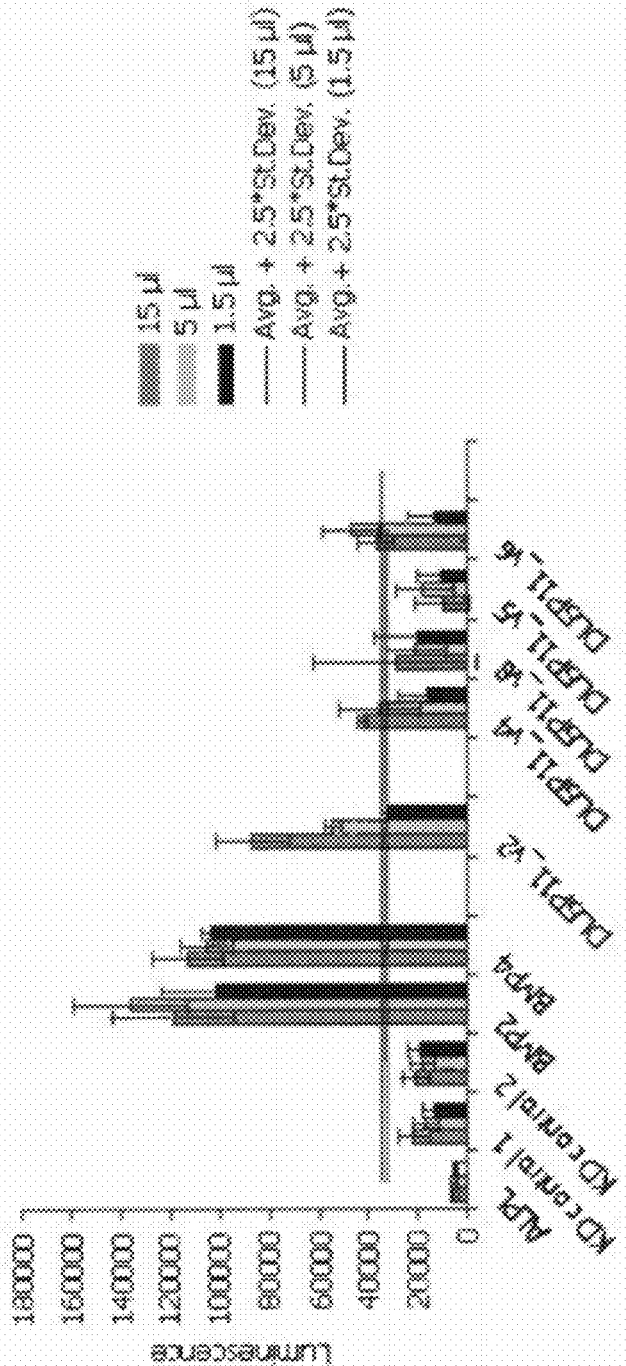
Figure 6G:
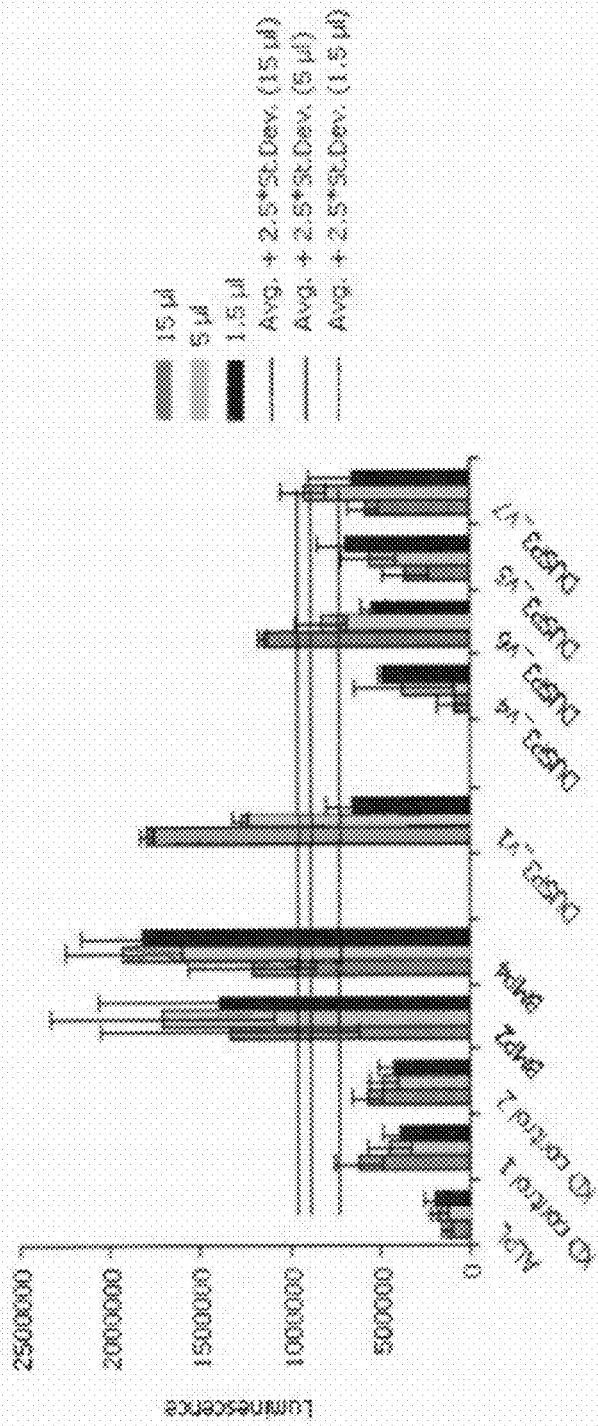
Figure 6H:
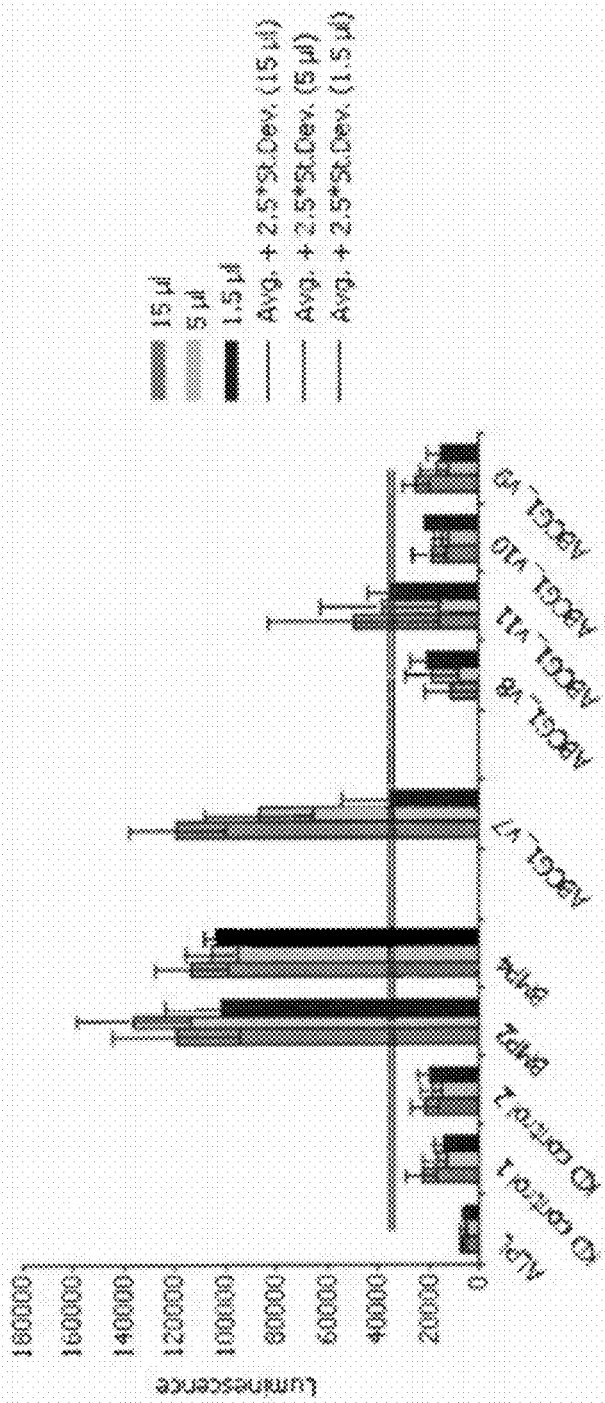
Figure 6I:
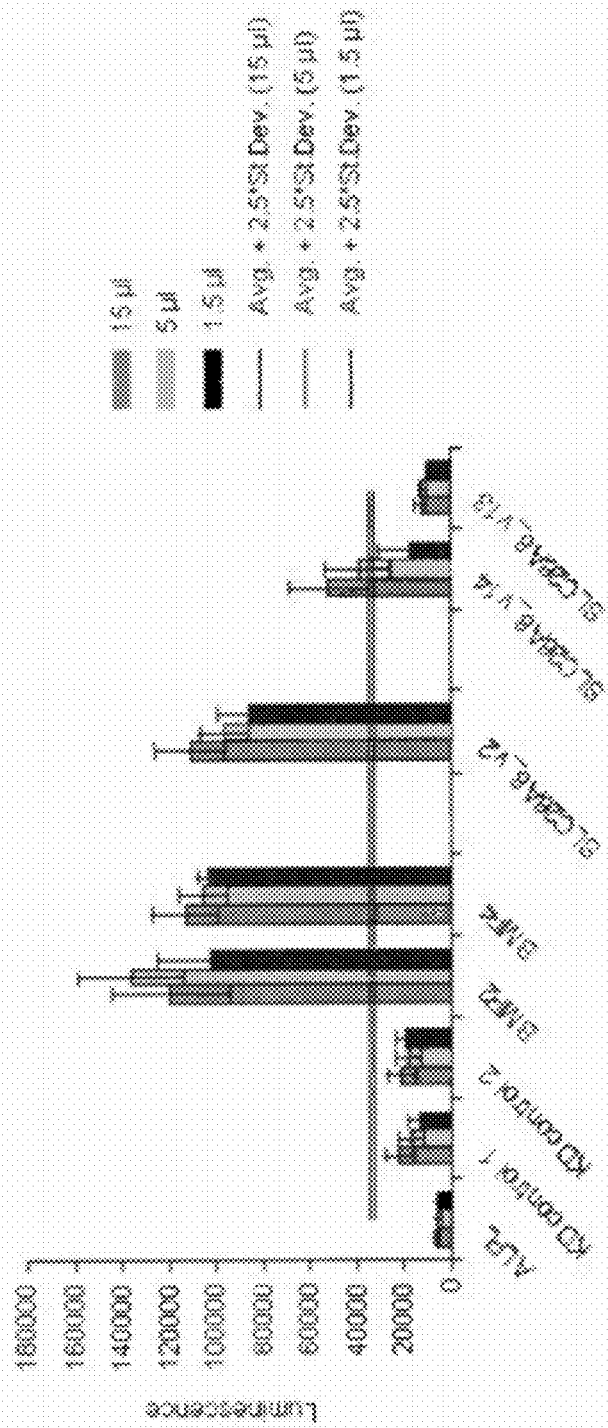
Figure 6J:
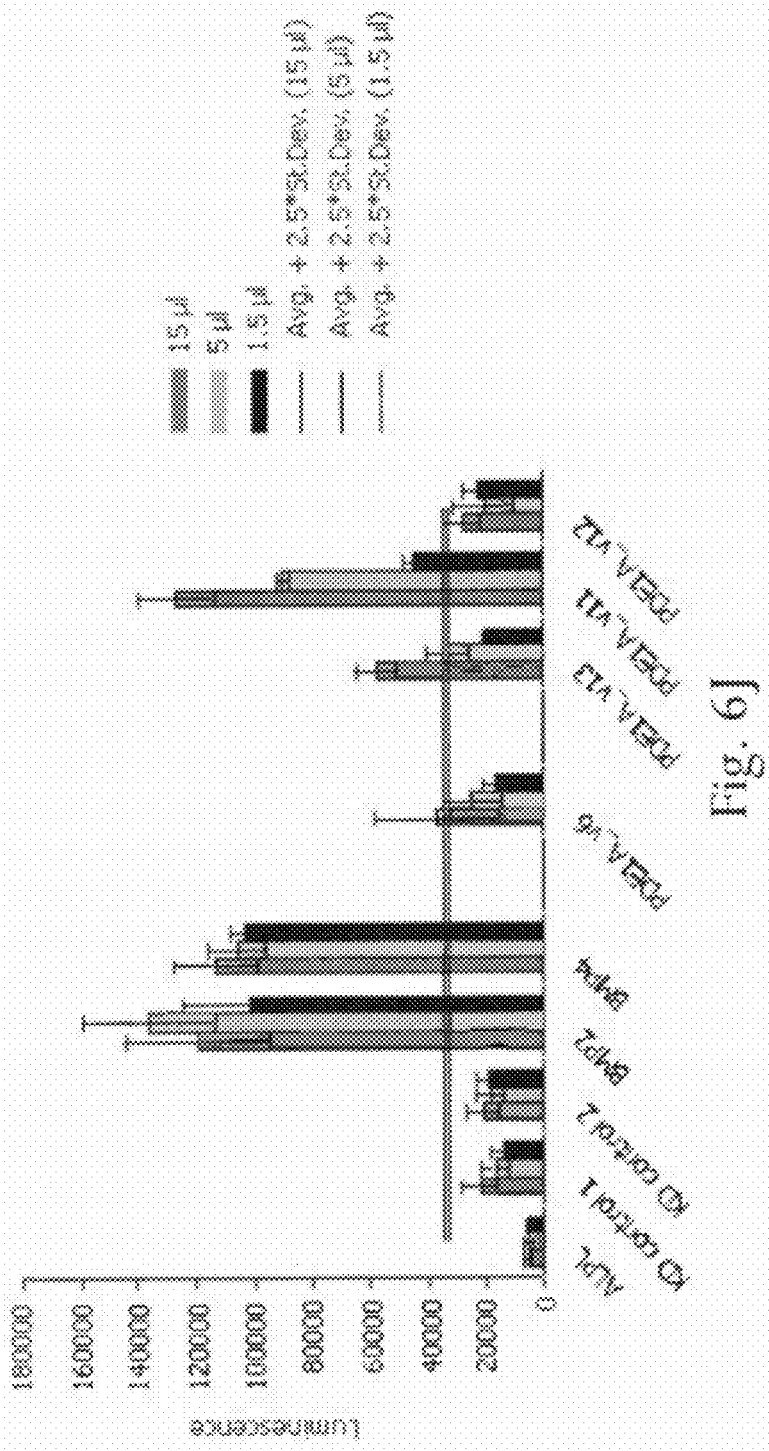
Figure 6K:
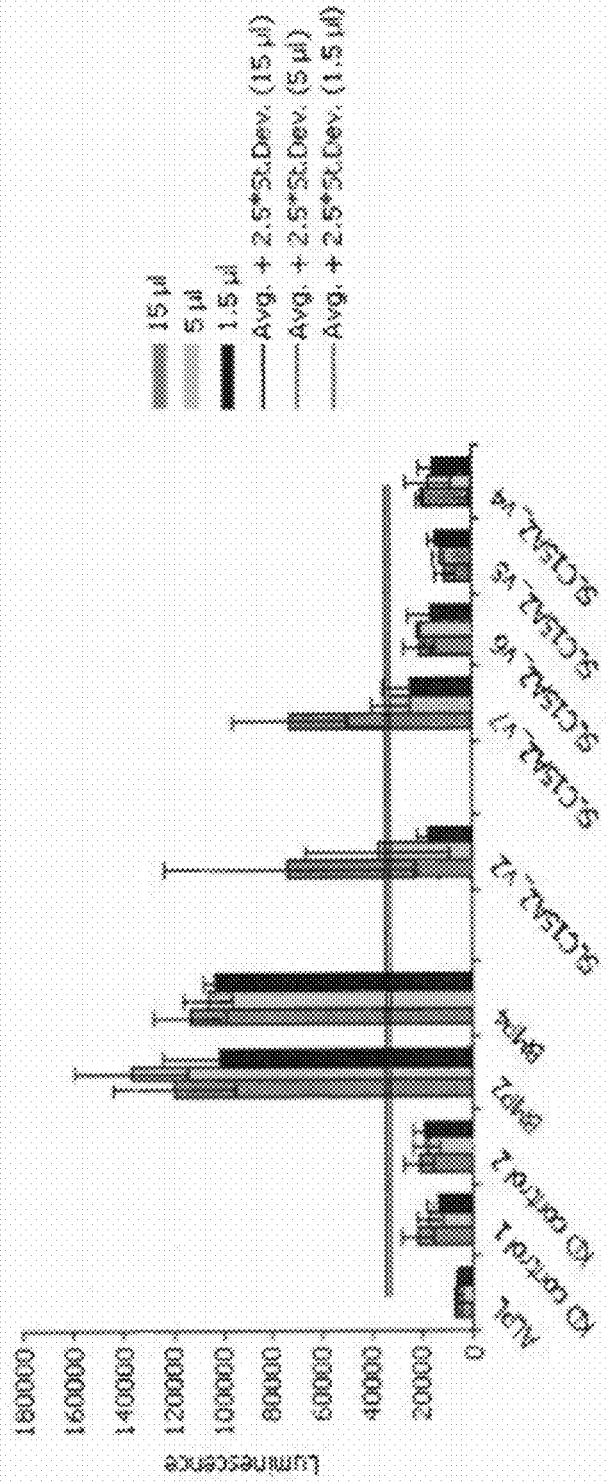
Figure 7A:
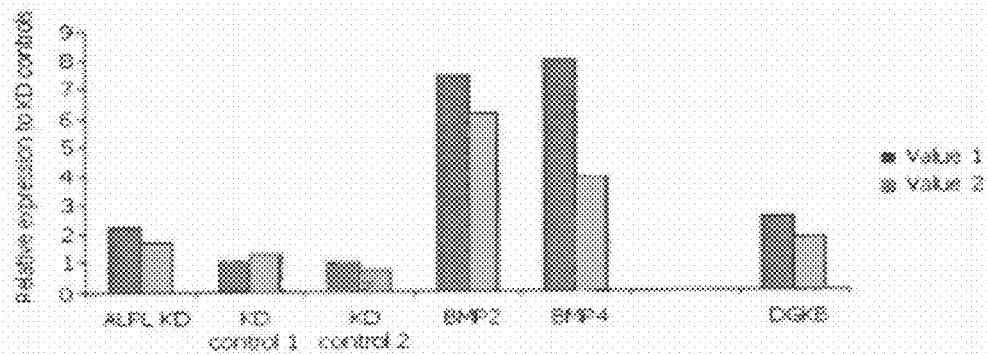
FIG. 7 (A-L): GAG analysis on chondrocytes in alginate cell culture 10 days post infection. The data are represented as relative GAG levels to the average of KD control 1 and KD control 2, being Ad-siRNA targeting PTGER4 and GRM7 respectively. Two individual data points are shown for every condition.
Figure 7B:
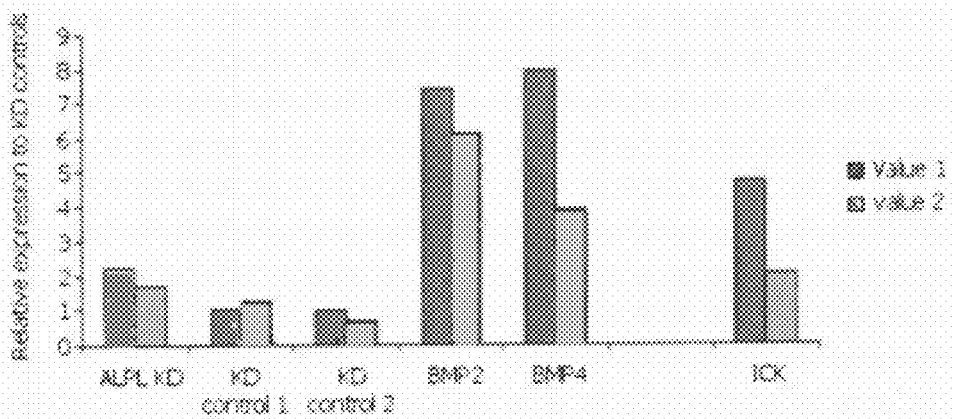
Figure 7C:
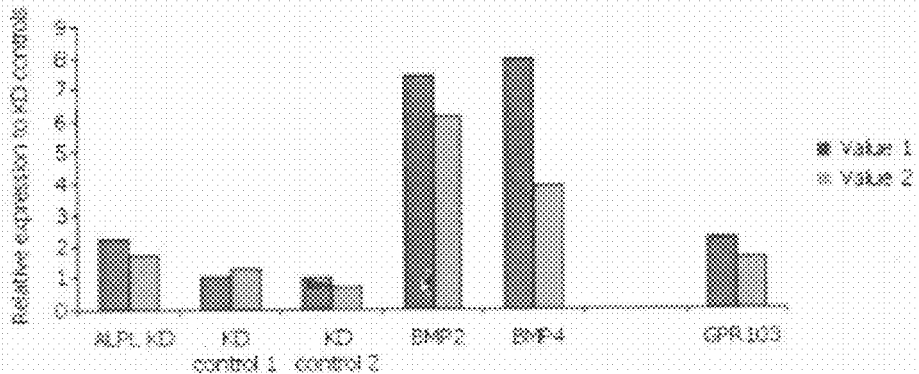
Figure 7D:
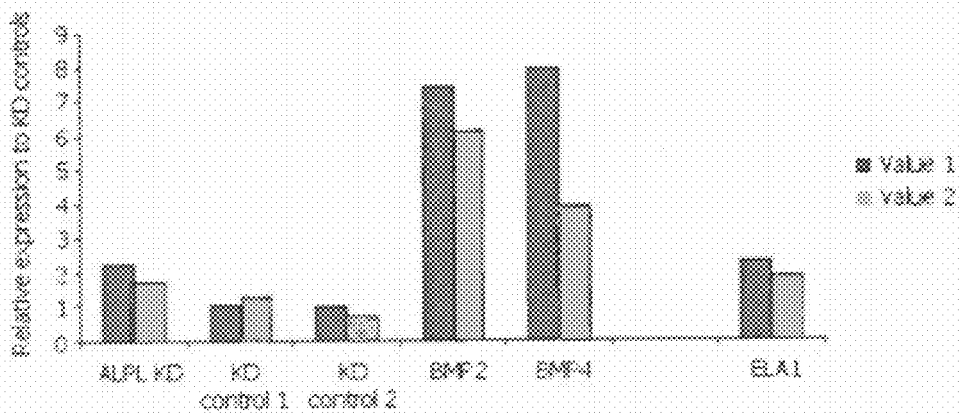
Figure 7E:
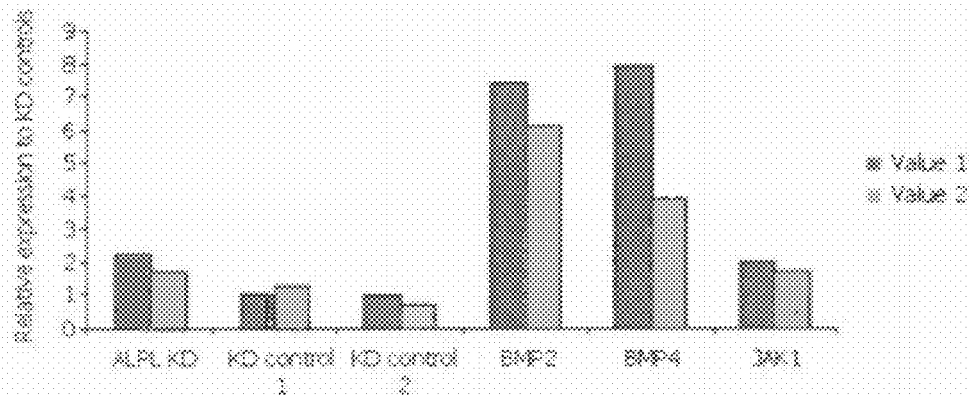
Figure 7F:
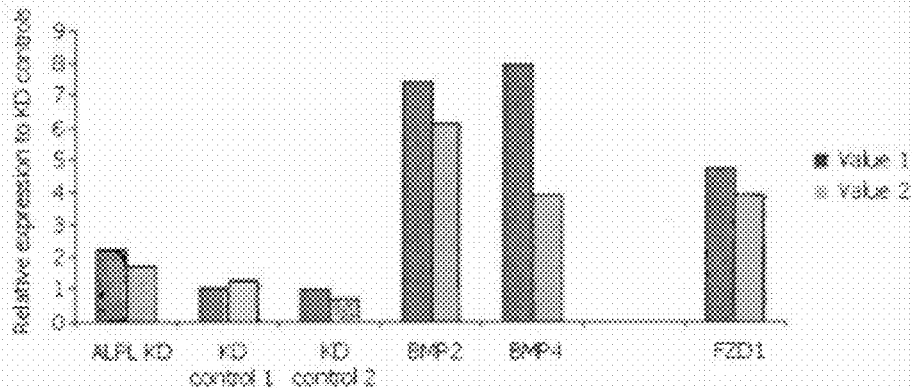
Figure 7G:
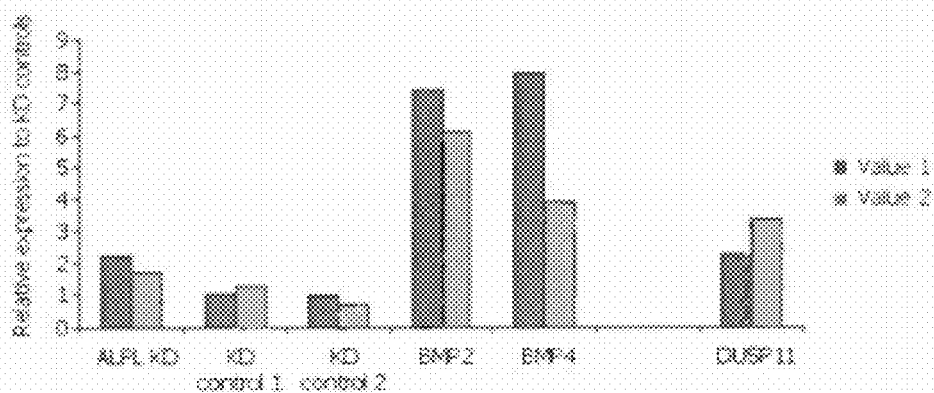
Figure 7H:
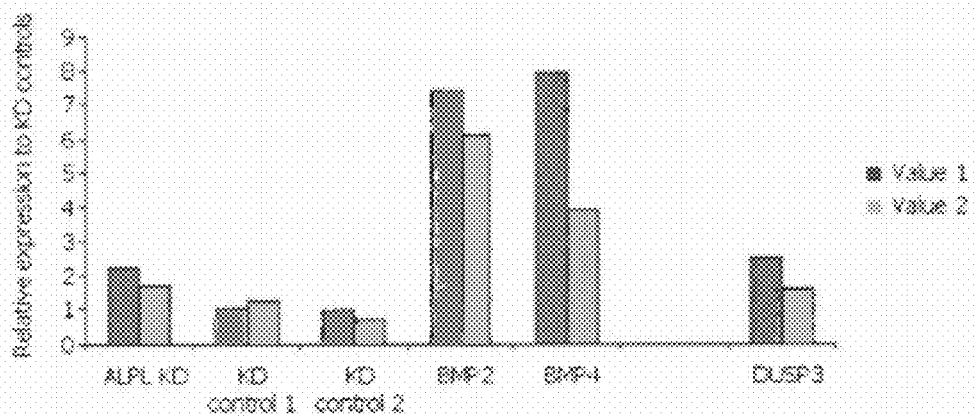
Figure 7I:
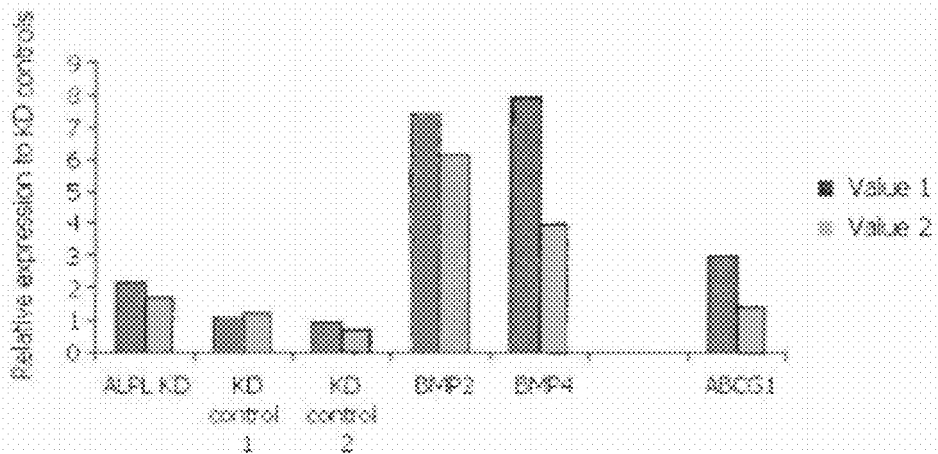
Figure 7J:
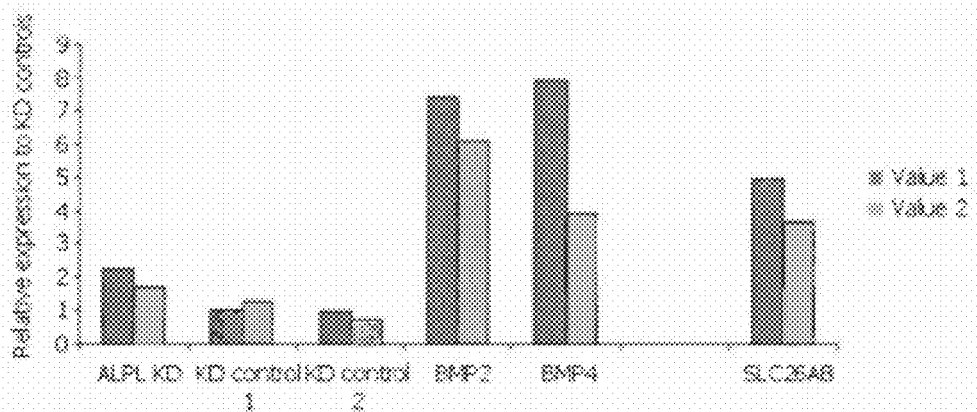
Figure 7K:
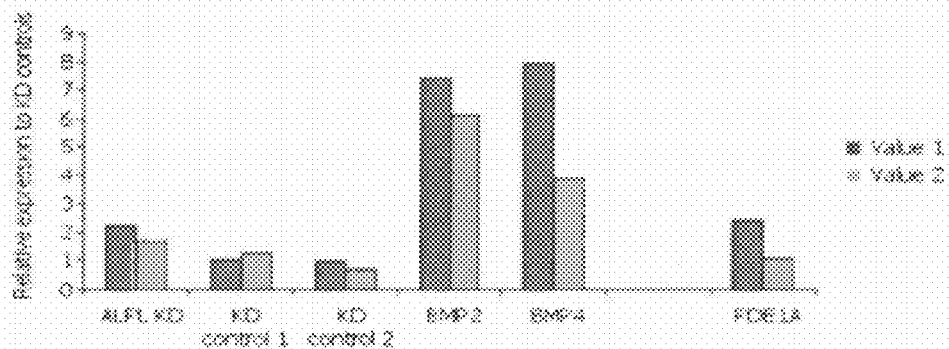
Figure 7L:
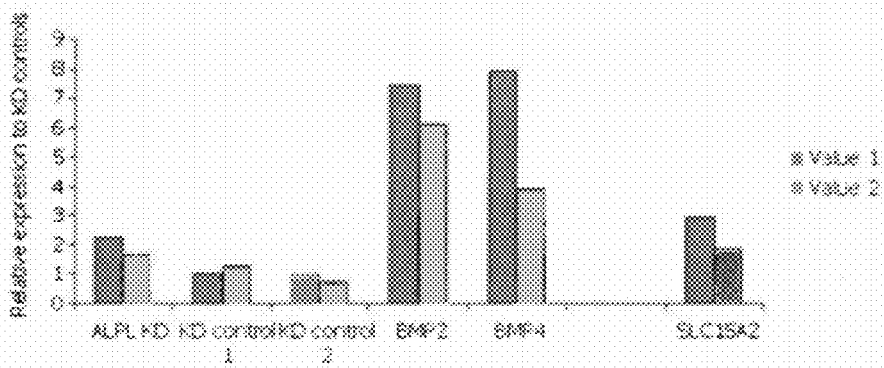
Figure 8A:
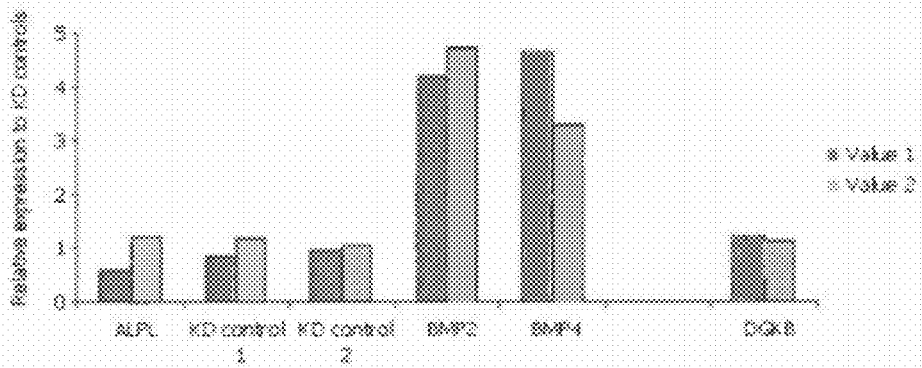
FIG. 8 (A-L): Hydroxyproline analysis on chondrocytes in alginate cell culture 10 days post infection. The data are represented as relative hydroxyproline levels to the average of KD control 1 and KD control 2, being Ad-siRNA targeting PTGER4 and GRM7 respectively. Two individual data points are shown for every condition.
Figure 8B:
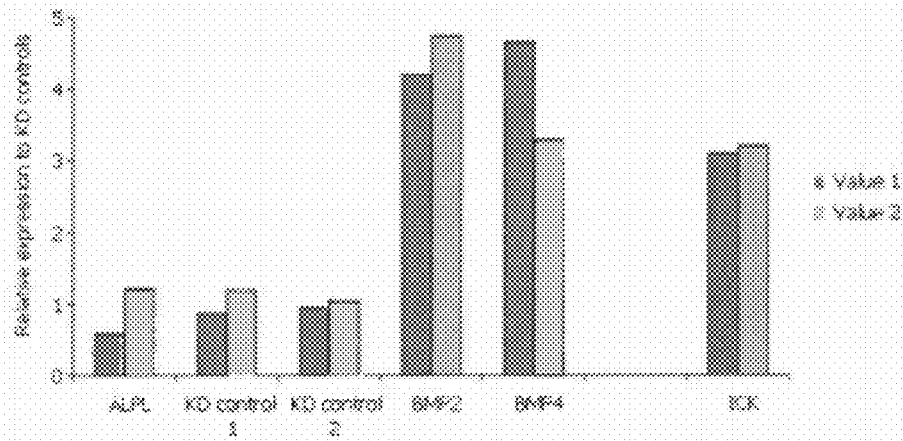
Figure 8C:
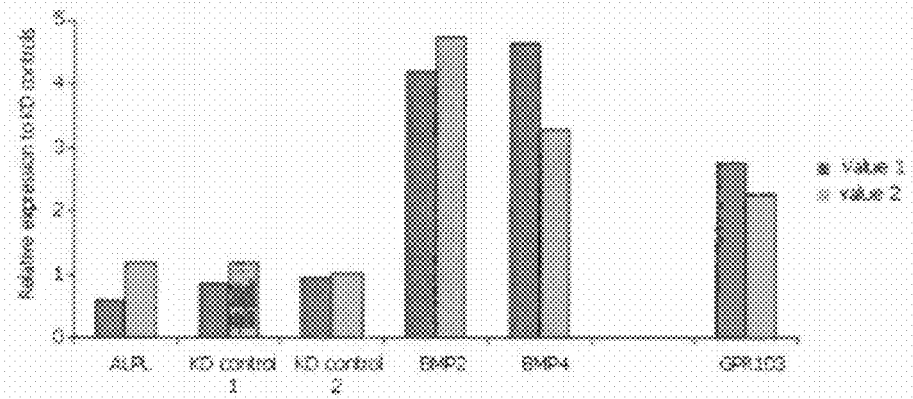
Figure 8D:
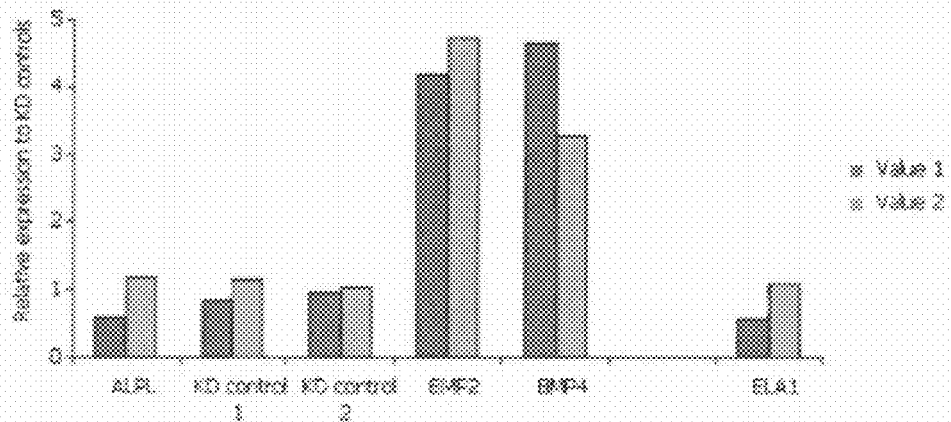
Figure 8E:
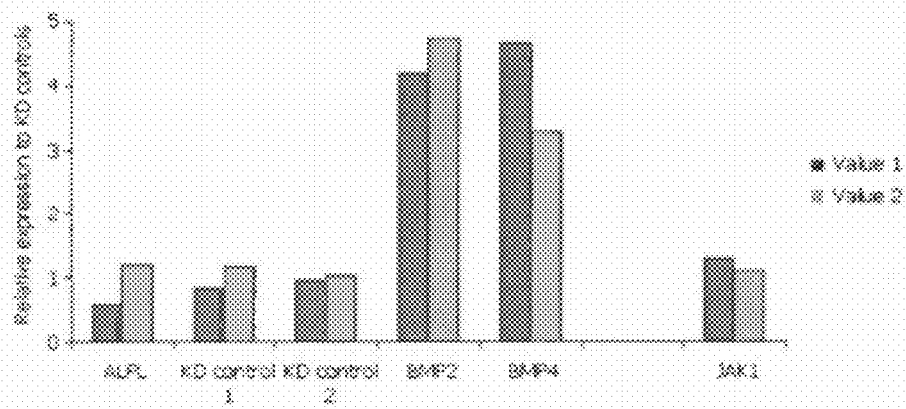
Figure 8F:
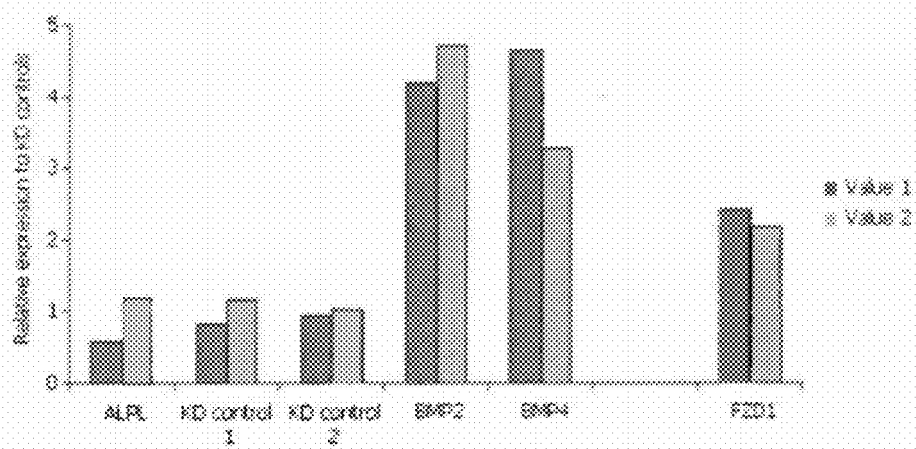
Figure 8G:
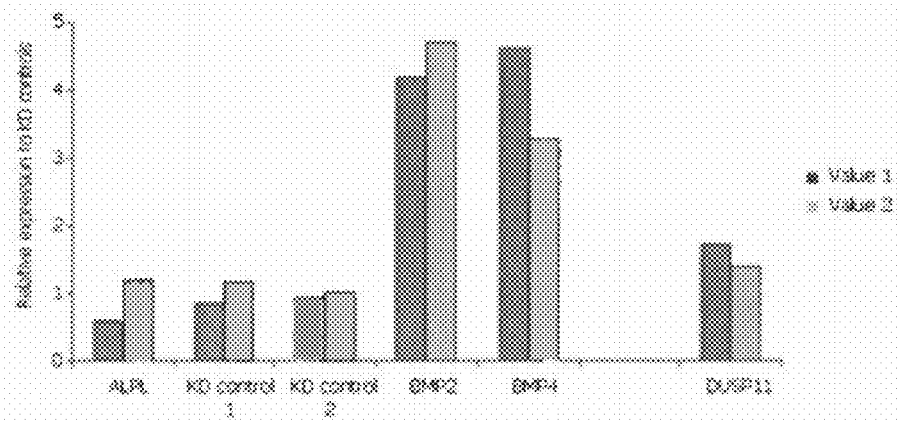
Figure 8H:
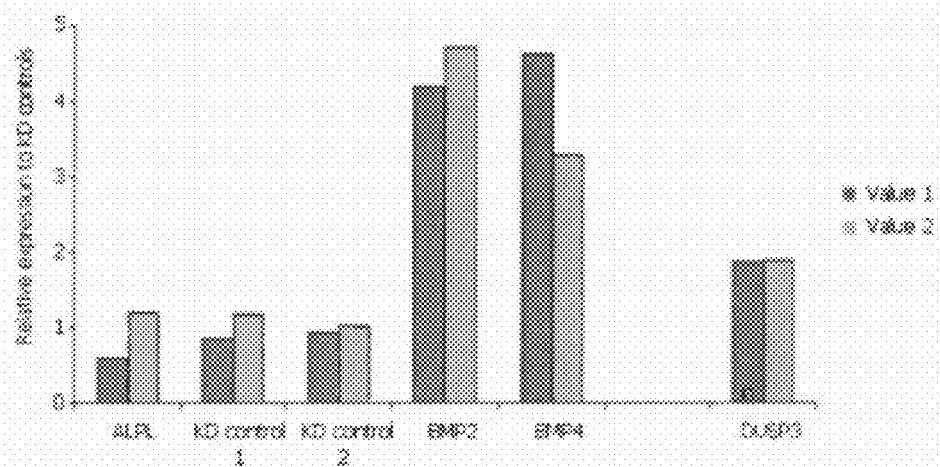
Figure 8I:
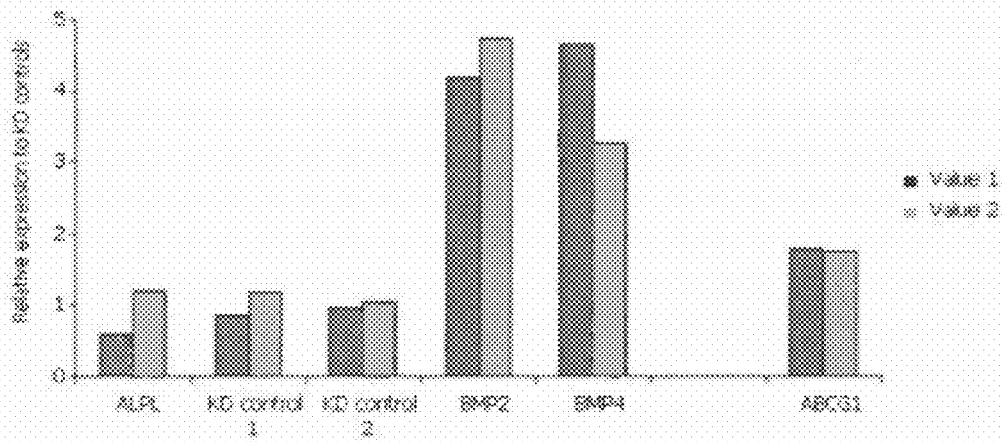
Figure 8J:
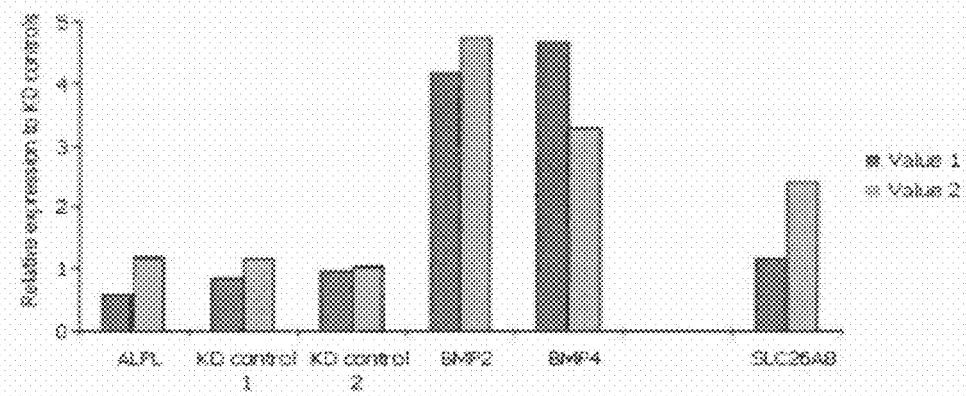
Figure 8K:
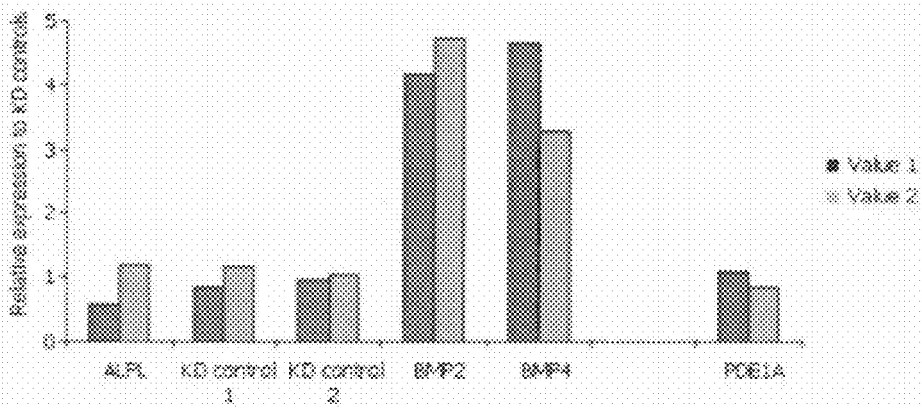
Figure 8L:
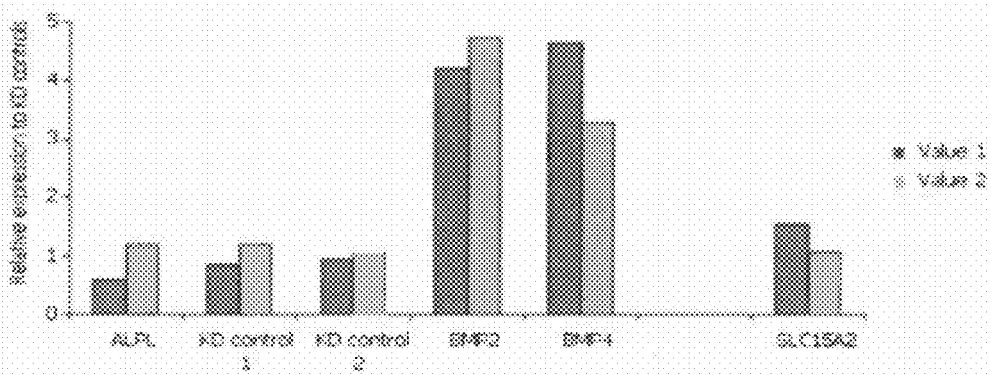
Figure 9A:
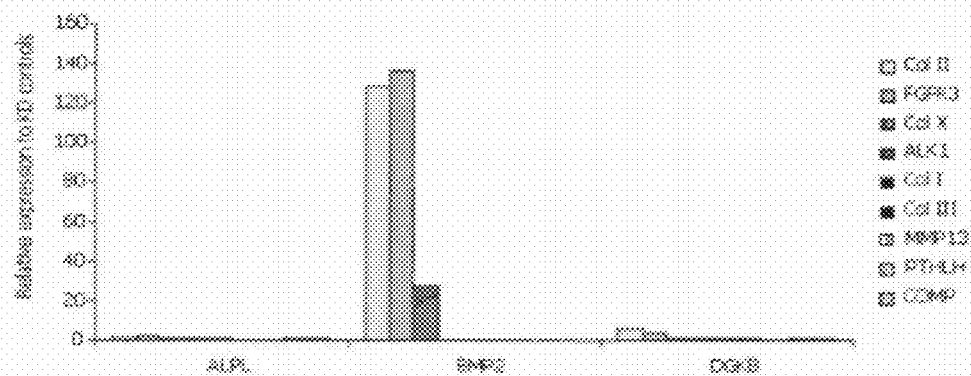
FIG. 9 (A-L): mRNA marker analysis on chondrocytes in alginate cell culture 10 days post infection. The cells are infected with either Ad5/ALPL and Ad5/BMP2 overexpressing viruses, and with an Ad-siRNA targeting the indicated gene. The data are represented as relative mRNA levels to the ALPL control.
Figure 9B:
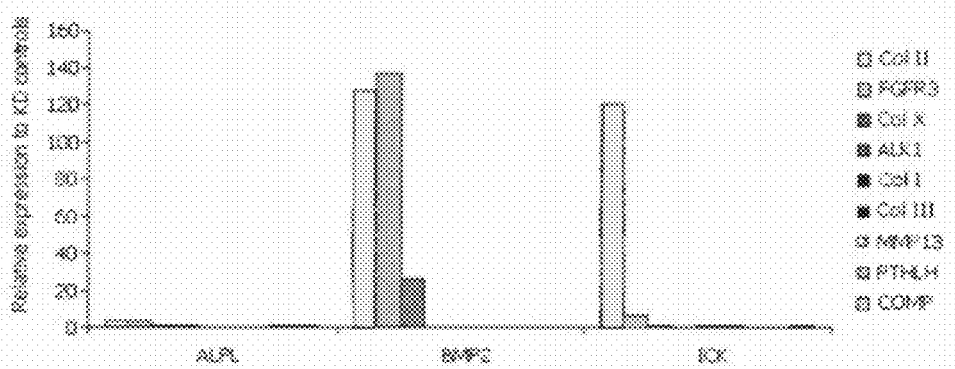
Figure 9C:
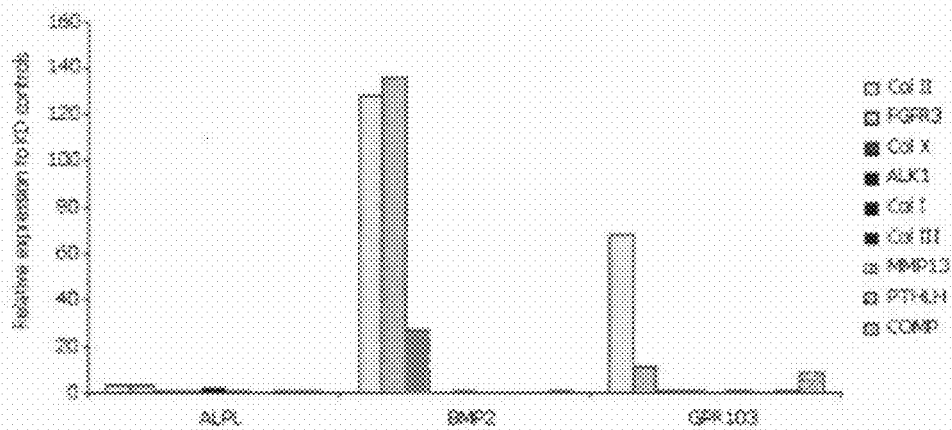
Figure 9D:
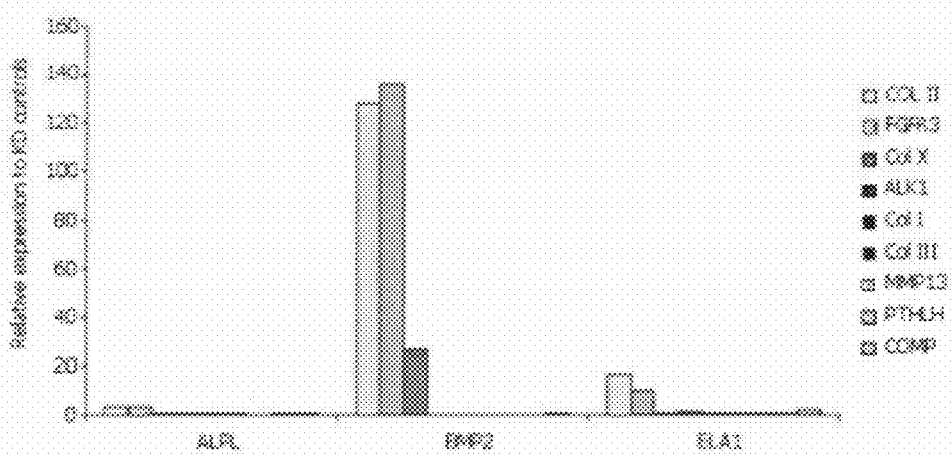
Figure 9E:
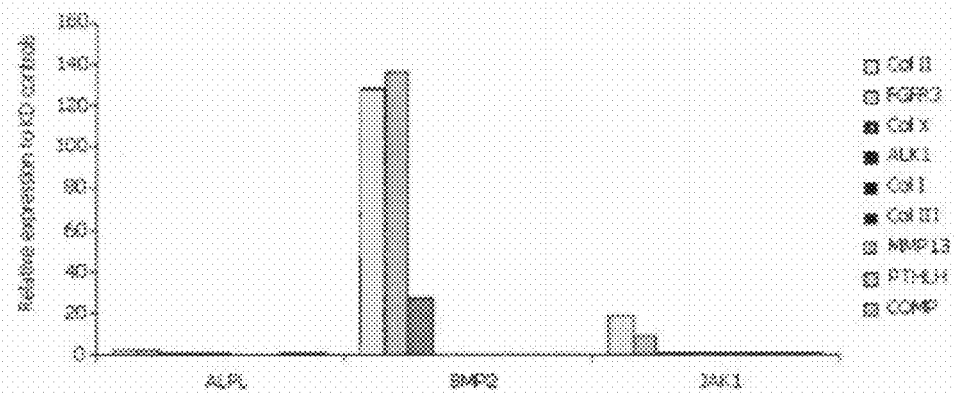
Figure 9F:
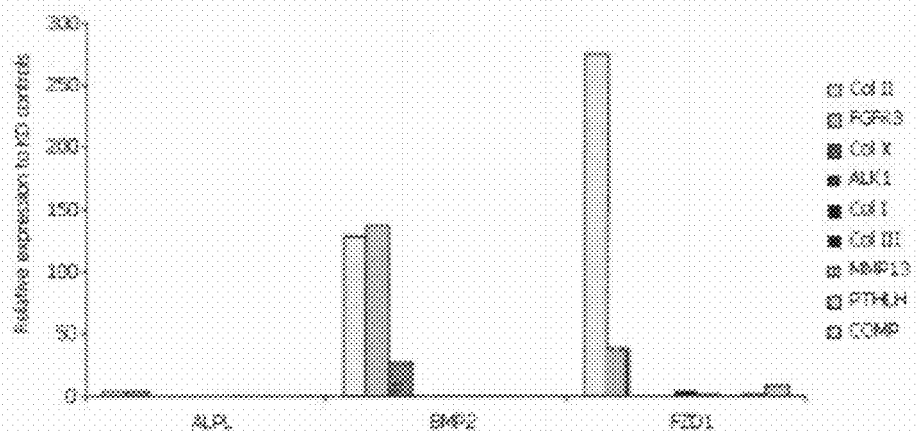
Figure 9G:
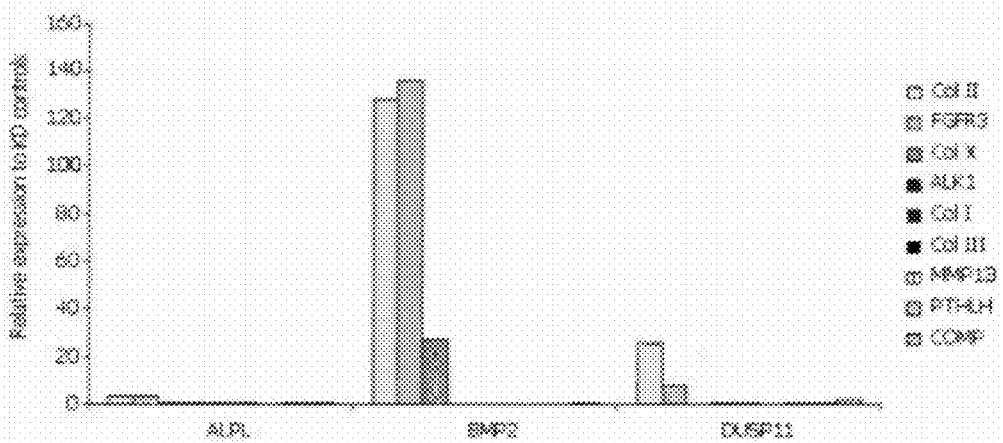
Figure 9H:
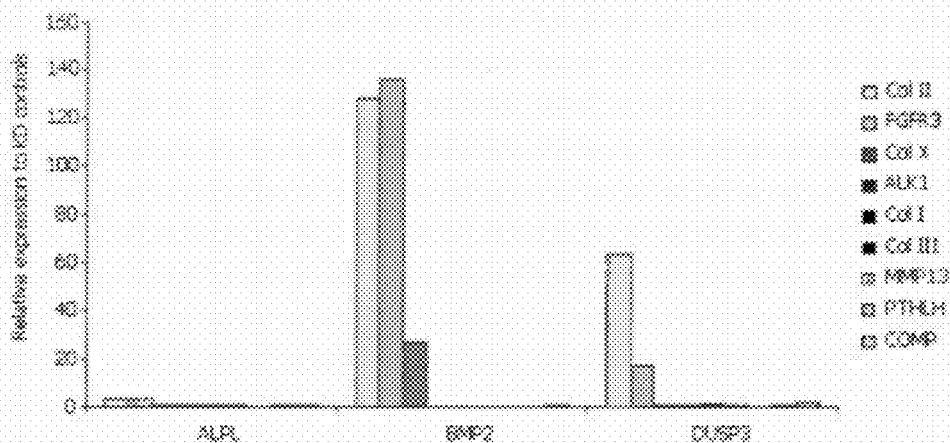
Figure 9I:
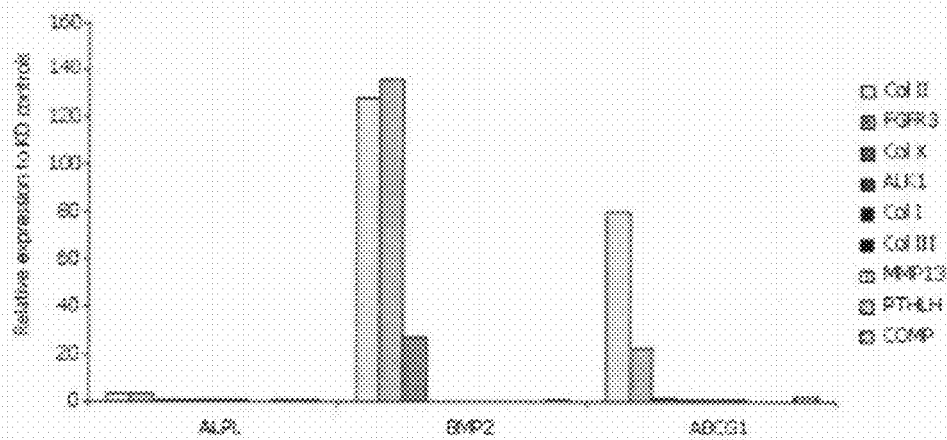
Figure 9J:
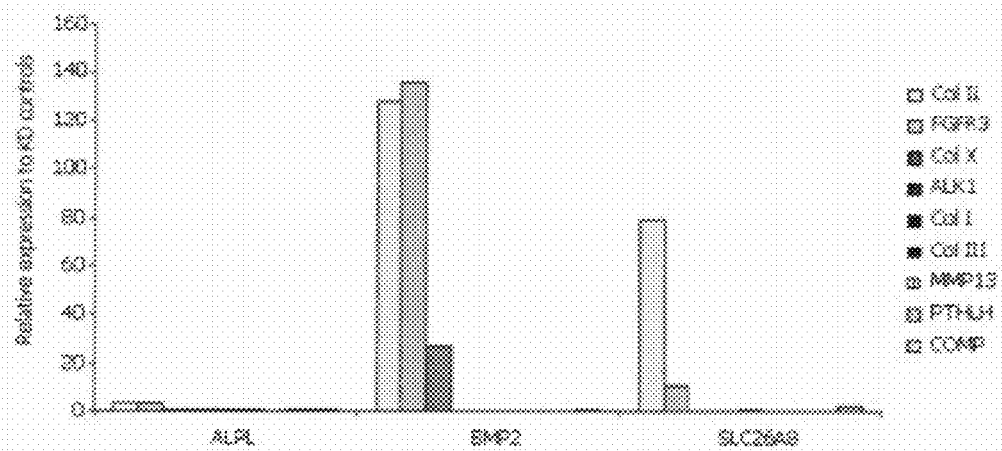
Figure 9K:
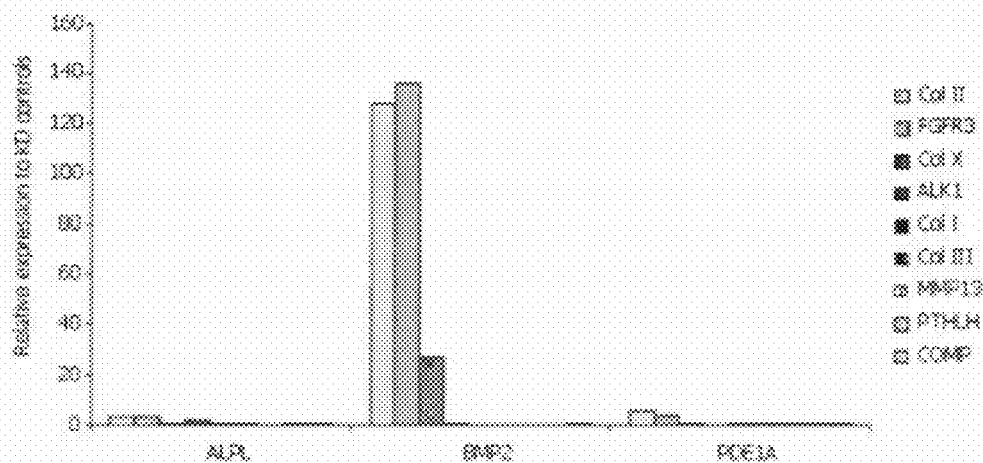
Figure 9L:
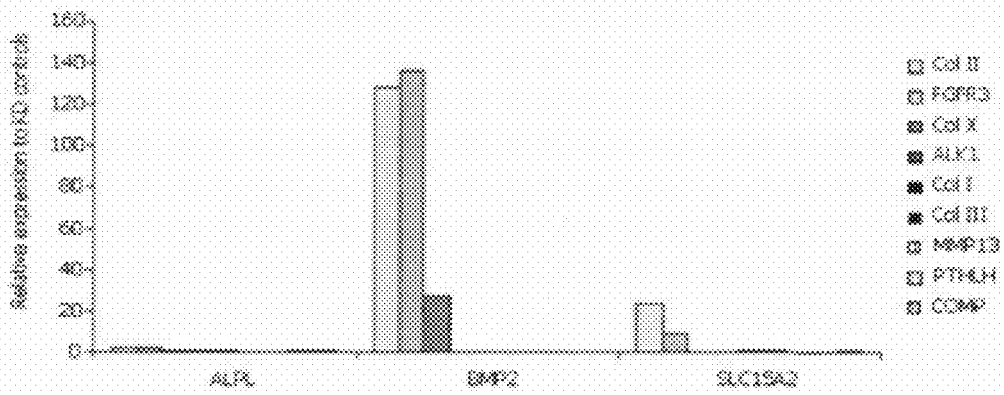

After 7 days, 10 μl of a 50 μg/ml 2-Phospho-L-ascorbic acid in assay culture medium is added to each well. Up-regulation of aggrecan is read at 10 dpi with Alcian blue staining: The medium is removed with a VacuSafe; 50 μl ice-cold MeOH is added with a multidrop and removed immediately with a VacuSafe; 80 μl of ice-cold MeOH is added with a multidrop to fixate the cells, and plates are incubated for 20 min at −20° C.; MeOH is removed with a VacuSafe; plates are air dried for 20 min. After washing once with 80 μl of PBS; 80 μl of 0.05% Alcian blue stain buffer (0.05% Alcian blue, Sigma, catalog number S-2889; 0.4 M $MgCl_2$/25 mM sodium acetate, pH 5.5) is added and plates are incubated overnight at RT. The next day cells are washed subsequently in 80 μl of 3% acetic acid, 25% ethanol/3% acetic acid, and 50% ethanol/3% acetic acid. Solutions are added with a multidrop and removed with a Vacusafe. After replacing 50% ethanol/3% acetic acid with 70% ethanol/3% acetic acid, each individual well is photographed with a SONY CCD camera, images are analyzed using a Galapagos Alcian blue quantification algorithm based on the separation of the blue signal through a color threshold procedure after a noise reduction filter. The amount of blue staining, which is proportional to aggrecan content, is expressed in pixel unit (see FIG. 4).

The propagated hits from Example 3 are used to transduce NHAc cells at three MOI's in duplicate in the chondrogenesis assay (see Example 1). The Ad-siRNAs have to score in duplicate in at least one MOI above threshold (average+2.5× standard deviation) to pass this secondary assay. In total, 101 out of 282 hits passed the Alcian blue assay for aggrecan (see Table 1). The results for some of the genes are shown in FIG. 5. Values represent the numerical output of the described algorithm and are correlated to Alcian blue staining levels. A clear induction of the aggrecan levels is observed upon infection of the Ad-siRNA targeting the indicated gene. The Ad-siRNA targeting FZD1 does not seem to induce Alcian blue staining.

TABLE 1

Overview of the 101 target sequences and their respective KD target sequences corresponding to the genes encoding the different polypeptides involved in chondrogenic differentiation. The GenBank numbers for the polypeptides and target gene symbols (general names) are also given.

| Hit ID | KD Target Sequence | Gene Symbol | GenBank Accession | Name | Class | KD Target Sequence SEQ ID NO |
|---|---|---|---|---|---|---|
| H33-006 | ATAAGCGGTTATCACTGCC | PCTK2 | NM_002595 | PCTAIRE protein kinase 2 | Kinase | 392 |
| H33-007 | GCTGGGATTCCAAGTGGAC | RYK | SK340-NM_002958 | RYK receptor-like tyrosine kinase | Kinase | 393 |
| H33-008 | AACTGTGCAGGGCCTCTCC | NTRK1 | NM_002529 | neurotrophic tyrosine kinase, receptor, type 1 | Kinase | 394 |
| H33-009 | GCTGCTGGATGTCATTCAC | CDK2 | NM_052827-NM_001798 | cyclin-dependent kinase 2 | Kinase | 395 |
| H33-010 | AGAGACACAGTGCCCATCC | PCK1 | NM_002591 | phosphoenolpyruvate carboxykinase 1 (soluble) | Kinase | 396 |
| H33-011 | ACTGAACCTCCGAAATGCC | NEK4 | SK256-NM_003157 | NIMA (never in mitosis gene a)-related kinase 4 | Kinase | 397 |
| H33-013 | GTGCTGGAGTGCTTCCATC | MAPKAPK3 | NM_004635 | mitogen-activated protein kinase-activated protein kinase 3 | Kinase | 398 |
| H33-020 | TTCAGACCTACCTTCAGTC | UMP-CMPK | NM_016308 | UMP-CMP kinase | Kinase | 399 |
| H33-025 | CCTGAATGTGACTGTGGAC | DGKB-INCENP | NM_020238-NM_004080-NM_145695 | diacylglycerol kinase, beta 90 kDa/inner centromere protein antigens 135/155 kDa | Kinase | 91 |
| H33-027 | GAGTCACACAGAGATGAGC | ROCK1 | NM_005406 | Rho-associated, coiled-coil containing protein kinase 1 | Kinase | 400 |
| H33-028 | CGATGTGCCTTCAAGATTC | PRKCN | SK489-NM_005813 | protein kinase C, nu | Kinase | 401 |

TABLE 1-continued

Overview of the 101 target sequences and their respective KD target sequences corresponding to the genes encoding the different polypeptides involved in chondrogenic differentiation. The GenBank numbers for the polypeptides and target gene symbols (general names) are also given.

| Hit ID | KD Target Sequence | Gene Symbol | GenBank Accession | Name | Class | KD Target Sequence SEQ ID NO |
|---|---|---|---|---|---|---|
| H33-031 | CAGTGGTTTGGGAATCTGC | PLK4-STK18 | SK341-NM_014264 | serine/threonine kinase 18 (STK18)/polo-like kinase 4 (Drosophila) | Kinase | 402 |
| H33-032 | GACTGACTGGCCTGAAGGC | ICK | NM_016513-NM_014920 | intestinal cell (MAK-like) kinase | Kinase | 92 |
| H33-034 | GATCTACACCACCTTCATC | GPR103 | AF411117-NM_198179 | G protein-coupled receptor 103 | GPCR | 101 |
| H33-036 | GTGACTACACAAGGACTCC | CCR2 | NM_000647 | chemokine (C-C motif) receptor 2 | GPCR | 403 |
| H33-040 | GACTGATTCGCTCTTTGCC | FPRL2 | NM_002030 | formyl peptide receptor-like 2 | GPCR | 404 |
| H33-041 | GGTGTATGGGCTCATGTAC | FZD1 | NM_003505 | frizzled homolog 1 (Drosophila) | GPCR | 108 |
| H33-042 | AGTGCAGCCTTGTGGGTTC | P2RY10 | NM_198333-NM_014499 | purinergic receptor P2Y, G-protein coupled, 10 | GPCR | 405 |
| H33-044 | TAACACTCACTGCACCTGC | EMR3 | NM_152939-NM_032571 | egf-like module containing, mucin-like, hormone receptor-like 3 | GPCR | 406 |
| H33-049 | TAACTGAAACTCAGCTAGC | PROZ | NM_003891 | protein Z, vitamin K-dependent plasma glycoprotein | Protease | 407 |
| H33-054 | ACTGAAGTAGCCCTCCTTC | THRB | NM_000461 | thyroid hormone receptor, beta (erythroblastic leukemia viral (v-erb-a) oncogene homolog 2, avian) | NHR | 408 |
| H33-056 | AGAACTGGGTGATGACAGC | ELA1 | NM_001971 | elastase 1, pancreatic | Protease | 116 |
| H33-058 | AGTGCAGTACAGCGATGAC | COL7A1 | NM_000094 | collagen, type VII, alpha 1 (epidermolysis bullosa, dystrophic, dominant and recessive) | Not classified | 409 |
| H33-059 | TTCACATCGCTGAGCACCC | CPZ | NM_003652 | carboxypeptidase Z | Protease | 410 |
| H33-061 | ATGAACTCTGTGATCCAGC | USP9Y | NM_004654 | ubiquitin specific protease 9, Y-linked (fat facets-like, Drosophila) | Protease | 123 |
| H33-063 | AGCCAGCAACGACATGTAC | CST3 | NM_000099 | cystatin C (amyloid angiopathy and cerebral hemorrhage) | Not classified | 411 |

TABLE 1-continued

Overview of the 101 target sequences and their respective KD target sequences corresponding to the genes encoding the different polypeptides involved in chondrogenic differentiation. The GenBank numbers for the polypeptides and target gene symbols (general names) are also given.

| Hit ID | KD Target Sequence | Gene Symbol | GenBank Accession | Name | Class | KD Target Sequence SEQ ID NO |
|---|---|---|---|---|---|---|
| H33-065 | GCTGCTGGGCATGTCCTTC | LNPEP | NM_005575 | leucyl/cystinyl aminopeptidase | Protease | 412 |
| H33-066 | TGTGATCGTCATCACAGTC | NLGN1 | NM_014932 | neuroligin 1 | Enzyme | 413 |
| H33-068 | AACATGATATGTGCTGGAC | KLK10 | NM_145888 NM_002776 | kallikrein 10 | Protease | 414 |
| H33-069 | CTGAGAAGGCTTCCACTGC | LOC119795 | XM_061692 | similar to glutamyl aminopeptidase (aminopeptidase A); gp160 | Protease | 415 |
| H33-070 | TGATACGTGGATCCAGGCC | LOC124221-MGC52282 | NM_178453 | similar to distal intestinal serine protease | Protease | 416 |
| H33-072 | CTACAGTGACAAGGCTAAC | OVTN-LOC159938 | XM_089945-NM_198185 | (similar to) oviductin protease | Protease | 417 |
| H33-073 | GAACTGGATAGCCCTCATC | LOC206008-RNF150 | XM_116274-XM_371709 | similar to KIAA1214 protein/ring finger protein 150 | Protease | 418 |
| H33-074 | CCCTGGTAAAGCTGCATTC | LOC220213 | XM_166659 | similar to evidence: NAS~ hypothetical protein/putative | Protease | 419 |
| H33-076 | GATGAAGGCTTCGGGCTTC | XYLB | NM_005108 | xylulokinase homolog (H. influenzae) | Kinase | 420 |
| H33-080 | TGTAAAGCTGGAAAGGGAC | PTEN | NM_000314 BC038293-AF017999 | putative protein tyrosine phosphatase homologue | Phosphatase | 421 |
| H33-081 | CTGAAGAAGCTGGAGTTGC | PTPN23 | NM_015466 | protein tyrosine phosphatase, non-receptor type 23/protein tyrosine phosphatase TD14 | Phosphatase | 422 |
| H33-082 | TTGGAATTCCAGTGTACCC | DUSP11 | NM_003584 | dual specificity phosphatase 11 (RNA/RNP complex 1-interacting) | Phosphatase | 132 |
| H33-083 | GCTAGTTATCGCCTACCTC | DUSP3 | NM_004090 | dual specificity phosphatase 3 (vaccinia virus phosphatase VH1-related) | Phosphatase | 139 |
| H33-084 | TCCTTGCAGCAGGCACATC | SLC24A1 | NM_004727 | solute carrier family 24 (sodium/potassium/calcium exchanger), member 1 | Ion Channel | 423 |

TABLE 1-continued

Overview of the 101 target sequences and their respective KD target sequences corresponding to the genes encoding the different polypeptides involved in chondrogenic differentiation. The GenBank numbers for the polypeptides and target gene symbols (general names) are also given.

| Hit ID | KD Target Sequence | Gene Symbol | GenBank Accession | Name | Class | KD Target Sequence SEQ ID NO |
|---|---|---|---|---|---|---|
| H33-092 | TCTGTGCGTGGACTGGAAC | GABRP | NM_014211 | gamma-aminobutyric acid (GABA) A receptor, pi | Ion Channel | 424 |
| H33-095 | CTTTGCTCGGAAGACGTTC | RAF1 | NM_002880 | v-raf-1 murine leukemia viral oncogene homolog 1 | Kinase | 425 |
| H33-096 | AGATTCCAGATGCAACCCC | JAK1 | SK185-NM_002227 | Janus kinase 1 (a protein tyrosine kinase) | Kinase | 148 |
| H33-098 | GAAGGCTTTGGAAAGTGTC | LOC167359-MGC42105 | XM_094437-NM_153361 | hypothetical protein MGC42105 | Kinase | 426 |
| H33-102 | GTGAACTCTGCTGCGACTC | PKD1L3-LOC162163 | XM_091397-NM_181536 | similar to KIAA1879 protein/polycystic kidney disease 1-like 3 | GPCR | 427 |
| H33-104 | GACAAGGCTATGATGCTGC | RPS6KA3 | NM_004586 | ribosomal protein S6 kinase, 90 kDa, polypeptide 3 | Kinase | 428 |
| H33-105 | GGATGTGTGGTGCTGTCAC | RBKS | NM_022128 | ribokinase | Kinase | 429 |
| H33-107 | CTGAACTACTGGTACAGCC | ABCG1 | NM_016818-NM_004915 | ATP-binding cassette, sub-family G (WHITE), member 1 | Transporter | 157 |
| H33-108 | CTCTGTGTTCCACTTCGGC | DPYD | NM_000110 | dihydropyrimidine dehydrogenase | Enzyme | 430 |
| H33-110 | CAGCAATGCAGAGTGTGAC | TNFRSF9 | NM_001561 | tumor necrosis factor receptor superfamily, member 9 | Other drugable or secreted | 431 |
| H33-114 | CAAAGCTGGCTACTACTAC | TNFSF14 | NM_172014-NM_003807 | tumor necrosis factor (ligand) superfamily, member 14 | Other drugable or secreted | 432 |
| H33-117 | CAGTGCAAAGAGCCCAAAC | GAPDS | NM_014364 | glyceraldehyde-3-phosphate dehydrogenase, testis-specific | Enzyme | 433 |
| H33-118 | GTATTCTGTACACCCTGGC | RDH11 | NM_016026 | retinol dehydrogenase 11 (all-trans and 9-cis) | Enzyme | 434 |
| H33-120 | GTGATCGACAGGATTGCTC | PRKAG3 | NM_017431 | protein kinase, AMP-activated, gamma 3 non-catalytic subunit | Kinase | 435 |

TABLE 1-continued

Overview of the 101 target sequences and their respective KD target sequences corresponding to the genes encoding the different polypeptides involved in chondrogenic differentiation. The GenBank numbers for the polypeptides and target gene symbols (general names) are also given.

| Hit ID | KD Target Sequence | Gene Symbol | GenBank Accession | Name | Class | KD Target Sequence SEQ ID NO |
|---|---|---|---|---|---|---|
| H33-130 | GCGAATTCCACCAG CATTC | SLC26 A8 | NM_052961 | solute carrier family 26, member 8 | Transporter | 165 |
| H33-138 | CACAGTGAAACCTT CCTGC | B4GAL T5 | NM_004776 | UDP-Gal: betaGlcNAc beta 1,4-galactosyltransferase, polypeptide 5 | Enzyme | 436 |
| H33-145 | ATCTGTGACACTGG ATCGC | LOC12 5836 | XM_064820 | similar to Aldose Reductase (E.C.1.1.1.21) | Enzyme | 437 |
| H33-147 | AGAGACTGGAGTT GTCAGC | GNPN AT1 | NM_198066 | glucosamine-phosphate N-acetyltransferase 1 | Enzyme | 438 |
| H33-152 | CCTGAGTTGAATGT CATAC | CYP17 A1 | NM_000102 | cytochrome P450, family 17, subfamily A, polypeptide 1 | Cytochrome P450 | 39 |
| H33-158 | CTGAACTAGTGACT ATCCC | MAGI-3 | NM_152900-NM_020965 | membrane-associated guanylate kinase-related | Kinase | 440 |
| H33-161 | ATAAGCACCGTGA GCGACC | LOC13 8967 | XM_071222 | similar to cytochrome P450 1A1 | Cytochrome P450 | 441 |
| H33-167 | CATTGGGCCACAG ACCTAC | ADOR A1 | NM_000674 | adenosine A1 receptor | GPCR | 442 |
| H33-168 | GATGAAGACAGCA ACCAAC | OPRK1 | NM_000912 | opioid receptor, kappa 1 | GPCR | 443 |
| H33-175 | AGCATATGATGACC TTGGC | CTSC | NM_148170-NM_001814 | cathepsin C | Protease | 444 |
| H33-180 | ATTCCACTACTACA GCTGC | H105E3 | NM_015922 | NAD(P) dependent steroid dehydrogenase-like | Enzyme | 445 |
| H33-182 | GAAACTGTGGCAG GCTAAC | LOC25 6519 | XM_171056 | similar to Putative serine/threonine-protein kinase D1044.3 in chromosome III | Kinase | 446 |
| H33-186 | CTGATGAAGGCCTT CGACC | LOC12 3326 | XM_063593 | similar to NADH-ubiquinone oxidoreductase PDSW subunit (Complex I-PDSW) (CI-PDSW) | Enzyme | 447 |
| H33-188 | TTGAAACAAGAGG AAGTCC | ACYP1 | XM_370768-NM_203488-NM_001107 | (similar to) acylphosphatase 1, erythrocyte (common) type | Phosphatase | 448 |

TABLE 1-continued

Overview of the 101 target sequences and their respective KD target sequences corresponding to the genes encoding the different polypeptides involved in chondrogenic differentiation. The GenBank numbers for the polypeptides and target gene symbols (general names) are also given.

| Hit ID | KD Target Sequence | Gene Symbol | GenBank Accession | Name | Class | KD Target Sequence SEQ ID NO |
|---|---|---|---|---|---|---|
| H33-190 | TGAACTTGCTCTGAGCTGC | KCNJ14 | NM_170720 NM_013348 | potassium inwardly-rectifying channel, subfamily J, member 14 | Ion Channel | 449 |
| H33-191 | ATCTGTAACCTCAGCACAC | PPP3CC | S46622 NM_005605 | protein phosphatase 3 (formerly 2B), catalytic subunit, gamma isoform (calcineurin A gamma) | Phosphatase | 450 |
| H33-192 | ACATTGACCAGGAAGTGAC | GGTLA4 | NM_178312 NM_178311 NM_080920 | gamma-glutamyltransferase-like activity 4 | Enzyme | 178 |
| H33-202 | GAAGCTAAGCCTCGGTTAC | PIK4CA | NM_058004 | phosphatidylinositol 4-kinase, catalytic, alpha polypeptide | Kinase | 451 |
| H33-204 | TAACCGTGGCATCTACCTC | TPP2 | NM_003291 | tripeptidyl peptidase II | Protease | 452 |
| H33-205 | TGACCACCTGGAGTATCAC | CST11 | NM_130794 | cystatin 11 | Not classified | 453 |
| H33-208 | GTGGACATCTTTGAGCTTC | GRIK4 | NM_014619 | glutamate receptor, ionotropic, kainate 4 | Ion Channel | 454 |
| H33-209 | GCTGAGAAGTACTTCCACC | ARHGEF16 | NM_014448 | Rho guanine exchange factor (GEF) 16 | Other drugable or secreted | 455 |
| H33-210 | AGACTACTGCAAGGGCGGC | STK23 | NM_014370 | serine/threonine kinase 23 | Kinase | 456 |
| H33-213 | GAGTATTTGCTGGCATTCC | SLCO1A2-CRLF2 | XM_372282 NM_134431 NM_022148 NM_021094 | solute carrier organic anion transporter family, member 1A2/cytokine receptor-like factor 2 | Protease | 457 |
| H33-217 | GAAGCTGAATTAGGGCTTC | PDE1A | NM_005019 | phosphodiesterase 1A, calmodulin-dependent | PDE | 184 |
| H33-219 | GGAGACACGGAATAAACTC | PPP1R12B | NM_032105 NM_002481 | protein phosphatase 1, regulatory (inhibitor) subunit 12B | Phosphatase | 458 |
| H33-222 | CCGAGACCACCTCAATGTC | ACAD8 | NM_014384 | acyl-Coenzyme A dehydrogenase family, member 8 | Enzyme | 459 |
| H33-223 | ATGGACATCTCCACGGGAC | PTPRN | NM_002846 | protein tyrosine phosphatase, receptor type, N | Phosphatase | 460 |

TABLE 1-continued

Overview of the 101 target sequences and their respective KD target sequences corresponding to the genes encoding the different polypeptides involved in chondrogenic differentiation. The GenBank numbers for the polypeptides and target gene symbols (general names) are also given.

| Hit ID | KD Target Sequence | Gene Symbol | GenBank Accession | Name | Class | KD Target Sequence SEQ ID NO |
|---|---|---|---|---|---|---|
| H33-230 | TATCCTGACCTTCCTGCGC | KCNG1 | NM_172318 NM_002237 | potassium voltage-gated channel, subfamily G, member 1 | Ion Channel | 461 |
| H33-236 | CACATGATCAAGCTAGGTC | LOC220763 | XM_055551 | similar to Heat shock protein HSP 90-beta (HSP 84) (HSP 90) | Kinase | 462 |
| H33-237 | GAAGCCAGGCATCTTCATC | SPOCK2 | NM_014767 | sparc/osteonectin, cwcv and kazal-like domains proteoglycan (testican) 2 | Enzyme | 463 |
| H33-238 | GCTGAAGTTATCCAGTCTC | PTPN13 | NM_080685 NM_080684 NM_080683 NM_006264 | protein tyrosine phosphatase, non-receptor type 13 (APO-1/CD95 (Fas)-associated phosphatase) | Phosphatase | 464 |
| H33-239 | AGCATTGGACCAGTTGATC | GABRG1 | NM_173536 | gamma-aminobutyric acid (GABA) A receptor, gamma 1 | Ion Channel | 465 |
| H33-243 | GTGATCTACGTGAACTGGC | DPP3 | NM_005700 | dipeptidylpeptidase 3 | Protease | 466 |
| H33-245 | GCCGACAGTGGTGCACTAC | LYPLA3 | NM_012320 | lysophospholipase 3 (lysosomal phospholipase A2) | Enzyme | 467 |
| H33-251 | AACATGATGGCTCAGAACC | CTSE | NM_148964 NM_001910 | cathepsin E | Protease | 468 |
| H33-253 | TACAGTGATGGATCATAGC | SULT1B1 | NM_014465 | sulfotransferase family, cytosolic, 1B, member 1 | Enzyme | 469 |
| H33-255 | ACCAATATGCCTACCTTCC | KLKB1 | NM_000892 | kallikrein B, plasma (Fletcher factor) 1 | Protease | 470 |
| H33-258 | ACTGTATCCCAGCAGTCCC | SENP7 | NM_020654 | sentrin/SUMO-specific protease | Protease | 471 |
| H33-259 | AAGCTGAACATAACCTTGC | PTPRR | NM_002849 | protein tyrosine phosphatase, receptor type, R | Phosphatase | 472 |

TABLE 1-continued

Overview of the 101 target sequences and their respective KD target sequences corresponding to the genes encoding the different polypeptides involved in chondrogenic differentiation. The GenBank numbers for the polypeptides and target gene symbols (general names) are also given.

| Hit ID | KD Target Sequence | Gene Symbol | GenBank Accession | Name | Class | KD Target Sequence SEQ ID NO |
|---|---|---|---|---|---|---|
| H33-261 | TTGAATAGCTCGGTGTCCC | LOC169014 | XM_095455 | similar to Mitogen-activated protein kinase 6 (Extracellular signal-regulated kinase 3) (ERK-3) (MAP kinase isoform p97) (p97-MAPK) | Kinase | 473 |
| H33-263 | GTGGAAGGCAAGATCTTCC | ABCD1-LOC388253-LOC391403 | XM_372940 XM_370972 NM_000033 | ATP-binding cassette, sub-family D (ALD), member 1/similar to Adrenoleukodystrophy protein (ALDP) | Transporter | 474 |
| H33-264 | TGTATGGCTGGTCGATCAC | ABCA7 | NM_033308 NM_019112 | ATP-binding cassette, sub-family A (ABC1), member 7 | Transporter | 475 |
| H33-269 | GCTGCGACAACTTCTGTTC | GPR110 | NM_153840 | G protein-coupled receptor 110 | GPCR | 476 |
| H33-276 | GCCCACGGTCTTCCACTAC | ACPT | NM_080791 NM_080789 NM_033068 | acid phosphatase, testicular | Phosphatase | 477 |
| H33-279 | GAAGCCATCTCCGACAATC | SLC15A2 | NM_021082 | solute carrier family 15 (H+/peptide transporter), member 2 | Transporter | 192 |
| H33-295 | GACTGAATCAGGCCTTCCC | PPIH | NM_006347 | peptidyl prolyl isomerase H (cyclophilin H) | Enzyme | 478 |

Example 5

Donor Dependency

The 282 hits identified by the ColII cELISA assay are further subject to a donor dependency test to demonstrate that the induction of ColII production by a given hit is not restricted to a single donor. In addition to the 11-year-old donor (donor I) previously used, NHAC's from multiple donors with ages of 24 (donor II), 41 (donor III), and 50 (donor IV), are obtained after informed consent (Cambrex, Verviers, Belgium). Cells are seeded as described in Examples 1 and 3. The propagated Ad-siRNAs are used to transduce NHAc cells from these different donors at three MOI's in duplicate in the chondrogenesis assay (see Examples 1 and 3). The Ad-siRNAs have to score at least once above threshold (average+2.5 times standard deviation) to pass this donor dependency test.

Out of 101 hits that passed the Alcian blue assay for aggrecan, 97 score positive in Donor IV. Of the remaining 4, 1 score positive in Donor II. The other 3 did not score in the other donors tested. In addition, 40 of the 101 hits score positive in all three additional donors. These results demonstrate that 98 out of these 101 hits function in a non-donor-dependent manner. Exceptions are H33-145; H33-182; and H33-263 (see Table 1). Indicated in this Table 1 are the Target Gene Symbol, Gene Bank Accession Number, and drugability class of the genes that correspond to the target sequences. The results for some of the genes are shown in Table 2. These data show that knocking down the RNA levels of the indicated genes induces collagen II levels in at least 2 donors. The values represent times standard deviation of the background.

TABLE 2 overview donor dependency data. N = 2 for every condition. All data points are represented as fold standard deviation of the background. All values above 2.5 are considered to be positive and are shaded grey.

| | Donor I cELISA | | | | | | Donor II cELISA | | | | | |
| --- | --- | --- | --- | --- | --- | --- | --- | --- | --- | --- | --- | --- |
| | 5 μl | | 1.5 μl | | 15 μl | | 5 μl | | 1.5 μl | | 15 μl | |
| NAME | 1 | 2 | 1 | 2 | 1 | 2 | 1 | 2 | 1 | 2 | 1 | 2 |
| Ad5C01Att01/A150100-ABCG1_v7 | 3.354 | 2.18 | 5.462 | 3.896 | 2.049 | 1.296 | 2.181 | 1.033 | 2.133 | -0.829 | 2.079 | 1.155 |
| Ad5C01Att01/A150100-DUSP11_v2 | 2.195 | 2.147 | 2.372 | 2.153 | 3.513 | 4.001 | 1.676 | 1.951 | 1.542 | 1.186 | 2.703 | 2.053 |
| Ad5C01Att01/A150100-ELA1_v2 | 4.825 | 3.735 | 7.646 | 6.06 | 3.162 | 2.691 | 2.195 | 1.382 | 2.664 | 1.064 | 2.649 | 1.3 |
| Ad5C01Att01/A150100-FZD1_v10 | 2.223 | 0.417 | 3.118 | 0.911 | 1.467 | 1.119 | 1.383 | -0.276 | 1.874 | -1.143 | 0.859 | -0.54 |
| Ad5C01Att01/A150100-GGTLA4_v6 | 1.927 | 2.09 | 3.149 | 2.859 | 2.427 | 1.669 | 3.286 | 1.201 | 3.086 | 1.233 | 3.274 | 2.064 |
| Ad5C01Att01/A150100-ICK_v1 | 4.542 | 1.537 | 7.24 | 4.168 | 3.381 | 1.479 | 2.467 | 0.923 | 2.4 | 0.3 | 3.077 | 1.536 |
| Ad5C01Att01/A150100-SLC15A2_v2 | 2.493 | 2.173 | 2.502 | 1.399 | 2.197 | 1.29 | 2.835 | 2.298 | 3.957 | 1.653 | 3.331 | 1.988 |
| Ad5C01Att01/A150100-SLC26A8_v2 | 2.193 | 2.643 | 1.674 | 2.539 | 2.295 | 2.841 | 2.286 | 3.247 | 2.013 | 1.936 | 0.873 | 1.807 |
| Ad5C01Att01/A150100-USP9Y_v1 | 3.927 | 3.561 | 5.565 | 4.123 | 4.315 | 2.85 | 2.54 | 1.386 | 2.86 | 2.183 | 1.819 | 0.501 |
| Ad5C01Att01/A150100-DGKB_v2 | 2.105 | 2.53 | 4.17 | 3.693 | 2.102 | 1.583 | 2.207 | -0.113 | 1.675 | -0.155 | 2.529 | 1.489 |
| Ad5C01Att01/A150100-DUSP3_v1 | 1.96 | 1.713 | 1.566 | 1.331 | 3.366 | 3.064 | 1.245 | -0.07 | 1.147 | -0.248 | 1.783 | 1.057 |
| Ad5C01Att01/A150100-GPR103_v6 | 2.375 | 1.354 | 2.989 | 1.369 | 2.229 | 2.395 | 2.13 | -0.561 | 1.551 | 0.057 | 1.682 | 1.643 |
| Ad5C01Att01/A150100-JAK1_v7 | 3.137 | 2.741 | 2.659 | 2.422 | 3.067 | 2.821 | 1.606 | 1.464 | 1.588 | 1.037 | 0.841 | 0.255 |
| Ad5C01Att01/A150100-PDE1A_v6 | 2.046 | 1.342 | 0.953 | 0.843 | 2.619 | 1.964 | 1.115 | -0.759 | 0.673 | 0.701 | 0.92 | 0.647 |

TABLE 2-continued overview donor dependency data. N = 2 for every condition. All data points are represented as fold standard deviation of the background. All values above 2.5 are considered to be positive and are shaded grey.

| NAME | Donor III cELISA 5 ml | | 1.5 ml | | Donor IV cELISA 5 ml | | 1.5 ml | | 15 ml | |
|---|---|---|---|---|---|---|---|---|---|---|
| | 1 | 2 | 1 | 2 | 1 | 2 | 1 | 2 | 1 | 2 |
| Ad5C01Att01/A150100-ABCG1_v7 | 1.778 | 2.521 | 2.623 | 3.452 | 3.522 | 2.558 | 4.203 | 3.486 | 5.958 | 5.694 |
| Ad5C01Att01/A150100-DUSP11_v2 | 5.351 | 5.183 | 4.174 | 4.277 | 4.78 | 5.948 | -0.079 | 0.375 | 9.032 | 8.322 |
| Ad5C01Att01/A150100-ELA1_v2 | 5.252 | 4.364 | 11.4 | 9.089 | 2.252 | 4.3 | 5.417 | 4.589 | 9.113 | 6.934 |
| Ad5C01Att01/A150100-FZD1_v10 | 2.745 | 2.503 | 1.277 | 3.962 | 2.747 | 1.504 | 2.476 | 2.485 | 3.647 | 2.608 |
| Ad5C01Att01/A150100-GGTLA4_v6 | 3.809 | 2.028 | 1.587 | 2.9 | 5.721 | 4.569 | 2.731 | 2.313 | 3.021 | 5.65 |
| Ad5C01Att01/A150100-ICK_v1 | 5.46 | 3.829 | 2.8 | 3.695 | 8.459 | 4.906 | 8.431 | 8.291 | 8.959 | 6.066 |
| Ad5C01Att01/A150100-SLC15A2_v2 | 5.187 | 3.679 | 0.798 | 2.389 | 7.693 | 4.805 | 3.919 | 1.849 | 11.45 | 12.756 |
| Ad5C01Att01/A150100-SLC26A8_v2 | 3.084 | 2.678 | 1.676 | 4.262 | 4.243 | 3.864 | 1.254 | 3.622 | 9.659 | 11.939 |
| Ad5C01Att01/A150100-USP9Y_v1 | 7.5 | 8.767 | 14.826 | 10.178 | 13.687 | 10.841 | 5.561 | 11.465 | 16.027 | 13.636 |
| Ad5C01Att01/A150100-DGKB_v2 | 3.057 | 2.328 | 2.344 | 2.387 | 5.193 | 2.838 | 5.542 | 5.286 | 3.015 | 2.833 |
| Ad5C01Att01/A150100-DUSP3_v1 | 3.853 | 2.903 | 2.457 | 5.035 | 4.61 | 5.799 | 1.481 | 1.093 | 12.646 | 10.915 |
| Ad5C01Att01/A150100-GPR103_v6 | 2.351 | 3.761 | 3.431 | 2.101 | 4.351 | 3.28 | 1.689 | 4.388 | 4.716 | 4.735 |
| Ad5C01Att01/A150100-JAK1_v7 | 4.918 | 3.861 | 6.981 | 11.349 | 6.971 | 8.313 | 1.549 | 1.534 | 10.357 | 7.485 |
| Ad5C01Att01/A150100-PDE1A_v6 | 0.262 | 1.923 | 1.406 | 2.757 | 0.7 | 1.866 | 0.161 | -0.019 | 4.478 | 3.966 |

Example 6

Quality Control of Target Ad-siRNAs

Target Ad-siRNAs are propagated using derivatives of PER.C6© cells (Crucell, Leiden, The Netherlands) at a 96-well plate level, followed by re-screening these viruses at several MOI's in the primary assay (see Example 1) and by sequencing the siRNAs encoded by the target Ad-siRNA viruses. PER.E2A cells are seeded in 96 well plates at a density of 40,000 cells per well in 180 µl PER.E2A medium. Cells are then incubated overnight at 39° C. in a 10% $CO_2$ humidified incubator. One day later, cells are infected with 1 µl of crude cell lysate from SILENCESELECT® stocks containing target Ad-siRNAs. Cells are incubated further at 34° C., 10% $CO_2$ until appearance of cytopathic effect (as revealed by the swelling and rounding up of the cells, typically 7 days post infection). The supernatant is collected and the virus crude lysate is treated with proteinase K: 12 µl crude lysate is added to 4 µl Lysis buffer (1× Expand High Fidelity buffer with MgCl₂ (Roche Molecular Biochemicals, Cat. No 1332465) supplemented with 1 mg/ml proteinase K (Roche Molecular Biochemicals, Cat No 745 723) and 0.45% Tween-20 (Roche Molecular Biochemicals, Cat No 1335465) in sterile PCR tubes. These are incubated at 55° C. for 2 h followed by a 15 min inactivation step at 95° C. For the PCR reaction, 1 µl lysate is added to a PCR master mix composed of 5 µl 10× Expand High Fidelity buffer with MgCl₂, 0.5 µl of dNTP mix (10 mM for each dNTP), 1 µl of 'Forward primer' (10 mM stock, sequence: 5' CCG TTT ACG TGG AGA CTC GCC, SEQ ID NO: 29), 1 µl of 'Reverse Primer' (10 mM stock, sequence: 5' CCC CCA CCT TAT ATA TAT TCT TTC C, SEQ ID NO: 30), 0.2 µl of Expand High Fidelity DNA polymerase (3.5 U/µl, Roche Molecular Biochemicals) and 41.3 µl of H₂O. PCR is performed in a PE Biosystems Gene-Amp PCR system 9700 as follows: the PCR mixture (50 µl in total) is incubated at 95° C. for 5 min; each cycle runs at 95° C. for 15 sec, 55° C. for 30 sec, 68° C. for 4 min, and is repeated for 35 cycles. A final incubation at 68° C. is performed for 7 min. 5 µl of the PCR mixture is mixed with 2 µl of 6× gel loading buffer, loaded on a 0.8% agarose gel containing 0.5 µg/µl ethidium bromide to resolve the amplification products. The size of the amplified fragments is estimated from a standard DNA ladder loaded on the same gel. The expected size is ~500 bp. For sequencing analysis, the siRNA constructs expressed by the target adenoviruses are amplified by PCR using primers complementary to vector sequences flanking the SapI site of the pIPspAdapt6-U6 plasmid. The sequence of the PCR fragments is determined and compared with the expected sequence. All sequences are found to be identical to the expected sequence.

Example 7

Evaluation of the on Target Effect of the Identified siRNA Sequences

To evaluate whether the identified siRNA sequences really increase collagen II and aggrecan levels through the knock down of the target mRNA, a second siRNA sequence is identified that exerts the same effect.

A number of additional siRNA sequences targeting the HIT sequences are designed and incorporated in adenoviruses according to WO 03/020931. After production of these adenoviruses, the Ad-siRNAs are infected at different volumes (1.5 µl, 5 µl and 15 µl) in the chondrocytes and their effect on collagen II is assessed as described in example 1. The threshold (average+2.5 standard deviation) is calculated for every volume. If a virus scores above the threshold for one or more of the different infection volumes, it is considered to be positive. The on target results are shown in FIG. 6. These results indicate that at least one additional siRNA, which targets the HIT sequence, can be identified. This underscores the on target effect of the siRNA sequences identified during the screening of the Silence Select library.

Example 8

Development of a Three-Dimensional-Alginate Culture System for a Quantitative Marker Analysis for Stable Cartilage and the Assessment of Glycosaminoglycans (GAG) and Hydroxyprolines (Hyp) Synthesis Principle of the Assay:

Normal human articular chondrocytes (NHAC's) grown in three-dimensional cultures are able to maintain a "differentiated state" as measured by the expression of Collagen type II and aggrecan. De-differentiated chondrocytes cultured in a two-dimensional system for a limited amount of passages can revert to a differentiated state when transferred into a three-dimensional culture system. This system was established to test the capability of siRNA adenoviruses (Ad-siRNA) 1) to induce a mRNA expression pattern that correlates with anabolic active chondrocytes and 2) to induce protein modification of collagen type II (hydroxyprolines) and aggrecan (glycosaminoglycans) involved in the stability of cartilage. Normal cartilage NHAC's are cultured in a two-dimensional culture system for two or three passages for cell expansion purposes. Cells are transduced with individual siRNA adenoviruses (Ad-siRNA) in the two-dimensional culture system and three days later are transferred into the three-dimensional alginate culture system. After 10 days in the alginate culture, various parameters can be assessed (e.g. mRNA marker analysis and protein modifications).

Assay Procedure

Using Ad-BMP2 (BMP2: "strong" collagen II inducer) and Ad-BMP7 (BMP7: "weak" collagen II inducer) as positive controls and Ad-ALPL as negative control the following protocol is set up (for both mRNA marker analysis and protein modification assessment): After two or three passages in monolayer culture conditions NHAC's are seeded at 2.10E+06 cells/T175 flask in 30 ml of chondrocyte growing medium (Cambrex) and transduced the following day with control-viruses (Ad-BMP2, Ad-BMP4, Ad-BMP7, Ad-ALPL) using an MOI of 2000. After three days, cells are trypsinised using the chondrocyte reagent pack (Cambrex) and washed once with 155 mM sodium chloride/20 mM Hepes ph 7.4 (Cambrex). Cells are re-suspended at a density of 2×10⁶ cells/ml in 1.2% sodium alginate (Cambrex). The cell suspension is transferred into a syringe attached to a 21-22 gauge needle and expelled in a drop-wise fashion into 102 mM calcium chloride/5 mM Hepes pH 7.4 (1 ml and 5 ml respectively in 24-well and 6-well plate) Five and 50 beads per well are produced respectively in the 24-well and 6-well plates. Plates containing the alginate beads are incubated for 10 minutes with gentle shaking every 2 minutes. The calcium chloride solution is aspirated with a Vacusafe system and beads are washed three times with the sodium chloride solution using the Vacusafe and once with DMEMF/12 supplemented with 10% heat inactivated fetal bovine serum (FBS-HI) and 1% penicillin/streptomycin. Alginate beads are finally re-suspended into 0.5 ml and 3 ml (respectively in 24-well and 6-well plate) of DMEMF/12 supplemented with 10% heat inactivated fetal calf serum (FBS-HI), 1% penicillin/streptomycin and 25 µg/ml of ascorbic acid (Fluka, Sigm101-128 and 401-594ldrich). The alginate cultures are incubated in a humidified incubator at 37° C. and 5% CO2 during 10 days with a medium refreshment every 48/72 h.

For each adenoviral transduction, 60 alginate beads are generated: 2×5 beads were cultured in 24-well plates for the GAGs/Hyps assessments and 50 beads are cultured in a single well of a 6-well plate for the mRNA expression pattern determination.

Control Viruses

Ad-BMP2; described in WO 03/018799

Ad-BMP7; Ad5 dE1/E2A adenoviruses that mediate the expression of full length bone morphogenetic protein 7 pre-protein (NP_001710).

Ad-BMP4; Ad5 dE1/E2A adenoviruses that mediate the expression of full length bone morphogenetic protein 4 pre-protein (see NP_570912).

Ad-ALPL; Ad5 dE1/E2A adenoviruses that mediate the expression of full length liver/bone/kidney alkaline phosphatase (NP_000469).

Example 9

Effect of Knock Down of Target Genes in Chondrocytes Embedded in Alginate Beads, on the Glycosaminoglycans (GAGs) Levels Chondrocytes are infected and embedded in alginate beads according to example 8. After 10 days in culture the alginate beads are treated with papain in order to solubilise the glycosaminoglycans prior to quantification: Beads cultured in the 24-well plates are washed once with a 50 mM Phosphate buffer pH 6.5 and incubated for 3 to 4 h at 65° C. with 250 μl/well of the same buffer containing 2 mM EDTA, 2 mM L-cystein and 126 μg/ml papain (Sigma). Complete digestion of the beads is assessed by microscopic observation. Papain digests are frozen at −20° C. until glycosaminoglycans quantification is performed.

The GAGs produced by the primary chondrocytes in the alginate culture system are measured using the Blyscan™ assay (Biocolor Ltd, Newtownabbey, Northern Ireland).

Principle of the Blyscan Assay

The Blyscan Assay is a quantitative dye-binding method for the analysis of sulfated GAGs. The dye label used in the assay is 1,9-dimethylmethylene blue employed under conditions that produce a specific label for the sulfated polysaccharides component of proteoglycans and/or the protein-free sulfated glycosaminoglycan chains. Aggrecan is the predominant proteoglycan in articular cartilage, representing ±90% of the cartilage proteoglycans. It is composed of a central core protein attached to ±50 keratan sulfate and ±100 chondroitin sulfate chains known as GAGs required for the biological function and the stability of aggrecan.

Assay Description

The papain digests generated after culturing the chondrocytes for 10 days in alginate beads (Example 7) are diluted in water 1:100, 1:200 if cells were originally transduced with the positives controls and 1:50, 1:100 if transduced with the negative controls. This dilution step allows readout values within the standard range of the assay. The GAG standard provided by the manufacturer contains 100 μg/ml of chondroitin 4-sulfate purified from bovine trachea. This standard is run in duplicate at four concentrations corresponding to 1, 2, 3 and 5 μg of GAGs. Standard and controls are individually diluted in 100 μl final volume in eppendorf tubes. One milliliter of the Blyscan Dye Reagent is added to each tube and incubated for 30 minutes at room temperature with continuous shaking. When formed, the GAG-dye complex becomes insoluble and is then separated from the remaining excess soluble unbound dye by centrifugation (10000×g for 10 minutes). Supernatant are discarded by inverting and careful draining of the tube contents. One milliliter of Blyscan Dissociation Reagent is added to each tube and incubated for one hour to one and a half hour with continuous shaking. This reagent brings the GAG-bound dye back into solution. The GAG content of the assayed samples is spectrophotometrically determined by the amount of dye recovered from the GAGs in the test sample. Two hundred microliters of the dissociation dye solutions are added to the wells of a 96-well plate and reading is performed on an automatic plate reader set at a dual wavelength (656 and 450 nm).

The GAGs concentrations measured in the Blyscan assay are normalized to DNA content by performing a fluorimetric Hoechst assay on the same papain digests. Hoechst 33342 dye reagent (Molecular Probes), a bisbenzimidasole dye that binds to adenine/thymine rich regions on DNA. Papain digests were diluted 1:1.7 and 1:3.3 in TE buffer, this dilution step allows readout values within the standard range of the assay. Purified calf thymus DNA (Sigm101-128 and 401-594ldrich) is used as standard DNA: the initial stock solution (2 μg/ml) is sequentially diluted in TE buffer in order to obtain the following concentration range: 1.5, 1.0, 0.75, 0.50, 0.2 μg/ml. Standard and test samples are diluted in TE to a final volume of 100 μl and added to a 96-well plate. One hundred microliters of Hoechst 33342 dye reagent are added to the wells, reading is performed on a multifunctional microplate reader (Fluostar Galaxy, BMG Labtechnologies GmbH) with an excitation wavelength set at 360 nm and an emission wavelength set at 440 nm.

When GAG concentrations are normalized to DNA content the resulting values expressed as the ratio GAG concentration (μg/ml)/DNA concentration (μg/ml) are used to calculate the assay window. This window is calculated as the ratio normalized GAG Ad-BMP2 (or Ad-BMP4)/normalized GAG Ad-ALPL.

The effect of the knock down of the 14 target genes on the GAG levels is assessed as described. The results are shown in FIG. 7. The results are expressed as fold induction of the GAG levels compared to the average of the normalized GAG values obtained for two negative control knock-down adenoviruses (Ad-PTGER4 and Ad-GRM7). Knock down of the mRNA of the respective genes results in an increase of the GAG levels.

Control Viruses

Ad-BMP2: described in WO 03/018799

Ad-BMP4: Ad5 dE1/E2A adenoviruses that mediate the expression of full length bone morphogenetic protein 4 preprotein (see NP_570912).

Ad-ALPL: Ad5 dE1/E2A adenoviruses that mediate the expression of full length liver/bone/kidney alkaline phosphatase (NP_000469).

Ad-PTGER4: Ad5 dE1/E2A adenoviruses that comprise the siRNA sequence CCATGCCTATTTCTACAGC (SEQ ID NO: 31) to knock down the prostaglandin E receptor 4 mRNA.

Ad-GRM7: Ad5 dE1/E2A adenoviruses that comprise the siRNA sequence TCAGTAACAGCTCCCAGAC (SEQ ID NO: 32) to knock down the metabotropic glutamate receptor 7 mRNA.

Example 10

Quantitative Analysis of Hydroxyprolines (Hyps)

In articular cartilage, approximately 95% of the collagen is type II collagen. Its polymers are the fibrils that form the basic cohesive framework of the tissue. The collagen biosynthesis involves several unique posttranslational modifications including hydroxylation of proline and lysine residues. These modifications are crucial for collagen stability and resistance to proteolytic enzymes.

Chondrocytes are infected and embedded in alginate beads according to example 8. After 10 days in culture the alginate beads are treated with papain: Beads cultured in the 24-well plates are washed once with a 50 mM Phosphate buffer pH 6.5 and incubated for 3 to 4 h at 65° C. with 250 μl/well of the same buffer containing 2 mM EDTA, 2 mM L-cystein and 126 μg/ml papain (Sigma). Complete digestion of the beads is assessed by microscopic observation. Papain digests are frozen at −20° C. until hydroxyproline quantification is performed.

Hydroxyproline assessment in the papain digests is performed by HPLC after acid hydrolysis and FMOC (9-fluorenylmethyl chloroformate) derivatisation of the samples. This method is described in "Bank R A, Jansen E J, Beekman B and Te Koppele J M. (1996) Amino acid analysis by reverse-phase high performance liquid chromatography: Improved derivatisation and detection conditions with 9-fluorenylmethyl chloroformate. Anal Biochem. 240 (2): 167-176.

The effect of the knock down of the 14 target genes on the hydroxyproline levels is assessed as described. The results are shown in FIG. 8. The results are expressed as fold induction compared to the average of Hyp concentrations measured for the two KD controls (Ad-PTGER4 and AD-GRM7). Knock down of the mRNA of the respective genes results in an increase of the hydroxyproline levels.

Control Viruses

Ad-BMP2; described in WO 03/018799

Ad-BMP4; Ad5 dE1/E2A adenoviruses that mediate the expression of full length bone morphogenetic protein 4 pre-protein (see NP_570912).

Ad-ALPL: Ad5 dE1/E2A adenoviruses that mediate the expression of full length liver/bone/kidney alkaline phosphatase (NP_000469).

Ad-PTGER4: Ad5 dE1/E2A adenoviruses that comprise the siRNA sequence CCATGCCTATTTCTACAGC (SEQ ID NO: 33) to knock down the prostaglandin E receptor 4 mRNA.

Ad-GRM7: Ad5 dE1/E2A adenoviruses that comprise the siRNA sequence TCAGTAACAGCTCCCAGAC (SEQ ID NO: 34) to knock down the metabotropic glutamate receptor 7 mRNA.

Example 11

Quantitative Analysis of Markers for Stable Cartilage

Assay General Principle:

Chondrocyte phenotypes can be categorized by characteristic patterns of gene expression. Quantitative RT-PCR techniques are used to monitor the expression pattern of a set of key marker molecules to define which phenotype is induced on the chondrocytes. Positive markers included collagen type II and FGFR3, typically expressed by cartilage chondrocytes. Negative makers included (1) collagens types I and III for dedifferentiated or fibroblast-like chondrocytes, a phenotype that can also be induced by retinoic acid or interleukin-1; (2) collagen X, PTHLH and ALK-1 for hypertrophic chondrocytes that are found in the calcified zone of adult cartilage and the lower hypertrophic zone of the fetal growth-plate cartilage; and (3) MMP13 as proteolytic enzyme involved in cartilage degradation. Functional cartilage chondrocytes should express high levels of positive markers but low or not detectable levels of negative markers.

Assay Description

Chondrocytes are infected and embedded in alginate beads according to example 8. After 10 days in culture the alginate beads are treated with 55 mM sodium citrate (Cambrex) in order to recover the chondrocytes from the alginate beads and harvest RNA: Incubation medium was removed from the 6-well plates with the Vacusafe and 5 ml of 55 mM sodium citrate are added to each well and incubated for 15 minutes at room temperature. The partially solubilised beads are gently mixed and transferred to a FALCON tube, wells are rinsed once with 2 ml of sodium citrate solution to collect the remaining beads and released cells. Tubes are laid on their side and gently mixed every 2-3 minutes until beads have completely solubilised (+/−15 minutes). Tubes are centrifuged at 1000 rpm for 10 minutes. Supernatant is discarded and the cell pellet is re-suspended in 2 ml of sodium citrate solution and left for 5 minutes. Six milliliters of 155 mM sodium chloride/20 mM Hepes ph 7.4 (Cambrex) are added to each tube prior to a 5 minutes centrifugation at 210 g. Cell pellet is lysed in 180 µl SV40 lysing buffer (Promega SV40 total RNA extraction kit) and frozen at −20° C. until RNA isolation is performed with the Promega SV40 total RNA extraction kit according to the manufacturer's instructions. Purified RNA is quantified using ribogreen reagent (Molecular Probes) and yeast RNA (Ambion) as standard RNA.

Purified RNA from chondrocytes transduced with control adenoviruses and cultured for 10 days in the alginate 3-dimensional culture system is used in a reverse transcription (RT) reaction. RNA is first diluted in water (Life Technologies-Invitrogen, Breda, The Netherlands) depending on the initial concentration of the sample: For RNA concentration below 25 ng/ml, samples are used undiluted, for RNA concentration between 25 and 50 ng/ml samples are diluted 1:2.5, For RNA concentration between 50 and 100 ng/ml samples are diluted 1:5 and for RNA concentration between 100 and 160 ng/ml samples are diluted 1:10. Two microliters of diluted/undiluted RNA are added to 5 µl of a reaction mix consisting of: 1× Taqman RT buffer, 5 mM $MgCl_2$, 500 µM dNTPs (2.5 mM each), 2.5 µM Random hexamers, 0.4 U/µl of RNAse inhibitor and 1.25 U/µl of MultiScribe Reverse Transcriptase (all reagents purchased from Applied Biosystems). The PCR reaction is performed in a Peltier Thermal Cycler-200 (BIOzym, Landgraaf, The Netherlands) as followed: the PCR total mixture (60 µl) is incubated 10 minutes at 25° C. followed by 30 minutes at 48° C., followed by 5 minutes at 95° C. Each reaction is run in parallel with a control that does not contain any RNAse inhibitor or Reverse Transcriptase.

Reverse transcription is followed by a quantitative PCR for specific amplification of the selected positive and negative marker genes, GAPDH is included as the endogenous control. Five microliters of cDNA (from RT reaction) are added to 20 µl of a PCR reaction mix consisting of: 1× Brilliant® SYBR® Green QPCR Master Mix (Sratagene Europe, Amsterdam, The Netherlands), 300 µM of each forward and reverse primers (table 3) (except for GAPDH and ALK-1, used at 100 µM) (Life Technologies-Invitrogen, Breda, The Netherlands) and 300 nM of reference dye (Stratagene) (diluted 1:100 in H2O). The PCR mixture (25 p. 1) is incubated for 10 minutes at 95° C. followed by 40 cycles: 15 seconds at 95° C. followed by 1 minute at 60° C. in the ABI PRISM® 7000 Sequence Detection System (Applied Biosystems, Nieuwerkerk A/D Ijssel, The Netherlands).

TABLE 3 primer sequences for the positive and negative markers:

| Primer | Gene | Primer sequence | SEQ ID NO |
|---|---|---|---|
| Forward | Collagen 2a1 L10347 | GGCAATAGCAGGTTCACGTACA | 35 |
| Reverse | Collagen 2a1 L10347 | CGATAACAGTCTTGCCCCACTT | 36 |

TABLE 3-continued primer sequences for the positive and negative markers:

| Primer | Gene | Primer sequence | SEQ ID NO |
|---|---|---|---|
| Forward | FGFR3 NM_000142 | ACGGCACACCCTACGTTACC | 37 |
| Reverse | FGFR3 NM_000142 | TGTGCAAGGAGAGAACCTCTAGCT | 38 |
| Forward | BMP-2 NM_001200 | CCAACACTGTGCGCAGCTT | 39 |
| Reverse | BMP-2 NM_001200 | AAGAATCTCCGGGTTGTTTTCC | 40 |
| Forward | ALK-1 NM_000020 | CAGTCTCATCCTGAAAGCATCTGA | 41 |
| Reverse | ALK-1 NM_000020 | TTTCCCACACACTCCACCAA | 42 |
| Forward | collagen 10a1 NM_000493 | TGGAGTGTTTTACGCTGAACGAT | 43 |
| Reverse | collagen 10a1 NM_000493 | CCTCTTACTGCTATACCTTTACTCTT TATGG | 44 |
| Forward | Collagen 1A1 NM_000088 | TGCCATCAAAGTCTTCTGCAA | 45 |
| Reverse | Collagen 1A1 NM_000088 | CGCCATACTCGAACTGGAATC | 46 |
| Forward | Collagen 3a1 NM_000090 | CACTATTATTTTGGCACAACAGGAA | 47 |
| Reverse | Collagen 3a1 NM_000090 | AGACACATATTTGGCATGGTTCTG | 48 |
| Forward | MMP13 NM_002427 | CAAGGGATCCAGTCTCTCTATGGT | 49 |
| Reverse | MMP13 NM_002427 | GGATAAGGAAGGGTCACATTTGTC | 50 |
| Forward | PTHLH NM_002820 | GCTCGGTGGAGGGTCTCA | 51 |
| Reverse | PTHLH NM_002820 | CTGTGTGGATTTCTGCGATCA | 52 |
| Forward | GAPDH NM_002046 | CATCCATGACAACTTTGGTATCG | 53 |
| Reverse | GAPDH NM_002046 | AGTCTTCTGGGTGGCAGTGAT | 54 |

Results are expressed for each tested marker gene as the relative expression in the sample (transduction with tested adenovirus) versus control (knock-down control adenoviruses) (Relative expression=$2^{ddCt}$, where ddCt= $dCt_{KD\ sample}-dCt_{KD\ control}$ and $dCt=Ct_{sample}-Ct_{GAPDH}$). The results for the 14 genes are shown in FIG. 9. The knock down of the mRNA of the respective genes results in expression of the positive markers, while the levels of the negative markers are either low or not detectable.

Control Viruses
Ad-BMP2; described in WO 03/018799
Ad-ALPL: Ad5 dE1/E2A adenoviruses that mediate the expression of full length liver/bone/kidney alkaline phosphatase (NP_000469).

Example 12

Expression of cDNA's in Human Cartilage

Upon identification of a modulator of cartilage synthesis, it is of the highest importance to evaluate whether the modulator is expressed in the tissue and the cells of interest. This can be achieved by measuring the RNA and/or protein levels. In recent years, RNA levels are being quantified through real time PCR technologies, whereby the RNA is first transcribed to cDNA and then the amplification of the cDNA of interest is monitored during a quantitative PCR reaction. The amplification plot and the resulting Ct value are indicators for the amount of a specific RNA transcript present in the sample. Ct values are determined in the presence or absence of the reverse transcriptase step (+RT versus -RT). An amplification signal in the -RT condition indicates the occurrence of non-specific PCR products originating from the genomic DNA. If the +RT Ct value is 3 Ct values higher than the -RT Ct value, then the investigated RNA is present in the sample.

To assess whether the polypeptides of the genes identified in the above assays are expressed in human cartilage, real time PCR with specific primers for the polynucleotides ("Assay on Demand" Applied Biosystems) is performed on human cartilage total RNA (Clinomics Biosciences). 2 samples of non-osteoarthritis and 2 of osteoarthritis patients are analyzed.

In short, 40 ng of RNA is transcribed to DNA using the MultiScribe Reverse Transcriptase (50 U/µl) enzyme (Applied BioSystems). The resulting cDNA is amplified with AmpliTaq Gold DNA polymerase (Applied BioSystems) during 40 cycles using an ABI PRISM® 7000 Sequence Detection System. Amplification of the transcript is detected via SybrGreen which results in a fluorescent signal upon intercalation in double stranded DNA.

Total RNA isolated from human cartilage is analyzed for the presence of transcripts listed in Table 4 via quantitative real time PCR.

For the genes listed in Table 4 the obtained Ct values indicate that they are detected in all RNA samples. ELA1 RNA is not detected in the real time PCR analysis, underscoring the need for additional patient analysis.

TABLE 4

| | Ct values | | | |
|---|---|---|---|---|
| | Normal Cartilage | | OA Cartilage | |
| TARGET | Ct Sample 1 | Ct Sample 2 | Ct Sample 1 | Ct Sample 2 |
| PDE1A | 30.8 | 28.5 | 30.7 | 30.2 |
| GPR103 | 33.1 | 33.3 | 38.4 | 37.4 |
| JAK1 | 26.2 | 24.1 | 27 | 26 |
| ICK | 36.3 | 33.8 | 36.1 | 35.5 |
| DGKB | 28.5 | 26.7 | 29.7 | 28.7 |
| DUSP3 | 27.1 | 24.2 | 27 | 27.1 |
| DUSP11 | 28.8 | 27.5 | 29.9 | 29.2 |
| SLC26A8 | 36.13 | 34.04 | 37.12 | 37.22 |
| SLC15A2 | 32.5 | 28.1 | 34.7 | 32.9 |
| ABCG1 | 29.7 | 28 | 31.1 | 29.5 |
| FZD1 | 28.1 | 25.4 | 34.1 | 27.1 |
| ELA1 | 40 | 40 | 40 | 39.1 |

Example 13

Identification of Small Molecules that Inhibit Target Kinase Activity

Compounds are screened for inhibition of the activity of the TARGETS that are kinase polypeptides. The affinity of the compounds to the polypeptides is determined in an experiment detecting changed reaction conditions after phosphorylation. The TARGET kinase polypeptides are incubated with its substrate and ATP in an appropriate buffer. The combination of these components results in the in vitro phosphorylation of the substrate. Sources of compounds include commercially available screening library, peptides in a phage display library or an antibody fragment library, and compounds that have been demonstrated to have binding affinity for a TARGET kinase.

The TARGET kinase polypeptides can be prepared in a number of ways depending on whether the assay will be run using cells, cell fractions or biochemically, on purified proteins. The polypeptides can be applied as complete polypeptides or as polypeptide fragments, which still comprise TARGET kinase catalytic activity.

Identification of small molecules inhibiting the activity of the TARGET kinase polypeptides is performed by measuring changes in levels of phosphorylated substrate or ATP. Since ATP is consumed during the phosphorylation of the substrate, its levels correlate with the kinase activity. Measuring ATP levels via chemiluminescent reactions therefore represents a method to measure kinase activity in vitro (Perkin Elmer). In a second type of assay, changes in the levels of phosphorylated substrate are detected with phosphospecific agents and are correlated to kinase activity. These levels are detected in solution or after immobilization of the substrate on a microtiter plate or other carrier. In solution, the phosphorylated substrate is detected via fluorescence resonance energy transfer (FRET) between the Eu labeled substrate and an APC labeled phosphospecific antibody (Perkin Elmer), via fluorescence polarization (FP) after binding of a phosphospecific antibody to the fluorescently labeled phosphorylated substrate (Panvera), via an Amplified Luminescent Proximity Homogeneous Assay (ALPHA) using the phosphorylated substrate and phosphospecific antibody, both coupled to ALPHA beads (Perkin Elmer) or using the IMAP binding reagent that specifically detects phosphate groups and thus alleviates the use of the phosphospecific antibody (Molecular Devices). Alternatively, the substrate is immobilized directly or by using biotin-streptavidin on a microtiter plate. After immobilization, the level of phosphorylated substrate is detected using a classical ELISA where binding of the phosphospecific antibody is either monitored via an enzyme such as horseradish peroxidase (HRP) or alkaline phosphates (AP) which are either directly coupled to the phosphospecific antibody or are coupled to a secondary antibody. Enzymatic activity correlates to phosphorylated substrate levels. Alternatively, binding of the Eu-labeled phosphospecific antibody to the immobilized phosphorylated substrate is determined via time resolved fluorescence energy (TRF) (Perkin Elmer). In addition, the substrate can be coated on FLASH plates (Perkin Elmer) and phosphorylation of the substrate is detected using $^{33}P$ labeled ATP or $^{125}I$ labeled phosphospecific antibody.

Small molecules are randomly screened or are preselected based upon drug class, (i.e. known kinase inhibitors), or upon virtual ligand screening (VLS) results. VLS uses virtual docking technology to test large numbers of small molecules in silico for their binding to the polypeptide of the invention. Small molecules are added to the kinase reaction and their effect on levels of phosphorylated substrate is measured with one or more of the above-described technologies.

Small molecules that inhibit the kinase activity are identified and are subsequently tested at different concentrations. $IC_{50}$ values are calculated from these dose response curves. Strong binders have an $IC_{50}$ in the nanomolar and even picomolar range. Compounds that have an $IC_{50}$ of at least 10 micromol or better (nmol to pmol) are applied in collagen II assay to check for their effect on the induction of chondrocyte anabolic stimulation.

Example 14

Ligand Screens for TARGET GPCRs

Example 14 A

Reporter Gene Screen

Mammalian cells such as Hek293 or CHO-K1 cells are either stably transfected with a plasmid harboring the luciferase gene under the control of a cAMP dependent promoter (CRE elements) or transduced with an adenovirus harboring a luciferase gene under the control of a cAMP dependent promoter. In addition reporter constructs can be used with the luciferase gene under the control of a $Ca^{2+}$ dependent promoter (NF-AT elements) or a promoter that is controlled by activated NF-κB. These cells, expressing the reporter construct, are then transduced with an adenovirus harboring the cDNA of a TARGET GPCR. Forty (40) hours after transduction the cells are treated with the following:

a) an agonist for the receptor and screened against a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of the SEQ ID NOs of the TARGET GPCRs; or b) a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NOs of the TARGET GPCRs.

Compounds, which decrease the agonist induced increase in luciferase activity or the constitutive activity, are considered to be antagonists or inverse agonists for a TARGET GPCR. These compounds are screened again for verification and screened against their effect on anabolic stimulation of chondrocytes. The compounds are also screened to verify binding to the GPCR. The binding and reporter activity assays can be performed in essentially any order to screen compounds.

In addition, cells expressing the NF-AT reporter gene can be transduced with an adenovirus harboring the cDNA encoding the α-subunit of $G_{15}$ or chimerical Gα subunits. $G_{15}$ is a promiscuous G protein of the $G_q$ class that couples to many different GPCRs and as such re-directs their signaling towards the release of intracellular $Ca^{2+}$ stores. The chimerical G alpha subunits are members of the $G_s$ and $G_{i/o}$ family by which the last 5 C-terminal residues are replaced by those of $G_{\alpha q}$, these chimerical G-proteins also redirect cAMP signaling to $Ca^{2+}$ signaling.

Example 14 B

FLIPR Screen

Mammalian cells such as Hek293 or CHO-K1 cells are stably transfected with an expression plasmid construct harboring the cDNA of a TARGET GPCR. Cells are seeded, grown, and selected until sufficient stable cells can be obtained. Cells are loaded with a $Ca^{2+}$ dependent fluorophore such as Fura3 or Fura4. After washing away the excess of fluorophore the cells are screened against a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NOs of the TARGET GPCRs, by simultaneously adding an agonist (alternatively no agonist need be added if the constitutive activity of the receptor is used) and a compound to the cells. Activation of the receptor is measured as an almost instantaneously increase in fluorescence due to the interaction of the fluorophore and the $Ca^{2+}$ that is released. Compounds that reduce or inhibit the agonist induced increase in fluorescence (or constitutive fluorescence) are considered to be antagonists or inverse agonists for the receptor they are screened against. These compounds are screened again to measure the amount of anabolic stimulation of chondrocytes as well as binding to a TARGET GPCR.

Example 14 C

AequoScreen

CHO cells, stably expressing Apoaequorin are stably transfected with a plasmid construct harboring the cDNA of a TARGET GPCR. Cells are seeded, grown, and selected until sufficient stable cells can be obtained. The cells are loaded with coelenterazine, a cofactor for apoaequorin. Upon receptor activation intracellular $Ca^{2+}$ stores are emptied and the aequorin will react with the coelenterazine in a light emitting process. The emitted light is a measure for receptor activation. The CHO, stable expressing both the apoaequorin and the receptor are screened against a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NOs of the TARGET GPCRs, by simultaneously adding an agonist (alternatively no agonist need be added if the constitutive activity of the receptor is used) and a compound to the cells. Activation of the receptor is measured as an almost instantaneously light flash due to the interaction of the apoaequorin, coelenterazine, and the $Ca^{2+}$ that is released. Compounds that reduce or inhibit the agonist induced increase in light or the constitutive activity are considered to be antagonists or inverse agonists for the receptor they are screened against. These compounds are screened again to measure the amount of anabolic stimulation of chondrocytes as well as binding to a TARGET GPCR.

In addition, CHO cells stable expressing the apoaequorin gene are stably transfected with a plasmid construct harboring the cDNA encoding the α-subunit of $G_{15}$ or chimerical $G_\alpha$ subunits. $G_{15}$ is a promiscuous G protein of the $G_q$ class that couples to many different GPCRs and as such redirects their signaling towards the release of intracellular $Ca^{2+}$ stores. The chimerical G alpha subunits are members of the $G_s$ and $G_{i/o}$ family by which the last 5 C-terminal residues are replaced by those of $G_{\alpha q}$, these chimerical G-proteins also redirect cAMP signaling to $Ca^{2+}$ signaling.

Example 14 D

Screening for Compounds that Bind to the GPCR Polypeptides (Displacement Experiment)

Compounds are screened for binding to the TARGET GPCR polypeptides. The affinity of the compounds to the polypeptides is determined in a displacement experiment. In brief, the GPCR polypeptides are incubated with a labeled (radiolabeled, fluorescent labeled) ligand that is known to bind to the polypeptide and with an unlabeled compound. The displacement of the labeled ligand from the polypeptide is determined by measuring the amount of labeled ligand that is still associated with the polypeptide. The amount associated with the polypeptide is plotted against the concentration of the compound to calculate $IC_{50}$ values. This value reflects the binding affinity of the compound to its TARGET, i.e. the TARGET GPCR polypeptides. Strong binders have an $IC_{50}$ in the nanomolar and even picomolar range. Compounds that have an $IC_{50}$ of at least 10 micromol or better (nmol to pmol) are applied an anabolic stimulation of chondrocytes assay to check for their effect on osteogenesis. The TARGET GPCR polypeptides can be prepared in a number of ways depending on whether the assay are run on cells, cell fractions or biochemically, on purified proteins.

Example 14 E

Screening for Compounds that Bind to a TARGET GPCR (Generic GPCR Screening Assay)

When a G protein receptor becomes constitutively active, it binds to a G protein ($G_q$, $G_s$, $G_i$, $G_o$) and stimulates the binding of GTP to the G protein. The G protein then acts as a GTPase and slowly hydrolyses the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTPγS can be used to monitor G protein coupling to membranes in the absence and presence of ligand. Moreover, a preferred approach is the use of a GPCR-G protein fusion protein. The strategy to generate a TARGET GPCR-G protein fusion protein is well known for those known in the art. Membranes expressing TARGET GPCR-G protein fusion protein are prepared for use in the direct identification of candidate compounds such as inverse agonist. Homogenized membranes with TARGET GPCR-G protein fusion protein are transferred in a 96-well plate. A pin-tool is used to transfer a candidate compound in each well plus [$^{35}$S]GTPγS, followed by incubation on a shaker for 60 minutes at room temperature. The assay is stopped by spinning of the plates at 4000 RPM for 15 minutes at 22° C. The plates are then aspirated and radioactivity is then read.

Example 14 F

Receptor Ligand Binding Study on Cell Surface

The receptor is expressed in mammalian cells (Hek293, CHO, COS7) by adenoviral transducing the cells (see U.S. Pat. No. 6,340,595). The cells are incubated with both labeled ligand (iodinated, tritiated, or fluorescent) and the unlabeled compound at various concentrations, ranging from 10 pM to 10 μM (3 hours at 4° C.: 25 mM HEPES, 140 mM NaCl, 1 mM CaCl$_2$, 5 mM MgCl$_2$ and 0.2% BSA, adjusted to pH 7.4). Reactions mixtures are aspirated onto PEI-treated GF/B glass filters using a cell harvester (Packard). The filters are washed twice with ice cold wash buffer (25 mM HEPES, 500 mM NaCl, 1 mM CaCl$_2$, 5 mM MgCl$_2$, adjusted to pH 7.4). Scintillant (MicroScint-10; 35 μl) is added to dried filters and the filters counted in a (Packard Topcount) scintillation counter. Data are analyzed and plotted using Prism software (GraphPad Software, San Diego, Calif.). Competition curves are analyzed and IC$_{50}$ values calculated. If one or more data points do not fall within the sigmoidal range of the competition curve or close to the sigmoidal range the assay is repeated and concentrations of labeled ligand and unlabeled compound adapted to have more data points close to or in the sigmoidal range of the curve.

Example 14 G

Receptor Ligand Binding Studies on Membrane Preparations

Membranes preparations are isolated from mammalian cells (Hek293, CHO, COS7) cells over expressing the receptor is done as follows: Medium is aspirated from the transduced cells and cells are harvested in 1×PBS by gentle scraping. Cells are pelleted (2500 rpm 5 min) and resuspended in 50 mM Tris pH 7.4 (10×10$^6$ cells/ml). The cell pellet is homogenized by sonicating 3×5 sec (UP50H; sonotrode MS1; max amplitude: 140 μm; max Sonic Power Thickness: 125 W/cm$^2$). Membrane fractions are prepared by centrifuging 20 min at maximal speed (13,000 rpm 15,000 to 20,000 g or rcf). The resulting pellet is resuspended in 500 μl 50 mM Tris pH 7.4 and sonicated again for 3×5 sec. The membrane fraction is isolated by centrifugation and finally resuspended in PBS. Binding competition and derivation of IC$_{50}$ values are determined as described above.

Example 14 H

Internalization Screen (1)

Activation of a GPCR-associated signal transduction pathway commonly leads to translocation of specific signal transduction molecules from the cytoplasm to the plasma membrane or from the cytoplasm to the nucleus. Norak has developed their transfluor assay based on agonist-induced translocation of receptor-β-arrestin-GFP complex from the cytosol to the plasma membrane and subsequent internalization of this complex, which occurs during receptor desensitization. A similar assay uses GFP tagged receptor instead of 3-arrestin. Hek293 cells are transduced with a TARGET GPCR vector that translates for a TARGET GPCR-eGFP fusion protein. 48 hours after transduction, the cells are set to fresh serum-free medium for 60 minutes and treated with a ligand for 15, 30, 60 or 120 minutes at 37° C. and 5% CO$_2$. After indicated exposure times, cells are washed with PBS and fixed with 5% paraformaldehyde for 20 minutes at RT. GFP fluorescence is visualized with a Zeiss microscope with a digital camera. This method aims for the identification of compounds that inhibit a ligand-mediated (constitutive activity-mediated) translocation of the fusion protein to intracellular compartments.

Example 14 I

Internalization Screen (2)

Various variations on translocation assays exists using β-arrestin and β-galactosidase enzyme complementation and BRET based assays with receptor as energy donor and β-arrestin as energy acceptor. Also the use of specific receptor antibodies labeled with pH sensitive dyes are used to detect agonist induced receptor translocation to acidic lysosomes. All of the translocation assays are used for screening for both agonistic and antagonistic acting ligands.

Example 14 J

Melanophore Assay (Arena Pharmaceutical)

The melanophore assay is based on the ability of GPCRs to alter the distribution of melanin containing melanosomes in *Xenopus* melanophores. The distribution of the melanosomes depends on the exogenous receptor that is either G$_{i/o}$ or G$_{s/q}$ coupled. The distribution of the melanosomes (dispersed or aggregated) is easily detected by measuring light absorption. This type of assay is used for both agonist as well as antagonist compound screens.

Example 15

Identification of Small Molecules that Inhibit Protease Activity

Compounds are screened for inhibition of the activity of the polypeptides of the present invention. The affinity of the compounds to the polypeptides is determined in an experiment detecting changes in levels of cleaved substrate. In brief, the polypeptides of the present invention are incubated with its substrate in an appropriate buffer. The combination of these components results in the cleavage of the substrate.

The polypeptides can be applied as complete polypeptides or as polypeptide fragments, which still comprise the catalytic activity of the polypeptide of the invention.

Cleavage of the substrate can be followed in several ways. In a first method, the substrate protein is heavily labeled with a fluorescent dye, like fluorescein, resulting in a complete quenching of the fluorescent signal. Cleavage of the substrate however, releases individual fragments, which contain less fluorescent labels. This results in the loss of quenching and the generation of a fluorescent signal, which correlates to the levels of cleaved substrate. Cleavage of the protein, which results in smaller peptide fragments, can also be measured using fluorescent polarization (FP). Alternatively, cleavage of the substrate can also be detected using fluorescence resonance energy transfer (FRET): a peptide substrate is labeled on both sides with either a quencher and fluorescent molecule, like DABCYL and EDANS. Upon cleavage of the substrate both molecules are separated resulting in fluorescent signal correlating to the levels of cleaved substrate. In addition, cleavage of a peptide substrate can also generate a new substrate for another enzymatic reaction, which is then detected via a fluorescent, chemiluminescent or colorimetric method.

Small molecules are randomly screened or are preselected based upon drug class, i.e. protease, or upon virtual ligand screening (VLS) results. VLS uses virtual docking technology to test large numbers of small molecules in silico for their binding to the polypeptide of the invention. Small molecules are added to the proteolytic reaction and their effect on levels of cleaved substrate is measured with the described technologies.

Small molecules that inhibit the protease activity are identified and are subsequently tested at different concentrations. IC50 values are calculated from these dose response curves. Strong binders have an IC50 in the nanomolar and even picomolar range. Compounds that have an IC50 of at least 10 micromol or better (nmol to pmol) are applied in amyloid beta secretion assay to check for their effect on the beta amyloid secretion and processing.

Example 16

Identification of Small Molecules that Inhibit Phosphodiesterase Activity

Compounds are screened for inhibition of the activity of the polypeptides of the present invention. The affinity of the compounds to the polypeptides is determined in an experiment detecting changes in levels of substrate or product. In brief, the polypeptides of the present invention are incubated with its substrate in an appropriate buffer. The combination of these components results in the conversion of the substrate into its product.

The polypeptides can be applied as complete polypeptides or as polypeptide fragments, which still comprise the catalytic activity of the polypeptide of the invention.

Conversion of cAMP or cGMP in AMP or GMP can be followed 1) by determining the cAMP or cGMP levels using e.g. ELISA, Alpha screen technology, Time resolved fluorescent technology, IMAP 2) by determining the levels of the products AMP and GMP using a colorimetric assay. The basis for the latter assay is the cleavage of cAMP or cGMP by a cyclic nucleotide phosphodiesterase. The 5'-nucleotide released is further cleaved into the nucleoside and phosphate by the enzyme 5'-nucleotidase. The phosphate released due to enzymatic cleavage is quantified using BIOMOL GREEN™ reagent in a modified Malachite Green assay.

Small molecules are randomly screened or are preselected based upon drug class, i.e. PDE, or upon virtual ligand screening (VLS) results. VLS uses virtual docking technology to test large numbers of small molecules in silico for their binding to the polypeptide of the invention. Small molecules are added to the PDE reaction and their effect on cyclic nucleotide levels is measured with the described technologies.

Small molecules that inhibit the PDE activity are identified and are subsequently tested at different concentrations. IC50 values are calculated from these dose response curves. Strong binders have an IC50 in the nanomolar and even picomolar range. Compounds that have an IC50 of at least 10 micromol or better (nmol to pmol) are applied in assays evaluating the anabolic activity of chondrocytes. This can be achieved by determining col2α1 and aggrecan levels produced by the chondrocytes.

We claim:

1. Method for identifying a compound that induces chondrocyte anabolic stimulation, comprising:
    (a) contacting a compound with a polypeptide comprising the amino acid sequence consisting of SEQ. ID. NO. 80 or 81, in an in vitro cell-free preparation;
    (b) measuring the binding affinity of said compound to said polypeptide;
    (c) selecting a compound based on its binding affinity to said polypeptide measured in step (b);
    (d) contacting said compound selected based on its binding affinity according to step (c) with a mammalian cell, which is in culture, and in which mammalian cell said polypeptide comprising the amino acid sequence of SEQ. ID. NO. 80 or 81 is expressed;
    (e) measuring in said culture containing said compound and mammalian cell of step (d), at least one protein that is expressed in said mammalian cell and that is an indicator of the anabolic stimulation of chondrocytes;
    (f) comparing said protein measurement in step (e) to the measurement of said protein in a culture of said mammalian cell that is not contacted with said compound; and
    (g) selecting a compound that increases said protein expressed by said mammalian cell, based on the comparing of step (f), as an inducer of chondrocyte anabolic stimulation in a mammalian cell.

2. The method according to claim 1, wherein said compound having binding affinity to said polypeptide exhibits a binding affinity of at least 10 micromolar.

3. The method of claim 1 wherein said protein that is an indicator is selected from the group consisting of collagen type II, alpha-1 (col2α1) and aggrecan.

4. The method according to claim 1, wherein said mammalian cell culture comprises chondrocytes.

5. A method for identifying a compound that induces chondrocyte anabolic stimulation, comprising (a) contacting a compound with a polypeptide comprising an amino acid sequence consisting of SEQ. ID. NO. 80 or 81, in an in vitro cell-free preparation; (b) measuring the binding affinity of said compound to said polypeptide; and (c) selecting a compound to confirm as an inducer of chondrocyte anabolic stimulation, which compound is selected based on its binding affinity for the polypeptide comprising an amino acid sequence consisting of SEQ. ID. NO. 80 or 81.

6. A method according to claim 5 further comprising
    (d) contacting said compound selected based on its binding affinity according to step (c) with a mammalian cell, which is in culture, and in which mammalian cell said polypeptide comprising the amino acid sequence consisting of SEQ. ID. NO. 80 or 81 is expressed; and
    (e) measuring, in said culture containing said compound and mammalian cell of step (d), protein expression of at least one protein that is expressed in said mammalian cell and that is a constituent of cartilage or that is required for the formation of cartilage; and
    (f) comparing said protein expression measurement in step (e) to the measurement of said protein expression in a culture of said mammalian cell that is not contacted with said compound; and
    (g) selecting a compound that increases said protein expression in said mammalian cell, based on the comparing of step (f), as an inducer of chondrocyte anabolic stimulation in a mammalian cell.

7. A method according to claim 6, wherein said protein that is a constituent of cartilage or that is required for the formation of cartilage is collagen type II, alpha-1 (col2α1) or aggrecan.

8. The method according to claim 6 wherein said compound having binding affinity to said polypeptide of SEQ. ID. NO. 80 or 81 exhibits a binding affinity of at least 10 micromolar.

9. The method according to claim 6, wherein said mammalian cells culture.

10. A method for identifying a compound that induces chondrocyte anabolic stimulation, comprising:
    (a) contacting a compound with a mammalian cell, which is in culture, and in which mammalian cell the polypeptide comprising the amino acid sequence consisting of SEQ. ID. NO. 80 or 81 is expressed;
    (b) measuring, in said culture containing said compound and mammalian cell of step (a), at least one protein that is expressed in said mammalian cell and that is an indicator of the anabolic stimulation of chondrocytes;
    (c) comparing said protein biochemical indicator measurement of step (b) to the said protein indicator measurement in a culture of said mammalian cell that is not contacted with said compound;
    (d) selecting a compound that increases said protein indicator expression by said mammalian cell, based on the comparing of step (c);
    (e) contacting said compound selected according to step (d) with a polypeptide comprising an amino acid sequence consisting of SEQ. ID. NO. 80 or 81, in an in vitro cell-free preparation;
    (f) measuring the binding affinity of said compound selected according to step (d) to said polypeptide contacted in step (e); and
    (g) selecting a compound as an inducer of chondrocyte anabolic stimulation, which compound is selected based on its binding affinity to said polypeptide measured in step (f).

11. The method according to claim 10 wherein said compound having binding affinity to said polypeptide of SEQ. ID. NO. 80 or 81 exhibits a binding affinity of at least 10 micromolar.

12. The method according to claim 10, wherein said mammalian cell culture comprises chondrocytes.

13. The method according to claim 10, wherein said protein that is expressed in said mammalian cell and that is an indicator of the anabolic stimulation of chondrocytes is a constituent of cartilage or is required for the formation of cartilage.

14. A method according to claim 13, wherein said protein that is a constituent of cartilage is collagen type II, alpha-1 (col2α1) or aggrecan.

* * * * *

SEQUENCE LISTING

```
<160> NUMBER OF SEQ ID NOS: 480

<210> SEQ ID NO 1
<211> LENGTH: 3536
<212> TYPE: DNA
<213> ORGANISM: Homo sapiens

<400> SEQUENCE: 1
atggggacga cggccccagg gcccattcac ctgctggagc tatgtgacca gaagctcatg      60
gagtttctct gcaacatgga taataaggac ttggtgtggc ttgaggagat ccaagaggag     120
gccgagcgca tgttcaccag agaattcagc aaagagccag agctgatgcc caaaacacct     180
tctcagaaga accgacggaa gaagagacgg atttcttatg ttcaggatga aaacagagat     240
cccatcagga gaaggttatc ccgcagaaag tctcggagca gccagctgag ctcccgacgc     300
ctccgcagca aggacagtgt agagaagctg gctacagtgg tcggggagaa cggctccgtt     360
ctgcggcgtg tgacccgtgc tgcggctgca gctgccgcgc ctaccatggc attggctgca     420
ccttcttcac ccacccctga gtctccacg atgctgacta agaagcccga ggataaccac     480
```

```
acccagtgcc agctggtgcc tgtggtggag atcggcatca gtgagcgcca gaatgctgag    540
cagcatgtca cccagctcat gtccaccgag cctctgcccc gcactctgtc cccgactcca    600
gcttcagcca cagctccaac ctcccagggc atcccgacat cagatgagga atcaacacct    660
aagaagtcga aggccaggat actggagtcc atcacagtga gctccctgat ggctacaccc    720 caggaccccca agggtcaagg ggtcgggacg gggcggtctg cgtctaagct caggattgcg    780
caggtctccc ctggcccacg ggactcgcca gcctttccag attctccatg gcgggagcgg    840
gtgctggctc ccatcctgcc ggataacttc tccacgccca cgggctctcg cacggactct    900
caatcggtgc ggcacagccc gatcgccccg tcttccccga gtccccaagt cttagcccag    960
aagtactctc tggtggccaa acaggaaagt gttgtccgca gggcgagcag aaggcttgcc   1020
aagaagactg ccgaagagcc agctgcctct ggccgcatca tctgtcacag ttacctggag   1080
aggctcctga atgttgaggt gccccagaaa gttggttctg agcagaagga acccccgag    1140 gaggctgagc ctgtggcggc agctgagcca gaggtccctg agaacaacgg aaataactcg   1200
tggccccaca atgacacgga gattgccaac agcacaccca acccgaagcc tgcagccagc   1260
agcccggaaa cacctctgc agggcagcaa gaggccaaga cggaccaagc agatggaccc    1320
agagagccac cgcagagtgc caggaggaag cgcagctaca gcaggccgt gagtgagctg    1380 gacgaggagc agcacctgga ggatgaggag ctgcagcccc ccaggagcaa gacccccttcc   1440 tcaccctgcc cagccagcaa ggtggtacgg cccctccgga cctttctgca cacagtgcag   1500
aggaaccaga tgctcatgac ccctacctca gccccacgca gcgtcatgaa gtcctttatt   1560
aagcgcaaca ctccctgcg catggacccc aaggagaagg agcggcagcg cctggagaat   1620
ctgcggcgga aggaggaggc cgagcagctg cgcaggcaga aggtggagga ggacaagcgg   1680
cggcggctgg aggaggtgaa gctgaagcgt gaggaacgcc tccgcaaggt gctgcaggcc   1740
cgcgagcggg tggagcagat gaaggaggag aagaagaagc agattgagca gaagtttgct   1800
cagatcgacg agaagactga aaggccaag gaggagcggc tggcagagga aaggccaag    1860 aaaaaggcgg cggccaagaa gatggaggag gtggaagcac gcaggaagca ggaagaggat   1920
gcacgtaggc tcaggtggct gcagcaggag gaggaagagc ggcggcacca agagctgctg   1980
cagaagaaga aggaagagga gcaggagcgg ctgcggaagg cggccgaggc taagcggctg   2040
gcagagcagc gggagcagga gcggcgggag caggagcggg gggagcagga gcggcgcgag   2100
caggagcggc gcgagcagga gcggcgggag caggagcggc gcgagcagga gcgacagctg   2160
gcagagcagg agcgtcggcg ggagcaggag cggctccaag ccgagaggga gctgcaggag   2220
cgggagaagg ccctgcggct gcagaaggag cagctgcaga gggaactgga ggagaagaag   2280
aagaaggaag agcagcagcg tctggctgag cggcagctgc aggaggagca agagaagaaa   2340
gccaaggagg cagcagggc cagcaaggcc ctgaatgtga ctgtggacgt gcagtctcca   2400
gcttgtacct catctcccat cactccgcaa gggcacaagg cccctcccca gatcaacccc   2460
cacaactacg ggatggatct gaatagcgac gactccaccg atgatgaggc ccatccccgg   2520
aagcccatcc ccacctgggc ccgaggcacc ccgctcagcc aggctatcat tcaccagtac   2580
taccagccac cgaaccttct ggagctcttt ggaaccattc tcccactgga cttggaggat   2640
atcttcaaga gagcaagcc ccgctatcac aagcgcacca gctctgctgt ctggaactca   2700
ccgcccctgc agggcgccag ggtcccccagc agcctggcct acagcctgaa gaagcactga   2760
ggctggcctg cggccttctt ggcagcctcg cctcctgtcc atgtctatct gtctgtctgt   2820
cggtctgtgt cttggtctgt tgccctcctt cttggcatgc cattgtggag ggcttggcca   2880
```

| | |
|---|---|
| ggtgtatata aacgtcctct gtgctgggtg tttctgctgc aggtggcagg tggccccagg | 2940 |
| cctgttttgga ggatgggctg ggtgggtggg tggggaagaa atgggcccag ccccacatgg | 3000 |
| cctgcagaca gtgctctgta aatagttgtt ttaatttagc tgaatgttag cattttagtc | 3060 |
| tttggcattt tagcgtttgg gaggtagatt aataaagtat attccttcaa gcctgctgtt | 3120 |
| gataccatga agactgggcg cctcagtccc agccctgtag ctgtgtgtct tgggccacca | 3180 |
| gtggcctgca ggacgaaggt actgttccat cacctgcggt gtgcctcagg atcaccaggt | 3240 |
| gcaggccccc accctcggag atgctgctgc agtgagtggt tccactgcct ggataaccct | 3300 |
| tgaggaacac gtcagttact gtcacgatgg ggcaggtgga gctccttcct attttttggg | 3360 |
| gtgctccctg tttgtaaagg ggagtttgtt cattgggaaa gacctgggtc ttgacacggc | 3420 |
| cctgccactt agtcccctac cctctccatt ccccaggctc cacccgtgct gctcaagtgc | 3480 |
| aaatggactt gagagtattt atgtgctggt gaagtatgag gtctgagtag aaaagg | 3536 |

<210> SEQ ID NO 2
<211> LENGTH: 3926
<212> TYPE: DNA
<213> ORGANISM: Homo sapiens

<400> SEQUENCE: 2

| | |
|---|---|
| atgacaaacc aggaaaaatg ggcccacctc agcccttcgg aatttttccca acttcagaaa | 60 |
| tatgctgagt attctacaaa gaaattaaag gatgttcttg aagaattcca tggtaatggt | 120 |
| gtgcttgcaa agtataatcc tgaagggaaa caagacattc ttaaccaaac aatagatttt | 180 |
| gaaggtttca aactattcat gaagacattc ctggaagccg agcttcctga tgatttcact | 240 |
| gcacacctttt tcatgtcatt tagcaacaag tttcctcatt ctagtccaat ggtaaaaagt | 300 |
| aagcctgctc tcctatcagg cggtctgaga atgaataaag gtgccatcac ccctccccga | 360 |
| actacttctc ctgcaaatac gtgttcccca gaagtaatcc atctgaagga cattgtctgt | 420 |
| tacctgtctc tgcttgaaag aggaagacct gaggataagc ttgagtttat gtttcgcctt | 480 |
| tatgacacgg atgggaatgg cttcctggac agctcggagc tagaaaatat catcagtcag | 540 |
| atgatgcatg ttgcagaata ccttgagtgg gatgtcactg aacttaatcc aatcctccat | 600 |
| gaaatgatgg aagaaattga ctatgatcat gatggaaccg tgtctctgga ggaatggatt | 660 |
| caaggaggaa tgacaacgat tccacttctt gtgctcctgg gcttagaaaa taacgtgaag | 720 |
| gatgatggac agcacgtgtg gcgactgaag cactttaaca aacctgccta ttgcaacctt | 780 |
| tgcctgaaca tgctgattgg cgtggggaag cagggcctct gctgttcctt ctgcaagtac | 840 |
| acagtccatg agcgctgtgt ggctcgagca cctccctctt gcatcaagac ctatgtgaag | 900 |
| tccaaaagga cactgatgt catgcaccat tactgggttg aaggtaactg cccaaccaag | 960 |
| tgtgataagt gccacaaaac tgttaaatgt taccagggcc tgacaggact gcattgtgtt | 1020 |
| tggtgtcaga tcacactgca taaaaatgt gcttctcatc taaaacctga atgtgactgt | 1080 |
| ggacctttga aggaccatat tttaccaccc acaacaatct gtccagtggt actgcagact | 1140 |
| ctgcccactt caggagtttc agttcctgag gaaagacaat caacagtgaa aaaggaaaag | 1200 |
| agtggttccc agcagccaaa caaagtgatt gacaagaata aaatgcaaag agccaactct | 1260 |
| gttactgtag atgacaagg cctgcaggtc actcctgtgc ctggtactca cccacttttta | 1320 |
| gttttttgtga accccaaaag tggtggaaaa caaggagaac gaatttacag aaaattccag | 1380 |
| tatcctattaa atcctcgtca ggtttacagt ctttctggaa atggaccaat gccagggtta | 1440 |
| aacttttttcc gtgatgttcc tgacttcaga gtgttagcct gtggtggaga tggaaccgtg | 1500 |

```
ggctgggttt tggattgcat agaaaaggcc aatgtaggca agcatcctcc agttgcgatt    1560
ctgcctcttg ggactggcaa tgatctagca agatgcctgc gatggggagg aggttacgaa    1620
ggtgagaatc tgatgaaaat tctaaaagac attgaaaaca gcacagaaat catgttggac    1680
aggtggaagt ttgaagtcat acctaatgac aaagatgaga aggagaccc agtgccttac     1740 agtatcatca ataattactt ttccattggc gtggatgcct ccattgcaca cagattccac    1800
atcatgagag aaaacaccc agagaaattc aacagtagaa tgaagaacaa attttggtat     1860
tttgagtttg gcacatctga aactttctca gccacctgca agaagctaca tgaatctgta    1920
gaaatagaat gtgatggagt acagatagat ttaataaaca tctctctgga aggaattgct    1980
attttgaata taccaagcat gcatggagga tccaatcttt ggggagagtc taagaaaaga    2040
cgaagccatc gacgaataga gaaaaagggg tctgacaaaa ggaccaccgt cacagatgcc    2100
aaagagttga agtttgcaag tcaagatctc agtgaccagc tgctggaggt ggtcggcttg    2160
gaaggagcca tggagatggg gcaaatatac acaggcctga aaagtgctgg ccggcggctg    2220
gctcagtgct cctgcgtggt catcaggacg agcaagtctc tgccaatgca aattgatggg    2280
gagccatgga tgcagacccc atgcacaata aaaattacac acaagaacca gccccaatg    2340 ctgatgggcc cgcctccaaa aaccggttta ttctgctccc tcgtcaaaag gacaagaaac    2400
cgaagcaagg aataatcctg tgttgtttca ctcttagaaa ttgaattagc ataattgggc    2460
catggaacac atatgctgga aatctttgaa ccatttcaag tctcctgctc atgcaaaatc    2520
atggaagtgg tttaacagtt tttgttacta agctaatgta aaattcagct attagaaaat    2580
ttattgtctc agttttata ggcatctttg catgaagaaa gcagaagttt acctgaagtg     2640
atactgcata ttttggtgc atgcattccc atagattttt acatctccca cccaactctt     2700
ccccaatttc cttttactaa cctgtgagaa aaacccgtga acatgaaaa aggaaatacc     2760 atgggaaacg tgattctcag tgtgattcca attattacga agcactaatc agtaacgcta    2820
caatgatcat aattgcagat tgctatacgt ttcccttta gaatcagtgt atcagtgacc     2880
tatgacttga ggagaaactt ttaattcgaa gatttatta aatagttgac tacaataacct    2940 tgctatatat acatagtttt tcttcaacat cttaactctt ctgagtggaa ataaaaatat    3000
caggcataag gttttctcat gctgaaaaat agaacgcggt ttttattttg cttagttttc    3060
tttttaattc cagaaataag tgaaaacatg ttacttgaca gtcaagtgtg gtaatatggc    3120
aagccttgtt cctttctgca tgagaatcta ggagagaatt cataaccaca ccaataacga    3180
aatagaagtt ttaaactatg tgcctaatca atgtgtttcc caccaaagat tcagaaaaca    3240
atgcttgaga gaaatgggtt aatgcataat taattaagca ttgtggagca aatttagggt    3300
tcctgtgatt aattttgtga tgactaaaat gctggaaagc aagtgagttg cccattaatt    3360
atgattaaaa ttctcacctt tcacagacag acaataagcc agacaacaca atcaaagctc    3420
aatagatgat ttcttgcttt tttcagtcat ttataaatat aggtgtaatt tttcatggat    3480
cagttaagta cacttgaagg aagtaaatga ttgtatcagt ttatttctag tataaatggg    3540
tacctgtaat aatactgagc tcttggaagc gaatcatgca tgcaattagc tccctcctcc    3600
tcacctactc cactcccatc tttatgacat ttcaaatgtt tatttggaaa caacagccta    3660
gatcactgtt gaaggtgttc atggcatagt tggagtctct gactgtttaa agaaatcaca    3720
gaacagtact tttctttag tgtttcatta agcctatgat gtaaaatgaa atgcttctga     3780
gcagtcttgt aatattgttc attcatattg acctgcatct catcattgca tgttttatgt    3840
tttcaaacat gccataagga aaacgagtgc ctgaactgca tgatttatta gtttctctcc    3900
```

```
actctgcatt aaagtgctaa tgattt                                        3926

<210> SEQ ID NO 3
<211> LENGTH: 3172
<212> TYPE: DNA
<213> ORGANISM: Homo sapiens

<400> SEQUENCE: 3
atgacaaacc aggaaaaatg ggcccacctc agcccttcgg aattttccca acttcagaaa     60
tatgctgagt attctacaaa gaaattaaag gatgttcttg aagaattcca tggtaatggt    120
gtgcttgcaa agtataatcc tgaagggaaa caagacattc ttaaccaaac aatagatttt    180
gaaggtttca aactattcat gaagacattc ctggaagccg agcttcctga tgatttcact    240
gcacaccttt tcatgtcatt tagcaacaag tttcctcatt ctagtccaat ggtaaaaagt    300
aagcctgctc tcctatcagg cggtctgaga atgaataaag gtgccatcac ccctccccga    360
actacttctc ctgcaaatac gtgttcccca gaagtaatcc atctgaagga cattgtctgt    420
tacctgtctc tgcttgaaag aggaagacct gaggataagc ttgagtttat gtttcgcctt    480
tatgacacgg atgggaatgg cttcctggac agctcggagc tagaaaatat catcagtcag    540
atgatgcatg ttgcagaata ccttgagtgg gatgtcactg aacttaatcc aatcctccat    600
gaaatgatga agaaattga ctatgatcat gatgaaccg tgtctctgga ggaatggatt    660
caaggaggaa tgacaacgat tccacttctt gtgctcctgg gcttagaaaa taacgtgaag    720
gatgatggac agcacgtgtg gcgactgaag cactttaaca aacctgccta ttgcaacctt    780
tgcctgaaca tgctgattgg cgtggggaag cagggcctct gctgttcctt ctgcaagtac    840
acagtccatg agcgctgtgt ggctcgagca cctccctctt gcatcaagac ctatgtgaag    900
tccaaaagga acactgatgt catgcaccat tactgggttg aaggtaactg cccaaccaag    960
tgtgataagt gccacaaaac tgttaaatgt taccagggcc tgacaggact gcattgtgtt   1020
tggtgtcaga tcacactgca taataaatgt gcttctcatc taaaacctga atgtgactgt   1080 ggaccttttga aggaccatat tttaccaccc acaacaatct gtccagtggt actgcagact   1140
ctgcccactt caggagtttc agttcctgag gaaagacaat caacagtgaa aaggaaaag   1200 agtggttccc agcagccaaa caaagtgatt gacaagaata aaatgcaaag agccaactct   1260
gttactgtag atggacaagg cctgcaggtc actcctgtgc ctggtactca cccactttta   1320 gttttttgtga accccaaaag tggtggaaaa caaggagaac gaatttacag aaaattccag   1380
tatctattaa atcctcgtca ggtttacagt ctttctggaa atggaccaat gccagggtta   1440
aactttttcc gtgatgttcc tgacttcaga gtgttagcct gtggtggaga tggaaccgtg   1500
ggctgggttt tggattgcat agaaaaggcc aatgtaggca agcatcctcc agttgcgatt   1560
ctgcctcttg ggactggcaa tgatctagca agatgcctgc gatggggagg aggttacgaa   1620
ggtgagaatc tgatgaaaat tctaaaagac attgaaaaca gcacagaaat catgttggac   1680
aggtggaagt ttgaagtcat acctaatgac aaagatgaga aaggagaccc agtgccttac   1740
agtatcatca ataattactt ttccattggc gtggatgcct ccattgcaca cagattccac   1800
atcatgagag aaaaacaccc agagaaattc aacagtagaa tgaagaacaa attttggtat   1860
tttgagtttg gcacatctga aactttctca gccacctgca agaagctaca tgaatctgta   1920
gaaatagaat gtgatggagt acagatagat ttaataaaca tctctctgga aggaattgct   1980
attttgaata taccaagcat gcatggagga tccaatcttt ggggagagtc taagaaaaga   2040
cgaagccatc gacgaataga gaaaaaaggg tctgacaaaa ggaccaccgt cacagatgcc   2100
```

```
aaagagttga agtttgcaag tcaagatctc agtgaccagc tgctggaggt ggtcggcttg    2160
gaaggagcca tggagatggg gcaaatatac acaggcctga aaagtgctgg ccggcggctg    2220
gctcagtgct cctgcgtggt catcaggacg agcaagtctc tgccaatgca aattgatggg    2280
gagccatgga tgcagacccc atgcacagtg agtacagagt agttgatatg ctatgtcaat    2340
ctcagttttg ctttcctctt tgactaaata accacaataa ctgatttttt tctttatttc    2400
ttttcaacct atcagcaaat agtcttttg ttgttgttgt tatgtgtgtg tcagagccac    2460
tacatttagg ctgtagacat tatataccct tggcaatgat ttagctcttg aatgtttgtg    2520
ctagcctaag tataaataga tcttttaaat agatcaatta taaaccatag atcaattata    2580
aactatggag ctaaacaaaa tattaataaa agtttatctg aaactttttt gtttatttca    2640
gagcacatta ttagaatatt atttgcgaga aatgcagacc taagcttata tgtgaactta    2700
tttctcagct tttctatgcc tccatttggg gatttgaggg ctttcttctc cataagaaaa    2760
aaatttctct ccagtttcta ccataattaa ttgtgttttc cagaatgagg tattatttaa    2820
ggcagacact gcccctctca aaaaaaatca gttttcattt gcatagtgaa tattttattg    2880
catttcaaaa acatgctagg aactgctttt ggcactggga gtagacacat gaacaagacc    2940
aacagtgtaa tttccttcaa gttacttaca ttcctataat agaggaccga ataaataaac    3000
aactacatga taaatataac ttcagactgt gagagttatt aaaaaataag gtgaaatgat    3060
gataagaagc tggattaggt gtggagaata aatactactt gagataaggg agacctcttt    3120
gaaaggacat agccaaaagc ttagtataaa attaaaaaaa ataaaaaaaa aa            3172

<210> SEQ ID NO 4
<211> LENGTH: 6228
<212> TYPE: DNA
<213> ORGANISM: Homo sapiens

<400> SEQUENCE: 4
cgggttcctg ctgcactacc atgcgccgtg cggcccgtgc gactcgccgg acctcgcggg      60
cgtccctgta cggagccctc ggccggtcct agcaggggatt gtccccattt ccagctccgg    120
agcgggcggc tgcgccccgc tcgtcgagga gctgcgctca cctcaggggc gggccccgc     180 ctgcgttcgc ggcgccaaga agagtattcc tttccactta caactaaata agacctgctt    240
ttgctggagc tgtgctaggc tgagggaatt ccacactgaa ttttacaagc gggatggatt    300
tctctaaggc agaagactga ttttggaaa tatgtatttg ggagacagtc acgtcctatt    360
gaataccttg tgctggtgct gccatcgaaa aatctggtta cactctgggg aggactgcta    420
ccactgcaga actgaaccac ttcggccgtg agatgagtgt ccggcctgag caggcacacc    480
atgaatagat acacaacaat caggcagctc ggggatggaa cctacggttc cgtcctgctg    540
ggaagaagca ttgagtctgg ggagctgatc gctattaaaa aaatgaaaag aaaattttat    600
tcctgggagg aatgcatgaa ccttcgggag gttaagtctt taaagaagct caaccatgcc    660
aatgtagtca aattaaaaga agttatcagg gaaaatgatc atctttattt tatcttcgag    720
tacatgaagg aaaatcttta ccagctcatt aaagagagaa ataagttgtt tcctgagtct    780
gctataagga atatcatgta tcagatatta caaggactcg catttattca caaacacggc    840
ttctttcatc gagacttaaa gcctgagaac ctcctctgca tgggaccaga acttgtgaaa    900
attgcagact ttggttttggc ccgagaaata cgatcaaaac ctccatatac agattatgta    960
tctaccagat ggtacagggc tccagaagta ctcctgaggt ctaccaacta cagctccccc   1020
attgacgtct gggcggtggg ctgcatcatg gcagaagttt acacccctca ggccactctt   1080
```

```
cctggagcca gtgaaattga cacaatattc aaaatttgcc aagtgctggg gacaccaaaa    1140
aagactgact ggcctgaagg ctatcaactt tcaagtgcaa tgaacttccg ttggccacag    1200
tgtgtaccca ataacttaaa gaccttgatt cccaatgcta gcagtgaagc agtccagctc    1260
ctgagagaca tgcttcagtg ggatcccaag aaacgaccaa cagctagtca ggcacttcga    1320
tatccttact tccaagttgg acacccacta ggcagcacca cacaaaacct tcaggattca    1380
gaaaaaccac agaaaggcat cctggaaaag gcaggcccac ctccttatat taagccagtc    1440
ccacctgccc agccaccagc caagccacac acacgaattt cttcacgaca gcatcaagcc    1500
agccagcccc ctctgcatct cacgtacccc tacaaagcag aggtctccag gacagatcac    1560
ccaagccatc tccaggagga caagccaagc ccgttgcttt tcccatccct ccacaacaag    1620
catccacagt cgaaaatcac agctggcctg gagcacaaaa atggtgagat aaagccaaag    1680
agtaggagaa ggtggggtct tatttccagg tcaacaaagg attcagatga ttgggctgac    1740
ttggatgact tggatttcag tccatccctc agcaggattg acctgaaaaa caagaaaaga    1800
cagagtgatg acactctctg caggtttgag agtgttttgg acctgaagcc ctctgagcct    1860
gtgggcacag gaaacagtgc ccccacccag acgtcatatc agcggcgaga cacgcccacc    1920
ctgagatctg cagccaagca gcactatttg aagcactctc gatacttgcc tgggatcagt    1980
ataagaaatg gcatactctc gaatccaggc aaggaattta ttccacctaa tccatggtct    2040
agttctggct tgtctggaaa atcttcaggg acaatgtcag taatcagcaa agtaaattca    2100
gttggttcca gctctacaag ttctagtgga ctgactggaa actatgtccc ttccttctg    2160 aaaaaagaaa tcggttctgc tatgcagagg gtacacctag cacctattcc agacccttcc    2220
cctggttatt cctcccctgaa ggccatgaga cctcatcctg ggcgaccatt cttccacacc    2280
cagcctagaa gcactcctgg gttgatacca cggcctccag ccgcccagcc agtgcatggc    2340
cggacagact gggcttccaa gtacgcatct cggcgatgac tgtctgcctt ggtgatgaat    2400
ctcttcctag ggagaagcag gatacttttcc ctcagctgac tggtgttcta cctgcaagat    2460
gtgcagaggg cataaaagca aatcaacact ttatagttat tcttctgaac taagacatgt    2520
caatattctt tttaaagtt ttttttaaa atattgattt gaatgcagta ggcttttttg    2580
tataaaatta ttttattcta aaactgggtc ccattatttt cttaaacaac agcattttgt    2640
atatatggat tatgttttag catttttatac agtcaacttt gtaatgaact ttttaaaaat    2700
taattgattt tccttttgggg ttccagataa tattttctac agattttgaa aaatgtaata    2760
atattaatgc agtattgcaa caggggtgca atttaaggct atgtgataga gggttattta    2820
ctcagtgtgt gcagatattt atgaagtggt gaaatttcaa gtgtggctca ctaggtactt    2880
caggccttct tggactgttg ttagaaaagt gatcctctgc tttttcttagt aggtcattgg    2940 tttgatttt ggataccact ctgctgttct aaaaggacta ttatattata taattcactt    3000
tgttttactt ttgttcccca gatgaaagaa ctctaagtaa atacatttta aaaatttt    3060 ctgacaccct ttaatgtggt tgcagatctc agatgaaacc aagcttaatt atactatgcc    3120
attatattct aatttattcc attttgaaa tcaagttgta tgtgtaccaa taaaagagat    3180
ttctgcttca aaaggctctc aacatgaagg ttaacacagt caatcaaact tacattcctg    3240
ccaagatgca tggccaaaaa actaagtatc aaagcagcag aaggttttg attatagtaa    3300 ctgagatgga atttttgtgcc tagctcagtt ctccagatct ggctaggagc agtcaatgac    3360
taatgttctg tcctagccaa attctcagga caatttgggg agcagaaaga gttatggcag    3420
aggttccact catctacaaa gtcacagtca catgccacat ttgatctcct aaccctggtg    3480
```

```
tagtttctttt caagagtgag aactttattt gttgggcaga ggctgttcca ttgagaggaa    3540
tgtttacagc agtttcaaaa atgacaaagt cagtttggag acagaaaaag acaaaaggtc    3600
cagtctcatc catctctata tggtacattt gcctcactta tggttgcctt aaaggcaaga    3660
gggaaggtca ccatcagtga acgcaatgca atctcaacag tgtattgatt catattctcc    3720
tagggctcaa actactctct attggttcca ggataatgac aaattgaacc atatgtaagt    3780 aatctttttat tttttatttt tttttgaga cagagtctca ctctgtcacc caggctggag    3840
tgcagtggcg cgatcttagc tctctgcaac ctctgcctcc caggttcaag cctcctgagt    3900
aactgggact acaggcgccc gccaccacgc ccagctaatt ttttgtattt ttagtagaga    3960
cggggtttca ctgtgttagc caggacggcc tcgatctcct gacctcgtga tccaccctcc    4020
tccacctccc aaagtactgg gattacaggc atgagccact gcacccagcc aagtgatcat    4080
ttttataggt taaaatgata ggtgaaatga atatagacac tttcatatgg ttcaacctaa    4140
tgacttggta aattattgcc ttggtgtatt aataatatgt tgcattctga acaaataacc    4200
atggcttcca aagggcccta acctaaaatc ggagagtaat ttatgctttg gagaatttga    4260
ctcaaatata tacttgacca agcaccatga tccctagggg catgagaaaa gcacataatg    4320
gatgtggatg tgataggtgg tcttttcctg ttaacaagct ggcagcaaag cttcagaaaa    4380
tatatatgca agcacaactt gaagctgaat tcatttctgt attatattct caactcgtta    4440
tctaaagcat cagaacatgt gttttcagag atgagtcctt tactataagg ttaatattta    4500 ttttcattt ctgtattata tatgaaaagt aaattaatgt gaaacctggc ccagcttgct    4560
ggaaagcagg ttttaaattg taaatattcc ttagaggagc aaatggattg tttaatacca    4620
tagtctcagt aatctagctt atataaggtc attacatttt ttaactgaaa aacctagtta    4680
cctgattatt gcacattata aaattgtttt tctaatactt tatagggccc aacttcagaa    4740
aatacttcgc ttttttctttt ttatgctttc gtttgtttac cagcaagcaa cttccctggg    4800
gaagccaaac acatattcat aaaaaaaatc aagtagctga tgtgcagttg agaaaactag    4860
aggactgaaa aaacaaattt taactagcaa atgctgtgaa ttactcttcc tccccttctc    4920
tgaaatgggt aaaggacaaa ttgtgtaaaa aaacctatgc actatagaag ggaatagtaa    4980
ccatttcttt tgtctctctg tttctgttct gactgagaac ctgcagccat ttcttgttac    5040
atgaaaacaa aatgctactt gttacctcta ttttttgtta ctatacaatt atgaaatgta    5100
atgtaagaca ccaacagaaa tgatataccct gtaactgtac ctatcaggac tatacctcat    5160
ttacagtcag aaagcttact gggatgtcag gaaatgatac agggttggtt ctcatttcgt    5220
gccgaaatga gacagaaatt cagtgacgaa ggtgcgttgt aggggtattg atgtgcccca    5280
ggtagtgcca gcagagtagg gaaaactgca tttgcataaa aactactctt gacatgattg    5340 ttcatttac aaaaaaattc cattaattac caagccctca cccagcccat gtgtgatagg    5400
atttatgtag gaagaaactt gattttcaaa taatttttta aatgtatctc ttgcctaaag    5460
gactatatac atctaataaa gtaacactgt gtcatcttct ggagttatca aaaattgtat    5520
acaatcaaga caacacaaga attattttat ttttgagtgc aaatacaggt actgttggag    5580
ttgatgggca ccatgctttc tcatgaagta gcatttccct accatcaagc cattgttttg    5640
tgccattcag gagaggaaaa aaggaattt atgctgtaca tttcagttca gtgtatgacc    5700
aaaagcaata tgtttataag aagatgtttg acatactaat tatttatat catttaaacc    5760 atactgtagc aacataatat atggagctaa tttgtagaat tattttacg atttccaaac    5820 aaatgtactg tactgttata taatttattg tgaggaccctt ctcatggaag ccattaggaa    5880
```

| | |
|---|---|
| aacaaactag aggtaaatat cacattaatc tgtattatca atttctcata gacactgtgc | 5940 |
| taatgtgaat tttaaatgac ctgcatcaag tcttctgatc tcagataact cagtacagat | 6000 |
| agcaattagt cagctgattt gattacaatg gagtaaccga caatatattt atttataaag | 6060 |
| cacatattca taataacgag aagaattcag aaaaccactt aagcaagacc cttctgaaat | 6120 |
| aaaaaatgtt gcttttttaaa tagtttgtcc taaggtgttt aaaacatgtc aaccttatgt | 6180 |
| aaggaaaaat ttcctggtcc aaataaagtt gaagtttaag aaaaattg | 6228 |

```
<210> SEQ ID NO 5
<211> LENGTH: 6095
<212> TYPE: DNA
<213> ORGANISM: Homo sapiens

<400> SEQUENCE: 5
```

| | |
|---|---|
| gcgccgtgcg gcccgtgcga ctcgccggac ctcgcgggcg tccctgtacg gagccctcgg | 60 |
| ccggtcctag cagggattgt ccccatttcc agctccggag cgggcggctg cgccccgctc | 120 |
| gtcgaggagc tgcgctcacc tcaggggcgg gccccgcct gcgttcgcgg cgccagcaga | 180 |
| agactgattt ttggaaatat gtatttggga gacagtcacg tcctattgaa taccttgtgc | 240 |
| tggtgctgcc atcgaaaaat ctggttacac tctggggagg actgctacca ctgcagaact | 300 |
| gaaccacttc ggccgtgaga tgagtgtccg gcctgagcag gcacaccatg aatagataca | 360 |
| caacaatcag gcagctcggg gatggaacct acggttccgt cctgctggga agaagcattg | 420 |
| agtctgggga gctgatcgct attaaaaaaa tgaaaagaaa atttttattcc tgggaggaat | 480 |
| gcatgaacct tcgggaggtt aagtctttaa agaagctcaa ccatgccaat gtagtcaaat | 540 |
| taaaagaagt tatcagggaa aatgatcatc tttattttat cttcgagtac atgaaggaaa | 600 |
| atctttacca gctcattaaa gagagaaata agttgtttcc tgagtctgct ataaggaata | 660 |
| tcatgtatca gatattacaa ggactcgcat ttattcacaa acacggcttc tttcatcgag | 720 |
| acttaaagcc tgagaacctc ctctgcatgg gaccagaact tgtgaaaatt gcagactttg | 780 |
| gtttggcccg agaaatacga tcaaaacctc catatacaga ttatgtatct accagatggt | 840 |
| acagggctcc agaagtactc ctgaggtcta ccaactacag ctcccccatt gacgtctggg | 900 |
| cggtgggctg catcatggca gaagtttaca ccctcaggcc actcttccct ggagccagtg | 960 |
| aaattgacac aatattcaaa atttgccaag tgctggggac accaaaaaag actgactggc | 1020 |
| ctgaaggcta tcaactttca agtgcaatga acttccgttg gccacagtgt gtacccaata | 1080 |
| acttaaagac cttgattccc aatgctagca gtgaagcagt ccagctcctg agagacatgc | 1140 |
| ttcagtggga tcccaagaaa cgaccaacag ctagtcaggc acttcgatat ccttacttcc | 1200 |
| aagttggaca cccactaggc agcaccacac aaaaccttca ggattcagaa aaaccacaga | 1260 |
| aaggcatcct ggaaaaggca ggcccacctc cttatattaa gccagtccca cctgcccagc | 1320 |
| caccagccaa gccacacaca cgaatttctt cacgacagca tcaagccagc cagccccctc | 1380 |
| tgcatctcac gtaccctac aaagcagagg tctccaggac agatcaccca agccatctcc | 1440 |
| aggaggacaa gccaagcccg ttgcttttcc catccctcca caacaagcat ccacagtcga | 1500 |
| aaatcacagc tggcctggag cacaaaaatg gtgagataaa gccaaagagt aggagaaggt | 1560 |
| ggggtcttat ttccaggtca acaaaggatt cagatgattg ggctgacttg gatgacttgg | 1620 |
| atttcagtcc atccctcagc aggattgacc tgaaaaacaa gaaaagacag agtgatgaca | 1680 |
| ctctctgcag gtttgagagt gttttggacc tgaagccctc tgagcctgtg ggcacaggaa | 1740 |
| acagtgcccc cacccagacg tcatatcagc ggcgagacac gcccacccta gatctgcag | 1800 |

```
ccaagcagca ctatttgaag cactctcgat acttgcctgg gatcagtata agaaatggca   1860
tactctcgaa tccaggcaag gaatttattc cacctaatcc atggtctagt tctggcttgt   1920
ctggaaaatc ttcagggaca atgtcagtaa tcagcaaagt aaattcagtt ggttccagct   1980
ctacaagttc tagtggactg actggaaact atgtcccttc ctttctgaaa aagaaatcg    2040 gttctgctat gcagagggta cacctagcac ctattccaga cccttcccct ggttattcct   2100
ccctgaaggc catgagacct catcctgggc gaccattctt ccacacccag cctagaagca   2160
ctcctgggtt gataccacgg cctccagccg cccagccagt gcatggccgg acagactggg   2220
cttccaagta cgcatctcgg cgatgactgt ctgccttggt gatgaatctc ttcctaggga   2280
gaagcaggat actttccctc agctgactgg tgttctacct gcaagatgtg cagagggcat   2340
aaaagcaaat caacacttta tagttattct tctgaactaa gacatgtcaa tattcttttt   2400
taaagttttt ttttaaaata ttgatttgaa tgcagtaggc ttttttgtat aaaattattt   2460
tattctaaaa ctgggtccca ttattttctt aaacaacagc attttgtata tatggattat   2520
gttttagcat tttatacagt caactttgta atgaactttt taaaaattaa ttgattttcc   2580 tttgggttc cagataatat tttctacaga ttttgaaaaa tgtaataata ttaatgcagt    2640
attgcaacag gggtgcaatt taaggctatg tgatagaggg ttatttactc agtgtgtgca   2700
gatatttatg aagtggtgaa atttcaagtg tggctcacta ggtacttcag gccttcttgg   2760
actgttgtta gaaaagtgat cctctgcttt tcttagtagg tcattggttt gatttttgga   2820
taccactctg ctgttctaaa aggactatta tattatataa ttcactttgt tttacttttg   2880
ttccccagat gaaagaactc taagtaaata cattttaaaa aatttttctg cacccctta    2940 atgtggttgc agatctcaga tgaaaccaag cttaattata ctatgccatt atattctaat   3000
ttattccatt tttgaaatca agttgtatgt gtaccaataa aagagatttc tgcttcaaaa   3060
ggctctcaac atgaaggtta acacagtcaa tcaaacttac attcctgcca agatgcatgg   3120
ccaaaaaact aagtatcaaa gcagcagaag gttttttgatt atagtaactg atggaatt    3180 ttgtgcctag ctcagttctc cagatctggc taggagcagt caatgactaa tgttctgtcc   3240
tagccaaatt ctcaggacaa tttggggagc agaaagagtt atggcagagg ttccactcat   3300
ctacaaagtc acagtcacat gccacatttg atctcctaac cctggtgtag tttcttcaa    3360 gagtgagaac tttatttgtt gggcagaggc tgttccattg agaggaatgt ttacagcagt   3420
ttcaaaaatg acaaagtcag tttggagaca gaaaaagaca aaggtccag tctcatccat    3480 ctctatatgg tacatttgcc tcacttatgg ttgccttaaa ggcaagaggg aaggtcacca   3540
tcagtgaacg caatgcaatc tcaacagtgt attgattcat attctcctag ggctcaaact   3600
actctctatt ggttccagga taatgacaaa ttgaaccata tgtaagtaat cttttatttt   3660 ttatttttt tttgagacag agtctcactc tgtcacccag gctggagtgc agtggcgcga   3720
tcttagctct ctgcaacctc tgcctcccag gttcaagcct cctgagtaac tgggactaca   3780
ggcgcccgcc accacgccca gctaattttt tgtattttta gtagagacgg ggtttcactg   3840
tgttagccag gacggcctcg atctcctgac ctcgtgatcc accctcctcc acctcccaaa   3900
gtactgggat tacaggcatg agccactgca cccagccaag tgatcatttt tataggttaa   3960
aatgataggt gaaatgaata tagacacttt catatggttc aacctaatga cttggtaaat   4020
tattgccttg gtgtattaat aatatgttgc attctgaaca ataaccatg cttccaaag    4080 ggccctaacc taaaatcgga gagtaattta tgctttggag aatttgactc aaatatatac   4140
ttgaccaagc accatgatcc ctaggggcat gagaaaagca cataatggat gtggatgtga   4200
```

```
taggtggtct tttcctgtta acaagctggc agcaaagctt cagaaaatat atatgcaagc    4260
acaacttgaa gctgaattca tttctgtatt atattctcaa ctcgttatct aaagcatcag    4320
aacatgtgtt ttcagagatg agtcctttac tataaggtta atatttattt tcattttctg    4380
tattatatat gaaaagtaaa ttaatgtgaa acctggccca gcttgctgga aagcaggttt    4440
taaattgtaa atattcctta gaggagcaaa tggattgttt aataccatag tctcagtaat    4500
ctagcttata taaggtcatt acatttttta actgaaaaac ctagttacct gattattgca    4560
cattataaaa ttgttttttct aatactttat agggcccaac ttcagaaaat acttcgcttt    4620
tttcttttta tgctttcgtt tgtttaccag caagcaactt ccctgggaa gccaaacaca     4680 tattcataaa aaaaatcaag tagctgatgt gcagttgaga aaactagagg actgaaaaaa    4740
caaattttaa ctagcaaatg ctgtgaatta ctcttcctcc ccttctctga aatgggtaaa    4800
ggacaaattg tgtaaaaaaa cctatgcact atagaaggga atagtaacca tttcttttgt    4860
ctctctgttt ctgttctgac tgagaacctg cagccatttc ttgttacatg aaaacaaaat    4920
gctacttgtt acctctattt tttgttacta tacaattatg aaatgtaatg taagacacca    4980
acagaaatga tatacctgta actgtaccta tcaggactat acctcattta cagtcagaaa    5040
gcttactggg atgtcaggaa atgatacagg gttggttctc atttcgtgcc gaaatgagac    5100
agaaattcag tgacgaaggt gcgttgtagg ggtattgatg tgccccaggt agtgccagca    5160
gagtagggaa aactgcattt gcataaaaac tactcttgac atgattgttc atttttacaaa   5220 aaaattccat taattaccaa gccctcaccc agcccatgtg tgataggatt tatgtaggaa    5280
gaaacttgat tttcaaataa ttttttaaat gtatctcttg cctaaaggac tatatacatc    5340
taataaagta acactgtgtc atcttctgga gttatcaaaa attgtataca atcaagacaa    5400
cacaagaatt attttatttt tgagtgcaaa tacaggtact gttggagttg atgggcacca    5460
tgctttctca tgaagtagca tttccctacc atcaagccat tgttttgtgc cattcaggag    5520
aggaaaaaaa ggaatttatg ctgtacattt cagttcagtg tatgaccaaa agcaatatgt    5580
ttataagaag atgtttgaca tactaattat tttatatcat ttaaaccata ctgtagcaac    5640
ataatatatg gagctaattt gtagaattat ttttacgatt tccaaacaaa tgtactgtac    5700
tgttatataa tttattgtga ggaccttctc atggaagcca ttaggaaaac aaactagagg    5760
taaatatcac attaatctgt attatcaatt tctcatagac actgtgctaa tgtgaatttt    5820
aaatgacctg catcaagtct tctgatctca gataactcag tacagatagc aattagtcag    5880
ctgatttgat tacaatggag taaccgacaa tatatttatt tataaagcac atattcataa    5940
taacgagaag aattcagaaa accacttaag caagacccctt ctgaaataaa aaatgttgct   6000
ttttaaatag tttgtcctaa ggtgtttaaa acatgtcaac cttatgtaag gaaaaatttc    6060
ctggtccaaa taaagttgaa gtttaagaaa aattg                              6095
```

<210> SEQ ID NO 6
<211> LENGTH: 1368
<212> TYPE: DNA
<213> ORGANISM: Homo sapiens

<400> SEQUENCE: 6

```
atgatctgct gcagtgctct gagccctagg attcatcttt cttttcaccg tagcctgact      60
ggcattgtat tagcaaactc atcactagac atcgtactac acgacacgta ctacgttgta    120
gcccactgcg ggggaaatgt taggcgcctg cattgcggtg gccccgcgtc ccggagcgc     180 acagcaatgc aggcgcttaa cattaccccg gagcagttct ctcggctgct gcgggaccac    240
```

```
aacctgacgc gggagcagtt catcgctctg taccggctgc gaccgctcgt ctacacccca      300
gagctgccgg gacgcgccaa gctggccctc gtgctcaccg gcgtgctcat cttcgccctg      360
gcactctttg gcaatgctct ggtgttctac gtggtgaccc gcagcaaggc catgcgcacc      420
gtcaccaaca tctttatctg ctccttggcg ctcagtgacc tgctcatcac cttcttctgc      480
attcccgtca ccatgctcca gaacatttcc gacaactggc tggggggtgc tttcatttgc      540
aagatggtgc catttgtcca gtctaccgct gttgtgacag aaatcctcac tatgacctgc      600
attgctgtgg aaaggcacca gggacttgtg catccttta aaatgaagtg caatacacc       660
aaccgaaggg ctttcacaat gctaggtgtg gtctggctgg tggcagtcat cgtaggatca      720
cccatgtggc acgtgcaaca acttgagatc aaatatgact tcctatatga aaggaacac       780
atctgctgct tagaagagtg gaccagccct gtgcaccaga gatctacac cacccttcatc     840
ctgtcatcct cttcctcctg cctcttatgg aagaagaaac gagctgtcat tatgatggtg      900
acagtggtgg ctctctttgc tgtgtgctgg gcaccattcc atgttgtcca tatgatgatt      960
gaatacagta attttgaaaa ggaatatgat gatgtcacaa tcaagatgat ttttgctatc     1020
gtgcaaatta ttggatttc caactccatc tgtaatccca ttgtctatgc atttatgaat     1080
gaaaacttca aaaaaatgt tttgtctgca gtttgttatt gcatagtaaa taaaaccttc     1140
tctccagcac aaaggcatgg aaattcagga attacaatga tgcggaagaa agcaaagttt     1200
tccctcagag agaatccagt ggaggaaacc aaaggagaag cattcagtga tggcaacatt     1260
gaagtcaaat tgtgtgaaca gacagaggag aagaaaaagc tcaaacgaca tcttgctctc     1320
tttaggtctg aactggctga gaattctcct ttagacagtg ggcattaa                  1368

<210> SEQ ID NO 7
<211> LENGTH: 1296
<212> TYPE: DNA
<213> ORGANISM: Homo sapiens

<400> SEQUENCE: 7
atgcaggcgc ttaacattac cccggagcag ttctctcggc tgctgcggga ccacaacctg       60
acgcgggagc agttcatcgc agttcatcgc ctgcgaccgc tcgtctacac cccagagctg      120
ccgggacgcg ccaagctggc cctcgtgctc accggcgtgc tcatcttcgc cctgcgctc       180
tttggcaatg ctctggtgtt ctacgtgtg acccgcagca aggccatgcg caccgtcacc      240
aacatcttta tctgctcctt ggcgctcagt gacctgctca tcaccttctt ctgcattccc      300
gtcaccatgc tccagaacat ttccgacaac tggctggggg gtgctttcat ttgcaagatg      360
gtgccatttg tccagtctac cgctgttgtg acagaaatcc tcactatgac ctgcattgct      420
gtggaaaggc accagggact tgtgcatcct tttaaaatga gtggcaata caccaaccga      480
agggctttca atgctaggt gtggtctgg ctggtggcag tcatcgtagg atcacccatg      540
tggcacgtgc aacaacttga gatcaaatat gacttcctat atgaaaagga acacatctgc      600
tgcttagaag agtggaccag ccctgtgcac cagaagatct acaccacctt catccttgtc      660
atcctcttcc tcctgcctct tatggtgatg cttattctgt acagtaaaat tggttatgaa      720
ctttggataa agaaaagagt tgggggatggt tcagtgcttc gaactattca tggaaaagaa      780
atgtccaaaa tagccaggaa gaagaaacga gctgtcatta tgatggtgac agtggtggct      840
ctctttgctg tgtgctgggc accattccat gttgtccata tgatgattga atacagtaat      900
tttgaaaagg aatatgatga tgtcacaatc aagatgattt ttgctatcgt gcaaattatt      960
ggattttcca actccatctg taatcccatt gtctatgcat ttatgaatga aaacttcaaa     1020
```

| | |
|---|---|
| aaaaatgttt tgtctgcagt ttgttattgc atagtaaata aaaccttctc tccagcacaa | 1080 |
| aggcatggaa attcaggaat tacaatgatg cggaagaaag caaagttttc cctcagagag | 1140 |
| aatccagtgg aggaaaccaa aggagaagca ttcagtgatg caacattga agtcaaattg | 1200 |
| tgtgaacaga cagaggagaa gaaaaagctc aaacgacatc ttgctctctt taggtctgaa | 1260 |
| ctggctgaga attctccttt agacagtggg cattaa | 1296 |

<210> SEQ ID NO 8
<211> LENGTH: 4350
<212> TYPE: DNA
<213> ORGANISM: Homo sapiens

<400> SEQUENCE: 8

| | |
|---|---|
| agttgaggga ttgacacaaa tggtcaggcg gcggcggcgg agaaggaggc ggaggcgcag | 60 |
| gggggagccg agcccgctgg gctgcggaga gttgcgctct ctacggggcc gcggccacta | 120 |
| gcgcggcgcc gccagccggg agccagcgag ccgagggcca ggaaggcggg acacgacccc | 180 |
| ggcgcgccct agccacccgg gttctccccg ccgcccgcgc ttcatgaatc gcaagtttcc | 240 |
| gcggcggcgg cggctgcggt acgcagaaca ggagccgggg gagcgggccg aaagcggctt | 300 |
| gggctcgacg gagggcaccc gcgcagaggt ctccctggcc gcaggggag ccgccgccgg | 360 |
| ccgtgccccct gcagcccca gcggagcggc gccaagagag gagccgagaa gtatggctg | 420 |
| aggaggaggc gcctaagaag tcccgggccg ccggcggtgg cgcgagctgg gaactttgtg | 480 |
| ccggggcgct ctcggcccgg ctggcggagg agggcagcgg ggacgccggt ggccgccgcc | 540 |
| gcccgccagt tgaccccgg cgattggcgc gccagctgct gctgctgctt tggctgctgg | 600 |
| aggctccgct gctgctgggg gtccgggccc aggcggcggg ccaggggcca ggccagggc | 660 |
| ccgggccggg gcagcaaccg ccgccgccgc ctcagcagca acagagcggg cagcagtaca | 720 |
| acggcgagcg gggcatctcc gtcccggacc acggctattg ccagcccatc tccatcccgc | 780 |
| tgtgcacgga catcgcgtac aaccagacca tcatgcccaa cctgctgggc cacacgaacc | 840 |
| aggaggacgc gggcctggag gtgcaccagt tctaccctct agtgaaagtg cagtgttccg | 900 |
| ctgagctcaa gttcttcctg tgctccatgt acgcgcccgt gtgcaccgtg ctagagcagg | 960 |
| cgctgccgcc ctgccgctcc ctgtgcgagc gcgcgcgcca gggctgcgag gcgctcatga | 1020 |
| acaagttcgg cttccagtgg ccagacacgc tcaagtgtga aagttcccg gtgcacggcg | 1080 |
| ccggcgagct gtgcgtgggc cagaacacgt ccgacaaggg cacccgacg ccctcgctgc | 1140 |
| ttccagagtt ctggaccagc aaccctcagc acggcggcgg agggcaccgt ggcggcttcc | 1200 |
| cgggggggcgc cggcgcgtcg gagcgaggca agttctcctg cccgcgcgcc ctcaaggtgc | 1260 |
| cctcctacct caactaccac ttcctggggg agaaggactg cggcgcacct tgtgagccga | 1320 |
| ccaaggtgta tgggctcatg tacttcgggc ccgaggagct gcgcttctcg cgcacctgga | 1380 |
| ttggcatttg gtcagtgctg tgctgcgcct ccacgctctt cacggtgctt acgtacctgg | 1440 |
| tggacatgcg gcgcttcagc tacccggagc ggcccatcat cttcttgtcc ggctgttaca | 1500 |
| cggccgtggc cgtggcctac atcgccggct tcctcctgga agaccgagtg gtgtgtaatg | 1560 |
| acaagttcgc cgaggacggg gcacgcactg tggcgcaggg caccaagaag gagggctgca | 1620 |
| ccatcctctt catgatgctc tacttcttca gcatggccag ctccatctgg tgggtgatcc | 1680 |
| tgtcgctcac ctggttcctg gcggctggca tgaagtgggg ccacgaggcc atcgaagcca | 1740 |
| actcacagta ttttcacctg gccgcctggg ctgtgccggc catcaagacc atcaccatcc | 1800 |
| tggcgctggg ccaggtggac ggcgatgtgc tgagcggagt gtgcttcgtg gggcttaaca | 1860 |

```
acgtggacgc gctgcgtggc ttcgtgctgg cgcccctctt cgtgtacctg tttatcggca    1920
cgtcctttct gctggccggc tttgtgtcgc tcttccgcat ccgcaccatc atgaagcacg    1980
atggcaccaa gaccgagaag ctggagaagc tcatggtgcg cattggcgtc ttcagcgtgc    2040
tgtacactgt gccagccacc atcgtcatcg cctgctactt ctacgagcag gccttccggg    2100
accagtggga acgcagctgg gtggcccaga gctgcaagag ctacgctatc ccctgccctc    2160
acctccaggc gggcggaggc gcccgccgc acccgcccat gagcccggac ttcacggtct    2220
tcatgattaa gtaccttatg acgctgatcg tgggcatcac gtcgggcttc tggatctggt    2280
ccggcaagac cctcaactcc tggaggaagt tctacacgag gctcaccaac agcaaacaag    2340
gggagactac agtctgagac ccggggctca gcccatgccc aggcctcggc cggggcgcag    2400
cgatccccca aagccagcgc cgtggagttc gtgccaatcc tgacatctcg aggtttcctc    2460
actagacaac tctcttcgc aggctccttt gaacaactca gctcctgcaa aagcttccgt    2520
ccctgaggca aaaggacacg aggggcccgac tgccagaggg aggatggaca gacctcttgc    2580
cctcacactc tggtaccagg actgttcgct tttatgattg taaatagcct gtgtaagatt    2640
tttgtaagta tatttgtatt taaatgacga ccgatcacgc gttttctttt ttcaaaagtt    2700
tttaattatt tagggcggtt taaccatttg aggcttttcc ttcttgccct tttcggagta    2760
ttgcaaagga gctaaaactg gtgtgcaacc gcacagcgct cctggtcgtc ctcgcgcgcc    2820
tctccctacc acgggtgctc gggacggctg ggcgccagct ccggggcgag ttcagcactg    2880
cggggtgcga ctagggctgc gctgccaggg tcacttcccg cctcctcctt ttgccccctc    2940
cccctccttc tgtcccctcc cttcttttcc tggcttgagg tagggctct taaggtacag    3000
aactccacaa accttccaaa tctggaggag ggccccata cattacaatt cctcccttgc    3060
tcggcggtgg attgcgaagg cccgtcccct cgacttcctg aagctggatt tttaactgtc    3120
cagaacttc ctccaacttc atgggggccc acgggtgtgg gcgctggcag tctcagcctc    3180
cctccacggt caccttcaac gcccagacac tcccttctcc caccttagtt ggttacaggg    3240
tgagtgagat aaccaatgcc aaactttttg aagtctaatt tttgaggggt gagctcattt    3300
cattctctag tgtctaaaac ctggtatggg tttggccagc gtcatggaaa gatgtggtta    3360
ctgagatttg ggaagaagca tgaagctttg tgtgggttgg aagagactga agatatgggt    3420
tataaaatgt taattctaat tgcatacgga tgcctggcaa ccttgccttt gagaatgaga    3480
cagcctgcgc ttagatttta ccggtctgta aatggaaat gttgaggtca cctggaaagc    3540
tttgttaagg agttgatgtt tgcttccctt aacaagacag caaaacgtaa acagaaattg    3600
aaaacttgaa ggatatttca gtgtcatgga cttcctcaaa atgaagtgct attttcttat    3660
ttttaatcaa ataactagac atatatcaga aactttaaaa tgtaaaagtt gtacactttc    3720
aacattttat tacgattatt attcagcagc acattctgag gggggaacaa ttcacaccac    3780
caataataac ctggtaagat ttcaggaggt aaagaaggtg aataattga cggggagata    3840
gcgcctgaaa taaacaaaat atgggcatgc atgctaaagg gaaatgtgt gcaggtctac    3900
tgcattaaat cctgtgtgct cctctttgg atttacagaa atgtgtcaaa tgtaaatctt    3960
tcaaagccat ttaaaatat tcactttagt tctctgtgaa gaagaggaga aaagcaatcc    4020
tcctgattgt attgttttaa actttaagaa tttatcaaaa tgccggtact taggacctaa    4080
atttatctat gtctgtcata cgctaaaatg atattggtct ttgaatttgg tatacattta    4140
ttctgttcac tatcacaaaa tcatctatat ttatagagga atagaagttt atatatatat    4200
aataccatat ttttaatttc acaaataaaa aattcaaagt tttgtacaaa attatatgga    4260
```

-continued

| | |
|---|---|
| ttttgtgcct gaaaataata gagcttgagc tgtctgaact attttacatt ttatggtgtc | 4320 |
| tcatagccaa tcccacagtg taaaaattca | 4350 |

<210> SEQ ID NO 9
<211> LENGTH: 952
<212> TYPE: DNA
<213> ORGANISM: Homo sapiens

<400> SEQUENCE: 9

| | |
|---|---|
| ttggtccaag caagaaggca gtggtctact ccatcggcaa catgctggtc ctttatggac | 60 |
| acagcaccca ggaccttccg gaaaccaatg cccgcgtagt cggagggact gaggccggga | 120 |
| ggaattcctg gccctctcag atttccctcc agtaccggtc tggaggttcc cggtatcaca | 180 |
| cctgtggagg gacccttatc agacagaact gggtgatgac agctgctcac tgcgtggatt | 240 |
| accagaagac tttccgcgtg gtggctggag accataacct gagccagaat gatggcactg | 300 |
| agcagtacgt gagtgtgcag aagatcgtgg tgcatccata ctggaacagc gataacgtgg | 360 |
| ctgccggcta tgacatcgcc ctgctgcgcc tgcccagag cgttaccctc aatagctatg | 420 |
| tccagctggg tgttctgccc caggaggag ccatcctggc taacaacagt ccctgctaca | 480 |
| tcacaggctg gggcaagacc aagaccaatg gcagctggc ccagaccctg cagcaggctt | 540 |
| acctgccctc tgtggactac gccatctgct ccagctcctc ctactggggc tccactgtga | 600 |
| agaacaccat ggtgtgtgct ggtggagatg gagttcgctc tggatgccag ggtgactctg | 660 |
| ggggcccccct ccattgcttg gtgaatggca agtattctgt ccatggagtg accagctttg | 720 |
| tgtccagccg gggctgtaat gtctccagga agcctacagt cttcacccag gtctctgctt | 780 |
| acatctcctg gataaataat gtcatcgcct ccaactgaac attttcctga gtccaacgac | 840 |
| cttcccaaaa tggttcttag atctgcaata ggacttgcga tcaaaagta aaacacattc | 900 |
| tgaaagacta ttgagccatt gatagaaaag caaataaaac tagatataca tt | 952 |

<210> SEQ ID NO 10
<211> LENGTH: 9372
<212> TYPE: DNA
<213> ORGANISM: Homo sapiens

<400> SEQUENCE: 10

| | |
|---|---|
| tgaataattg aactttgttt atttctccat atttttgcag tggtaattcc attataaaac | 60 |
| ctaatgaaac aatgttttta tagatggtgt ggaaagactt ttctgggctc agaggtgaaa | 120 |
| ctgacccttg tgtatcagca gcatttctga ctgactgaga gagtgtagtg attaacagag | 180 |
| ttgtgatgtt agttaagaaa cttagatttg ccattgtagc ttttctacca attagcagat | 240 |
| tgtttaactc actgaaattg taaagtggta gacgtggact tagtcattac tgggcagctt | 300 |
| atgaattgta ttcatttact catgatgtaa aaatggttag tctccacttt taaggctcta | 360 |
| gttctagtgg ctaaataggt acttatttat acagtatgat aactgctgta ttaaaataca | 420 |
| tgtctcaaat gtggaatagt agaagaggtg aagaaaatca tagtttgagg tagaatactg | 480 |
| tttgctggtc ttaaaaactg tggtattttg gtgattccat aaattaggtc agatacttcc | 540 |
| actggaggga aacagtttaa aggatatatg tgatactatt aatagaatga ggaagacaca | 600 |
| ccagatattt aggagggaat tagcgagctt gaaactaaga gctggtttga atgagactgg | 660 |
| gtcataagtg atttcaagta ccagattaag gcactgagat tttatttta agcactgaag | 720 |
| tcagattttt tccttttaaa agaaaggatt catgatgaaa tctgcttttt gttttgcaga | 780 |
| gagcttggag ataattctgg tggctgtgtg gagtatgtgt tggaggtatt aaattttcac | 840 |

```
agtatatata aggcagcaat tgataggcct ttcacagatt cttctgataa ctacataaag      900
agacaaaaaa aagaaaaaag agcaaagatc tgtgctgtgt caagtatgac agccatcact      960
catggctctc cagtaggagg gaacgacagc cagggccagg ttcttgatgg ccagtctcag     1020
catctcttcc aacagaacca gacttcatca cctgattctt ccaatgagaa ttccgtagca     1080
actcctcctc cagaggaaca agggcaaggt gatgccccac cacagcatga agatgaagag     1140
cctgcatttc cacatactga gctggcaaac ctggatgaca tgatcaacag gcctcgatgg     1200
gtggttcctg ttttgccaaa agggaatta gaagtgcttt tagaagctgc tattgatctt     1260
agtgtaaaag gccttgatgt taaaagtgaa gcatgccaac gttttttttcg agatggacta     1320
acaatatctt tcactaaaat tcttatggat gaggctgtga gtggctggaa gtttgaaatt     1380
catagatgta ttattaacaa tactcatcgc ctagtggagc tttgtgtggc caagttgtcc     1440
caagattggt ttccacttct agaacttctc gccatggcct taaatcctca ctgcaagttt     1500
catatctaca atggtacacg tccgtgtgaa ttaatttcct caaatgctca gttgcctgaa     1560
gaagaattat ttgctcgttc ttcagatcct cgatcaccaa aaggttggct agtggatctc     1620
atcaataaat ttggcacatt aaatgggttc cagattttgc atgatcgttt ttttaatgga     1680
tcagcattaa atattcaaat aattgcagct cttattaaac catttggaca atgctatgag     1740
tttctcagtc aacatacact gaaaaagtac ttcattccag ttatagaaat agttccacat     1800
ttattggaaa acttaactga tgaagaactg aaaaaggagg caagaatga agccaaaaat     1860
gatgcccttt caatgattat taaatctttg aagaacttag cttcaagaat ttcaggacaa     1920
gatgagacta taaaaaattt ggaaattttt aggttaaaga tgatactcag attgttgcaa     1980
atttcctctt ttaatggaaa gatgaatgca ctgaatgaaa taaataaggt tatatctagt     2040
gtatcatatt atactcatcg gcatagtaat cctgaggagg aagaatggct gacagctgag     2100
cgaatggcag aatggataca gcaaataat atccttatcca tagtcttgca agacagtctt     2160
catcaaccac aatatgtaga aaagctagag aaaattcttc gttttgtgat taaagaaaag     2220
gctcttacat tacaggacct tgataatatc tgggcagcac aggcaggaaa acatgaagcc     2280
attgtgaaga atgtacatga tctgctagca aagttggctt gggattttc tcctggacaa     2340
cttgatcatc ttttttgattg ctttaaggca agttggacaa atgcaagtaa aaagcaacgt     2400
gaaaagctcc ttgagttgat acgccgtctt gcagaagatg ataaagatgg tgtgatggca     2460
cacaaagtgt tgaaccttct ttggaacctg gctcagagtg atgatgtgcc tgtagacatc     2520
atggaccttg ctcttagtgc ccacataaaa atactagatt atagttgttc ccaggatcga     2580
gatgcacaga agatccagtg gatagatcac tttatagaag aacttcgcac aaatgacaag     2640
tgggtaattc ctgctctgaa acaaataaga gaaatttgta gtttgtttgg tgaagcatct     2700
caaaatttga gtcaaactca gcgaagtccc cacatatttt atcgccatga tttaatcaac     2760
cagcttcaac aaaatcatgc tttagttact ttggtagcag aaaaccttgc aacctacatg     2820
aatagcatca gattgtatgc tggagatcat aagactatg atccacaaac agtgaggctt     2880
ggaagtcgat acagtcatgt tcaagaagtt caagaacgac taaacttcct tagatttta     2940
ctgaaggatg gccaactgtg gctctgtgct cctcaggcaa acaaatatg gaagtgctta     3000
gcagaaaatg cagtttatct ttgtgatcgt gaagcctgtt ttaagtggta ttccaagtta     3060
atggggatg aaccagactt ggatcctgat attaataagg acttctttga agtaatgta     3120
cttcagcttg atccttccct tttaactgaa aatggaatga aatgctttga aagatttttc     3180
aaagctgtca attgtcgaga aaggaaacta atagcaaaaa gaagatccta tatgatggat     3240
```

```
gatttggaat taattggact agactacctt tggagggttg tgattcagag tagtgacgag    3300
attgctaaca gagctataga tcttcttaaa gagatataca caaaccttgg cccaagatta    3360
aaagccaatc aggtggttat ccatgaagac ttcattcagt cttgctttga tcgtttaaaa    3420
gcatcatatg atacactgtg tgttttttgat ggtgacaaaa acagcattaa ttgtgcaaga   3480
caagaagcca ttcgaatggt tagagtatta actgttataa aagagtacat taatgaatgt    3540
gacagtgatt atcacaagga aagaatgatt ttacctatgt cgagagcatt ttgtggcaaa    3600
cacctctctc ttatagttcg gtttccaaac cagggcagac aggttgatga gttggatata    3660
tggtttcata cgaatgacac aattggttca gtacggcgat gtattgttaa tcgtattaaa    3720
gccaatgtag cccacaaaaa aattgaactt tttgtgggtg gtgagctgat agattctgaa    3780
aatgacagaa agctaattgg acaattaaac ttaaaagata atctctaat tacagccaaa     3840
cttacacaaa taaatttcaa tatgccatca agtcctgata gctcttccga ttcctcaact    3900
gcatctcctg gaaaccaccg taatcattac aatgatggtc ccaatctaaa ggtggaaagt    3960
tgtttgcctg gggtgataat gtcagtgcat cccaaataca tctctttcct ttggcaattt    4020
gcaaacttag gtagcaacct gaatatgcca cctcttaaaa atggagcaag agtacttatg    4080
aaacttatgc caccagatag aacagctgta gaaaaattac gaactgtttg tttggaccat    4140
gcaaccttg gagaaggcaa acttagtcca ccccttgact ccctttttctt tggtccttct    4200
gcctcccaag ttctatacct aacagaggta gtttatgcct tgttaatgcc tgctggtgtg    4260
cctctaactg atgggtcctc tgactttcaa gttcacttct tgaaaagtgg tggcttacct    4320
cttgtactga gtatgctaat aagaaataac ttcttgccaa atacagatat ggaaactcga    4380
aggggtgctt atttaaatgc tcttaaaata gccaaactgt tgttaactgc gattggctat    4440
ggccatgttc gagctgtagc agaagcttgt cagccagttg tagatggtac agaccccata    4500
acacagatta accaagttac tcatgatcaa gcagtggtgc tacaaagtgc ccttcagagc    4560
attcctaatc cctcatccga gtgcgtactt agaaatgagt ccatacttct tgctcaggaa    4620
atatctaatg aggcttcaag atatatgcct gatatttgtg taattagggc tatacagaaa    4680
attatctggg catcagcatg tggggcatta ggactatttt ttagcccaaa tgaagaaata    4740
actaaaattt atcagatgac caccaatgga agcaataagc tggaggtgga agatgaacaa    4800
gtttgttgtg aagcactgga agtgatgacc ttatgttttg ctttacttcc aacagcgttg    4860
gatgcactta gtaaagaaaa agcctggcag accttcatca ttgacttatt attgcactgt    4920
ccaagcaaaa ctgttcgtca gttggcacag gagcagttct ttttaatgtg caccagatgt    4980
tgcatgggac acaggcctct gcttttcttc attactttac tctttaccat actggggagc    5040
acagcaagag agaagggtaa atattcaggt gattatttca cacttttacg gcaccttctc    5100
aattatgctt acaatggcaa tattaacata cccaatgctg aagttcttct tgtcagtgaa    5160
attgattggc tcaaaaggat tagggataat gttaaaaaca caggtgaaac aggtgtcgaa    5220
gagccaatac tggaaggcca ccttggggta caaaagagt tattggcctt tcaaacttct    5280
gagaaaaagt atcactttgg ttgtgaaaaa ggaggtgcta atctcattaa agaattaatt    5340
gatgatttca tctttcccgc atccaaagtt tacctgcagt atttaagaag tggagaacta    5400
ccagctgagc aggctattcc agtctgtagt tcacccgtta ccatcaatgc cggttttgag    5460
ctacttgtag cattagctat tggctgtgtg aggaatctca acagatagt agactgtttg    5520
actgaaatgt attacatggg cacagcaatt actacttgtg aagcacttac tgagtgggaa    5580
tatctgcccc ctgttggacc ccgcccacca aaaggatttg tgggactcaa aaatgctggt   5640
```

```
gctacgtgtt acatgaactc tgtgatccag cagctataca tgattccttc tatcaggaac    5700
agtattcttg caattgaagg cacaggtagt gatttacacg atgatatgtt cggggatgag    5760
aagcaggaca gtgagagtaa tgttgatccc cgagatgatg tatttggata tcctcatcaa    5820
tttgaagaca agccagcatt aagtaagaca gaagatagga aagagtataa tattggtgtc    5880
ctaagacacc ttcaggtcat ctttggtcat ttagctgctt cccaactaca atactatgta    5940
cccagaggat tttggaaaca gttcaggctt tggggtgaac ctgttaatct ccgtgaacaa    6000
catgatgcct tagagttttt taattctttg gtggatagtt tagatgaagc tttaaaagct    6060
ttaggacacc cggctatact aagtaaagtc ctaggaggct cctttgctga tcagaagatc    6120
tgccagggct gcccacatag gtttgaatgt gaagaatctt ttacaacttt gaatgtggat    6180
attagaaatc atcaaaatct tcttgactct ttggaacagt atatcaaagg agatttattg    6240
gaaggtgcaa atgcatatca ttgtgaaaaa tgtgataaaa aggttgacac agtaaagcgc    6300
ctgctaatta aaaaattgcc tcgggttctt gctatccaac tcaaacgatt tgactatgac    6360
tgggaaagag aatgtgcaat taaattcaat gattattttg aatttcctcg agagctggat    6420
atgggacctt acacagtagc aggtgttgca aacctggaaa gggataatgt aaactcagaa    6480
aatgagttga ttgaacagaa agagcagtct gacaatgaaa ctgcaggagg cacaaagtac    6540
agacttgtag gagtgcttgt acacagtggt caagcaagcg gtgggcatta ttattcttac    6600
atcattcaaa ggaatggtaa agatgatcag acagatcact ggtataaatt tgatgatgga    6660
gatgtaacag aatgcaaaat ggatgatgat gaagaaatga aaaatcagtg ttttggtgga    6720
gagtacatgg gagaagtatt tgatcacatg atgaagcgca tgtcatatag gcgacagaag    6780
aggtggtgga atgcttacat accttttat gaacaaatgg atatgataga tgaagatgat    6840
gagatgataa gatacatatc agagctaact attgcaagac cccatcagat cattatgtca    6900
ccagccattg agagaagtgt acggaaacaa aatgtgaaat ttatgcataa ccgattgcaa    6960
tatagtttag agtattttca gtttgtgaaa aaactgctta catgtaatgg tgtttattta    7020
aaccctgctc cagggcagga ttatttgttg cctgaagcag aagaaattac tatgattagt    7080
attcagcttg ctgctagatt cctctttacc actggatttc acaccaagaa aatagttcgt    7140
ggtcctgcca gtgactggta tgatgcactg tgcgttcttc tccgtcacag caaaaatgta    7200 cgttttggt ttactcataa tgtcctttt aatgtatcaa atcgcttctc tgaatacctc    7260
ctggagtgcc ctagtgcaga agtgaggggt gcatttgcaa aacttatagt gtttattgca    7320 cactttcct tgcaagatgg gtcttgtcct tctccttttg catctccagg accttctagt    7380
caggcatgtg ataacttgag cttgagtgac cacttactaa gagccacact aaatctcttg    7440
agaagggaag tttcagagca tggacatcat ttacagcaat atttaatttt gtttgtaatg    7500
tatgccaatt taggtgtggc agaaaaaaca cagcttctga aattgaatgt acctgctacc    7560
tttatgcttg tgtctttaga cgagggacca ggtcctccaa tcaaatatca gtatgctgaa    7620
ttaggcaagt tatattcagt agtgtctcag ctgattcgtt gttgcaatgt gtcatcaaca    7680
atgcagtctt caatcaatgg taatccccct ctccccaatc ctttcggtga ccttaattta    7740
tcacagccta atgccaat tcagcagaat gtgttagaca tttttatttgt gagaacaagt    7800 tatgtgaaga aaattattga agactgcagt aactcagagg ataccatcaa attacttcgc    7860
ttttgctctt gggagaatcc tcagttctca tctactgtcc tcagcgaact tctctggcag    7920
gttgcatatt catatcccta tgaacttcgg ccatatttag atctactttt ccaaattta    7980 ctgattgagg actcctggca gactcacaga attcataatg cacttaaagg aattccagat    8040
```

| | |
|---|---:|
| gacagagatg ggctgttcga tacaatacag cgctcgaaga atcactatca aaaacgagca | 8100 |
| tatcagtgca taaaatgtat ggtagctcta tttagcagtt gtcctgttgc ttaccagatc | 8160 |
| ttacagggta acggagatct aaaagaaaa tggacctggg cagtggaatg gctaggagat | 8220 |
| gaacttgaaa gaagaccata tactggcaat cctcagtata gttacaacaa ttggtctcct | 8280 |
| ccagtacaaa gcaatgaaac agcaaatggt tatttcttag aaagatcaca tagtgctagg | 8340 |
| atgacacttg caaaagcttg tgaactctgt ccagaagagg agccagatga ccaggatgcc | 8400 |
| ccagatgagc atgagccctc tccatcagaa gatgccccat tatatcctca ttcacctgcc | 8460 |
| tctcagtatc aacagaataa tcatgtacat ggacagccat atacaggacc agcagcacat | 8520 |
| cacttgaaca accctcagaa acaggccaa cgaacacaag aaaattatga aggcaatgaa | 8580 |
| gaagtatcct cacctcagat gaaggatcag tgaaaagcaa taattaactg cttcctttat | 8640 |
| gactatgcac taaggtctta tagtccaaac tttctctgtg tctggctagt attgaaaact | 8700 |
| agataaactg ctccaaacca acatggagta aagagcatat tcactggttt atttgcagta | 8760 |
| atttgcaatt tgtcagtgta taagacacat gcagggtgaa gtgtacagag ttttgtaaca | 8820 |
| aatgactggt cctaatctgt aaatgagaaa ggtatatata ctatgttaat gtctgactgt | 8880 |
| taattcttaa gcaagaaact tttttgatg aaaacaagtc agatctacac agtcacacaa | 8940 |
| ttattttttg ttgtgttcac tacattgtgc aattgatatt gcctgctttg agcagtttgg | 9000 |
| tcaacttacc aacttccccc caaaaaggg aacataaaag agcccatctt tgtcagttta | 9060 |
| caccaatagt ttcttgttaa tccttctttc ctggatatat aaggctggtg gtaacttttg | 9120 |
| aattatatgg ttgatgtgga aaattggcag tgtaacattt ctagatactt tcattacct | 9180 |
| ttttattctg gtatataggc taaccacttt aaagctattc ttatgctgta acagttagca | 9240 |
| tggcttcaca ctgtttgtgt agccaagagg acagaattac atgaatgaca gtgcccagag | 9300 |
| tgacagctgt atattgctca gagcttttat ttcttatacc tagaataaat ataaatggg | 9360 |
| ggaaaaaaaa aa | 9372 |

<210> SEQ ID NO 11
<211> LENGTH: 1593
<212> TYPE: DNA
<213> ORGANISM: Homo sapiens

<400> SEQUENCE: 11

| | |
|---|---:|
| ctgggagcgc ggcgtaggtg gctgccgagt cttttcctgt ttagggtctt atcctggcat | 60 |
| tgagggcgcc ggactggcgc ttttggccgg cttggcattg ggtgggcggc ttcttgggac | 120 |
| ccacatgagc cagtggcatc atccccgcag tggctgggc cggagacgcg acttttcagg | 180 |
| acgctcctca gccaagaaga agggcggaaa ccacatcccc gaaaggtgga aagactatct | 240 |
| cccagttgga cagcggatgc ctgggactcg tttcattgct ttcaaagttc ctttgcaaaa | 300 |
| gagttttgaa aagaaacttg ctccagaaga atgcttttcc cctttggatc ttttttaacaa | 360 |
| aatccgagaa caaatgaag aacttggact gattattgat ttaacatata ctcaacgcta | 420 |
| ttataaacca gaggatttgc cagaaactgt tccttactta aaaattttta cagttggaca | 480 |
| tcaagtgcct gatgatgaga ctattttaa attcaaacac gctgttaatg gttttttgaa | 540 |
| agaaaataaa gataatgata aacttattgg tgtccactgt acccatggtt taacaggac | 600 |
| tggctacctc atttgcagat atttgattga tgtagaaggc gtgaggccag atgatgcaat | 660 |
| tgaattattc aataggtgcc ggggacattg cttagaaaga caaaactaca ttgaagacct | 720 |
| tcagaatggt cctatcagaa agaattggaa ttccagtgta cccaggtcaa gtgattttga | 780 |

| | |
|---|---:|
| agactcagca catctcatgc aaccagtcca caataagcct gttaaacaag gacctaggta | 840 |
| taatctacat cagatccagg gtcactcagc tcctcgacat ttccacaccc agacccaaag | 900 |
| tttgcaacaa tcagtcagaa aattttcaga gaatccacat gtttaccaga gacaccatct | 960 |
| ccctcctcct ggtcccctg gagaggacta ttcacacagg aggtattctt ggaatgtgaa | 1020 |
| gcccaatgcc agtcgggcag cccaggatag aagaaggtgg tatccttata attactccag | 1080 |
| actctcctat ccagcctgtt gggaatggac ccagtgatac aaacctgtcc tggaattcta | 1140 |
| cctggagacc agagctggcc tgaaaattac tggtgtgact tttaattagt tcaggtctaa | 1200 |
| tcaggtttct ttattgttcc cttatgtatt caagcttaag gaaaaattgc attgctgttt | 1260 |
| acctctttgc tgataaattt gcagtaatta cagcattgca ggaaaaacaa tctgttattc | 1320 |
| cagtcttaaa tttttctaaa agaagacaat atttagaac tgaagcattg agaacttccc | 1380 |
| ttgcaaatta tttttaaaat tctatcttgt ttttctatgt atttctttct gactagactt | 1440 |
| gtgatatgcg tgtgtttatg tacagaaatt tttagtgttt ttgttatgtt ctgttattga | 1500 |
| cccaaaggcc atctttattt tctataactg ttcaaaattt atattaaaat ctacttagga | 1560 |
| gataatttct ttagaaaaaa aaaaaaaaaa aaa | 1593 |

<210> SEQ ID NO 12
<211> LENGTH: 4116
<212> TYPE: DNA
<213> ORGANISM: Homo sapiens

<400> SEQUENCE: 12

| | |
|---|---:|
| cgccgctctc cgcctcgctt gctcctgccg ggcgtgcagg gccccgccgc cgccatgtcg | 60 |
| ggctcgttcg agctctcggt gcaggatctc aacgacctgc tctcggacgg cagcggctgc | 120 |
| tacagcctcc cgagccagcc ctgcaacgag gtcaccccgc ggatctacgt gggcaacgcg | 180 |
| tctgtggctc aggacatccc caagctgcag aaactaggca tcacccatgt gctgaacgcg | 240 |
| gctgagggca ggtccttcat gcacgtcaac accaatgcca acttctacaa ggactccggc | 300 |
| atcacatacc tgggcatcaa ggccaacgac acacaggagt tcaacctcag cgcttacttt | 360 |
| gaaagggctg ccgacttcat tgaccaggct ttggctcaaa agaatggccg ggtgctcgtc | 420 |
| cactgccggg aaggttatag ccgctcccca acgctagtta tcgcctacct catgatgcgg | 480 |
| cagaagatgg acgtcaagtc tgccctgagc atcgtgaggc agaaccgtga gatcggcccc | 540 |
| aacgatggct tcctggccca gctctgccag ctcaatgaca gactagccaa ggagggaag | 600 |
| ttgaaaccct agggcacccc caccgcctct gctcgagagg tccgtggggg aggccgtggg | 660 |
| caaaggtgtc ccgagctgcc atgtttagga aacacactgt accctgctcc cagcatcaca | 720 |
| aggcacttgt ctacaagtgt gtcccaacac agtcctgggc cactttcccc accctgggga | 780 |
| gcacataaag aagcttgcca agggggggcgt ccttgctccc cagttgtcct gtttctgtaa | 840 |
| cttatgatgt ctttttccctg agatgggggc tcagaggggg aaggcctgtg gcctgcatgc | 900 |
| ttcccgatgg cccacggcag gaggtgtgtg gaagtgtaag gcctaagatg ctcacagagg | 960 |
| tccctcatga cctcccttcc ccaactcccg aatcctctct tgagtgtgga cctcaacacc | 1020 |
| ttgagcccta gtaaaggaac tatgcaaatg caggccactc tccccaccac gtctgtgccc | 1080 |
| cgcactgtcc ccacagcctt ccacaccctg tgcataggca gccctctcac gtcttgaggt | 1140 |
| ccgaagctgg ggtgggggtg tccgtcagtt attagtggat ggagattccc acagcaaggc | 1200 |
| tgcatttgaa tgatttcctt aggatgaatg gtccctacac aaagaggcct tgtgggcaaa | 1260 |
| cctggagaac cctcctaaat ccatagagtt ttcaaaatgt gaatctttgg aagcctttgag | 1320 |

```
ttcagaatct gctgctctgg aatatttccc ttcgatctta tctcagtcac ttcgttttg    1380 agaagagtga tgccttgggc atgctttttt tttttctttt tttagaaaac agggagttga    1440
agtccaacct atttaaaaac cccaccattt ggagaattac aagggttttg tcctgaattg    1500
tagtgttggc aagcccaagc cactcgtgct aactgctttt tgtctcggtt gctattccaa    1560
gaacagaagg aggaagttgg ccaattacag cgtgtgtgca tggatgtgtg tgggggggcgt    1620 gcctctcaga aacgcggcca aagacaagc agggaagtga aaggtcccag gcacacaccc     1680
tgcccattgc aggtggctct tacagctctc tggtgccagc acgggatccc tgaagtgact    1740
cagccaggca gacatgagac atggcggagt gtccaaatgg atcctttatt ggtggtagag    1800
caaaaaaacc caaacacgat aaaccttca aaagactttc taaggatgat attggaatgc      1860
accagccctc acatgtgtat gcacatttgc cagaatataa gagttttgtt ttaaatacag    1920
tcttgttagg atttacgtt attgttatta tggaaagtga ttgtgatgct atttatcttc      1980
agggtcactc tgggcaaaga gaaggtcctc agccatgccc ccagcacctt gcacataggt    2040
gtctgataaa agtttaagaa attaaacact ttttgagcac caaatatata tagggcattg     2100
ttctggtggg tgtgtcacgc tcccagaaga ctgaatttat ggtaggatca ctcgcaaggc    2160
cttgtgaagg agtcttacct aaaacaaaag aaatatcagg acttttgtt gactattac      2220 aactcagttt tacatttaaa ttcaggcagt gttaatatgc caaggtaggg aatgtgcctt    2280
tttcagagtt ggccaggagc tcctggctgg gacacggaga ggcaggtgtg gcgtaaggcc    2340
tcactcccgg ctgtgaaggt ctctgatcac acagaagcag ccctgcccag cctggtcatt    2400
tgctgtccgc ttttctctgt gaccacagca gccctgaaca accagtatgt gtcttcttct    2460
ccagatagtg aaaaggtgt ccagataaac ccacctaagt gaaatggcca tcctctaaac    2520
tgggtacctc actgcacagc ttctaggtag ccttccaact taatctaact tgagcctcac    2580
agtaaccctg taaagttagt agagcttgtt cttgtattgt gaccttttt aaaaaaaagg     2640 aactgaggtt cagaatgatt aagggcctgg cccccagggt tgtccagctc cataaggtgg    2700
agctgggcaa gattttgggt ttgctgctcc ctgaagctgg attctttcat acgatactct    2760
ttctcaagaa ggggctccc tgggatctcc aggtgtactg cacttaccct caatccagcc     2820
ccggagaagc aagtgaaaag ggtgggtccc tcataggcta gaatgtgcag ctcttcttcc    2880
aggtgggatg tagcaccca agtagagct ttctgctctg ctcctggaaa aggctaggga      2940 gctgggctg gggctcccct cccatgacca ggcagtggtc accccatggg acaggcacag    3000
ctacttacgc gaacacagca ggttggtgtg gctggctaac taggacctct cgaaagtctc    3060
tgtgggggca tgagggagaa aaggccattg ggagaattac tgcctttact ttgggactac    3120
ttttatgctg ataacttggg atttcttgat agtccttcac ccctgaaacc ccgtatttac    3180
ttaacaagat ttagctctta gttcttcaag taaaattaaa gtctcttgtg taagagccaa    3240
cacatgccca gctgcggatg ggagctgttc ctggacagcc ttctactgcc tgggaagtga    3300
tggaacagga actcagggtg cccttacccc ctccccagac ctgttccctt tctttgactg    3360
acagagcacc atccaggcaa aattagagcg ccaaatggtt ttcttctcaa tcttaaagca    3420 gtatacctt ccacaggctc gtctgtgtcc ctgccactct gagttatcca gaaaccacca     3480
cctacaaatg aggggactca tctagaagac ctcaaggtc cccttttggc tctgagggt      3540 ctctaataat ccccacttgg aattcagcac cgcaaggaaa ttatgggtat gtgagccata    3600
atatgatggc cagcaggtgg cgctgccttc caccagtggt gatggatggt ttggaaaggg    3660
aatgttggtg ccttttgtgc cacaagttaa gatgctactg ttttaaagga aaaaaaaaa     3720
```

| | |
|---|---|
| aaaaagtact gatcttcaat atgaagacat gagcttttct cgcaggaaat tttcttttc | 3780 |
| acagaactgg tgtcaggaat cactgaaggg ctaaccgtga tagtccttgc aagtaagtca | 3840 |
| aggttttatc ctgattggaa atagaagaca tttccggttg agagaacaga ttcgttggaa | 3900 |
| gcttaacttt tgttgcctct taacgccacc aaattttagg gtaatttgat tatgaaagag | 3960 |
| tgaattttc tggacagaaa agggagagct accaaattgt ttttttcttt ttaaaaggaa | 4020 |
| gtttaatgtc cgttgtatca caaatcagtg ttaaaacacc agaactttag ccaaaataaa | 4080 |
| tgtcttacat tacaaaggta aaaaaaaaaa aaaaaa | 4116 |

<210> SEQ ID NO 13
<211> LENGTH: 3540
<212> TYPE: DNA
<213> ORGANISM: Homo sapiens

<400> SEQUENCE: 13

| | |
|---|---|
| ccagtttgct tcttggagaa cactggacag ctgaataaat gcagtatcta aatataaaag | 60 |
| aggactgcaa tgccatggct ttctgtgcta aaatgaggag ctccaagaag actgaggtga | 120 |
| acctggaggc ccctgagcca ggggtggaag tgatcttcta tctgtcggac agggagcccc | 180 |
| tccggctggg cagtggagag tacacagcag aggaactgtg catcagggct gcacaggcat | 240 |
| gccgtatctc tcctctttgt cacaacctct ttgccctgta tgacgagaac accaagctct | 300 |
| ggtatgctcc aaatcgcacc atcaccgttg atgacaagat gtccctccgg ctccactacc | 360 |
| ggatgaggtt ctatttcacc aattggcatg aaccaacga caatgagcag tcagtgtggc | 420 |
| gtcattctcc aaagaagcag aaaaatggct acgagaaaaa aagattcca gatgcaaccc | 480 |
| ctctccttga tgccagctca ctggagtatc tgtttgctca gggacagtat gatttggtga | 540 |
| aatgcctggc tcctattcga gaccccaaga ccgagcagga tggacatgat attgagaacg | 600 |
| agtgtctagg gatggctgtc ctggccatct cacactatgc catgatgaag aagatgcagt | 660 |
| tgccagaact gcccaaggac atcagctaca agcgatatat tccagaaaca ttgaataagt | 720 |
| ccatcagaca gaggaacctt ctcaccagga tgcggataaa taatgttttc aaggatttcc | 780 |
| taaaggaatt taacaacaag accatttgtg acagcagcgt gtccacgcat gacctgaagg | 840 |
| tgaaatactt ggctaccttg gaaactttga caaaacatta cggtgctgaa atatttgaga | 900 |
| cttccatgtt actgatttca tcagaaaatg agatgaattg gtttcattcg aatgacggtg | 960 |
| gaaacgttct ctactacgaa gtgatggtga ctgggaatct tggaatccag tggaggcata | 1020 |
| aaccaaatgt tgtttctgtt gaaaaggaaa aaaataaact gaagcggaaa aaactggaaa | 1080 |
| ataaagacaa gaaggatgag gagaaaaaca agatccggga agagtggaac aattttttcat | 1140 |
| tcttccctga aatcactcac attgtaataa aggagtctgt ggtcagcatt aacaagcagg | 1200 |
| acaacaagaa aatggaactg aagctctctt cccacgagga ggccttgtcc tttgtgtccc | 1260 |
| tggtagatgg ctacttccgg ctcacagcag atgcccatca ttacctctgc accgacgtgg | 1320 |
| ccccccgtt gatcgtccac aacatacaga atggctgtca tggtccaatc tgtacagaat | 1380 |
| acgccatcaa taaattgcgg caagaaggaa gcgaggaggg gatgtacgtg ctgaggtgga | 1440 |
| gctgcaccga ctttgacaac atcctcatga ccgtcacctg ctttgagaag tctgagcagg | 1500 |
| tgcagggtgc ccagaagcag ttcaagaact ttcagatcga ggtgcagaag ggccgctaca | 1560 |
| gtctgcacgg ttcggaccgc agcttcccca gcttgggaga cctcatgagc cacctcaaga | 1620 |
| agcagatcct gcgcacggat aacatcagct tcatgctaaa acgctgctgc cagcccaagc | 1680 |
| cccgagaaat ctccaacctg ctggtggcta ctaagaaagc ccaggagtgg cagcccgtct | 1740 |

```
accccatgag ccagctgagt ttcgatcgga tcctcaagaa ggatctggtg cagggcgagc    1800
accttgggag aggcacgaga acacacatct attctgggac cctgatggat acaaggatg     1860 acgaaggaac ttctgaagag aagaagataa aagtgatcct caaagtctta gaccccagcc    1920
acagggatat ttccctggcc ttcttcgagg cagccagcat gatgagacag gtctcccaca    1980
aacacatcgt gtacctctat ggcgtctgtg tccgcgacgt ggagaatatc atggtggaag    2040
agtttgtgga aggggggtcct ctggatctct tcatgcaccg gaaaagtgat gtccttacca    2100
caccatggaa attcaaagtt gccaaacagc tggccagtgc cctgagctac ttggaggata    2160
aagacctggt ccatggaaat gtgtgtacta aaaacctcct cctggcccgt gagggaatcg    2220
acagtgagtg tggcccattc atcaagctca gtgaccccgg catccccatt acggtgctgt    2280
ctaggcaaga atgcattgaa cgaatcccat ggattgctcc tgagtgtgtt gaggactcca    2340
agaacctgag tgtggctgct gacaagtgga gctttggaac cacgctctgg gaaatctgct    2400
acaatggcga gatccccttg aaagacaaga cgctgattga gaaagagaga ttctatgaaa    2460
gccggtgcag gccagtgaca ccatcatgta aggagctggc tgacctcatg acccgctgca    2520
tgaactatga ccccaatcag aggccttttct tccgagccat catgagagac attaataagc    2580
ttgaagagca gaatccagat attgtttcca gaaaaaaaaa ccagccaact gaagtggacc    2640
ccacacattt tgagaagcgc ttcctaaaga ggatccgtga cttgggagag gccactttg     2700 ggaaggttga gctctgcagg tatgacccccg aagacaatac aggggagcag gtggctgtta    2760
aatctctgaa gcctgagagt ggaggtaacc acatagctga tctgaaaaag gaaatcgaga    2820
tcttaaggaa cctctatcat gagaacattg tgaagtacaa aggaatctgc acagaagacg    2880
gaggaaatgg tattaagctc atcatggaat ttctgccttc gggaagcctt aaggaatatc    2940
ttccaaagaa taagaacaaa ataaacctca acagcagct aaaatatgcc gttcagattt     3000 gtaagggggat ggactatttg ggttctcggc aatacgttca ccgggacttg gcagcaagaa    3060
atgtccttgt tgagagtgaa caccaagtga aaattggaga cttcggttta accaaagcaa    3120
ttgaaaccga taaggagtat tacaccgtca aggatgaccg ggacagccct gtgttttggt    3180
atgctccaga atgtttaatg caatctaaat tttatattgc ctctgacgtc tggtcttttg    3240
gagtcactct gcatgagctg ctgacttact gtgattcaga ttctagtccc atggctttgt    3300
tcctgaaaat gataggccca acccatggcc agatgacagt cacaagactt gtgaatacgt    3360
taaaagaagg aaaacgcctg ccgtgcccac ctaactgtcc agatgaggtt tatcagctta    3420
tgagaaaatg ctgggaattc caaccatcca atcggacaag cttcagaac cttattgaag     3480 gatttgaagc acttttaaaa taagaagcat gaataacatt taaattccac agattatcaa    3540
```

<210> SEQ ID NO 14
<211> LENGTH: 3541
<212> TYPE: DNA
<213> ORGANISM: Homo sapiens

<400> SEQUENCE: 14

```
tccagtttgc ttcttggaga acactggaca gctgaataaa tgcagtatct aaatataaaa      60
gaggactgca atgccatggc tttctgtgct aaaatgagga gctccaagaa gactgaggtg     120
aacctggagg cccctgagcc aggggtggaa gtgatcttct atctgtcgga cagggagccc     180
ctccggctgg gcagtggaga gtacacagca gaggaactgt gcatcagggc tgcacaggca     240
tgccgtatct ctcctctttg tcacaacctc tttgccctgt atgacgagaa caccaagctc     300
tggtatgctc caaatcgcac catcaccgtt gatgacaaga tgtccctccg gctccactac     360
```

```
cggatgaggt tctatttcac caattggcat ggaaccaacg acaatgagca gtcagtgtgg    420
cgtcattctc caaagaagca gaaaaatggc tacgagaaaa aaaagattcc agatgcaacc    480
cctctccttg atgccagctc actggagtat ctgtttgctc agggacagta tgatttggtg    540
aaatgcctgg ctcctattcg agaccccaag accgagcagg atggacatga tattgagaac    600
gagtgtctag ggatggctgt cctggccatc tcacactatg ccatgatgaa gaagatgcag    660
ttgccagaac tgcccaagga catcagctac aagcgatata ttccagaaac attgaataag    720
tccatcagac agaggaacct tctcaccagg atgcggataa ataatgtttt caaggatttc    780
ctaaaggaat taacaacaa gaccatttgt gacagcagcg tgtccacgca tgacctgaag    840
gtgaaatact tggctacctt ggaaactttg acaaaacatt acggtgctga aatatttgag    900
acttccatgt tactgatttc atcagaaaat gagatgaatt ggtttcattc gaatgacggt    960
ggaaacgttc tctactacga agtgatggtg actgggaatc ttggaatcca gtggaggcat   1020
aaaccaaatg ttgtttctgt tgaaaaggaa aaaataaac tgaagcggaa aaaactggaa   1080
aataaagaca agaaggatga ggagaaaaac aagatccggg aagagtggaa caattttca   1140 ttcttccctg aaatcactca cattgtaata aaggagtctg tggtcagcat taacaagcag   1200
gacaacaaga aaatggaact gaagctctct tcccacgagg aggccttgtc ctttgtgtcc   1260
ctggtagatg gctacttccg gctcacagca gatgcccatc attacctctg caccgacgtg   1320
gcccccccgt tgatcgtcca caacatacag aatggctgtc atggtccaat ctgtacagaa   1380
tacgccatca ataaattgcg gcaagaagga gcgaggagg ggatgtacgt gctgaggtgg   1440
agctgcaccg actttgacaa catcctcatg accgtcacct gctttgagaa gtctgagcag   1500
gtgcagggtg cccagaagca gttcaagaac tttcagatcg aggtgcagaa gggccgctac   1560
agtctgcacg gttcggaccg cagcttcccc agcttgggag acctcatgag ccacctcaag   1620
aagcagatcc tgcgcacgga taacatcagc ttcatgctaa aacgctgctg ccagcccaag   1680
ccccgagaaa tctccaacct gctggtggct actaagaaag cccaggagtg gcagcccgtc   1740
taccccatga gccagctgag tttcgatcgg atcctcaaga aggatctggt gcagggcgag   1800
caccttggga gaggcacgag aacacacatc tattctggga ccctgatgga ttacaaggat   1860
gacgaaggaa cttctgaaga gaagaagata aaagtgatcc tcaaagtctt agaccccagc   1920
cacagggata tttccctggc cttcttcgag gcagccagca tgatgagaca ggtctcccac   1980
aaacacatcg tgtacctcta tggcgtctgt gtccgcgacg tggagaatat catggtggaa   2040
gagtttgtgg aagggggtcc tctggatctc ttcatgcacc ggaaaagtga tgtccttacc   2100
acaccatgga aattcaaagt tgccaaacag ctggccagtg ccctgagcta cttggaggat   2160
aaagacctgg tccatggaaa tgtgtgtact aaaaaccctcc tcctggcccg tgagggaatc   2220
gacagtgagt gtggcccatt catcaagctc agtgaccccg gcatccccat tacggtgctg   2280
tctaggcaag aatgcattga cgaatccca tggattgctc ctgagtgtgt tgaggactcc   2340
aagaacctga gtgtggctgc tgacaagtgg agctttggaa ccacgctctg gaaatctgc   2400 tacaatggcg agatccccct tgaaagacaag acgctgattg agaaagagag attctatgaa   2460
agccggtgca ggccagtgac accatcatgt aaggagctgg ctgacctcat gacccgctgc   2520
atgaactatg accccaatca gaggccttc ttccgagcca tcatgagaga cattaataag   2580
cttgaagagc agaatccaga tattgttcc agaaaaaaaa accagccaac tgaagtggac   2640
cccacacatt tgagaagcg cttcctaaag aggatccgtg acttgggaga gggccacttt   2700
gggaaggttg agctctgcag gtatgacccc gaagacaata cagggagca ggtggctgtt   2760
```

| | |
|---|---:|
| aaatctctga agcctgagag tggaggtaac cacatagctg atctgaaaaa ggaaatcgag | 2820 |
| atcttaagga acctctatca tgagaacatt gtgaagtaca aaggaatctg cacagaagac | 2880 |
| ggaggaaatg gtattaagct catcatggaa tttctgcctt cgggaagcct aaggaatat | 2940 |
| cttccaaaga ataagaacaa aataaacctc aaacagcagc taaaatatgc cgttcagatt | 3000 |
| tgtaaggga tggactattt gggttctcgg caatacgttc accgggactt ggcagcaaga | 3060 |
| aatgtccttg ttgagagtga acaccaagtg aaaattggag acttcggttt aaccaaagca | 3120 |
| attgaaccg ataaggagta ttacaccgtc aaggatgacc gggacagccc tgtgttttgg | 3180 |
| tatgctccag aatgtttaat gcaatctaaa ttttatattg cctctgacgt ctggtctttt | 3240 |
| ggagtcactc tgcatgagct gctgacttac tgtgattcag attctagtcc catggctttg | 3300 |
| ttcctgaaaa tgataggccc aacccatggc cagatgacag tcacaagact tgtgaatacg | 3360 |
| ttaaaagaag gaaaacgcct gccgtgccca cctaactgtc cagatgaggt ttatcagctt | 3420 |
| atgagaaaat gctgggaatt ccaaccatcc aatcggacaa gctttcagaa ccttattgaa | 3480 |
| ggatttgaag cacttttaaa ataagaagca tgaataacat ttaaattcca cagattatca | 3540 |
| a | 3541 |

<210> SEQ ID NO 15
<211> LENGTH: 2982
<212> TYPE: DNA
<213> ORGANISM: Homo sapiens

<400> SEQUENCE: 15

| | |
|---|---:|
| cgcaccccgc gcagcggctg agccgggagc cagcgcagcc tcggccccgc agctcaagcc | 60 |
| tcgtccccgc cgccgccgcc gccgccgccg ccgccgcccc cggggcatgg cctgtctgat | 120 |
| ggccgctttc tcggtcggca ccgccatgaa tgccagcagt tactctgcag agatgacgga | 180 |
| gcccaagtcg gtgtgtgtct cggtggatga ggtggtgtcc agcaacatgg aggccactga | 240 |
| gacggacctg ctgaatggac atctgaaaaa agtagataat aaccctcacgg aagcccagcg | 300 |
| cttctcctcc ttgcctcgga gggcagctgt gaacattgaa ttcagggacc tttcctattc | 360 |
| ggttcctgaa ggaccctggt ggaggaagaa aggatacaag accctcctga aggaatttc | 420 |
| cgggaagttc aatagtggtg agttggtggc cattatgggt ccttccgggg ccggaaagtc | 480 |
| cacgctgatg aacatcctgg ctggatacag ggagacgggc atgaagggg ccgtcctcat | 540 |
| caacggcctg ccccgggacc tgcgctgctt ccggaaggtg tcctgctaca tcatgcagga | 600 |
| tgacatgctg ctgccgcatc tcactgtgca ggaggccatg atggtgtcgg cacatctgaa | 660 |
| gcttcaggag aaggatgaag gcagaaggga aatggtcaag gagatactga cagcgctggg | 720 |
| cttgctgtct tgccgccaaca cgcggaccgg gagcctgtca ggtggtcagc gcaagcgcct | 780 |
| ggccatcgcg ctggagctgg tgaacaaccc tccagtcatg ttcttcgatg agcccaccag | 840 |
| cggcctggac agcgcctcct gcttccaggt ggtctcgctg atgaagggc tcgctcaagg | 900 |
| gggtcgctcc atcattgca ccatccacca gcccagcgcc aaactcttcg agctgttcga | 960 |
| ccagctttac gtcctgagtc aaggacaatg tgtgtaccgg ggaaaagtct gcaatcttgt | 1020 |
| gccatatttg agggatttgg gtctgaactg cccaacctac cacaacccag cagattttgt | 1080 |
| catggaggtt gcatccggcg agtacggtga tcagaacagt cggctggtga gagcggttcg | 1140 |
| ggagggcatg tgtgactcag accacaagag agacctcggg ggtgatgccg aggtgaaccc | 1200 |
| tttctcttgg caccggccct ctgaagagga ctcctcgtcc atggaaggct gccacagctt | 1260 |
| ctctgccagc tgcctcacgc agttctgcat cctcttcaag aggaccttcc tcagcatcat | 1320 |

| | |
|---|---|
| gagggactcg gtcctgacac acctgcgcat cacctcgcac attgggatcg gcctcctcat | 1380 |
| tggcctgctg tacttgggga tcgggaacga agccaagaag gtcttgagca actccggctt | 1440 |
| cctcttcttc tccatgctgt tcctcatgtt cgcggccctc atgcctactg ttctgacatt | 1500 |
| tcccctggag atgggagtct ttcttcggga acacctgaac tactggtaca gcctgaaggc | 1560 |
| ctactacctg gccaagacca tggcagacgt gcccttcag atcatgttcc cagtggccta | 1620 |
| ctgcagcatc gtgtactgga tgacgtcgca gccgtccgac gccgtgcgct ttgtgctgtt | 1680 |
| tgccgcgctg ggcaccatga cctccctggt ggcacagtcc ctgggcctgc tgatcggagc | 1740 |
| cgcctccacg tccctgcagg tggccacttt cgtgggccca gtgacagcca tcccggtgct | 1800 |
| cctgttctcg gggttcttcg tcagcttcga caccatcccc acgtacctac agtggatgtc | 1860 |
| ctacatctcc tatgtcaggt atgggttcga agggtcatc ctctccatct atggcttaga | 1920 |
| ccgggaagat ctgcactgtg acatcgacga gacgtgccac ttccagaagt cggaggccat | 1980 |
| cctgcgggag ctggacgtgg aaaatgccaa gctgtacctg gacttcatcg tactcggat | 2040 |
| tttcttcatc tccctccgcc tcattgccta ttttgtcctc aggtacaaaa tccgggcaga | 2100 |
| gaggtaaaac acctgaatgc caggaaacag gaagattaga cactgtggcc gagggcacgt | 2160 |
| ctagaatcga ggaggcaagc ctgtgcccga ccgacgacac agagactctt ctgatccaac | 2220 |
| ccctagaacc gcgttgggtt tgtgggtgtc tcgtgctcag ccactctgcc cagctgggtt | 2280 |
| ggatcttctc tccattcccc tttctagctt taactaggaa gatgtaggca gattggtggt | 2340 |
| ttttttttt ttaacataca gaattttaaa taccacaact ggggcagaat ttaaagctgc | 2400 |
| aacacagctg gtgatgagag gcttcctcag tccagtcgct ccttagcacc aggcaccgtg | 2460 |
| ggtcctggat gggggaactgc aagcagcctc tcagctgatg gctgcacagt cagatgtctg | 2520 |
| gtggcagaga gtccgagcat ggagcgattc cattttatga ctgttgtttt tcacattttc | 2580 |
| atctttctaa ggtgtgtctc ttttccaatg agaagtcatt tttgcaagcc aaaagtcgat | 2640 |
| caatcgcatt cattttaaga aattatacct ttttagtact tgctgaagaa tgattcaggg | 2700 |
| taaatcacat actttgttta gagaggcgag gggtttaacc gagtcaccca gctggtctca | 2760 |
| tacatagaca gcacttgtga aggattgaat gcaggttcca ggtggaggga agacgtggac | 2820 |
| accatctcca ctgagccatg cagacatttt taaaagctat acaaaaaatt gtgagaagac | 2880 |
| attggccaac tctttcaaag tcttttcttt tccacgtgct tcttatttta agcgaaatat | 2940 |
| attgtttgtt tcttcctaaa aaaaaaaaa aaaaaaaaa aa | 2982 |

<210> SEQ ID NO 16
<211> LENGTH: 3018
<212> TYPE: DNA
<213> ORGANISM: Homo sapiens

<400> SEQUENCE: 16

| | |
|---|---|
| cgcaccccgc gcagcggctg agccgggagc cagcgcagcc tcggccccgc agctcaagcc | 60 |
| tcgtccccgc cgccgccgcc gccgccgccg ccgccgcccc cggggcatgg cctgtctgat | 120 |
| ggccgctttc tcggtcggca ccgccatgaa tgccagcagt tactctgcag agatgacgga | 180 |
| gcccaagtcg gtgtgtgtct cggtggatga ggtggtgtcc agcaacatgg aggccactga | 240 |
| gacggacctg ctgaatggac atctgaaaaa agtagataat aacctcacgg aagcccagcg | 300 |
| cttctcctcc ttgcctcgga gggcagctgt gaacattgaa ttcagggacc tttcctattc | 360 |
| ggttcctgaa ggaccctggt ggaggaagaa aggatacaag accctcctga aggaatttc | 420 |
| cgggaagttc aatagtggtg agttggtggc cattatgggt ccttccgggg ccgggaagtc | 480 |

```
cacgctgatg aacatcctgg ctggatacag ggagacgggc atgaaggggg ccgtcctcat    540
caacggcctg ccccgggacc tgcgctgctt ccggaaggtg tcctgctaca tcatgcagga    600
tgacatgctg ctgccgcatc tcactgtgca ggaggccatg atggtgtcgg cacatctgaa    660
gcttcaggag aaggatgaag gcagaaggga aatggtcaag gagatactga cagcgctggg    720
cttgctgtct tgcgccaaca cgcggaccgg gagcctgtca ggtggtcagc gcaagcgcct    780
ggccatcgcg ctggagctgg tgaacaaccc tccagtcatg ttcttcgatg agcccaccag    840
cggcctggac agcgcctcct gcttccaggt ggtctcgctg atgaaagggc tcgctcaagg    900
gggtcgctcc atcatttgca ccatccacca gcccagcgcc aaactcttcg agctgttcga    960
ccagctttac gtcctgagtc aaggacaatg tgtgtaccgg ggaaaagtct gcaatcttgt   1020
gccatatttg agggatttgg gtctgaactg cccaacctac cacaacccag cagattttgt   1080
catggaggtt gcatccggcg agtacggtga tcagaacagt cggctggtga gagcggttcg   1140
ggagggcatg tgtgactcag accacaagag agacctcggg ggtgatgccg aggtgaaccc   1200
ttttctttgg caccggccct ctgaagaggt aaagcagaca aaacgattaa aggggttgag   1260
aaaggactcc tcgtccatgg aaggctgcca cagcttctct gccagctgcc tcacgcagtt   1320
ctgcatcctc ttcaagagga ccttcctcag catcatgagg gactcggtcc tgacacacct   1380
gcgcatcacc tcgcacattg ggatcggcct cctcattggc ctgctgtact ggggatcgg    1440
gaacgaagcc aagaaggtct tgagcaactc cggcttcctc ttcttctcca tgctgttcct   1500
catgttcgcg gccctcatgc ctactgttct gacatttccc ctggagatgg gagtctttct   1560
tcgggaacac ctgaactact ggtacagcct gaaggcctac tacctggcca agaccatggc   1620
agacgtgccc tttcagatca tgttcccagt ggcctactgc agcatcgtgt actgatgac    1680
gtcgcagccg tccgacgccg tgcgctttgt gctgttgcc gcgctgggca ccatgacctc   1740
cctggtggca cagtccctgg gcctgctgat cggagccgcc tccacgtccc tgcaggtggc   1800
cactttcgtg ggcccagtga cagccatccc ggtgctcctg ttctcggggt tcttcgtcag   1860
cttcgacacc atccccacgt acctacagtg gatgtcctac atctcctatg tcaggtatgg   1920
gttcgaaggg gtcatcctct ccatctatgg cttagaccgg gaagatctgc actgtgacat   1980
cgacgagacg tgccacttcc agaagtcgga ggcatcctg cgggagctgg acgtggaaaa   2040
tgccaagctg tacctggact tcatcgtact cgggattttc ttcatctccc tccgcctcat   2100
tgcctatttt gtcctcaggt acaaaatccg ggcagagagg taaaacacct gaatgccagg   2160
aaacaggaag attagacact gtggccgagg gcacgtctag aatcgaggag gcaagcctgt   2220
gcccgaccga cgacacagag actcttctga tccaaccct agaaccgcgt tgggtttgtg   2280
ggtgtctcgt gctcagccac tctgcccagc tgggttggat cttctctcca ttcccctttc   2340
tagctttaac taggaagatg taggcagatt ggtggttttt ttttttttaa catacagaat   2400
tttaaatacc acaactgggg cagaatttaa agctgcaaca cagctggtga tgagaggctt   2460
cctcagtcca gtcgctcctt agcaccaggc accgtgggtc ctggatgggg aactgcaagc   2520
agcctctcag ctgatggctg cacagtcaga tgtctggtgg cagagagtcc gagcatggag   2580
cgattccatt ttatgactgt tgttttttcac attttcatct ttctaaggtg tgtctctttt   2640
ccaatgagaa gtcatttttg caagccaaaa gtcgatcaat cgcattcatt ttaagaaatt   2700
ataccttttt agtacttgct gaagaatgat tcagggtaaa tcacatactt tgtttagaga   2760
ggcgaggggt ttaaccgagt cacccagctg gtctcataca tagacagcac ttgtgaagga   2820
ttgaatgcag gttccaggtg gagggaagac gtggacacca tctccactga gccatgcaga   2880
```

-continued

| | |
|---|---|
| catttttaaa agctatacaa aaaattgtga gaagacattg gccaactctt tcaaagtctt | 2940 |
| tcttttttcca cgtgcttctt attttaagcg aaatatattg tttgtttctt cctaaaaaaa | 3000 |
| aaaaaaaaaa aaaaaaaa | 3018 |

<210> SEQ ID NO 17
<211> LENGTH: 2983
<212> TYPE: DNA
<213> ORGANISM: Homo sapiens

<400> SEQUENCE: 17

| | |
|---|---|
| gcgaggggca agcccggatt cctgccggcc gcctttctgc gcgcgccgga gagagagacg | 60 |
| cggtggggac agggatgcgc atttcacttc cccgagctcc ggagagggat ggcggggtgt | 120 |
| cggcgagttc actgctggac acagttacta atgccagcag ttactctgca gagatgacgg | 180 |
| agcccaagtc ggtgtgtgtc tcggtggatg aggtggtgtc cagcaacatg gaggccactg | 240 |
| agacggacct gctgaatgga catctgaaaa agtagagaaa taacctcacg gaagcccagc | 300 |
| gcttctcctc cttgcctcgg agggcagctg tgaacattga attcagggac cttttcctatt | 360 |
| cggttcctga aggaccctgg tggaggaaga aggatacaa gaccctcctg aaaggaattt | 420 |
| ccgggaagtt caatagtggt gagttggtgg ccattatggg tccttccggg gccgggaagt | 480 |
| ccacgctgat gaacatcctg gctggataca gggagacggg catgaagggg gccgtcctca | 540 |
| tcaacggcct gccccgggac ctgcgctgct tccggaaggt gtcctgctac atcatgcagg | 600 |
| atgacatgct gctgccgcat ctcactgtgc aggaggccat gatggtgtcg gcacatctga | 660 |
| agcttcagga aaggatgaa ggcagaaggg aaatggtcaa ggagatactg acagcgctgg | 720 |
| gcttgctgtc ttgcgccaac acgcggaccg ggagcctgtc aggtggtcag cgcaagcgcc | 780 |
| tggccatcgc gctggagctg gtgaacaacc ctccagtcat gttcttcgat gagcccacca | 840 |
| gcggcctgga cagcgcctcc tgcttccagg tggtctcgct gatgaaaggg ctcgctcaag | 900 |
| ggggtcgctc catcatttgc accatccacc agcccagcgc caaactcttc gagctgttcg | 960 |
| accagcttta cgtcctgagt caaggacaat gtgtgtaccg gggaaaagtc tgcaatcttg | 1020 |
| tgccatatt gagggatttg ggtctgaact gcccaaccta ccacaaccca gcagattttg | 1080 |
| tcatggaggt tgcatccggc gagtacggtg atcagaacag tcggctggtg agagcggttc | 1140 |
| gggagggcat gtgtgactca gaccacaaga gagacctcgg gggtgatgcc gaggtgaacc | 1200 |
| cttttctttg gcaccggccc tctgaagagg actcctcgtc catggaaggc tgccacagct | 1260 |
| tctctgccag ctgcctcacg cagttctgca tcctcttcaa gaggaccttc ctcagcatca | 1320 |
| tgagggactc ggtcctgaca cacctgcgca tcacctcgca cattgggatc ggcctcctca | 1380 |
| ttggcctgct gtacttgggg atcgggaacg aagccaagaa ggtcttgagc aactccggct | 1440 |
| tcctcttctt ctccatgctg ttcctcatgt tcgcggccct catgcctact gttctgacat | 1500 |
| tcccctgga gatgggagtc tttcttcggg aacacctgaa ctactggtac agcctgaagg | 1560 |
| cctactacct ggccaagacc atggcagacg tgcccttttca gatcatgttc ccagtggcct | 1620 |
| actgcagcat cgtgtactgg atgacgtcgc agccgtccga cgccgtgcgc tttgtgctgt | 1680 |
| ttgccgcgct gggcaccatg acctcccttgg tggcacagtc cctgggcctg ctgatcggag | 1740 |
| ccgcctccac gtccctgcag gtggccactt tcgtgggccc agtgacagcc atcccggtgc | 1800 |
| tcctgttctc ggggttcttc gtcagcttcg acaccatccc cacgtaccta cagtggatgt | 1860 |
| cctacatctc ctatgtcagg tatgggttcg aaggggtcat cctctccatc tatgcttag | 1920 |
| accgggaaga tctgcactgt gacatcgacg agacgtgcca cttccagaag tcggaggcca | 1980 |

```
tcctgcggga gctggacgtg gaaaatgcca agctgtacct ggacttcatc gtactcggga    2040
ttttcttcat ctccctccgc ctcattgcct attttgtcct caggtacaaa atccgggcag    2100
agaggtaaaa cacctgaatg ccaggaaaca ggaagattag acactgtggc cgagggcacg    2160
tctagaatcg aggaggcaag cctgtgcccg accgacgaca cagagactct tctgatccaa    2220
cccctagaac cgcgttgggt tgtgggtgt ctcgtgctca gccactctgc ccagctgggt    2280
tggatcttct ctccattccc cttctagct ttaactagga agatgtaggc agattggtgg    2340
tttttttttt tttaacatac agaattttaa ataccacaac tggggcagaa tttaaagctg    2400
caacacagct ggtgatgaga ggcttcctca gtccagtcgc tccttagcac caggcaccgt    2460
gggtcctgga tggggaactg caagcagcct ctcagctgat ggctgcacag tcagatgtct    2520
ggtggcagag agtccgagca tggagcgatt ccattttatg actgttgttt ttcacatttt    2580 catcttttcta aggtgtgtct cttttccaat gagaagtcat ttttgcaagc caaaagtcga    2640
tcaatcgcat tcatttaag aaattatacc tttttagtac ttgctgaaga atgattcagg    2700
gtaaatcaca tactttgttt agagaggcga ggggtttaac cgagtcaccc agctggtctc    2760
atacatagac agcacttgtg aaggattgaa tgcaggttcc aggtggaggg aagacgtgga    2820
caccatctcc actgagccat gcagacattt ttaaaagcta tacaaaaaat tgtgagaaga    2880
cattggccaa ctcttttcaaa gtctttcttt tccacgtgc ttcttatttt aagcgaaata    2940
tattgtttgt ttcttcctaa aaaaaaaaaa aaaaaaaaaa aaa                      2983

<210> SEQ ID NO 18
<211> LENGTH: 3142
<212> TYPE: DNA
<213> ORGANISM: Homo sapiens

<400> SEQUENCE: 18
agacactgaa tcatcatttg tagtttgggg ggctttacat gcctgcagtg gtgaaaactg      60
aaattttgtc ccacttaagg gagtttcttc ttcccttat taattgcaaa ataaatatat     120
gtcacttcag agggcagcag ctggactacc tatgtttgtg cgctacacc aacctgaact     180 tcgcttcctg agacctaaga ttcagccccg tgctcagcag acatcaggga tcaccgactc     240
tgtgccagga gctgttcttg atgctgggaa cgcaggggtg gacaaaacag agaaagccct     300
gccctcagaa tgccagcagt tactctgcag agatgacgga gcccaagtcg gtgtgtgtct     360
cggtggatga ggtggtgtcc agcaacatgg aggccactga gacggacctg ctgaatggac     420
atctgaaaaa agtagataat aacctcacgg aagcccagcg cttctcctcc ttgcctcgga     480
gggcagctgt gaacattgaa ttcagggacc tttcctattc ggttcctgaa ggaccctggt     540
ggaggaagaa aggatacaag accctcctga aggaatttc cgggaagttc aatagtggtg     600
agttggtggc cattatgggt ccttccgggg ccgggaagtc cacgctgatg aacatcctgg     660
ctggatacag ggagacgggc atgaagggg ccgtcctcat caacggcctg ccccgggacc     720
tgcgctgctt ccggaaggtg tcctgctaca tcatgcagga tgacatgctg ctgccgcatc     780
tcactgtgca ggaggccatg atggtgtcgg cacatctgaa gcttcaggag aaggatgaag     840
gcagaaggga aatggtcaag gagatactga cagcgctggg cttgctgtct tgcgccaaca     900
cgcggaccgg gagcctgtca ggtggtcagc gcaagcgcct ggccatcgcg ctggagctgg     960
tgaacaaccc tccagtcatg ttcttcgatg agcccaccag cggcctggac agcgcctcct    1020
gcttccaggt ggtctcgctg atgaaggggc tcgctcaagg gggtcgctcc atcatttgca    1080
ccatccacca gcccagcgcc aaactcttcg agctgttcga ccagctttac gtcctgagtc    1140
```

```
aaggacaatg tgtgtaccgg ggaaaagtct gcaatcttgt gccatatttg agggatttgg    1200
gtctgaactg cccaacctac cacaacccag cagattttgt catggaggtt gcatccggcg    1260
agtacggtga tcagaacagt cggctggtga gagcggttcg ggagggcatg tgtgactcag    1320
accacaagag agacctcggg ggtgatgccg aggtgaaccc ttttctttgg caccggccct    1380
ctgaagagga ctcctcgtcc atggaaggct gccacagctt ctctgccagc tgcctcacgc    1440
agttctgcat cctcttcaag aggaccttcc tcagcatcat gagggactcg gtcctgacac    1500
acctgcgcat cacctcgcac attgggatcg gcctcctcat tggcctgctg tacttgggga    1560
tcgggaacga agccaagaag gtcttgagca actccggctt cctcttcttc tccatgctgt    1620
tcctcatgtt cgcggccctc atgcctactg ttctgacatt tccctgag atgggagtct    1680 ttcttcggga cacctgaac tactggtaca gcctgaaggc ctactacctg ccaagacca    1740 tggcagacgt gcccttcag atcatgttcc cagtggccta ctgcagcatc gtgtactgga    1800
tgacgtcgca gccgtccgac gccgtgcgct ttgtgctgtt gccgcgctg ggcaccatga    1860 cctccctggt ggcacagtcc ctgggcctgc tgatcggagc cgcctccacg tccctgcagg    1920
tggccacttt cgtgggccca gtgacagcca tcccggtgct cctgttctcg ggttcttcg    1980 tcagcttcga caccatcccc acgtacctac agtggatgtc ctacatctcc tatgtcaggt    2040
atgggttcga aggggtcatc ctctccatct atggcttaga ccgggaagat ctgcactgtg    2100
acatcgacga gacgtgccac ttccagaagt cggaggccat cctgcgggag ctggacgtgg    2160
aaaatgccaa gctgtacctg gacttcatcg tactcgggat tttcttcatc tccctccgcc    2220
tcattgccta ttttgtcctc aggtacaaaa tccgggcaga gaggtaaaac acctgaatgc    2280
caggaaacag gaagattaga cactgtggcc gagggcacgt ctagaatcga ggaggcaagc    2340
ctgtgcccga ccgacgacac agagactctt ctgatccaac ccctagaacc gcgttgggtt    2400
tgtgggtgtc tcgtgctcag ccactctgcc cagctgggtt ggatcttctc tccattcccc    2460
tttctagctt taactaggaa gatgtaggca gattggtggt tttttttttt ttaacataca    2520
gaattttaaa taccacaact ggggcagaat ttaaagctgc aacacagctg gtgatgagag    2580
gcttcctcag tccagtcgct ccttagcacc aggcaccgtg ggtcctggat ggggaactgc    2640
aagcagcctc tcagctgatg gctgcacagt cagatgtctg gtggcagaga gtccgagcat    2700
ggagcgattc catttatga ctgttgtttt tcacattttc atctttctaa ggtgtgtctc    2760
ttttccaatg agaagtcatt tttgcaagcc aaaagtcgat caatcgcatt catttttaaga    2820 aattatacct ttttagtact tgctgaagaa tgattcaggg taaatcacat actttgttta    2880
gagaggcgag gggtttaacc gagtcaccca gctggtctca tacatagaca gcacttgtga    2940
aggattgaat gcaggttcca ggtggaggga agacgtggac accatctcca ctgagccatg    3000
cagacatttt taaagctat acaaaaaatt gtgagaagac attggccaac tctttcaaag    3060
tctttctttt tccacgtgct tcttatttta agcgaaatat attgtttgtt tcttcctaaa    3120
aaaaaaaaaa aaaaaaaaaa aa                                              3142

<210> SEQ ID NO 19
<211> LENGTH: 3060
<212> TYPE: DNA
<213> ORGANISM: Homo sapiens

<400> SEQUENCE: 19
acttcagagg gcagcagctg gactacctat gtttgtggcg ctacaccaac ctgaacttcg     60
cttcctgaga cctaagattc agccccgtgc tcagcagaca tcagggatca ccgactctgt    120
```

```
gccaggagct gttcttgatg ctgggaacgc aggggtggac aaaacagaga aagccctgcc    180
ctcagtgaga aatatgctgt catgtaaatt gcttttttccc ctatagaatg ccagcagtta   240
ctctgcagag atgacggagc ccaagtcggt gtgtgtctcg gtggatgagg tggtgtccag    300
caacatggag gccactgaga cggacctgct gaatggacat ctgaaaaaag tagataataa    360
cctcacggaa gcccagcgct tctcctcctt gcctcggagg gcagctgtga acattgaatt    420
cagggacctt tcctattcgg ttcctgaagg accctggtgg aggaagaaag gatacaagac    480
cctcctgaaa ggaatttccg ggaagttcaa tagtggtgag ttggtggcca ttatgggtcc    540
ttccggggcc gggaagtcca cgctgatgaa catcctggct ggatacaggg agacgggcat    600 gaaggggggcc gtcctcatca acggcctgcc ccgggacctg cgctgcttcc ggaaggtgtc    660
ctgctacatc atgcaggatg acatgctgct gccgcatctc actgtgcagg aggccatgat    720
ggtgtcggca catctgaagc ttcaggagaa ggatgaaggc agaagggaaa tggtcaagga    780
gatactgaca gcgctgggct tgctgtcttg cgccaacacg cggaccggga gcctgtcagg    840
tggtcagcgc aagcgcctgg ccatcgcgct ggagctggtg aacaaccctc cagtcatgtt    900
cttcgatgag cccaccagcg gcctggacag cgcctcctgc ttccaggtgg tctcgctgat    960
gaaagggctc gctcaagggg gtcgctccat catttgcacc atccaccagc ccagcgccaa   1020
actcttcgag ctgttcgacc agctttacgt cctgagtcaa ggacaatgtg tgtaccgggg   1080
aaaagtctgc aatcttgtgc catatttgag ggatttgggt ctgaactgcc aacctacca   1140 caacccagca gattttgtca tggaggttgc atccggcgag tacggtgatc agaacagtcg   1200
gctggtgaga gcggttcggg agggcatgtg tgactcagac cacaagagag acctcggggg   1260
tgatgccgag gtgaaccctt tcctttggca ccggccctct gaagaggact cctcgtccat   1320
ggaaggctgc cacagcttct ctgccagctg cctcacgcag ttctgcatcc tcttcaagag   1380
gaccttcctc agcatcatga gggactcggt cctgacacac ctgcgcatca cctcgcacat   1440
tgggatcggc ctcctcattg gcctgctgta cttggggatc gggaacgaag ccaagaaggt   1500
cttgagcaac tccggcttcc tcttcttctc catgctgttc ctcatgttcg cggccctcat   1560
gcctactgtt ctgacatttc ccctggagat gggagtcttt cttcgggaac acctgaacta   1620
ctggtacagc ctgaaggcct actacctggc caagaccatg gcagacgtgc cctttcagat   1680
catgttccca gtggcctact gcagcatcgt gtactggatg acgtcgcagc cgtccgacgc   1740
cgtgcgcttt gtgctgtttg ccgcgctggg caccatgacc tccctggtgg cacagtccct   1800
gggcctgctg atcggagccg cctccacgtc cctgcaggtg gccactttcg tgggcccagt   1860
gacagccatc ccggtgctcc tgttctcggg gttcttcgtc agcttcgaca ccatccccac   1920
gtacctacag tggatgtcct acatctccta tgtcaggtat gggttcgaag gggtcatcct   1980
ctccatctat ggcttagacc gggaagatct gcactgtgac atcgacgaga cgtgccactt   2040
ccagaagtcg gaggccatcc tgcgggagct ggacgtggaa aatgccaagc tgtacctgga   2100
cttcatcgta ctcgggattt tcttcatctc cctccgcctc attgcctatt ttgtcctcag   2160
gtacaaaatc cggcagagaa ggtaaaacac ctgaatgcca ggaaacagga agattagaca   2220
ctgtggccga gggcacgtct agaatcgagg aggcaagcct gtcccgacc gacgacacag    2280 agactcttct gatccaaccc ctagaaccgc gttgggtttg tgggtgtctc gtgctcagcc    2340
actctgccca gctgggttgg atcttctctc cattccccctt tctagctttta actaggaaga   2400 tgtaggcaga ttggtggttt ttttttttttt aacatacaga atttttaaata ccacaactgg    2460 ggcagaattt aaagctgcaa cacagctggt gatgagaggc ttcctcagtc cagtcgctcc    2520
```

| | |
|---|---|
| ttagcaccag gcaccgtggg tcctggatgg ggaactgcaa gcagcctctc agctgatggc | 2580 |
| tgcacagtca gatgtctggt ggcagagagt ccgagcatgg agcgattcca ttttatgact | 2640 |
| gttgttttc acattttcat ctttctaagg tgtgtctctt ttccaatgag aagtcatttt | 2700 |
| tgcaagccaa aagtcgatca atcgcattca ttttaagaaa ttatacccttt ttagtacttg | 2760 |
| ctgaagaatg attcagggta aatcacatac tttgtttaga gaggcgaggg gtttaaccga | 2820 |
| gtcacccagc tggtctcata catagacagc acttgtgaag gattgaatgc aggttccagg | 2880 |
| tggagggaag acgtggacac catctccact gagccatgca gacatttttta aaagctatac | 2940 |
| aaaaaattgt gagaagacat tggccaactc tttcaaagtc tttcttttc cacgtgcttc | 3000 |
| ttattttaag cgaaatatat tgtttgtttc ttcctaaaaa aaaaaaaaaa aaaaaaaaa | 3060 |

<210> SEQ ID NO 20
<211> LENGTH: 2946
<212> TYPE: DNA
<213> ORGANISM: Homo sapiens
<400> SEQUENCE: 20

| | |
|---|---|
| gctttataaa ggggagtttc cctgcacaag ctctctctct tgtctgccgc catgtgagac | 60 |
| atgcctttca ccttccgcca tgatcatgag gcttccccag ccacatggaa ctaatgccag | 120 |
| cagttactct gcagagatga cggagcccaa gtcggtgtgt gtctcggtgg atgaggtggt | 180 |
| gtccagcaac atggaggcca ctgagacgga cctgctgaat ggacatctga aaaagtaga | 240 |
| taataacctc acgaagccc agcgcttctc ctccttgcct cggagggcag ctgtgaacat | 300 |
| tgaattcagg gaccttttcct attcggttcc tgaaggaccc tggtggagga agaaaggata | 360 |
| caagacccctc ctgaaaggaa tttccgggaa gttcaatagt ggtgagttgg tggccattat | 420 |
| gggtccttcc ggggccggga agtccacgct gatgaacatc ctggctggat acaggggagac | 480 |
| gggcatgaag ggggccgtcc tcatcaacgg cctgccccgg gacctgcgct gcttccggaa | 540 |
| ggtgtcctgc tacatcatgc aggatgacat gctgctgccg catctcactg tgcaggaggc | 600 |
| catgatggtg tcggcacatc tgaagcttca ggagaaggat gaaggcagaa gggaaatggt | 660 |
| caaggagata ctgacagcgc tgggcttgct gtcttgcgcc aacacgcgga ccgggagcct | 720 |
| gtcaggtggt cagcgcaagc gcctggccat cgcgctggag ctggtgaaca ccctccagt | 780 |
| catgttcttc gatgagccca ccagcggcct ggacagcgcc tcctgcttcc aggtggtctc | 840 |
| gctgatgaaa gggctcgctc aagggggtcg ctccatcatt tgcaccatcc accagcccag | 900 |
| cgccaaactc ttcgagctgt tcgaccagct ttacgtcctg agtcaaggac aatgtgtgta | 960 |
| ccggggaaaa gtctgcaatc ttgtgccata tttgagggat ttgggtctga actgcccaac | 1020 |
| ctaccacaac ccagcagatt ttgtcatgga ggttgcatcc ggcgagtacg gtgatcagaa | 1080 |
| cagtcggctg gtgagagcgg ttcgggaggg catgtgtgac tcagaccaca agagagacct | 1140 |
| cgggggtgat gccgaggtga acccttttct ttggcaccgg ccctctgaag aggactcctc | 1200 |
| gtccatggaa ggctgccaca gcttctctgc cagctgcctc acgcagttct gcatcctctt | 1260 |
| caagaggacc ttcctcagca tcatgaggga ctcggtcctg acacacctgc gcatcacctc | 1320 |
| gcacattggg atcggcctcc tcattggcct gctgtacttg gggatcggga acgaagccaa | 1380 |
| gaaggtcttg agcaactccg gcttcctctt cttctccatg ctgttcctca tgttcgcggc | 1440 |
| cctcatgcct actgttctga catttccccct ggagatggga gtctttcttc gggaacacct | 1500 |
| gaactactgg tacagcctga aggcctacta cctggccaag accatggcag acgtgccctt | 1560 |
| tcagatcatg ttcccagtgg cctactgcag catcgtgtac tggatgacgt cgcagccgtc | 1620 |

```
cgacgccgtg cgctttgtgc tgtttgccgc gctgggcacc atgacctccc tggtggcaca    1680
gtccctgggc ctgctgatcg gagccgcctc cacgtccctg caggtggcca ctttcgtggg    1740
cccagtgaca gccatcccgg tgctcctgtt ctcggggttc ttcgtcagct tcgacaccat    1800
ccccacgtac ctacagtgga tgtcctacat ctcctatgtc aggtatgggt tcgaaggggt    1860
catcctctcc atctatggct tagaccggga agatctgcac tgtgacatcg acgagacgtg    1920
ccacttccag aagtcggagg ccatcctgcg ggagctggac gtggaaaatg ccaagctgta    1980
cctggacttc atcgtactcg ggattttctt catctccctc cgcctcattg cctattttgt    2040
cctcaggtac aaaatccggg cagagaggta aaacacctga atgccaggaa acaggaagat    2100
tagacactgt ggccgagggc acgtctagaa tcgaggaggc aagcctgtgc ccgaccgacg    2160
acacagagac tcttctgatc caaccctag aaccgcgttg ggtttgtggg tgtctcgtgc     2220
tcagccactc tgcccagctg ggttggatct tctctccatt ccctttcta gctttaacta    2280 ggaagatgta ggcagattgg tggttttttt ttttttaaca tacagaattt taaataccac    2340
aactggggca gaatttaaag ctgcaacaca gctggtgatg agaggcttcc tcagtccagt    2400
cgctccttag caccaggcac cgtgggtcct ggatggggaa ctgcaagcag cctctcagct    2460
gatggctgca cagtcagatg tctggtggca gagagtccga gcatggagcg attccatttt    2520
atgactgttt ttttcacat tttcatcttt ctaaggtgtg tctcttttcc aatgagaagt     2580 cattttgca agccaaaagt cgatcaatcg cattcatttt aagaaattat accttttag      2640 tacttgctga agaatgattc agggtaaatc acatactttg tttagagagg cgagggttt     2700 aaccgagtca cccagctggt ctcatacata gacagcactt gtgaaggatt gaatgcaggt    2760
tccaggtgga gggaagacgt ggacaccatc tccactgagc catgcagaca tttttaaaag    2820
ctatacaaaa aattgtgaga agacattggc caactctttc aaagtctttc ttttccacg    2880 tgcttcttat tttaagcgaa atatattgtt tgtttcttcc taaaaaaaaa aaaaaaaaa    2940 aaaaaa                                                               2946
```

<210> SEQ ID NO 21
<211> LENGTH: 3498
<212> TYPE: DNA
<213> ORGANISM: Homo sapiens

<400> SEQUENCE: 21

```
ttctttccaa gggtctctgg gtgaggcccg tgaccttccc aagcctctcc ctgtcttgtg      60
aaacctgggc gtgatatacc tccctttag ggctgctgcg atcatttagg cagattaaac     120
ctcataagtg gtttcccata caagaaagat gctagcagtg caacagacag aacacttacc     180
tgcctgccct cccgccagga ggtggtcttc caacttttgc ccggagtcta cagagggtgg     240
gccctctctg ctggggctcc gggacatggt caggagaggt tggtctgtct gtaccgccat     300
tctcttggcc agactgtggt gtctggtccc tactcacacc ttcctgtcag agtatccaga     360
ggccgcagag tatccacacc ctggctgggt gtactggcta cagatggctg tggctccagg     420
tcacctgcgt gcctgggtga tgagaaataa tgtcacaaca aatatcccat ctgcattctc     480
tgggacactg acccatgaag agaaagcagt tctcacagtt tttacaggca cagccacagc     540
cgtgcatgta caggtggcag ctttagcttc tgctaaactg gagagctcag tgtttgtgac     600
agactgcgtg tcctgcaaaa tcgaaaatgt ctgtgattca gctcttcagg gaaaagggt      660 gccgatgtct ggcctacagg gctcaagcat tgtcatcatg cccccatcca accgtccact     720
cgccagtgcg gcatcctgca cgtggtcagt ccaagtccag ggagggcccc atcacctggg     780
```

```
ggtggtcgct atcagtggca aagtcttgtc agcagctcat ggggcaggaa gggcctatgg    840
ttgggggttt cctggcgatc ccatggagga aggatacaag accctcctga aaggaatttc    900
cgggaagttc aatagtggtg agttggtggc cattatgggt ccttccgggg ccgggaagtc    960
cacgctgatg aacatcctgg ctggatacag ggagacgggc atgaaggggg ccgtcctcat   1020
caacggcctg ccccgggacc tgcgctgctt ccggaaggtg tcctgctaca tcatgcagga   1080
tgacatgctg ctgccgcatc tcactgtgca ggaggccatg atggtgtcgg cacatctgaa   1140
gcttcaggag aaggatgaag gcagaaggga aatggtcaag gagatactga cagcgctggg   1200
cttgctgtct tgcgccaaca cgcggaccgg gagcctgtca ggtggtcagc gcaagcgcct   1260
ggccatcgcg ctggagctgg tgaacaaccc tccagtcatg ttcttcgatg agcccaccag   1320
cggcctggac agcgcctcct gcttccaggt ggtctcgctg atgaaagggc tcgctcaagg   1380
gggtcgctcc atcatttgca ccatccacca gcccagcgcc aaactcttcg agctgttcga   1440
ccagctttac gtcctgagtc aaggacaatg tgtgtaccgg ggaaaagtct gcaatcttgt   1500
gccatatttg agggatttgg gtctgaactg cccaacctac cacaacccag cagattttgt   1560
catggaggtt gcatccggcg agtacggtga tcagaacagt cggctggtga gagcggttcg   1620
ggagggcatg tgtgactcag accacaagag agacctcggg ggtgatgccg aggtgaaccc   1680
ttttctttgg caccggccct ctgaagaggt aaagcagaca aaacgattaa aggggttgag   1740
aaaggactcc tcgtccatgg aaggctgcca cagcttctct gccagctgcc tcacgcagtt   1800
ctgcatcctc ttcaagagga ccttcctcag catcatgagg gactcggtcc tgacacacct   1860
gcgcatcacc tcgcacattg ggatcggcct cctcattggc ctgctgtact ggggatcgg   1920
gaacgaagcc aagaaggtct tgagcaactc cggcttcctc ttcttctcca tgctgttcct   1980
catgttcgcg gccctcatgc ctactgttct gacatttccc ctggagatgg gagtctttct   2040
tcgggaacac ctgaactact ggtacagcct gaaggcctac tacctggcca agaccatggc   2100
agacgtgccc tttcagatca tgttcccagt ggcctactgc agcatcgtgt actggatgac   2160
gtcgcagccg tccgacgccg tgcgctttgt gctgtttgcc gcgctgggca ccatgacctc   2220
cctggtggca cagtccctgg gcctgctgat cggagccgcc tccacgtccc tgcaggtggc   2280
cactttcgtg ggcccagtga cagccatccc ggtgctcctg ttctcggggt tcttcgtcag   2340
cttcgacacc atccccacgt acctacagtg gatgtcctac atctcctatg tcaggtatgg   2400
gttcgaaggg gtcatcctct ccatctatgg cttagaccgg gaagatctgc actgtgacat   2460
cgacgagacg tgccacttcc agaagtcgga ggccatcctg cgggagctgg acgtggaaaa   2520
tgccaagctg tacctggact tcatcgtact cgggattttc ttcatctccc tccgcctcat   2580
tgcctatttt gtcctcaggt acaaaatccg ggcagagagg taaaacacct gaatgccagg   2640
aaacaggaag attagacact gtggccgagg gcacgtctag aatcgaggag gcaagcctgt   2700
gcccgaccga cgacacagag actcttctga tccaaccccct agaaccgcgt tgggtttgtg   2760
ggtgtctcgt gctcagccac tctgcccagc tgggttggat cttctctcca ttccccttc   2820
tagctttaac taggaagatg taggcagatt ggtggttttt tttttttttaa catacagaat   2880
tttaaatacc acaactgggg cagaatttaa agctgcaaca cagctggtga tgagaggctt   2940
cctcagtcca gtcgctcctt agcaccaggc accgtgggtc ctggatgggg aactgcaagc   3000
agcctctcag ctgatggctg cacagtcaga tgtctggtgg cagagagtcc gagcatggag   3060
cgattccatt ttatgactgt tgttttttcac attttcatct ttctaaggtg tgtctctttt   3120
ccaatgagaa gtcattttg caagccaaaa gtcgatcaat cgcattcatt ttaagaaatt   3180
```

| | |
|---|---|
| atacctttt agtacttgct gaagaatgat tcagggtaaa tcacatactt tgtttagaga | 3240 |
| ggcgagggt ttaaccgagt cacccagctg gtctcataca tagacagcac ttgtgaagga | 3300 |
| ttgaatgcag gttccaggtg gagggaagac gtggacacca tctccactga gccatgcaga | 3360 |
| cattttaaa agctatacaa aaaattgtga gaagacattg gccaactctt tcaaagtctt | 3420 |
| tcttttcca cgtgcttctt attttaagcg aaatatattg tttgtttctt cctaaaaaaa | 3480 |
| aaaaaaaaaa aaaaaaaa | 3498 |

<210> SEQ ID NO 22
<211> LENGTH: 3400
<212> TYPE: DNA
<213> ORGANISM: Homo sapiens

<400> SEQUENCE: 22

| | |
|---|---|
| ggaaccgccg ccggtatccg cgtccgcagc gccgccagcc aggcgagagc cgtgtgggat | 60 |
| cccagcgccc gcactcccgc ccccgccaag gagccaggaa tggcacaact agagaggagc | 120 |
| gccatctctg gcttcagctc taagtccagg cgaaactcat tcgcatatga tgttaagcgt | 180 |
| gaagtataca atgaggagac cttcaacag gaacacaaaa ggaaggcctc ctcttctggg | 240 |
| aacatgaaca tcaacatcac caccttcaga caccacgtcc agtgccgctg ctcatggcac | 300 |
| aggttcctac gatgcgtgct tacaatcttt cccttcctag aatggatgtg tatgtatcga | 360 |
| ttaaaggatt ggcttctggg agacttactt gctggtataa gtgttggcct tgtgcaagtt | 420 |
| ccccaaggcc tgacacttag tttgctggca aggcaactga ttcctcctct caacatcgct | 480 |
| tatgcagctt tctgttcttc ggtaatctat gtaattttg gatcgtgtca tcaaatgtcc | 540 |
| attggttcct tcttcctggt gagtgctctg ctgatcaacg ttctgaaagt gagcccattc | 600 |
| aacaacggtc aactggtcat gggatctttc gtcaagaatg agttttcggc ccctcctac | 660 |
| cttatgggct ataataaatc cttgagtgtg gtggcaacca caacttttct gactgggatt | 720 |
| attcagctaa taatgggcgt attgggtttg ggcttcattg ccacttacct tccggagtct | 780 |
| gcaatgagtg cttacctggc tgctgtggca cttcatatca tgctgtccca gctgactttc | 840 |
| atctttggga ttatgattag tttccatgcc ggtcccatct ccttcttcta tgacataatt | 900 |
| aattactgtg tagctctccc aaaagcgaat tccaccagca ttctagtatt tctaactgtt | 960 |
| gttgttgctc tgcgaatcaa caaatgtatc agaatttctt tcaatcagta tcccattgag | 1020 |
| tttcccatgg aatttattct gattattggc ttcactgtga ttgcaaacaa gataagcatg | 1080 |
| gccacagaaa ccagccagac gcttattgac atgattcctt atagctttct gcttcctgta | 1140 |
| acaccagatt tcagccttct tcccaagata attttacaag ccttctcctt atctttggtg | 1200 |
| agctcctttc tgctcatatt tctgggcaag aagattgcca gtcttcacaa ttacagtgtc | 1260 |
| aattccaacc aggatttaat agccatcggc ctttgcaatg tcgtcagttc atttttcaga | 1320 |
| tcttgtgtgt ttactggtgc tattgctagg actattatcc aggataaatc tggaggaaga | 1380 |
| caacagtttg catctctggt aggcgcaggt gtgatgctgc tcctgatggt gaagatggga | 1440 |
| cactttttct acacactgcc aaatgctgtg ctggctggta ttattctgag caacgtcatt | 1500 |
| ccctaccttg aaaccatttc taacctaccc agcctgtgga ggcaggacca atatgactgt | 1560 |
| gctctttgga tgatgacatt ctcatcttca attttcctgg gactggacat tggactaatt | 1620 |
| atctcagtag tttctgcttt cttcatcacc actgttcgtt cacacagagc taagattctt | 1680 |
| ctcctgggtc aaatccctaa caccaacatt tatagaagca tcaatgatta tcgggagatc | 1740 |
| atcaccattc ctgggggtgaa aatcttccag tgctgcagct caattacatt tgtaaatgtt | 1800 |

```
tactacctaa agcataagct gttaaaagag gttgatatgg taaaggtgcc tcttaaagaa    1860
gaagaaattt tcagcttgtt taattcaagt gacaccaatc tacaaggagg aaagatttgc    1920
aggtgtttct gcaactgtga tgatctggag ccgctgccca ggattcttta cacagagcga    1980
tttgaaaata aactggatcc cgaagcatcc tccattaacc tgattcactg ctcacatttt    2040
gagagcatga acacaagcca aactgcatcc gaagaccaag tgccatacac agtatcgtcc    2100
gtgtctcaga aaatcaagg gcaacagtat gaggaggtgg aggaagtttg cttcctaat     2160 aactcatcaa gaaacagctc accaggactg cctgatgtgg cggaaagcca ggggaggaga    2220
tcactcatcc cttactcaga tgcgtctcta ctgcccagtg tccacaccat catcctggat    2280
ttctccatgg tacactacgt ggattcacgg gggttagtcg tattaagaca gatatgcaat    2340
gcctttcaaa acgccaacat tttgatactc attgcagggt gtcactcttc catagtcagg    2400
gcatttgaga ggaatgattt ctttgacgct ggcatcacca agacccagct gttcctcagc    2460
gttcacgacg ccgtgctgtt tgccttgtca aggaaggtca taggctcctc tgagttaagc    2520
atcgatgaat ccgagacagt gatacgggaa acctactcag aaacagacaa gaatgacaat    2580
tcaagatata aaatgagcag cagttttcta ggaagccaaa aaaatgtaag tccaggcttc    2640
atcaagatcc aacagcctgt agaagaggag tcggagttgg atttggagct ggaatcagaa    2700
caagaggctg ggctgggtct ggacctagac ctggatcggg agctggagcc tgaaatggag    2760
cccaaggctg agaccgagac caagacccag accgagatgg agcccagcc tgagactgag     2820 cctgagatgg agcccaaccc caaatctagg ccaagagctc acactttcc tcagcagcgt     2880 tactggccta tgtatcatcc gtctatggct tccacccagt ctcagactca gactcggaca    2940
tggtcagtgg agaggagacg ccatcctatg gattcatact caccagaggg caacagcaat    3000
gaagatgtct aggagatgaa ctagaaataa ggggtcagat aatgctggca aatcctccta    3060
cccaaaaagg ggtcaattgt ccagagacct agactggata cgaactagca gtacttcctt    3120
cctgactgtg actcctacta cctgccagcc ttcttccttg ctctgcgctg ggatcatact    3180
cccaaatcac attactaaat gccaacaatt atctctgaat tccctatcca ggctcccctc    3240
atttcacctt cagcatatat tctagtcatg aatttccttc ttcacacacc ccacatctct    3300
gggctttgtg ccagaccatc tctaacttaa tcctctcatc cctgttcccc tttctccaaa    3360
gagatgaagc tcaaataaaa tgtataactc tagtaaaaaa                          3400

<210> SEQ ID NO 23
<211> LENGTH: 977
<212> TYPE: DNA
<213> ORGANISM: Homo sapiens

<400> SEQUENCE: 23
attgaatgca gcaagggtct ggaggctgag gaccaggcag acaaacattc agagttgctg      60
gaatgcgaca gagacaggga gtcagactgg tcatgcaagg ccagctctgg ggtctcggca     120
ggtggtccgc gacatgacct ccgagttctt ctctgcccag ctccgggccc agatctctga     180
cgacaccact caccccgatct cctactacaa gcccgagttc tacatgccgg atgacggggg     240
cactgctcac ctgtctgtgg tcgcagagga cggcagtgct gtgtccgcca ccagcaccat     300
caacctctac tttggctcca aggtgcgctc cccagtcagc gggatcctgc tcaataatga     360
aatggatgac ttcagctcta ccagcatcac caacgagttt ggggtacccc cctcacctgc     420
caatttcatc cagccaggga agcagccgct ctcgtccatg tgcccgacga tcatggtggg     480
ccaggacggc caggtccgga tggtggtggg agctgccggg gcacgcagga tcaccatggc     540
```

```
cactgcactg gccatcatct acaacctctg gttcggctat gacgtgaagt gggccgtgga    600
ggagccccgg ctgcacaacc agcttctgcc caacgtcacg acagtggaga gaaacattga    660
ccaggaagtg actgcagccc tggagacccg gcaccatcac acccagatca cgtccacctt    720
cattgctgtg gtgcaagcca tcgtccgcat ggctggtggc tgggcagctg cctcggactc    780
caggaaaggt ggggaacctg ctggctactg attgctccag gcggacaagg ctgacaagca    840
atccaggaac aaaatactca ccaggacgag gaagaggact ttgggggaca ggcttctcct    900
gtgagcagca gagcagcaca ataaatgagg ccactgtgcc aggctccagg tggcctccct    960
ggcctgtctc cccactc    977

<210> SEQ ID NO 24
<211> LENGTH: 1049
<212> TYPE: DNA
<213> ORGANISM: Homo sapiens

<400> SEQUENCE: 24
ctcgagagct gggctctgcg tcctcgtcca gccgccaact cggccaaagg cgaagccagc     60
agtttcttct gctgccgggc aacgcgcctt ttaaacctga gggagtgggc gcgtgagcac    120
ttaatggcgc cggtgacaga gtgagcttaa cggattaata agcgcagcca ggccagctct    180
ggggtctcgg caggtggtcc gcgacatgac ctccgagttc ttctctgccc agctccgggc    240
ccagatctct gacgacacca ctcacccgat ctcctactac aagcccgagt tctacatgcc    300
ggatgacggg ggcactgctc acctgtctgt ggtcgcagag gacggcagtg ctgtgtccgc    360
caccagcacc atcaacctct actttggctc caaggtgcgc tccccagtca gcgggatcct    420
gctcaataat gaaatggatg acttcagctc taccagcatc accaacgagt ttggggtacc    480
cccctcacct gccaatttca tccagccagg gaagcagccg ctctcgtcca tgtgcccgac    540
gatcatggtg ggccaggacg gccaggtccg gatggtggtg ggagctgccg ggggcacgca    600
gatcaccatg gccactgcac tggccatcat ctacaacctc tggttcggct atgacgtgaa    660
gtgggccgtg gaggagcccc ggctgcacaa ccagcttctg cccaacgtca cgacagtgga    720
gagaaacatt gaccaggaag tgactgcagc cctggagacc cggcaccatc acacccagat    780
cacgtccacc ttcattgctg tggtgcaagc catcgtccgc atggctggtg gctgggcagc    840
tgcctcggac tccaggaaag gtggggaacc tgctggctac tgattgctcc aggcggacaa    900
ggctgacaag caatccagga acaaaatact caccaggacg aggaagagga ctttggggga    960
caggcttctc ctgtgagcag cagagcagca caataaatga ggccactgtg ccaggctcca   1020
ggtggcctcc ctggcctgtc tccccactc   1049

<210> SEQ ID NO 25
<211> LENGTH: 1108
<212> TYPE: DNA
<213> ORGANISM: Homo sapiens

<400> SEQUENCE: 25
attgaatgca gcaagggtct ggaggctgag gaccaggcag acaaacattc agagttgctg     60
gaatgcgaca gagacaggga gtcagactgg tcatgcaagg tcctgggcct gcccttgggt    120
cctggggagc cacggaaggt tgtgggtgcc agagggttgt ggtcagagcc acagtcaggg    180
gccttctgag acctgtgccc cctccccacc ctccctcccc acctccctag gccagctctg    240
gggtctcggc aggtggtccg cgacatgacc tccgagttct tctctgccca gctccgggcc    300
cagatctctg acgacaccac tcacccgatc tcctactaca agcccgagtt ctacatgccg    360
```

```
gatgacgggg gcactgctca cctgtctgtg gtcgcagagg acggcagtgc tgtgtccgcc    420
accagcacca tcaacctcta ctttggctcc aaggtgcgct ccccagtcag cgggatcctg    480
ctcaataatg aaatggatga cttcagctct accagcatca ccaacgagtt tggggtaccc    540
ccctcacctg ccaatttcat ccagccaggg aagcagccgc tctcgtccat gtgcccgacg    600
atcatggtgg gccaggacgg ccaggtccgg atggtggtgg gagctgccgg gggcacgcag    660
atcaccatgg ccactgcact ggccatcatc tacaacctct ggttcggcta tgacgtgaag    720
tgggccgtgg aggagccccg gctgcacaac cagcttctgc ccaacgtcac gacagtggag    780
agaaacattg accaggaagt gactgcagcc ctggagaccc ggcaccatca cacccagatc    840
acgtccacct tcattgctgt ggtgcaagcc atcgtccgca tggctggtgg ctgggcagct    900
gcctcggact ccaggaaagg tggggaacct gctggctact gattgctcca ggcggacaag    960
gctgacaagc aatccaggaa caaaatactc accaggacga ggaagaggac tttggggggac   1020 aggcttctcc tgtgagcagc agagcagcac aataaatgag gccactgtgc caggctccag   1080
gtggcctccc tggcctgtct ccccactc                                      1108

<210> SEQ ID NO 26
<211> LENGTH: 2414
<212> TYPE: DNA
<213> ORGANISM: Homo sapiens

<400> SEQUENCE: 26
gtcagagtct tccctcagct ttgtacatca gcactgtttt gatagataag agaggctact     60
gtataagtgt gtaagatttg taatggactg aggaatgctt gttctagctg ctgaaactga    120
ctgtaactgt attgtcttag gagcatcatc atggggtcta gtgccacaga gattgaagaa    180
ttggaaaaca ccacttttaa gtatcttaca ggagaacaga ctgaaaaaat gtggcagcgc    240
ctgaaaggaa tactaagatg cttggtgaag cagctggaaa gaggtgatgt taacgtcgtc    300
gacttaaaga agaatattga atatgcggca tctgtgctgg aagcagttta tatcgatgaa    360
acaagaagac ttctggatac tgaagatgag ctcagtgaca ttcagactga ctcagtccca    420
tctgaagtcc gggactggtt ggcttctacc tttacacgga aaatggggat gacaaaaaag    480
aaacctgagg aaaaaccaaa atttcggagc attgtgcatg ctgttcaagc tggaattttt    540
gtggaaagaa tgtaccgaaa acatatcat atggttggtt tggcatatcc agcagctgtc    600
atcgtaacat taaggatgt tgataaatgg tcttttcgatg tatttgccct aaatgaagca    660
agtggagagc atagtctgaa gtttatgatt tatgaactgt ttaccagata tgatcttatc    720
aaccgtttca agattcctgt ttcttgccta atcaccttg cagaagcttt agaagttggt    780
tacagcaagt acaaaaatcc atatcacaat ttgattcatg cagctgatgt cactcaaact    840
gtgcattaca taatgcttca tacaggtatc atgcactggc tcactgaact ggaaatttta    900
gcaatggtct ttgctgctgc cattcatgat tatgagcata cagggacaac aaacaacttt    960
cacattcaga caaggtcaga tgttgccatt ttgtataatg atcgctctgt ccttgagaat   1020
caccacgtga gtgcagctta tcgacttatg caagaagaag aaatgaatat cttgataaat   1080
ttatccaaag atgactggag ggatcttcgg aacctagtga ttgaaatggt tttatctaca   1140
gacatgtcag gtcacttcca gcaaattaaa aatataagaa acagtttgca gcagcctgaa   1200
gggattgaca gagccaaaac catgtccctg attctccacg cagcagacat cagccaccca   1260
gccaaatcct ggaagctgca ttatcggtgg accatggccc taatgaagga gttttttcctg   1320 cagggagata aagaagctga attagggctt ccattttccc cactttgtga tcggaagtca   1380
```

-continued

| | |
|---|---|
| accatggtgg cccagtcaca aataggtttc atcgatttca tagtagagcc aacatttct | 1440 |
| cttctgacag actcaacaga gaaaattgtt attcctctta tagaggaagc ctcaaaagcc | 1500 |
| gaaacttctt cctatgtggc aagcagctca accaccattg tggggttaca cattgctgat | 1560 |
| gcactaagac gatcaaatac aaaaggctcc atgagtgatg ggtcctattc cccagactac | 1620 |
| tcccttgcag cagtggacct gaagagtttc aagaacaacc tggtggacat cattcagcag | 1680 |
| aacaaagaga ggtggaaaga gttagctgca caaggtgaat ctgatcttca taagaactca | 1740 |
| gaagacttag taaatgctga agaaaaacat gatgagacac attcataggc ccgaaacacc | 1800 |
| ttaaagactt ctgtcatttt aaacatgaga ggacaatgaa atcagcatga aacatccta | 1860 |
| aattctcaac tttccacaaa gctatggctc ttctttcaac atagaattgg attgggccat | 1920 |
| tttaattgac tcctatacaa ggaattaaga agaacataaa ttttgagcta gtaactctgg | 1980 |
| ccaaataaat acactcaagt ttttatcaga gttttggcc agtgcttctg ccattttttt | 2040 |
| ccctccacaa tttggccttc ttcaatcaag ccagataaat ttttgagaca aaagtcagac | 2100 |
| agttttaat ttttcttgct ttgaaccctg tcataatgac tgtgcaatac atgtgcagaa | 2160 |
| gatgaggtat tttaaaattt acttccttgc actgtcttac acagagtgct ataactataa | 2220 |
| atttttcaag gtcttaaata aaaggaagca aaaacaaaat tattgaaaaa ttttttttgt | 2280 |
| tgtgctgggg aatatactat ttagattgtc cttcttattt taaatgcatg gaacagaat | 2340 |
| gacaggggggg atgctgagga gctggttgaa gcatcagagc aatgctacag tccaacaatg | 2400 |
| gagcattaga tccc | 2414 |

<210> SEQ ID NO 27
<211> LENGTH: 2009
<212> TYPE: DNA
<213> ORGANISM: Homo sapiens

<400> SEQUENCE: 27

| | |
|---|---|
| gaattctgat gtgcttcagt gcacagaaca gtaacagatg agctgctttt ggggagagct | 60 |
| tgagtactca gtcggagcat catcatgggg tctagtgcca cagagattga agaattggaa | 120 |
| aacaccactt ttaagtatct tacaggagaa cagactgaaa aaatgtggca gcgcctgaaa | 180 |
| ggaatactaa gatgcttggt gaagcagctg gaaagaggtg atgttaacgt cgtcgactta | 240 |
| aagaagaata ttgaatatgc ggcatctgtg ctggaagcag tttatatcga tgaaacaaga | 300 |
| agacttctgg atactgaaga tgagctcagt gacattcaga ctgactcagt cccatctgaa | 360 |
| gtccgggact ggttggcttc tacctttaca cggaaaatgg ggatgacaaa aaagaaacct | 420 |
| gaggaaaaac caaaatttcg gagcattgtg catgctgttc aagctggaat ttttgtggaa | 480 |
| agaatgtacc gaaaaacata tcatatggtt ggtttggcat atccagcagc tgtcatcgta | 540 |
| acattaaagg atgttgataa atggtctttc gatgtatttg ccctaaatga agcaagtgga | 600 |
| gagcatagtc tgaagtttat gatttatgaa ctgtttacca gatatgatct tatcaaccgt | 660 |
| ttcaagattc ctgtttcttg cctaatcacc tttgcagaag ctttagaagt tggttacagc | 720 |
| aagtacaaaa atccatatca caatttgatt catgcagctg atgtcactca aactgtgcat | 780 |
| tacataatgc ttcatacagg tatcatgcac tggctcactg aactggaaat tttagcaatg | 840 |
| gtctttgctg ctgccattca tgattatgag catacaggga caacaaacaa ctttcacatt | 900 |
| cagacaaggt cagatgttgc cattttgtat aatgatcgct ctgtccttga gaatcaccac | 960 |
| gtgagtgcag cttatcgact tatgcaagaa gaagaaatga atatcttgat aaatttatcc | 1020 |
| aaagatgact ggagggatct tcggaaccta gtgattgaaa tggttttatc tacagacatg | 1080 |

```
tcaggtcact tccagcaaat taaaaatata agaaacagtt tgcagcagcc tgaagggatt    1140
gacagagcca aaaccatgtc cctgattctc cacgcagcag acatcagcca cccagccaaa    1200
tcctggaagc tgcattatcg gtggaccatg gccctaatgg aggagttttt cctgcaggga    1260
gataaagaag ctgaattagg gcttccattt tccccacttt gtgatcggaa gtcaaccatg    1320
gtggcccagt cacaaatagg tttcatcgat ttcatagtag agccaacatt ttctcttctg    1380
acagactcaa cagagaaaat tgttattcct cttatagagg aagcctcaaa agccgaaact    1440
tcttcctatg tggcaagcag ctcaaccacc attgtggggt tacacattgc tgatgcacta    1500
agacgatcaa atacaaaagg ctccatgagt gatgggtcct attccccaga ctactccctt    1560
gcagcagtgg acctgaagag tttcaagaac aacctggtgg acatcattca gcagaacaaa    1620
gagaggtgga aagagttagc tgcacaagaa gcaagaacca gttcacagaa gtgtgagttt    1680
attcatcagt aaacaccttt aagtaaaacc tcgtgcatgg tggcagctct aatttgacca    1740
aaagacttgg agattttgat tatgcttgct ggaaatctac cctgtcctgt gtgagacagg    1800 aaatctatt ttgcagattg ctcaataagc atcatgagcc acataaataa cagctgtaaa    1860
ctccttaatt caccgggctc aactgctacc gaacagattc atctagtggc tacatcagca    1920
ccttgtgctt tcagatatct gtttcaatgg cattttgtgg catttgtctt taccgagtgc    1980
caataaattt tctttgagca gctaaaaaa                                      2009

<210> SEQ ID NO 28
<211> LENGTH: 2846
<212> TYPE: DNA
<213> ORGANISM: Homo sapiens

<400> SEQUENCE: 28
aaatgcttga ggagagagag agagtaagga gccagccatg aatcctttcc agaaaaatga      60
gtccaaggaa actctttttt cacctgtctc cattgaagag gtaccacctc gaccacctag     120
ccctccaaag aagccatctc cgacaatctg tggctccaac tatccactga gcattgcctt     180
cattgtggtg aatgaattct gcgagcgctt ttcctattat ggaatgaaag ctgtgctgat     240
cctgtatttc ctgtatttcc tgcactggaa tgaagatacc tccacatcta tataccatgc     300
cttcagcagc ctctgttatt ttactcccat cctgggagca gccattgctg actcgtggtt     360
gggaaaattc aagacaatca tctatctctc cttggtgtat gtgcttggcc atgtgatcaa     420
gtccttgggt gccttaccaa tactgggagg acaagtggta cacacagtcc tatcattgat     480
cggcctgagt ctaatagctt tggggacagg aggcatcaaa ccctgtgtgg cagcttttgg     540
tggagaccag tttgaagaaa aacatgcaga ggaacggact agatacttct cagtcttcta     600
cctgtccatc aatgcaggga gcttgatttc tacatttatc acacccatgc tgagaggaga     660
tgtgcaatgt tttgggagaag actgctatgc attggctttt ggagttccag gactgctcat     720
ggtaattgca cttgttgtgt ttgcaatggg aagcaaaata tacaataaac caccccctga     780
aggaaacata gtggctcaag ttttcaaatg tatctggttt gctatttcca atcgtttcaa     840
gaaccgttct ggagacattc caaagcgaca gcactggcta gactgggcgg ctgagaaata     900
tccaaagcag ctcattatgg atgtaaaggc actgaccagg gtactattcc tttatatccc     960
attgcccatg ttctgggctc ttttggatca gcagggttca cgatggactt tgcaagccat    1020
caggatgaat aggaatttgg ggttttttgt gcttcagccg gaccagatgc aggttctaaa    1080
tccccttctg gttcttatct tcatcccgtt gtttgacttt gtcatttatc gtctggtctc    1140
caagtgtgga attaacttct catcacttag gaaaatggct gttggtatga tcctagcatg    1200
```

```
cctggcattt gcagttgcgg cagctgtaga gataaaaata aatgaaatgg ccccagccca    1260
gccaggtccc caggaggttt tcctacaagt cttgaatctg gcagatgatg aggtgaaggt    1320
gacagtggtg ggaaatgaaa acaattctct gttgatagag tccatcaaat cctttcagaa    1380
aacaccacac tattccaaac tgcacctgaa aacaaaaagc caggattttc acttccacct    1440
gaaatatcac aatttgtctc tctacactga gcattctgtg caggagaaga actggtacag    1500
tcttgtcatt cgtgaagatg ggaacagtat ctccagcatg atggtaaagg atacagaaag    1560
cagaacaacc aatgggatga caaccgtgag gtttgttaac actttgcata agatgtcaa    1620 catctccctg agtacagata cctctctcaa tgttggtgaa gactatggtg tgtctgctta    1680
tagaactgtg caaagaggag aatacccctgc agtgcactgt agaacagaag ataagaactt    1740
ttctctgaat ttgggtcttc tagactttgg tgcagcatat ctgtttgtta ttactaataa    1800
caccaatcag ggtcttcagg cctggaagat tgaagacatt ccagccaaca aaatgtccat    1860
tgcgtggcag ctaccacaat atgccctggt tacagctggg gaggtcatgt tctctgtcac    1920
aggtcttgag ttttcttatt ctcaggctcc ctctggcatg aaatctgtgc tccaggcagc    1980
ttggctattg acaattgcag ttgggaatat catcgtgctt gttgtggcac agttcagtgg    2040
cctggtacag tgggccgaat tcattttgtt ttcctgcctc ctgctggtga tctgcctgat    2100
cttctccatc atgggctact actatgttcc tgtaaagaca gaggatatgc ggggtccagc    2160
agataagcac attcctcaca tccaggggaa catgatcaaa ctagagacca agaagacaaa    2220
actctgatga ctccctagat tctgtcctga ccccaattcc tggccctgtc ttgaagcatt    2280 tttttttcttc tactggatta gacaagagag atagcagcat atcagagctg atctcctcca    2340
cctttctcca atgacagaag ttccaggact ggttttccag tacatctta aacaaggccc      2400 cagagactct atgtctgccc gtccatcagt gaactcatta aaacttgtgc agtgttgctg    2460
gagctggcct ggtgtctcca aatgaccatg aaaaatacaca cgtataatgg agatcattct    2520
ctgtgggtat gcaaagttat gggaattcct ttataggtaa ctgccattta ggactgatgg    2580
ccctaatttt tgaggtgctg atttagaggc aaaattgcag aataacaaag aaatggtatt    2640
tcaagttttt tttttataa gcaatgtaat tatgctattc acaggggcct caagaattgg    2700
tatgtatgat gtgatctggt ccagccaggg cctggcttgt cagctctcta ggtttgatat    2760
gactttagta aatttgtcaa tatagatggt aggaagcaga atgccatttt attaaaacac    2820
aggagaagtt aaaaaaaaaa aaaaaa                                         2846

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
ccgtttacgt ggagactcgc c                                              21

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
cccccacctt atatatattc tttcc                                          25
```

-continued

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 31
ccatgcctat ttctacagc                                               19

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
tcagtaacag ctcccagac                                               19

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 33
ccatgcctat ttctacagc                                               19

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 34
tcagtaacag ctcccagac                                               19

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
ggcaatagca ggttcacgta ca                                           22

<210> SEQ ID NO 36
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 36
cgataacagt cttgccccac tt                                           22

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
acggcacacc ctacgttacc                                           20

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
tgtgcaagga gagaacctct agct                                      24

<210> SEQ ID NO 39
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 39
ccaacactgt gcgcagctt                                            19

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 40
aagaatctcc gggttgtttt cc                                        22

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
cagtctcatc ctgaaagcat ctga                                      24

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
tttcccacac actccaccaa                                           20

<210> SEQ ID NO 43
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 43
tggagtgttt tacgctgaac gat                                       23

<210> SEQ ID NO 44
<211> LENGTH: 31

```
<212> TYPE: DNA
<213> ORGANISM: Artificial Sequence
<220> FEATURE:
<223> OTHER INFORMATION: Synthetic oligonucleotide

<400> SEQUENCE: 44
cctcttactg ctataccttt actctttatg g                               31

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 45
tgccatcaaa gtcttctgca a                                          21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
cgccatactc gaactggaat c                                          21

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 47
cactattatt ttggcacaac aggaa                                      25

<210> SEQ ID NO 48
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 48
agacacatat ttggcatggt tctg                                       24

<210> SEQ ID NO 49
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 49
caagggatcc agtctctcta tggt                                       24

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 50
ggataaggaa gggtcacatt tgtc                                       24
```

<210> SEQ ID NO 51
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 51
gctcggtgga gggtctca                                                   18

<210> SEQ ID NO 52
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 52
ctgtgtggat ttctgcgatc a                                               21

<210> SEQ ID NO 53
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 53
catccatgac aactttggta tcg                                             23

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 54
agtcttctgg gtggcagtga t                                               21

<210> SEQ ID NO 55
<211> LENGTH: 919
<212> TYPE: PRT
<213> ORGANISM: Homo sapiens

<400> SEQUENCE: 55

Met Gly Thr Thr Ala Pro Gly Pro Ile His Leu Leu Glu Leu Cys Asp
1               5                   10                  15

Gln Lys Leu Met Glu Phe Leu Cys Asn Met Asp Asn Lys Asp Leu Val
            20                  25                  30

Trp Leu Glu Glu Ile Gln Glu Ala Glu Arg Met Phe Thr Arg Glu
        35                  40                  45

Phe Ser Lys Glu Pro Glu Leu Met Pro Lys Thr Pro Ser Gln Lys Asn
    50                  55                  60

Arg Arg Lys Lys Arg Arg Ile Ser Tyr Val Gln Asp Glu Asn Arg Asp
65                  70                  75                  80

Pro Ile Arg Arg Arg Leu Ser Arg Lys Ser Arg Ser Ser Gln Leu
                85                  90                  95

Ser Ser Arg Arg Leu Arg Ser Lys Asp Ser Val Glu Lys Leu Ala Thr
            100                 105                 110

Val Val Gly Glu Asn Gly Ser Val Leu Arg Arg Val Thr Arg Ala Ala
        115                 120                 125

```
Ala Ala Ala Ala Ala Thr Met Ala Leu Ala Pro Ser Ser Pro
    130             135             140

Thr Pro Glu Ser Pro Thr Met Leu Thr Lys Lys Pro Glu Asp Asn His
145             150             155             160

Thr Gln Cys Gln Leu Val Pro Val Val Glu Ile Gly Ile Ser Glu Arg
                165             170             175

Gln Asn Ala Glu Gln His Val Thr Gln Leu Met Ser Thr Glu Pro Leu
            180             185             190

Pro Arg Thr Leu Ser Pro Thr Pro Ala Ser Ala Thr Ala Pro Thr Ser
        195             200             205

Gln Gly Ile Pro Thr Ser Asp Glu Glu Ser Thr Pro Lys Lys Ser Lys
    210             215             220

Ala Arg Ile Leu Glu Ser Ile Thr Val Ser Ser Leu Met Ala Thr Pro
225             230             235             240

Gln Asp Pro Lys Gly Gln Gly Val Gly Thr Arg Ser Ala Ser Lys
                245             250             255

Leu Arg Ile Ala Gln Val Ser Pro Gly Pro Arg Asp Ser Pro Ala Phe
            260             265             270

Pro Asp Ser Pro Trp Arg Glu Arg Val Leu Ala Pro Ile Leu Pro Asp
        275             280             285

Asn Phe Ser Thr Pro Thr Gly Ser Arg Thr Asp Ser Gln Ser Val Arg
    290             295             300

His Ser Pro Ile Ala Pro Ser Ser Pro Ser Pro Gln Val Leu Ala Gln
305             310             315             320

Lys Tyr Ser Leu Val Ala Lys Gln Glu Ser Val Val Arg Arg Ala Ser
                325             330             335

Arg Arg Leu Ala Lys Lys Thr Ala Glu Glu Pro Ala Ala Ser Gly Arg
            340             345             350

Ile Ile Cys His Ser Tyr Leu Glu Arg Leu Leu Asn Val Glu Val Pro
        355             360             365

Gln Lys Val Gly Ser Glu Gln Lys Glu Pro Pro Glu Glu Ala Glu Pro
    370             375             380

Val Ala Ala Glu Pro Glu Val Pro Glu Asn Asn Gly Asn Asn Ser
385             390             395             400

Trp Pro His Asn Asp Thr Glu Ile Ala Asn Ser Thr Pro Asn Pro Lys
                405             410             415

Pro Ala Ala Ser Ser Pro Glu Thr Pro Ser Ala Gly Gln Gln Glu Ala
            420             425             430

Lys Thr Asp Gln Ala Asp Gly Pro Arg Glu Pro Gln Ser Ala Arg
        435             440             445

Arg Lys Arg Ser Tyr Lys Gln Ala Val Ser Glu Leu Asp Glu Glu Gln
    450             455             460

His Leu Glu Asp Glu Glu Leu Gln Pro Arg Ser Lys Thr Pro Ser
465             470             475             480

Ser Pro Cys Pro Ala Ser Lys Val Val Arg Pro Leu Arg Thr Phe Leu
                485             490             495

His Thr Val Gln Arg Asn Gln Met Leu Met Thr Pro Thr Ser Ala Pro
            500             505             510

Arg Ser Val Met Lys Ser Phe Ile Lys Arg Asn Thr Pro Leu Arg Met
        515             520             525

Asp Pro Lys Glu Lys Glu Arg Gln Arg Leu Glu Asn Leu Arg Arg Lys
    530             535             540

Glu Glu Ala Glu Gln Leu Arg Arg Gln Lys Val Glu Glu Asp Lys Arg
```

```
            545                 550                 555                 560
Arg Arg Leu Glu Glu Val Lys Leu Lys Arg Glu Glu Leu Arg Lys
                565                 570                 575

Val Leu Gln Ala Arg Glu Arg Val Gln Met Lys Glu Glu Lys Lys
            580                 585                 590

Lys Gln Ile Glu Gln Lys Phe Ala Gln Ile Asp Glu Lys Thr Glu Lys
        595                 600                 605

Ala Lys Glu Glu Arg Leu Ala Glu Glu Lys Ala Lys Lys Ala Ala
        610                 615                 620

Ala Lys Lys Met Glu Glu Val Glu Ala Arg Arg Lys Gln Glu Glu Asp
625                 630                 635                 640

Ala Arg Arg Leu Arg Trp Leu Gln Gln Glu Glu Glu Arg Arg His
                645                 650                 655

Gln Glu Leu Leu Gln Lys Lys Glu Glu Gln Glu Arg Leu Arg
                660                 665                 670

Lys Ala Ala Glu Ala Lys Arg Leu Ala Glu Gln Arg Glu Gln Glu Arg
        675                 680                 685

Arg Glu Gln Glu Arg Arg Glu Gln Glu Arg Arg Glu Gln Glu Arg Arg
690                 695                 700

Glu Gln Glu Arg Arg Glu Gln Glu Arg Arg Glu Gln Glu Arg Gln Leu
705                 710                 715                 720

Ala Glu Gln Glu Arg Arg Arg Glu Gln Glu Arg Leu Gln Ala Glu Arg
                725                 730                 735

Glu Leu Gln Glu Arg Glu Lys Ala Leu Arg Leu Gln Lys Glu Gln Leu
                740                 745                 750

Gln Arg Glu Leu Glu Glu Lys Lys Lys Glu Glu Gln Arg Leu
        755                 760                 765

Ala Glu Arg Gln Leu Gln Glu Gln Glu Lys Lys Ala Lys Glu Ala
        770                 775                 780

Ala Gly Ala Ser Lys Ala Leu Asn Val Thr Val Asp Val Gln Ser Pro
785                 790                 795                 800

Ala Cys Thr Ser Ser Pro Ile Thr Pro Gln Gly His Lys Ala Pro Pro
                805                 810                 815

Gln Ile Asn Pro His Asn Tyr Gly Met Asp Leu Asn Ser Asp Asp Ser
            820                 825                 830

Thr Asp Asp Glu Ala His Pro Arg Lys Pro Ile Pro Thr Trp Ala Arg
        835                 840                 845

Gly Thr Pro Leu Ser Gln Ala Ile Ile His Gln Tyr Tyr Gln Pro Pro
    850                 855                 860

Asn Leu Leu Glu Leu Phe Gly Thr Ile Leu Pro Leu Asp Leu Glu Asp
865                 870                 875                 880

Ile Phe Lys Lys Ser Lys Pro Arg Tyr His Lys Arg Thr Ser Ser Ala
                885                 890                 895

Val Trp Asn Ser Pro Pro Leu Gln Gly Ala Arg Val Pro Ser Ser Leu
                900                 905                 910

Ala Tyr Ser Leu Lys Lys His
            915

<210> SEQ ID NO 56
<211> LENGTH: 804
<212> TYPE: PRT
<213> ORGANISM: Homo sapiens

<400> SEQUENCE: 56

Met Thr Asn Gln Glu Lys Trp Ala His Leu Ser Pro Ser Glu Phe Ser
```

-continued

```
1               5                   10                  15
Gln Leu Gln Lys Tyr Ala Glu Tyr Ser Thr Lys Lys Leu Lys Asp Val
                20                  25                  30

Leu Glu Glu Phe His Gly Asn Gly Val Leu Ala Lys Tyr Asn Pro Glu
                35                  40                  45

Gly Lys Gln Asp Ile Leu Asn Gln Thr Ile Asp Phe Glu Gly Phe Lys
        50                  55                  60

Leu Phe Met Lys Thr Phe Leu Glu Ala Glu Leu Pro Asp Asp Phe Thr
65                  70                  75                  80

Ala His Leu Phe Met Ser Phe Ser Asn Lys Phe Pro His Ser Ser Pro
                85                  90                  95

Met Val Lys Ser Lys Pro Ala Leu Leu Ser Gly Gly Leu Arg Met Asn
                100                 105                 110

Lys Gly Ala Ile Thr Pro Pro Arg Thr Thr Ser Pro Ala Asn Thr Cys
            115                 120                 125

Ser Pro Glu Val Ile His Leu Lys Asp Ile Val Cys Tyr Leu Ser Leu
            130                 135                 140

Leu Glu Arg Gly Arg Pro Glu Asp Lys Leu Glu Phe Met Phe Arg Leu
145                 150                 155                 160

Tyr Asp Thr Asp Gly Asn Gly Phe Leu Asp Ser Ser Glu Leu Glu Asn
                165                 170                 175

Ile Ile Ser Gln Met Met His Val Ala Glu Tyr Leu Glu Trp Asp Val
                180                 185                 190

Thr Glu Leu Asn Pro Ile Leu His Glu Met Met Glu Glu Ile Asp Tyr
            195                 200                 205

Asp His Asp Gly Thr Val Ser Leu Glu Glu Trp Ile Gln Gly Gly Met
            210                 215                 220

Thr Thr Ile Pro Leu Leu Val Leu Leu Gly Leu Glu Asn Asn Val Lys
225                 230                 235                 240

Asp Asp Gly Gln His Val Trp Arg Leu Lys His Phe Asn Lys Pro Ala
                245                 250                 255

Tyr Cys Asn Leu Cys Leu Asn Met Leu Ile Gly Val Gly Lys Gln Gly
                260                 265                 270

Leu Cys Cys Ser Phe Cys Lys Tyr Thr Val His Glu Arg Cys Val Ala
            275                 280                 285

Arg Ala Pro Pro Ser Cys Ile Lys Thr Tyr Val Lys Ser Lys Arg Asn
            290                 295                 300

Thr Asp Val Met His His Tyr Trp Val Glu Gly Asn Cys Pro Thr Lys
305                 310                 315                 320

Cys Asp Lys Cys His Lys Thr Val Lys Cys Tyr Gln Gly Leu Thr Gly
                325                 330                 335

Leu His Cys Val Trp Cys Gln Ile Thr Leu His Asn Lys Cys Ala Ser
                340                 345                 350

His Leu Lys Pro Glu Cys Asp Cys Gly Pro Leu Lys Asp His Ile Leu
            355                 360                 365

Pro Pro Thr Thr Ile Cys Pro Val Val Leu Gln Thr Leu Pro Thr Ser
370                 375                 380

Gly Val Ser Val Pro Glu Glu Arg Gln Ser Thr Val Lys Lys Glu Lys
385                 390                 395                 400

Ser Gly Ser Gln Gln Pro Asn Lys Val Ile Asp Lys Asn Lys Met Gln
            405                 410                 415

Arg Ala Asn Ser Val Thr Val Asp Gly Gln Gly Leu Asn Val Thr Pro
            420                 425                 430
```

Val Pro Gly Thr His Pro Leu Leu Val Phe Val Asn Pro Lys Ser Gly
        435                 440                 445

Gly Lys Gln Gly Glu Arg Ile Tyr Arg Lys Phe Gln Tyr Leu Leu Asn
    450                 455                 460

Pro Arg Gln Val Tyr Ser Leu Ser Gly Asn Gly Pro Met Pro Gly Leu
465                 470                 475                 480

Asn Phe Phe Arg Asp Val Pro Asp Phe Arg Val Leu Ala Cys Gly Gly
                485                 490                 495

Asp Gly Thr Val Gly Trp Val Leu Asp Cys Ile Glu Lys Ala Asn Val
            500                 505                 510

Gly Lys His Pro Pro Val Ala Ile Leu Pro Leu Gly Thr Gly Asn Asp
        515                 520                 525

Leu Ala Arg Cys Leu Arg Trp Gly Gly Gly Tyr Glu Gly Glu Asn Leu
530                 535                 540

Met Lys Ile Leu Lys Asp Ile Glu Asn Ser Thr Glu Ile Met Leu Asp
545                 550                 555                 560

Arg Trp Lys Phe Glu Val Ile Pro Asn Asp Lys Asp Glu Lys Gly Asp
                565                 570                 575

Pro Val Pro Tyr Ser Ile Ile Asn Asn Tyr Phe Ser Ile Gly Val Asp
            580                 585                 590

Ala Ser Ile Ala His Arg Phe His Ile Met Arg Glu Lys His Pro Glu
        595                 600                 605

Lys Phe Asn Ser Arg Met Lys Asn Lys Phe Trp Tyr Phe Glu Phe Gly
610                 615                 620

Thr Ser Glu Thr Phe Ser Ala Thr Cys Lys Lys Leu His Glu Ser Val
625                 630                 635                 640

Glu Ile Glu Cys Asp Gly Val Gln Ile Asp Leu Ile Asn Ile Ser Leu
                645                 650                 655

Glu Gly Ile Ala Ile Leu Asn Ile Pro Ser Met His Gly Gly Ser Asn
            660                 665                 670

Leu Trp Gly Glu Ser Lys Lys Arg Ser His Arg Ile Glu Lys
        675                 680                 685

Lys Gly Ser Asp Lys Arg Thr Thr Val Thr Asp Ala Lys Glu Leu Lys
690                 695                 700

Phe Ala Ser Gln Asp Leu Ser Asp Gln Leu Leu Glu Val Val Gly Leu
705                 710                 715                 720

Glu Gly Ala Met Glu Met Gly Gln Ile Tyr Thr Gly Leu Lys Ser Ala
                725                 730                 735

Gly Arg Arg Leu Ala Gln Cys Ser Cys Val Val Ile Arg Thr Ser Lys
            740                 745                 750

Ser Leu Pro Met Gln Ile Asp Gly Glu Pro Trp Met Gln Thr Pro Cys
        755                 760                 765

Thr Ile Lys Ile Thr His Lys Asn Gln Ala Pro Met Leu Met Gly Pro
770                 775                 780

Pro Pro Lys Thr Gly Leu Phe Cys Ser Leu Val Lys Arg Thr Arg Asn
785                 790                 795                 800

Arg Ser Lys Glu

<210> SEQ ID NO 57
<211> LENGTH: 773
<212> TYPE: PRT
<213> ORGANISM: Homo sapiens

<400> SEQUENCE: 57

Met Thr Asn Gln Glu Lys Trp Ala His Leu Ser Pro Ser Glu Phe Ser

-continued

```
1               5                   10                  15
Gln Leu Gln Lys Tyr Ala Glu Tyr Ser Thr Lys Lys Leu Lys Asp Val
                20                  25                  30

Leu Glu Glu Phe His Gly Asn Gly Val Leu Ala Lys Tyr Asn Pro Glu
                35                  40                  45

Gly Lys Gln Asp Ile Leu Asn Gln Thr Ile Asp Phe Glu Gly Phe Lys
                50                  55                  60

Leu Phe Met Lys Thr Phe Leu Glu Ala Glu Leu Pro Asp Asp Phe Thr
65                      70                  75                  80

Ala His Leu Phe Met Ser Phe Ser Asn Lys Phe Pro His Ser Ser Pro
                        85                  90                  95

Met Val Lys Ser Lys Pro Ala Leu Leu Ser Gly Gly Leu Arg Met Asn
                100                 105                 110

Lys Gly Ala Ile Thr Pro Pro Arg Thr Thr Ser Pro Ala Asn Thr Cys
                115                 120                 125

Ser Pro Glu Val Ile His Leu Lys Asp Ile Val Cys Tyr Leu Ser Leu
                130                 135                 140

Leu Glu Arg Gly Arg Pro Glu Asp Lys Leu Glu Phe Met Phe Arg Leu
145                     150                 155                 160

Tyr Asp Thr Asp Gly Asn Gly Phe Leu Asp Ser Ser Glu Leu Glu Asn
                        165                 170                 175

Ile Ile Ser Gln Met Met His Val Ala Glu Tyr Leu Glu Trp Asp Val
                180                 185                 190

Thr Glu Leu Asn Pro Ile Leu His Glu Met Met Glu Glu Ile Asp Tyr
                195                 200                 205

Asp His Asp Gly Thr Val Ser Leu Glu Glu Trp Ile Gln Gly Gly Met
                210                 215                 220

Thr Thr Ile Pro Leu Leu Val Leu Leu Gly Leu Glu Asn Asn Val Lys
225                     230                 235                 240

Asp Asp Gly Gln His Val Trp Arg Leu Lys His Phe Asn Lys Pro Ala
                        245                 250                 255

Tyr Cys Asn Leu Cys Leu Asn Met Leu Ile Gly Val Gly Lys Gln Gly
                260                 265                 270

Leu Cys Cys Ser Phe Cys Lys Tyr Thr Val His Glu Arg Cys Val Ala
                275                 280                 285

Arg Ala Pro Pro Ser Cys Ile Lys Thr Tyr Val Lys Ser Lys Arg Asn
                290                 295                 300

Thr Asp Val Met His His Tyr Trp Val Glu Gly Asn Cys Pro Thr Lys
305                     310                 315                 320

Cys Asp Lys Cys His Lys Thr Val Lys Cys Tyr Gln Gly Leu Thr Gly
                        325                 330                 335

Leu His Cys Val Trp Cys Gln Ile Thr Leu His Asn Lys Cys Ala Ser
                340                 345                 350

His Leu Lys Pro Glu Cys Asp Cys Gly Pro Leu Lys Asp His Ile Leu
                355                 360                 365

Pro Pro Thr Thr Ile Cys Pro Val Val Leu Gln Thr Leu Pro Thr Ser
                370                 375                 380

Gly Val Ser Val Pro Glu Glu Arg Gln Ser Thr Val Lys Lys Glu Lys
385                     390                 395                 400

Ser Gly Ser Gln Gln Pro Asn Lys Val Ile Asp Lys Asn Lys Met Gln
                        405                 410                 415

Arg Ala Asn Ser Val Thr Val Asp Gly Gln Gly Leu Gln Val Thr Pro
                420                 425                 430
```

```
Val Pro Gly Thr His Pro Leu Leu Val Phe Val Asn Pro Lys Ser Gly
        435                 440                 445

Gly Lys Gln Gly Glu Arg Ile Tyr Arg Lys Phe Gln Tyr Leu Leu Asn
        450                 455                 460

Pro Arg Gln Val Tyr Ser Leu Ser Gly Asn Gly Pro Met Pro Gly Leu
465                 470                 475                 480

Asn Phe Phe Arg Asp Val Pro Asp Phe Arg Val Leu Ala Cys Gly Gly
                485                 490                 495

Asp Gly Thr Val Gly Trp Val Leu Asp Cys Ile Glu Lys Ala Asn Val
        500                 505                 510

Gly Lys His Pro Pro Val Ala Ile Leu Pro Leu Gly Thr Gly Asn Asp
        515                 520                 525

Leu Ala Arg Cys Leu Arg Trp Gly Gly Gly Tyr Glu Gly Glu Asn Leu
530                 535                 540

Met Lys Ile Leu Lys Asp Ile Glu Asn Ser Thr Glu Ile Met Leu Asp
545                 550                 555                 560

Arg Trp Lys Phe Glu Val Ile Pro Asn Asp Lys Asp Glu Lys Gly Asp
                565                 570                 575

Pro Val Pro Tyr Ser Ile Ile Asn Asn Tyr Phe Ser Ile Gly Val Asp
            580                 585                 590

Ala Ser Ile Ala His Arg Phe His Ile Met Arg Glu Lys His Pro Glu
            595                 600                 605

Lys Phe Asn Ser Arg Met Lys Asn Lys Phe Trp Tyr Phe Glu Phe Gly
        610                 615                 620

Thr Ser Glu Thr Phe Ser Ala Thr Cys Lys Lys Leu His Glu Ser Val
625                 630                 635                 640

Glu Ile Glu Cys Asp Gly Val Gln Ile Asp Leu Ile Asn Ile Ser Leu
                645                 650                 655

Glu Gly Ile Ala Ile Leu Asn Ile Pro Ser Met His Gly Gly Ser Asn
            660                 665                 670

Leu Trp Gly Glu Ser Lys Lys Arg Ser His Arg Ile Glu Lys
            675                 680                 685

Lys Gly Ser Asp Lys Arg Thr Thr Val Thr Asp Ala Lys Glu Leu Lys
        690                 695                 700

Phe Ala Ser Gln Asp Leu Ser Asp Gln Leu Leu Glu Val Val Gly Leu
705                 710                 715                 720

Glu Gly Ala Met Glu Met Gly Gln Ile Tyr Thr Gly Leu Lys Ser Ala
                725                 730                 735

Gly Arg Arg Leu Ala Gln Cys Ser Cys Val Val Ile Arg Thr Ser Lys
            740                 745                 750

Ser Leu Pro Met Gln Ile Asp Gly Glu Pro Trp Met Gln Thr Pro Cys
        755                 760                 765

Thr Val Ser Thr Glu
    770

<210> SEQ ID NO 58
<211> LENGTH: 632
<212> TYPE: PRT
<213> ORGANISM: Homo sapiens

<400> SEQUENCE: 58

Met Asn Arg Tyr Thr Thr Ile Arg Gln Leu Gly Asp Gly Thr Tyr Gly
1               5                   10                  15

Ser Val Leu Leu Gly Arg Ser Ile Glu Ser Gly Glu Leu Ile Ala Ile
            20                  25                  30
```

-continued

```
Lys Lys Met Lys Arg Lys Phe Tyr Ser Trp Glu Glu Cys Met Asn Leu
         35                  40                  45

Arg Glu Val Lys Ser Leu Lys Lys Leu Asn His Ala Asn Val Val Lys
 50                  55                  60

Leu Lys Glu Val Ile Arg Glu Asn Asp His Leu Tyr Phe Ile Phe Glu
 65                  70                  75                  80

Tyr Met Lys Glu Asn Leu Tyr Gln Leu Ile Lys Glu Arg Asn Lys Leu
                 85                  90                  95

Phe Pro Glu Ser Ala Ile Arg Asn Ile Met Tyr Gln Ile Leu Gln Gly
             100                 105                 110

Leu Ala Phe Ile His Lys His Gly Phe Phe His Arg Asp Leu Lys Pro
             115                 120                 125

Glu Asn Leu Leu Cys Met Gly Pro Glu Leu Val Lys Ile Ala Asp Phe
         130                 135                 140

Gly Leu Ala Arg Glu Ile Arg Ser Lys Pro Pro Tyr Thr Asp Tyr Val
145                 150                 155                 160

Ser Thr Arg Trp Tyr Arg Ala Pro Glu Val Leu Leu Arg Ser Thr Asn
                 165                 170                 175

Tyr Ser Ser Pro Ile Asp Val Trp Ala Val Gly Cys Ile Met Ala Glu
             180                 185                 190

Val Tyr Thr Leu Arg Pro Leu Phe Pro Gly Ala Ser Glu Ile Asp Thr
             195                 200                 205

Ile Phe Lys Ile Cys Gln Val Leu Gly Thr Pro Lys Lys Thr Asp Trp
210                 215                 220

Pro Glu Gly Tyr Gln Leu Ser Ser Ala Met Asn Phe Arg Trp Pro Gln
225                 230                 235                 240

Cys Val Pro Asn Asn Leu Lys Thr Leu Ile Pro Asn Ala Ser Ser Glu
                 245                 250                 255

Ala Val Gln Leu Leu Arg Asp Met Leu Gln Trp Asp Pro Lys Lys Arg
             260                 265                 270

Pro Thr Ala Ser Gln Ala Leu Arg Tyr Pro Tyr Phe Gln Val Gly His
             275                 280                 285

Pro Leu Gly Ser Thr Thr Gln Asn Leu Gln Asp Ser Glu Lys Pro Gln
290                 295                 300

Lys Gly Ile Leu Glu Lys Ala Gly Pro Pro Tyr Ile Lys Pro Val
305                 310                 315                 320

Pro Pro Ala Gln Pro Ala Lys Pro His Thr Arg Ile Ser Ser Arg
                 325                 330                 335

Gln His Gln Ala Ser Gln Pro Leu His Leu Thr Tyr Pro Tyr Lys
             340                 345                 350

Ala Glu Val Ser Arg Thr Asp His Pro Ser His Leu Gln Glu Asp Lys
             355                 360                 365

Pro Ser Pro Leu Leu Phe Pro Ser Leu His Asn Lys His Pro Gln Ser
370                 375                 380

Lys Ile Thr Ala Gly Leu Glu His Lys Asn Gly Glu Ile Lys Pro Lys
385                 390                 395                 400

Ser Arg Arg Arg Trp Gly Leu Ile Ser Arg Ser Thr Lys Asp Ser Asp
                 405                 410                 415

Asp Trp Ala Asp Leu Asp Asp Leu Asp Phe Ser Pro Ser Leu Ser Arg
             420                 425                 430

Ile Asp Leu Lys Asn Lys Lys Arg Gln Ser Asp Asp Thr Leu Cys Arg
             435                 440                 445

Phe Glu Ser Val Leu Asp Leu Lys Pro Ser Glu Pro Val Gly Thr Gly
450                 455                 460
```

```
Asn Ser Ala Pro Thr Gln Thr Ser Tyr Gln Arg Arg Asp Thr Pro Thr
465                 470                 475                 480

Leu Arg Ser Ala Ala Lys Gln His Tyr Leu Lys His Ser Arg Tyr Leu
            485                 490                 495

Pro Gly Ile Ser Ile Arg Asn Gly Ile Leu Ser Asn Pro Gly Lys Glu
            500                 505                 510

Phe Ile Pro Pro Asn Pro Trp Ser Ser Gly Leu Ser Gly Lys Ser
            515                 520                 525

Ser Gly Thr Met Ser Val Ile Ser Lys Val Asn Ser Val Gly Ser Ser
            530                 535                 540

Ser Thr Ser Ser Ser Gly Leu Thr Gly Asn Tyr Val Pro Ser Phe Leu
545                 550                 555                 560

Lys Lys Glu Ile Gly Ser Ala Met Gln Arg Val His Leu Ala Pro Ile
            565                 570                 575

Pro Asp Pro Ser Pro Gly Tyr Ser Ser Leu Lys Ala Met Arg Pro His
            580                 585                 590

Pro Gly Arg Pro Phe Phe His Thr Gln Pro Arg Ser Thr Pro Gly Leu
            595                 600                 605

Ile Pro Arg Pro Pro Ala Ala Gln Pro Val His Gly Arg Thr Asp Trp
            610                 615                 620

Ala Ser Lys Tyr Ala Ser Arg Arg
625                 630

<210> SEQ ID NO 59
<211> LENGTH: 632
<212> TYPE: PRT
<213> ORGANISM: Homo sapiens

<400> SEQUENCE: 59

Met Asn Arg Tyr Thr Thr Ile Arg Gln Leu Gly Asp Gly Thr Tyr Gly
1               5                   10                  15

Ser Val Leu Leu Gly Arg Ser Ile Glu Ser Gly Glu Leu Ile Ala Ile
            20                  25                  30

Lys Lys Met Lys Arg Lys Phe Tyr Ser Trp Glu Glu Cys Met Asn Leu
            35                  40                  45

Arg Glu Val Lys Ser Leu Lys Lys Leu Asn His Ala Asn Val Val Lys
50                  55                  60

Leu Lys Glu Val Ile Arg Glu Asn Asp His Leu Tyr Phe Ile Phe Glu
65                  70                  75                  80

Tyr Met Lys Glu Asn Leu Tyr Gln Leu Ile Lys Glu Arg Asn Lys Leu
            85                  90                  95

Phe Pro Glu Ser Ala Ile Arg Asn Ile Met Tyr Gln Ile Leu Gln Gly
            100                 105                 110

Leu Ala Phe Ile His Lys His Gly Phe Phe His Arg Asp Leu Lys Pro
            115                 120                 125

Glu Asn Leu Leu Cys Met Gly Pro Glu Leu Val Lys Ile Ala Asp Phe
            130                 135                 140

Gly Leu Ala Arg Glu Ile Arg Ser Lys Pro Pro Tyr Thr Asp Tyr Val
145                 150                 155                 160

Ser Thr Arg Trp Tyr Arg Ala Pro Glu Val Leu Leu Arg Ser Thr Asn
            165                 170                 175

Tyr Ser Ser Pro Ile Asp Val Trp Ala Val Gly Cys Ile Met Ala Glu
            180                 185                 190

Val Tyr Thr Leu Arg Pro Leu Phe Pro Gly Ala Ser Glu Ile Asp Thr
            195                 200                 205
```

```
Ile Phe Lys Ile Cys Gln Val Leu Gly Thr Pro Lys Lys Thr Asp Trp
    210                 215                 220
Pro Glu Gly Tyr Gln Leu Ser Ser Ala Met Asn Phe Arg Trp Pro Gln
225                 230                 235                 240
Cys Val Pro Asn Asn Leu Lys Thr Leu Ile Pro Asn Ala Ser Ser Glu
                245                 250                 255
Ala Val Gln Leu Leu Arg Asp Met Leu Gln Trp Asp Pro Lys Lys Arg
            260                 265                 270
Pro Thr Ala Ser Gln Ala Leu Arg Tyr Pro Tyr Phe Gln Val Gly His
        275                 280                 285
Pro Leu Gly Ser Thr Thr Gln Asn Leu Gln Asp Ser Glu Lys Pro Gln
    290                 295                 300
Lys Gly Ile Leu Glu Lys Ala Gly Pro Pro Tyr Ile Lys Pro Val
305                 310                 315                 320
Pro Pro Ala Gln Pro Ala Lys Pro His Thr Arg Ile Ser Ser Arg
                325                 330                 335
Gln His Gln Ala Ser Gln Pro Pro Leu His Leu Thr Tyr Pro Tyr Lys
            340                 345                 350
Ala Glu Val Ser Arg Thr Asp His Pro Ser His Leu Gln Glu Asp Lys
        355                 360                 365
Pro Ser Pro Leu Leu Phe Pro Ser Leu His Asn Lys His Pro Gln Ser
    370                 375                 380
Lys Ile Thr Ala Gly Leu Glu His Lys Asn Gly Glu Ile Lys Pro Lys
385                 390                 395                 400
Ser Arg Arg Arg Trp Gly Leu Ile Ser Arg Ser Thr Lys Asp Ser Asp
                405                 410                 415
Asp Trp Ala Asp Leu Asp Asp Leu Asp Phe Ser Pro Ser Leu Ser Arg
            420                 425                 430
Ile Asp Leu Lys Asn Lys Lys Arg Gln Ser Asp Asp Thr Leu Cys Arg
        435                 440                 445
Phe Glu Ser Val Leu Asp Leu Lys Pro Ser Glu Pro Val Gly Thr Gly
    450                 455                 460
Asn Ser Ala Pro Thr Gln Thr Ser Tyr Gln Arg Arg Asp Thr Pro Thr
465                 470                 475                 480
Leu Arg Ser Ala Ala Lys Gln His Tyr Leu Lys His Ser Arg Tyr Leu
                485                 490                 495
Pro Gly Ile Ser Ile Arg Asn Gly Ile Leu Ser Asn Pro Gly Lys Glu
            500                 505                 510
Phe Ile Pro Pro Asn Pro Trp Ser Ser Ser Gly Leu Ser Gly Lys Ser
        515                 520                 525
Ser Gly Thr Met Ser Val Ile Ser Lys Val Asn Ser Val Gly Ser Ser
    530                 535                 540
Ser Thr Ser Ser Ser Gly Leu Thr Gly Asn Tyr Val Pro Ser Phe Leu
545                 550                 555                 560
Lys Lys Glu Ile Gly Ser Ala Met Gln Arg Val His Leu Ala Pro Ile
                565                 570                 575
Pro Asp Pro Ser Pro Gly Tyr Ser Ser Leu Lys Ala Met Arg Pro His
            580                 585                 590
Pro Gly Arg Pro Phe Phe His Thr Gln Pro Arg Ser Thr Pro Gly Leu
        595                 600                 605
Ile Pro Arg Pro Pro Ala Ala Gln Pro Val His Gly Arg Thr Asp Trp
    610                 615                 620
Ala Ser Lys Tyr Ala Ser Arg Arg
```

-continued

```
             625                 630
```

<210> SEQ ID NO 60
<211> LENGTH: 455
<212> TYPE: PRT
<213> ORGANISM: Homo sapiens
<400> SEQUENCE: 60

```
Met Ile Cys Cys Ser Ala Leu Ser Pro Arg Ile His Leu Ser Phe His
1               5                   10                  15

Arg Ser Leu Thr Gly Ile Val Leu Ala Asn Ser Ser Leu Asp Ile Val
            20                  25                  30

Leu His Asp Thr Tyr Tyr Val Ala His Cys Gly Gly Asn Val Arg
        35                  40                  45

Arg Leu His Cys Gly Gly Pro Ala Ser Arg Glu Arg Thr Ala Met Gln
    50                  55                  60

Ala Leu Asn Ile Thr Pro Glu Gln Phe Ser Arg Leu Leu Arg Asp His
65                  70                  75                  80

Asn Leu Thr Arg Glu Gln Phe Ile Ala Leu Tyr Arg Leu Arg Pro Leu
                85                  90                  95

Val Tyr Thr Pro Glu Leu Pro Gly Arg Ala Lys Leu Ala Leu Val Leu
            100                 105                 110

Thr Gly Val Leu Ile Phe Ala Leu Ala Leu Phe Gly Asn Ala Leu Val
        115                 120                 125

Phe Tyr Val Val Thr Arg Ser Lys Ala Met Arg Thr Val Thr Asn Ile
130                 135                 140

Phe Ile Cys Ser Leu Ala Leu Ser Asp Leu Leu Ile Thr Phe Phe Cys
145                 150                 155                 160

Ile Pro Val Thr Met Leu Gln Asn Ile Ser Asp Asn Trp Leu Gly Gly
                165                 170                 175

Ala Phe Ile Cys Lys Met Val Pro Phe Val Gln Ser Thr Ala Val Val
            180                 185                 190

Thr Glu Ile Leu Thr Met Thr Cys Ile Ala Val Glu Arg His Gln Gly
        195                 200                 205

Leu Val His Pro Phe Lys Met Lys Trp Gln Tyr Thr Asn Arg Arg Ala
    210                 215                 220

Phe Thr Met Leu Gly Val Val Trp Leu Val Ala Val Ile Val Gly Ser
225                 230                 235                 240

Pro Met Trp His Val Gln Gln Leu Glu Ile Lys Tyr Asp Phe Leu Tyr
                245                 250                 255

Glu Lys Glu His Ile Cys Cys Leu Glu Glu Trp Thr Ser Pro Val His
            260                 265                 270

Gln Lys Ile Tyr Thr Thr Phe Ile Leu Ser Ser Ser Ser Cys Leu
        275                 280                 285

Leu Trp Lys Lys Lys Arg Ala Val Ile Met Met Val Thr Val Val Ala
    290                 295                 300

Leu Phe Ala Val Cys Trp Ala Pro Phe His Val His Met Met Ile
305                 310                 315                 320

Glu Tyr Ser Asn Phe Glu Lys Glu Tyr Asp Asp Val Thr Ile Lys Met
                325                 330                 335

Ile Phe Ala Ile Val Gln Ile Ile Gly Phe Ser Asn Ser Ile Cys Asn
            340                 345                 350

Pro Ile Val Tyr Ala Phe Met Asn Glu Asn Phe Lys Lys Asn Val Leu
        355                 360                 365

Ser Ala Val Cys Tyr Cys Ile Val Asn Lys Thr Phe Ser Pro Ala Gln
```

```
                370             375             380
Arg His Gly Asn Ser Gly Ile Thr Met Met Arg Lys Lys Ala Lys Phe
385                 390                 395                 400

Ser Leu Arg Glu Asn Pro Val Glu Glu Thr Lys Gly Glu Ala Phe Ser
                405                 410                 415

Asp Gly Asn Ile Glu Val Lys Leu Cys Glu Gln Thr Glu Glu Lys Lys
                420                 425                 430

Lys Leu Lys Arg His Leu Ala Leu Phe Arg Ser Glu Leu Ala Glu Asn
            435                 440                 445

Ser Pro Leu Asp Ser Gly His
    450                 455

<210> SEQ ID NO 61
<211> LENGTH: 431
<212> TYPE: PRT
<213> ORGANISM: Homo sapiens

<400> SEQUENCE: 61

Met Gln Ala Leu Asn Ile Thr Pro Glu Gln Phe Ser Arg Leu Leu Arg
1               5                   10                  15

Asp His Asn Leu Thr Arg Glu Gln Phe Ile Ala Val His Arg Leu Arg
                20                  25                  30

Pro Leu Val Tyr Thr Pro Glu Leu Pro Gly Arg Ala Lys Leu Ala Leu
            35                  40                  45

Val Leu Thr Gly Val Leu Ile Phe Ala Leu Ala Leu Phe Gly Asn Ala
        50                  55                  60

Leu Val Phe Tyr Val Val Thr Arg Ser Lys Ala Met Arg Thr Val Thr
65                  70                  75                  80

Asn Ile Phe Ile Cys Ser Leu Ala Leu Ser Asp Leu Leu Ile Thr Phe
                85                  90                  95

Phe Cys Ile Pro Val Thr Met Leu Gln Asn Ile Ser Asp Asn Trp Leu
            100                 105                 110

Gly Gly Ala Phe Ile Cys Lys Met Val Pro Phe Val Gln Ser Thr Ala
        115                 120                 125

Val Val Thr Glu Ile Leu Thr Met Thr Cys Ile Ala Val Glu Arg His
130                 135                 140

Gln Gly Leu Val His Pro Phe Lys Met Lys Trp Gln Tyr Thr Asn Arg
145                 150                 155                 160

Arg Ala Phe Thr Met Leu Gly Val Val Trp Leu Val Ala Val Ile Val
                165                 170                 175

Gly Ser Pro Met Trp His Val Gln Gln Leu Glu Ile Lys Tyr Asp Phe
            180                 185                 190

Leu Tyr Glu Lys Glu His Ile Cys Cys Leu Glu Glu Trp Thr Ser Pro
        195                 200                 205

Val His Gln Lys Ile Tyr Thr Thr Phe Ile Leu Val Ile Leu Phe Leu
210                 215                 220

Leu Pro Leu Met Val Met Leu Ile Leu Tyr Ser Lys Ile Gly Tyr Glu
225                 230                 235                 240

Leu Trp Ile Lys Lys Arg Val Gly Asp Gly Ser Val Leu Arg Thr Ile
                245                 250                 255

His Gly Lys Glu Met Ser Lys Ile Ala Arg Lys Lys Arg Ala Val
            260                 265                 270

Ile Met Met Val Thr Val Val Ala Leu Phe Ala Val Cys Trp Ala Pro
        275                 280                 285

Phe His Val Val His Met Met Ile Glu Tyr Ser Asn Phe Glu Lys Glu
```

```
                 290                 295                 300
Tyr Asp Asp Val Thr Ile Lys Met Ile Phe Ala Ile Val Gln Ile Ile
305                 310                 315                 320

Gly Phe Ser Asn Ser Ile Cys Asn Pro Ile Val Tyr Ala Phe Met Asn
                325                 330                 335

Glu Asn Phe Lys Lys Asn Val Leu Ser Ala Val Cys Tyr Cys Ile Val
                340                 345                 350

Asn Lys Thr Phe Ser Pro Ala Gln Arg His Gly Asn Ser Gly Ile Thr
                355                 360                 365

Met Met Arg Lys Lys Ala Lys Phe Ser Leu Arg Glu Asn Pro Val Glu
        370                 375                 380

Glu Thr Lys Gly Glu Ala Phe Ser Asp Gly Asn Ile Glu Val Lys Leu
385                 390                 395                 400

Cys Glu Gln Thr Glu Lys Lys Lys Leu Lys Arg His Leu Ala Leu
                405                 410                 415

Phe Arg Ser Glu Leu Ala Glu Asn Ser Pro Leu Asp Ser Gly His
                420                 425                 430

<210> SEQ ID NO 62
<211> LENGTH: 647
<212> TYPE: PRT
<213> ORGANISM: Homo sapiens

<400> SEQUENCE: 62

Met Ala Glu Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
                20                  25                  30

Glu Gly Ser Gly Asp Ala Gly Arg Arg Pro Pro Val Asp Pro
                35                  40                  45

Arg Arg Leu Ala Arg Gln Leu Leu Leu Leu Trp Leu Leu Glu Ala
50                  55                  60

Pro Leu Leu Gly Val Arg Ala Gln Ala Gly Gln Gly Pro Gly
65                  70                  75                  80

Gln Gly Pro Gly Pro Gly Gln Gln Pro Pro Pro Gln Gln Gln
                85                  90                  95

Gln Ser Gly Gln Gln Tyr Asn Gly Glu Arg Gly Ile Ser Val Pro Asp
                100                 105                 110

His Gly Tyr Cys Gln Pro Ile Ser Ile Pro Leu Cys Thr Asp Ile Ala
                115                 120                 125

Tyr Asn Gln Thr Ile Met Pro Asn Leu Leu Gly His Thr Asn Gln Glu
                130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
                165                 170                 175

Cys Thr Val Leu Glu Gln Ala Leu Pro Pro Cys Arg Ser Leu Cys Glu
                180                 185                 190

Arg Ala Arg Gln Gly Cys Glu Ala Leu Met Asn Lys Phe Gly Phe Gln
                195                 200                 205

Trp Pro Asp Thr Leu Lys Cys Glu Lys Phe Pro Val His Gly Ala Gly
                210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
```

245                 250                 255
Gly His Arg Gly Gly Phe Pro Gly Gly Ala Gly Ala Ser Glu Arg Gly
                260                 265                 270

Lys Phe Ser Cys Pro Arg Ala Leu Lys Val Pro Ser Tyr Leu Asn Tyr
            275                 280                 285

His Phe Leu Gly Glu Lys Asp Cys Gly Ala Pro Cys Glu Pro Thr Lys
        290                 295                 300

Val Tyr Gly Leu Met Tyr Phe Gly Pro Glu Glu Leu Arg Phe Ser Arg
305                 310                 315                 320

Thr Trp Ile Gly Ile Trp Ser Val Leu Cys Cys Ala Ser Thr Leu Phe
                325                 330                 335

Thr Val Leu Thr Tyr Leu Val Asp Met Arg Arg Phe Ser Tyr Pro Glu
            340                 345                 350

Arg Pro Ile Ile Phe Leu Ser Gly Cys Tyr Thr Ala Val Ala Val Ala
        355                 360                 365

Tyr Ile Ala Gly Phe Leu Leu Glu Asp Arg Val Val Cys Asn Asp Lys
    370                 375                 380

Phe Ala Glu Asp Gly Ala Arg Thr Val Ala Gln Gly Thr Lys Lys Glu
385                 390                 395                 400

Gly Cys Thr Ile Leu Phe Met Met Leu Tyr Phe Phe Ser Met Ala Ser
                405                 410                 415

Ser Ile Trp Trp Val Ile Leu Ser Leu Thr Trp Phe Leu Ala Ala Gly
            420                 425                 430

Met Lys Trp Gly His Glu Ala Ile Glu Ala Asn Ser Gln Tyr Phe His
        435                 440                 445

Leu Ala Ala Trp Ala Val Pro Ala Ile Lys Thr Ile Thr Ile Leu Ala
    450                 455                 460

Leu Gly Gln Val Asp Gly Asp Val Leu Ser Gly Val Cys Phe Val Gly
465                 470                 475                 480

Leu Asn Asn Val Asp Ala Leu Arg Gly Phe Val Leu Ala Pro Leu Phe
                485                 490                 495

Val Tyr Leu Phe Ile Gly Thr Ser Phe Leu Leu Ala Gly Phe Val Ser
            500                 505                 510

Leu Phe Arg Ile Arg Thr Ile Met Lys His Asp Gly Thr Lys Thr Glu
        515                 520                 525

Lys Leu Glu Lys Leu Met Val Arg Ile Gly Val Phe Ser Val Leu Tyr
    530                 535                 540

Thr Val Pro Ala Thr Ile Val Ile Ala Cys Tyr Phe Tyr Glu Gln Ala
545                 550                 555                 560

Phe Arg Asp Gln Trp Glu Arg Ser Trp Val Ala Gln Ser Cys Lys Ser
                565                 570                 575

Tyr Ala Ile Pro Cys Pro His Leu Gln Ala Gly Gly Gly Ala Pro Pro
            580                 585                 590

His Pro Pro Met Ser Pro Asp Phe Thr Val Phe Met Ile Lys Tyr Leu
        595                 600                 605

Met Thr Leu Ile Val Gly Ile Thr Ser Gly Phe Trp Ile Trp Ser Gly
    610                 615                 620

Lys Thr Leu Asn Ser Trp Arg Lys Phe Tyr Thr Arg Leu Thr Asn Ser
625                 630                 635                 640

Lys Gln Gly Glu Thr Thr Val
                645

<210> SEQ ID NO 63
<211> LENGTH: 258

-continued

```
<212> TYPE: PRT
<213> ORGANISM: Homo sapiens

<400> SEQUENCE: 63

Met Leu Val Leu Tyr Gly His Ser Thr Gln Asp Leu Pro Glu Thr Asn
1               5                   10                  15

Ala Arg Val Val Gly Gly Thr Glu Ala Gly Arg Asn Ser Trp Pro Ser
            20                  25                  30

Gln Ile Ser Leu Gln Tyr Arg Ser Gly Gly Ser Arg Tyr His Thr Cys
        35                  40                  45

Gly Gly Thr Leu Ile Arg Gln Asn Trp Val Met Thr Ala Ala His Cys
    50                  55                  60

Val Asp Tyr Gln Lys Thr Phe Arg Val Val Ala Gly Asp His Asn Leu
65                  70                  75                  80

Ser Gln Asn Asp Gly Thr Glu Gln Tyr Val Ser Val Gln Lys Ile Val
                85                  90                  95

Val His Pro Tyr Trp Asn Ser Asn Val Ala Ala Gly Tyr Asp Ile
            100                 105                 110

Ala Leu Leu Arg Leu Ala Gln Ser Val Thr Leu Asn Ser Tyr Val Gln
        115                 120                 125

Leu Gly Val Leu Pro Gln Glu Gly Ala Ile Leu Ala Asn Asn Ser Pro
    130                 135                 140

Cys Tyr Ile Thr Gly Trp Gly Lys Thr Lys Thr Asn Gly Gln Leu Ala
145                 150                 155                 160

Gln Thr Leu Gln Gln Ala Tyr Leu Pro Ser Val Asp Tyr Ala Ile Cys
                165                 170                 175

Ser Ser Ser Ser Tyr Trp Gly Ser Thr Val Lys Asn Thr Met Val Cys
            180                 185                 190

Ala Gly Gly Asp Gly Val Arg Ser Gly Cys Gln Gly Asp Ser Gly Gly
        195                 200                 205

Pro Leu His Cys Leu Val Asn Gly Lys Tyr Ser Val His Gly Val Thr
    210                 215                 220

Ser Phe Val Ser Arg Gly Cys Asn Val Ser Arg Lys Pro Thr Val
225                 230                 235                 240

Phe Thr Gln Val Ser Ala Tyr Ile Ser Trp Ile Asn Asn Val Ile Ala
                245                 250                 255

Ser Asn

<210> SEQ ID NO 64
<211> LENGTH: 2555
<212> TYPE: PRT
<213> ORGANISM: Homo sapiens

<400> SEQUENCE: 64

Met Thr Ala Ile Thr His Gly Ser Pro Val Gly Gly Asn Asp Ser Gln
1               5                   10                  15

Gly Gln Val Leu Asp Gly Gln Ser Gln His Leu Phe Gln Gln Asn Gln
            20                  25                  30

Thr Ser Ser Pro Asp Ser Ser Asn Glu Asn Ser Val Ala Thr Pro Pro
        35                  40                  45

Pro Glu Glu Gln Gly Gln Gly Asp Ala Pro Gln His Glu Asp Glu
    50                  55                  60

Glu Pro Ala Phe Pro His Thr Glu Leu Ala Asn Leu Asp Asp Met Ile
65                  70                  75                  80

Asn Arg Pro Arg Trp Val Val Pro Val Leu Pro Lys Gly Glu Leu Glu
                85                  90                  95
```

Val Leu Leu Glu Ala Ala Ile Asp Leu Ser Val Lys Gly Leu Asp Val
            100                 105                 110

Lys Ser Glu Ala Cys Gln Arg Phe Phe Arg Asp Gly Leu Thr Ile Ser
            115                 120                 125

Phe Thr Lys Ile Leu Met Asp Glu Ala Val Ser Gly Trp Lys Phe Glu
            130                 135                 140

Ile His Arg Cys Ile Ile Asn Asn Thr His Arg Leu Val Glu Leu Cys
145                 150                 155                 160

Val Ala Lys Leu Ser Gln Asp Trp Phe Pro Leu Leu Glu Leu Leu Ala
                165                 170                 175

Met Ala Leu Asn Pro His Cys Lys Phe His Ile Tyr Asn Gly Thr Arg
                180                 185                 190

Pro Cys Glu Leu Ile Ser Ser Asn Ala Gln Leu Pro Glu Glu Glu Leu
            195                 200                 205

Phe Ala Arg Ser Ser Asp Pro Arg Ser Pro Lys Gly Trp Leu Val Asp
            210                 215                 220

Leu Ile Asn Lys Phe Gly Thr Leu Asn Gly Phe Gln Ile Leu His Asp
225                 230                 235                 240

Arg Phe Phe Asn Gly Ser Ala Leu Asn Ile Gln Ile Ala Ala Leu
                245                 250                 255

Ile Lys Pro Phe Gly Gln Cys Tyr Glu Phe Leu Ser Gln His Thr Leu
            260                 265                 270

Lys Lys Tyr Phe Ile Pro Val Ile Glu Ile Val Pro His Leu Leu Glu
            275                 280                 285

Asn Leu Thr Asp Glu Glu Leu Lys Lys Glu Ala Lys Asn Glu Ala Lys
            290                 295                 300

Asn Asp Ala Leu Ser Met Ile Ile Lys Ser Leu Lys Asn Leu Ala Ser
305                 310                 315                 320

Arg Ile Ser Gly Gln Asp Glu Thr Ile Lys Asn Leu Glu Ile Phe Arg
                325                 330                 335

Leu Lys Met Ile Leu Arg Leu Leu Gln Ile Ser Ser Phe Asn Gly Lys
            340                 345                 350

Met Asn Ala Leu Asn Glu Ile Asn Lys Val Ile Ser Ser Val Ser Tyr
            355                 360                 365

Tyr Thr His Arg His Ser Asn Pro Glu Glu Glu Trp Leu Thr Ala
            370                 375                 380

Glu Arg Met Ala Glu Trp Ile Gln Gln Asn Asn Ile Leu Ser Ile Val
385                 390                 395                 400

Leu Gln Asp Ser Leu His Gln Pro Gln Tyr Val Glu Lys Leu Glu Lys
                405                 410                 415

Ile Leu Arg Phe Val Ile Lys Glu Lys Ala Leu Thr Leu Gln Asp Leu
            420                 425                 430

Asp Asn Ile Trp Ala Ala Gln Ala Gly Lys His Glu Ala Ile Val Lys
            435                 440                 445

Asn Val His Asp Leu Leu Ala Lys Leu Ala Trp Asp Phe Ser Pro Gly
            450                 455                 460

Gln Leu Asp His Leu Phe Asp Cys Phe Lys Ala Ser Trp Thr Asn Ala
465                 470                 475                 480

Ser Lys Lys Gln Arg Glu Lys Leu Leu Glu Leu Ile Arg Arg Leu Ala
                485                 490                 495

Glu Asp Asp Lys Asp Gly Val Met Ala His Lys Val Leu Asn Leu Leu
            500                 505                 510

Trp Asn Leu Ala Gln Ser Asp Asp Val Pro Val Asp Ile Met Asp Leu

```
                515                 520                 525
Ala Leu Ser Ala His Ile Lys Ile Leu Asp Tyr Ser Cys Ser Gln Asp
530                 535                 540

Arg Asp Ala Gln Lys Ile Gln Trp Ile Asp His Phe Ile Glu Glu Leu
545                 550                 555                 560

Arg Thr Asn Asp Lys Trp Val Ile Pro Ala Leu Lys Gln Ile Arg Glu
                565                 570                 575

Ile Cys Ser Leu Phe Gly Glu Ala Ser Gln Asn Leu Ser Gln Thr Gln
                580                 585                 590

Arg Ser Pro His Ile Phe Tyr Arg His Asp Leu Ile Asn Gln Leu Gln
                595                 600                 605

Gln Asn His Ala Leu Val Thr Leu Val Ala Glu Asn Leu Ala Thr Tyr
                610                 615                 620

Met Asn Ser Ile Arg Leu Tyr Ala Gly Asp His Glu Asp Tyr Asp Pro
625                 630                 635                 640

Gln Thr Val Arg Leu Gly Ser Arg Tyr Ser His Val Gln Glu Val Gln
                645                 650                 655

Glu Arg Leu Asn Phe Leu Arg Phe Leu Leu Lys Asp Gly Gln Leu Trp
                660                 665                 670

Leu Cys Ala Pro Gln Ala Lys Gln Ile Trp Lys Cys Leu Ala Glu Asn
                675                 680                 685

Ala Val Tyr Leu Cys Asp Arg Glu Ala Cys Phe Lys Trp Tyr Ser Lys
                690                 695                 700

Leu Met Gly Asp Glu Pro Asp Leu Asp Pro Asp Ile Asn Lys Asp Phe
705                 710                 715                 720

Phe Glu Ser Asn Val Leu Gln Leu Asp Pro Ser Leu Leu Thr Glu Asn
                725                 730                 735

Gly Met Lys Cys Phe Glu Arg Phe Phe Lys Ala Val Asn Cys Arg Glu
                740                 745                 750

Arg Lys Leu Ile Ala Lys Arg Ser Tyr Met Met Asp Asp Leu Glu
                755                 760                 765

Leu Ile Gly Leu Asp Tyr Leu Trp Arg Val Val Ile Gln Ser Ser Asp
770                 775                 780

Glu Ile Ala Asn Arg Ala Ile Asp Leu Leu Lys Glu Ile Tyr Thr Asn
785                 790                 795                 800

Leu Gly Pro Arg Leu Lys Ala Asn Gln Val Val Ile His Glu Asp Phe
                805                 810                 815

Ile Gln Ser Cys Phe Asp Arg Leu Lys Ala Ser Tyr Asp Thr Leu Cys
                820                 825                 830

Val Phe Asp Gly Asp Lys Asn Ser Ile Asn Cys Ala Arg Gln Glu Ala
                835                 840                 845

Ile Arg Met Val Arg Val Leu Thr Val Ile Lys Glu Tyr Ile Asn Glu
                850                 855                 860

Cys Asp Ser Asp Tyr His Lys Glu Arg Met Ile Leu Pro Met Ser Arg
865                 870                 875                 880

Ala Phe Cys Gly Lys His Leu Ser Leu Ile Val Arg Phe Pro Asn Gln
                885                 890                 895

Gly Arg Gln Val Asp Glu Leu Asp Ile Trp Phe His Thr Asn Asp Thr
                900                 905                 910

Ile Gly Ser Val Arg Arg Cys Ile Val Asn Arg Ile Lys Ala Asn Val
                915                 920                 925

Ala His Lys Lys Ile Glu Leu Phe Val Gly Gly Glu Leu Ile Asp Ser
                930                 935                 940
```

-continued

```
Glu Asn Asp Arg Lys Leu Ile Gly Gln Leu Asn Leu Lys Asp Lys Ser
945                 950                 955                 960

Leu Ile Thr Ala Lys Leu Thr Gln Ile Asn Phe Asn Met Pro Ser Ser
                965                 970                 975

Pro Asp Ser Ser Asp Ser Ser Thr Ala Ser Pro Gly Asn His Arg
            980                 985                 990

Asn His Tyr Asn Asp Gly Pro Asn Leu Lys Val Glu Ser Cys Leu Pro
            995                 1000                1005

Gly Val Ile Met Ser Val His Pro Lys Tyr Ile Ser Phe Leu Trp
        1010                1015                1020

Gln Phe Ala Asn Leu Gly Ser Asn Leu Asn Met Pro Pro Leu Lys
        1025                1030                1035

Asn Gly Ala Arg Val Leu Met Lys Leu Met Pro Pro Asp Arg Thr
        1040                1045                1050

Ala Val Glu Lys Leu Arg Thr Val Cys Leu Asp His Ala Asn Leu
        1055                1060                1065

Gly Glu Gly Lys Leu Ser Pro Pro Leu Asp Ser Leu Phe Phe Gly
        1070                1075                1080

Pro Ser Ala Ser Gln Val Leu Tyr Leu Thr Glu Val Val Tyr Ala
        1085                1090                1095

Leu Leu Met Pro Ala Gly Val Pro Leu Thr Asp Gly Ser Ser Asp
        1100                1105                1110

Phe Gln Val His Phe Leu Lys Ser Gly Gly Leu Pro Leu Val Leu
        1115                1120                1125

Ser Met Leu Ile Arg Asn Asn Phe Leu Pro Asn Thr Asp Met Glu
        1130                1135                1140

Thr Arg Arg Gly Ala Tyr Leu Asn Ala Leu Lys Ile Ala Lys Leu
        1145                1150                1155

Leu Leu Thr Ala Ile Gly Tyr Gly His Val Arg Ala Val Ala Glu
        1160                1165                1170

Ala Cys Gln Pro Val Val Asp Gly Thr Asp Pro Ile Thr Gln Ile
        1175                1180                1185

Asn Gln Val Thr His Asp Gln Ala Val Val Leu Gln Ser Ala Leu
        1190                1195                1200

Gln Ser Ile Pro Asn Pro Ser Ser Glu Cys Val Leu Arg Asn Glu
        1205                1210                1215

Ser Ile Leu Leu Ala Gln Glu Ile Ser Asn Glu Ala Ser Arg Tyr
        1220                1225                1230

Met Pro Asp Ile Cys Val Ile Arg Ala Ile Gln Lys Ile Ile Trp
        1235                1240                1245

Ala Ser Ala Cys Gly Ala Leu Gly Leu Phe Phe Ser Pro Asn Glu
        1250                1255                1260

Glu Ile Thr Lys Ile Tyr Gln Met Thr Thr Asn Gly Ser Asn Lys
        1265                1270                1275

Leu Glu Val Glu Asp Glu Gln Val Cys Cys Glu Ala Leu Glu Val
        1280                1285                1290

Met Thr Leu Cys Phe Ala Leu Leu Pro Thr Ala Leu Asp Ala Leu
        1295                1300                1305

Ser Lys Glu Lys Ala Trp Gln Thr Phe Ile Ile Asp Leu Leu Leu
        1310                1315                1320

His Cys Pro Ser Lys Thr Val Arg Gln Leu Ala Gln Glu Gln Phe
        1325                1330                1335

Phe Leu Met Cys Thr Arg Cys Cys Met Gly His Arg Pro Leu Leu
        1340                1345                1350
```

```
Phe Phe Ile Thr Leu Leu Phe Thr Ile Leu Gly Ser Thr Ala Arg
1355                1360                1365

Glu Lys Gly Lys Tyr Ser Gly Asp Tyr Phe Thr Leu Leu Arg His
1370                1375                1380

Leu Leu Asn Tyr Ala Tyr Asn Gly Asn Ile Asn Ile Pro Asn Ala
1385                1390                1395

Glu Val Leu Leu Val Ser Glu Ile Asp Trp Leu Lys Arg Ile Arg
1400                1405                1410

Asp Asn Val Lys Asn Thr Gly Glu Thr Gly Val Glu Glu Pro Ile
1415                1420                1425

Leu Glu Gly His Leu Gly Val Thr Lys Glu Leu Leu Ala Phe Gln
1430                1435                1440

Thr Ser Glu Lys Lys Tyr His Phe Gly Cys Glu Lys Gly Gly Ala
1445                1450                1455

Asn Leu Ile Lys Glu Leu Ile Asp Asp Phe Ile Phe Pro Ala Ser
1460                1465                1470

Lys Val Tyr Leu Gln Tyr Leu Arg Ser Gly Glu Leu Pro Ala Glu
1475                1480                1485

Gln Ala Ile Pro Val Cys Ser Ser Pro Val Thr Ile Asn Ala Gly
1490                1495                1500

Phe Glu Leu Leu Val Ala Leu Ala Ile Gly Cys Val Arg Asn Leu
1505                1510                1515

Lys Gln Ile Val Asp Cys Leu Thr Glu Met Tyr Tyr Met Gly Thr
1520                1525                1530

Ala Ile Thr Thr Cys Glu Ala Leu Thr Glu Trp Glu Tyr Leu Pro
1535                1540                1545

Pro Val Gly Pro Arg Pro Pro Lys Gly Phe Val Gly Leu Lys Asn
1550                1555                1560

Ala Gly Ala Thr Cys Tyr Met Asn Ser Val Ile Gln Gln Leu Tyr
1565                1570                1575

Met Ile Pro Ser Ile Arg Asn Ser Ile Leu Ala Ile Glu Gly Thr
1580                1585                1590

Gly Ser Asp Leu His Asp Asp Met Phe Gly Asp Glu Lys Gln Asp
1595                1600                1605

Ser Glu Ser Asn Val Asp Pro Arg Asp Asp Val Phe Gly Tyr Pro
1610                1615                1620

His Gln Phe Glu Asp Lys Pro Ala Leu Ser Lys Thr Glu Asp Arg
1625                1630                1635

Lys Glu Tyr Asn Ile Gly Val Leu Arg His Leu Gln Val Ile Phe
1640                1645                1650

Gly His Leu Ala Ala Ser Gln Leu Gln Tyr Tyr Val Pro Arg Gly
1655                1660                1665

Phe Trp Lys Gln Phe Arg Leu Trp Gly Glu Pro Val Asn Leu Arg
1670                1675                1680

Glu Gln His Asp Ala Leu Glu Phe Phe Asn Ser Leu Val Asp Ser
1685                1690                1695

Leu Asp Glu Ala Leu Lys Ala Leu Gly His Pro Ala Ile Leu Ser
1700                1705                1710

Lys Val Leu Gly Gly Ser Phe Ala Asp Gln Lys Ile Cys Gln Gly
1715                1720                1725

Cys Pro His Arg Phe Glu Cys Glu Glu Ser Phe Thr Thr Leu Asn
1730                1735                1740

Val Asp Ile Arg Asn His Gln Asn Leu Leu Asp Ser Leu Glu Gln
```

```
                    1745                1750                1755

Tyr Ile Lys Gly Asp Leu Leu Glu Gly Ala Asn Ala Tyr His Cys
        1760                1765                1770

Glu Lys Cys Asp Lys Lys Val Asp Thr Val Lys Arg Leu Leu Ile
        1775                1780                1785

Lys Lys Leu Pro Arg Val Leu Ala Ile Gln Leu Lys Arg Phe Asp
        1790                1795                1800

Tyr Asp Trp Glu Arg Glu Cys Ala Ile Lys Phe Asn Asp Tyr Phe
        1805                1810                1815

Glu Phe Pro Arg Glu Leu Asp Met Gly Pro Tyr Thr Val Ala Gly
        1820                1825                1830

Val Ala Asn Leu Glu Arg Asp Asn Val Asn Ser Glu Asn Glu Leu
        1835                1840                1845

Ile Glu Gln Lys Glu Gln Ser Asp Asn Glu Thr Ala Gly Gly Thr
        1850                1855                1860

Lys Tyr Arg Leu Val Gly Val Leu Val His Ser Gly Gln Ala Ser
        1865                1870                1875

Gly Gly His Tyr Tyr Ser Tyr Ile Ile Gln Arg Asn Gly Lys Asp
        1880                1885                1890

Asp Gln Thr Asp His Trp Tyr Lys Phe Asp Asp Gly Asp Val Thr
        1895                1900                1905

Glu Cys Lys Met Asp Asp Asp Glu Glu Met Lys Asn Gln Cys Phe
        1910                1915                1920

Gly Gly Glu Tyr Met Gly Glu Val Phe Asp His Met Met Lys Arg
        1925                1930                1935

Met Ser Tyr Arg Arg Gln Lys Arg Trp Trp Asn Ala Tyr Ile Pro
        1940                1945                1950

Phe Tyr Glu Gln Met Asp Met Ile Asp Glu Asp Asp Glu Met Ile
        1955                1960                1965

Arg Tyr Ile Ser Glu Leu Thr Ile Ala Arg Pro His Gln Ile Ile
        1970                1975                1980

Met Ser Pro Ala Ile Glu Arg Ser Val Arg Lys Gln Asn Val Lys
        1985                1990                1995

Phe Met His Asn Arg Leu Gln Tyr Ser Leu Glu Tyr Phe Gln Phe
        2000                2005                2010

Val Lys Lys Leu Leu Thr Cys Asn Gly Val Tyr Leu Asn Pro Ala
        2015                2020                2025

Pro Gly Gln Asp Tyr Leu Leu Pro Glu Ala Glu Glu Ile Thr Met
        2030                2035                2040

Ile Ser Ile Gln Leu Ala Ala Arg Phe Leu Phe Thr Thr Gly Phe
        2045                2050                2055

His Thr Lys Lys Ile Val Arg Gly Pro Ala Ser Asp Trp Tyr Asp
        2060                2065                2070

Ala Leu Cys Val Leu Leu Arg His Ser Lys Asn Val Arg Phe Trp
        2075                2080                2085

Phe Thr His Asn Val Leu Phe Asn Val Ser Asn Arg Phe Ser Glu
        2090                2095                2100

Tyr Leu Leu Glu Cys Pro Ser Ala Glu Val Arg Gly Ala Phe Ala
        2105                2110                2115

Lys Leu Ile Val Phe Ile Ala His Phe Ser Leu Gln Asp Gly Ser
        2120                2125                2130

Cys Pro Ser Pro Phe Ala Ser Pro Gly Pro Ser Ser Gln Ala Cys
        2135                2140                2145
```

-continued

Asp Asn Leu Ser Leu Ser Asp His Leu Arg Ala Thr Leu Asn
2150                2155                2160

Leu Leu Arg Arg Glu Val Ser Glu His Gly His Leu Gln Gln
2165                2170                2175

Tyr Phe Asn Leu Phe Val Met Tyr Ala Asn Leu Gly Val Ala Glu
2180                2185                2190

Lys Thr Gln Leu Leu Lys Leu Asn Val Pro Ala Thr Phe Met Leu
2195                2200                2205

Val Ser Leu Asp Glu Gly Pro Gly Pro Pro Ile Lys Tyr Gln Tyr
2210                2215                2220

Ala Glu Leu Gly Lys Leu Tyr Ser Val Val Ser Gln Leu Ile Arg
2225                2230                2235

Cys Cys Asn Val Ser Ser Thr Met Gln Ser Ser Ile Asn Gly Asn
2240                2245                2250

Pro Pro Leu Pro Asn Pro Phe Gly Asp Leu Asn Leu Ser Gln Pro
2255                2260                2265

Ile Met Pro Ile Gln Gln Asn Val Leu Asp Ile Leu Phe Val Arg
2270                2275                2280

Thr Ser Tyr Val Lys Lys Ile Ile Glu Asp Cys Ser Asn Ser Glu
2285                2290                2295

Asp Thr Ile Lys Leu Leu Arg Phe Cys Ser Trp Glu Asn Pro Gln
2300                2305                2310

Phe Ser Ser Thr Val Leu Ser Glu Leu Leu Trp Gln Val Ala Tyr
2315                2320                2325

Ser Tyr Thr Tyr Glu Leu Arg Pro Tyr Leu Asp Leu Leu Phe Gln
2330                2335                2340

Ile Leu Leu Ile Glu Asp Ser Trp Gln Thr His Arg Ile His Asn
2345                2350                2355

Ala Leu Lys Gly Ile Pro Asp Asp Arg Asp Gly Leu Phe Asp Thr
2360                2365                2370

Ile Gln Arg Ser Lys Asn His Tyr Gln Lys Arg Ala Tyr Gln Cys
2375                2380                2385

Ile Lys Cys Met Val Ala Leu Phe Ser Ser Cys Pro Val Ala Tyr
2390                2395                2400

Gln Ile Leu Gln Gly Asn Gly Asp Leu Lys Arg Lys Trp Thr Trp
2405                2410                2415

Ala Val Glu Trp Leu Gly Asp Glu Leu Glu Arg Arg Pro Tyr Thr
2420                2425                2430

Gly Asn Pro Gln Tyr Ser Tyr Asn Asn Trp Ser Pro Pro Val Gln
2435                2440                2445

Ser Asn Glu Thr Ala Asn Gly Tyr Phe Leu Glu Arg Ser His Ser
2450                2455                2460

Ala Arg Met Thr Leu Ala Lys Ala Cys Glu Leu Cys Pro Glu Glu
2465                2470                2475

Glu Pro Asp Asp Gln Asp Ala Pro Asp Glu His Glu Pro Ser Pro
2480                2485                2490

Ser Glu Asp Ala Pro Leu Tyr Pro His Ser Pro Ala Ser Gln Tyr
2495                2500                2505

Gln Gln Asn Asn His Val His Gly Gln Pro Tyr Thr Gly Pro Ala
2510                2515                2520

Ala His His Leu Asn Asn Pro Gln Lys Thr Gly Gln Arg Thr Gln
2525                2530                2535

Glu Asn Tyr Glu Gly Asn Glu Glu Val Ser Ser Pro Gln Met Lys
2540                2545                2550

Asp Gln
    2555

<210> SEQ ID NO 65
<211> LENGTH: 330
<212> TYPE: PRT
<213> ORGANISM: Homo sapiens

<400> SEQUENCE: 65

Met Ser Gln Trp His His Pro Arg Ser Gly Trp Gly Arg Arg Asp
1               5                   10                  15

Phe Ser Gly Arg Ser Ser Ala Lys Lys Gly Gly Asn His Ile Pro
            20                  25                  30

Glu Arg Trp Lys Asp Tyr Leu Pro Val Gly Gln Arg Met Pro Gly Thr
            35                  40                  45

Arg Phe Ile Ala Phe Lys Val Pro Leu Gln Lys Ser Phe Glu Lys Lys
50                  55                  60

Leu Ala Pro Glu Glu Cys Phe Ser Pro Leu Asp Leu Phe Asn Lys Ile
65                  70                  75                  80

Arg Glu Gln Asn Glu Glu Leu Gly Leu Ile Ile Asp Leu Thr Tyr Thr
                85                  90                  95

Gln Arg Tyr Tyr Lys Pro Glu Asp Leu Pro Glu Thr Val Pro Tyr Leu
            100                 105                 110

Lys Ile Phe Thr Val Gly His Gln Val Pro Asp Asp Glu Thr Ile Phe
        115                 120                 125

Lys Phe Lys His Ala Val Asn Gly Phe Leu Lys Glu Asn Lys Asp Asn
130                 135                 140

Asp Lys Leu Ile Gly Val His Cys Thr His Gly Leu Asn Arg Thr Gly
145                 150                 155                 160

Tyr Leu Ile Cys Arg Tyr Leu Ile Asp Val Glu Gly Val Arg Pro Asp
                165                 170                 175

Asp Ala Ile Glu Leu Phe Asn Arg Cys Arg Gly His Cys Leu Glu Arg
            180                 185                 190

Gln Asn Tyr Ile Glu Asp Leu Gln Asn Gly Pro Ile Arg Lys Asn Trp
        195                 200                 205

Asn Ser Ser Val Pro Arg Ser Ser Asp Phe Glu Asp Ser Ala His Leu
210                 215                 220

Met Gln Pro Val His Asn Lys Pro Val Lys Gln Gly Pro Arg Tyr Asn
225                 230                 235                 240

Leu His Gln Ile Gln Gly His Ser Ala Pro Arg His Phe His Thr Gln
                245                 250                 255

Thr Gln Ser Leu Gln Gln Ser Val Arg Lys Phe Ser Glu Asn Pro His
            260                 265                 270

Val Tyr Gln Arg His His Leu Pro Pro Gly Pro Pro Gly Glu Asp
        275                 280                 285

Tyr Ser His Arg Arg Tyr Ser Trp Asn Val Lys Pro Asn Ala Ser Arg
290                 295                 300

Ala Ala Gln Asp Arg Arg Arg Trp Tyr Pro Tyr Asn Tyr Ser Arg Leu
305                 310                 315                 320

Ser Tyr Pro Ala Cys Trp Glu Trp Thr Gln
                325                 330

<210> SEQ ID NO 66
<211> LENGTH: 185
<212> TYPE: PRT
<213> ORGANISM: Homo sapiens

```
<400> SEQUENCE: 66

Met Ser Gly Ser Phe Glu Leu Ser Val Gln Asp Leu Asn Asp Leu Leu
1               5                   10                  15

Ser Asp Gly Ser Gly Cys Tyr Ser Leu Pro Ser Gln Pro Cys Asn Glu
            20                  25                  30

Val Thr Pro Arg Ile Tyr Val Gly Asn Ala Ser Val Ala Gln Asp Ile
        35                  40                  45

Pro Lys Leu Gln Lys Leu Gly Ile Thr His Val Leu Asn Ala Ala Glu
    50                  55                  60

Gly Arg Ser Phe Met His Val Asn Thr Asn Ala Asn Phe Tyr Lys Asp
65                  70                  75                  80

Ser Gly Ile Thr Tyr Leu Gly Ile Lys Ala Asn Asp Thr Gln Glu Phe
                85                  90                  95

Asn Leu Ser Ala Tyr Phe Glu Arg Ala Ala Asp Phe Ile Asp Gln Ala
            100                 105                 110

Leu Ala Gln Lys Asn Gly Arg Val Leu Val His Cys Arg Glu Gly Tyr
        115                 120                 125

Ser Arg Ser Pro Thr Leu Val Ile Ala Tyr Leu Met Met Arg Gln Lys
    130                 135                 140

Met Asp Val Lys Ser Ala Leu Ser Ile Val Arg Gln Asn Arg Glu Ile
145                 150                 155                 160

Gly Pro Asn Asp Gly Phe Leu Ala Gln Leu Cys Gln Leu Asn Asp Arg
                165                 170                 175

Leu Ala Lys Glu Gly Lys Leu Lys Pro
            180                 185

<210> SEQ ID NO 67
<211> LENGTH: 1154
<212> TYPE: PRT
<213> ORGANISM: Homo sapiens

<400> SEQUENCE: 67

Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
        35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
        115                 120                 125

His Ser Pro Lys Lys Gln Lys Asn Gly Tyr Glu Lys Lys Ile Pro
    130                 135                 140

Asp Ala Thr Pro Leu Leu Asp Ala Ser Ser Leu Glu Tyr Leu Phe Ala
145                 150                 155                 160

Gln Gly Gln Tyr Asp Leu Val Lys Cys Leu Ala Pro Ile Arg Asp Pro
                165                 170                 175
```

-continued

```
Lys Thr Glu Gln Asp Gly His Asp Ile Glu Asn Glu Cys Leu Gly Met
                180                 185                 190

Ala Val Leu Ala Ile Ser His Tyr Ala Met Met Lys Lys Met Gln Leu
            195                 200                 205

Pro Glu Leu Pro Lys Asp Ile Ser Tyr Lys Arg Tyr Ile Pro Glu Thr
        210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

Thr Leu Glu Thr Leu Thr Lys His Tyr Gly Ala Glu Ile Phe Glu Thr
        275                 280                 285

Ser Met Leu Leu Ile Ser Ser Glu Asn Glu Met Asn Trp Phe His Ser
    290                 295                 300

Asn Asp Gly Gly Asn Val Leu Tyr Tyr Glu Val Met Val Thr Gly Asn
305                 310                 315                 320

Leu Gly Ile Gln Trp Arg His Lys Pro Asn Val Val Ser Val Glu Lys
                325                 330                 335

Glu Lys Asn Lys Leu Lys Arg Lys Lys Leu Glu Asn Lys Asp Lys Lys
            340                 345                 350

Asp Glu Glu Lys Asn Lys Ile Arg Glu Glu Trp Asn Asn Phe Ser Phe
        355                 360                 365

Phe Pro Glu Ile Thr His Ile Val Ile Lys Glu Ser Val Val Ser Ile
    370                 375                 380

Asn Lys Gln Asp Asn Lys Lys Met Glu Leu Lys Leu Ser Ser His Glu
385                 390                 395                 400

Glu Ala Leu Ser Phe Val Ser Leu Val Asp Gly Tyr Phe Arg Leu Thr
                405                 410                 415

Ala Asp Ala His His Tyr Leu Cys Thr Asp Val Ala Pro Pro Leu Ile
            420                 425                 430

Val His Asn Ile Gln Asn Gly Cys His Gly Pro Ile Cys Thr Glu Tyr
        435                 440                 445

Ala Ile Asn Lys Leu Arg Gln Glu Gly Ser Glu Glu Gly Met Tyr Val
    450                 455                 460

Leu Arg Trp Ser Cys Thr Asp Phe Asp Asn Ile Leu Met Thr Val Thr
465                 470                 475                 480

Cys Phe Glu Lys Ser Glu Gln Val Gln Gly Ala Gln Lys Gln Phe Lys
                485                 490                 495

Asn Phe Gln Ile Glu Val Gln Lys Gly Arg Tyr Ser Leu His Gly Ser
            500                 505                 510

Asp Arg Ser Phe Pro Ser Leu Gly Asp Leu Met Ser His Leu Lys Lys
        515                 520                 525

Gln Ile Leu Arg Thr Asp Asn Ile Ser Phe Met Leu Lys Arg Cys Cys
    530                 535                 540

Gln Pro Lys Pro Arg Glu Ile Ser Asn Leu Leu Val Ala Thr Lys Lys
545                 550                 555                 560

Ala Gln Glu Trp Gln Pro Val Tyr Pro Met Ser Gln Leu Ser Phe Asp
                565                 570                 575

Arg Ile Leu Lys Lys Asp Leu Val Gln Gly Glu His Leu Gly Arg Gly
            580                 585                 590

Thr Arg Thr His Ile Tyr Ser Gly Thr Leu Met Asp Tyr Lys Asp Asp
        595                 600                 605
```

Glu Gly Thr Ser Glu Glu Lys Lys Ile Lys Val Ile Leu Lys Val Leu
                610                 615                 620

Asp Pro Ser His Arg Asp Ile Ser Leu Ala Phe Phe Glu Ala Ala Ser
625                 630                 635                 640

Met Met Arg Gln Val Ser His Lys His Ile Val Tyr Leu Tyr Gly Val
                645                 650                 655

Cys Val Arg Asp Val Glu Asn Ile Met Val Glu Glu Phe Val Glu Gly
                660                 665                 670

Gly Pro Leu Asp Leu Phe Met His Arg Lys Ser Asp Val Leu Thr Thr
                675                 680                 685

Pro Trp Lys Phe Lys Val Ala Lys Gln Leu Ala Ser Ala Leu Ser Tyr
                690                 695                 700

Leu Glu Asp Lys Asp Leu Val His Gly Asn Val Cys Thr Lys Asn Leu
705                 710                 715                 720

Leu Leu Ala Arg Glu Gly Ile Asp Ser Glu Cys Gly Pro Phe Ile Lys
                725                 730                 735

Leu Ser Asp Pro Gly Ile Pro Ile Thr Val Leu Ser Arg Gln Glu Cys
                740                 745                 750

Ile Glu Arg Ile Pro Trp Ile Ala Pro Glu Cys Val Glu Asp Ser Lys
                755                 760                 765

Asn Leu Ser Val Ala Ala Asp Lys Trp Ser Phe Gly Thr Thr Leu Trp
770                 775                 780

Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
                820                 825                 830

Asn Gln Arg Pro Phe Phe Arg Ala Ile Met Arg Asp Ile Asn Lys Leu
                835                 840                 845

Glu Glu Gln Asn Pro Asp Ile Val Ser Arg Lys Lys Asn Gln Pro Thr
850                 855                 860

Glu Val Asp Pro Thr His Phe Glu Lys Arg Phe Leu Lys Arg Ile Arg
865                 870                 875                 880

Asp Leu Gly Glu Gly His Phe Gly Lys Val Glu Leu Cys Arg Tyr Asp
                885                 890                 895

Pro Glu Asp Asn Thr Gly Glu Gln Val Ala Val Lys Ser Leu Lys Pro
                900                 905                 910

Glu Ser Gly Gly Asn His Ile Ala Asp Leu Lys Lys Glu Ile Glu Ile
                915                 920                 925

Leu Arg Asn Leu Tyr His Glu Asn Ile Val Lys Tyr Lys Gly Ile Cys
                930                 935                 940

Thr Glu Asp Gly Gly Asn Gly Ile Lys Leu Ile Met Glu Phe Leu Pro
945                 950                 955                 960

Ser Gly Ser Leu Lys Glu Tyr Leu Pro Lys Asn Lys Asn Lys Ile Asn
                965                 970                 975

Leu Lys Gln Gln Leu Lys Tyr Ala Val Gln Ile Cys Lys Gly Met Asp
                980                 985                 990

Tyr Leu Gly Ser Arg Gln Tyr Val His Arg Asp Leu Ala Ala Arg Asn
                995                 1000                1005

Val Leu Val Glu Ser Glu His Gln Val Lys Ile Gly Asp Phe Gly
        1010                1015                1020

Leu Thr Lys Ala Ile Glu Thr Asp Lys Glu Tyr Tyr Thr Val Lys

```
                1025                1030                1035

Asp Asp Arg Asp Ser Pro Val Phe Trp Tyr Ala Pro Glu Cys Leu
    1040                1045                1050

Met Gln Ser Lys Phe Tyr Ile Ala Ser Asp Val Trp Ser Phe Gly
    1055                1060                1065

Val Thr Leu His Glu Leu Leu Thr Tyr Cys Asp Ser Asp Ser Ser
    1070                1075                1080

Pro Met Ala Leu Phe Leu Lys Met Ile Gly Pro Thr His Gly Gln
    1085                1090                1095

Met Thr Val Thr Arg Leu Val Asn Thr Leu Lys Glu Gly Lys Arg
    1100                1105                1110

Leu Pro Cys Pro Pro Asn Cys Pro Asp Glu Val Tyr Gln Leu Met
    1115                1120                1125

Arg Lys Cys Trp Glu Phe Gln Pro Ser Asn Arg Thr Ser Phe Gln
    1130                1135                1140

Asn Leu Ile Glu Gly Phe Glu Ala Leu Leu Lys
    1145                1150

<210> SEQ ID NO 68
<211> LENGTH: 1141
<212> TYPE: PRT
<213> ORGANISM: Homo sapiens

<400> SEQUENCE: 68

Met Ala Phe Cys Ala Lys Met Arg Ser Ser Lys Lys Thr Glu Val Asn
1               5                   10                  15

Leu Glu Ala Pro Glu Pro Gly Val Glu Val Ile Phe Tyr Leu Ser Asp
                20                  25                  30

Arg Glu Pro Leu Arg Leu Gly Ser Gly Glu Tyr Thr Ala Glu Glu Leu
            35                  40                  45

Cys Ile Arg Ala Ala Gln Ala Cys Arg Ile Ser Pro Leu Cys His Asn
        50                  55                  60

Leu Phe Ala Leu Tyr Asp Glu Asn Thr Lys Leu Trp Tyr Ala Pro Asn
65                  70                  75                  80

Arg Thr Ile Thr Val Asp Asp Lys Met Ser Leu Arg Leu His Tyr Arg
                85                  90                  95

Met Arg Phe Tyr Phe Thr Asn Trp His Gly Thr Asn Asp Asn Glu Gln
            100                 105                 110

Ser Val Trp Arg His Ser Pro Lys Lys Gln Lys Asn Gly Tyr Glu Lys
        115                 120                 125

Lys Lys Ile Pro Asp Ala Thr Pro Leu Leu Asp Ala Ser Ser Leu Glu
    130                 135                 140

Tyr Leu Phe Ala Gln Gly Gln Tyr Asp Leu Val Lys Cys Leu Ala Pro
145                 150                 155                 160

Ile Arg Asp Pro Lys Thr Glu Gln Asp Gly His Asp Ile Glu Asn Glu
                165                 170                 175

Cys Leu Gly Met Ala Val Leu Ala Ile Ser His Tyr Ala Met Met Lys
            180                 185                 190

Lys Met Gln Leu Pro Glu Leu Pro Lys Asp Ile Ser Tyr Lys Arg Tyr
        195                 200                 205

Ile Pro Glu Thr Leu Asn Lys Ser Ile Arg Gln Arg Asn Leu Leu Thr
    210                 215                 220

Arg Met Arg Ile Asn Asn Val Phe Lys Asp Phe Leu Lys Glu Phe Asn
225                 230                 235                 240

Asn Lys Thr Ile Cys Asp Ser Ser Val Ser Thr His Asp Leu Lys Val
```

-continued

```
                245                 250                 255
Lys Tyr Leu Ala Thr Leu Glu Thr Leu Thr Lys His Tyr Gly Ala Glu
                260                 265                 270

Ile Phe Glu Thr Ser Met Leu Leu Ile Ser Ser Glu Asn Glu Met Asn
                275                 280             285

Trp Phe His Ser Asn Asp Gly Gly Asn Val Leu Tyr Tyr Glu Val Met
                290                 295                 300

Val Thr Gly Asn Leu Gly Ile Gln Trp Arg His Lys Pro Asn Val Val
305                 310                 315                 320

Ser Val Glu Lys Glu Lys Asn Lys Leu Lys Arg Lys Lys Leu Glu Asn
                325                 330                 335

Lys Asp Lys Lys Asp Glu Glu Lys Asn Lys Ile Arg Glu Glu Trp Asn
                340                 345                 350

Asn Phe Ser Phe Phe Pro Glu Ile Thr His Ile Val Ile Lys Glu Ser
                355                 360                 365

Val Val Ser Ile Asn Lys Gln Asp Asn Lys Lys Met Glu Leu Lys Leu
                370                 375             380

Ser Ser His Glu Glu Ala Leu Ser Phe Val Ser Leu Val Asp Gly Tyr
385                 390                 395                 400

Phe Arg Leu Thr Ala Asp Ala His His Tyr Leu Cys Thr Asp Val Ala
                405                 410                 415

Pro Pro Leu Ile Val His Asn Ile Gln Asn Gly Cys His Gly Pro Ile
                420                 425                 430

Cys Thr Glu Tyr Ala Ile Asn Lys Leu Arg Gln Glu Gly Ser Glu Glu
                435                 440                 445

Gly Met Tyr Val Leu Arg Trp Ser Cys Thr Asp Phe Asp Asn Ile Leu
                450                 455                 460

Met Thr Val Thr Cys Phe Glu Lys Ser Glu Gln Val Gln Gly Ala Gln
465                 470                 475             480

Lys Gln Phe Lys Asn Phe Gln Ile Glu Val Gln Lys Gly Arg Tyr Ser
                485                 490                 495

Leu His Gly Ser Asp Arg Ser Phe Pro Ser Leu Gly Asp Leu Met Ser
                500                 505                 510

His Leu Lys Lys Gln Ile Leu Arg Thr Asp Asn Ile Ser Phe Met Leu
                515                 520                 525

Lys Arg Cys Cys Gln Pro Lys Pro Arg Glu Ile Ser Asn Leu Leu Val
                530                 535             540

Ala Thr Lys Lys Ala Gln Glu Trp Gln Pro Val Tyr Pro Met Ser Gln
545                 550                 555                 560

Leu Ser Phe Asp Arg Ile Leu Lys Lys Asp Leu Val Gln Gly Glu His
                565                 570                 575

Leu Gly Arg Gly Thr Arg Thr His Ile Tyr Ser Gly Thr Leu Met Asp
                580                 585                 590

Tyr Lys Asp Asp Glu Gly Thr Ser Glu Glu Lys Lys Ile Lys Val Ile
                595                 600                 605

Leu Lys Val Leu Asp Pro Ser His Arg Asp Ile Ser Leu Ala Phe Phe
                610                 615             620

Glu Ala Ala Ser Met Met Arg Gln Val Ser His Lys His Ile Val Tyr
625                 630                 635                 640

Leu Tyr Gly Val Cys Val Arg Asp Val Glu Asn Ile Met Val Glu Glu
                645                 650                 655

Phe Val Glu Gly Gly Pro Leu Asp Leu Phe Met His Arg Lys Ser Asp
                660                 665                 670
```

-continued

```
Val Leu Thr Thr Pro Trp Lys Phe Lys Val Ala Lys Gln Leu Ala Ser
            675                 680                 685

Ala Leu Ser Tyr Leu Glu Asp Lys Asp Leu Val His Gly Asn Val Cys
    690                 695                 700

Thr Lys Asn Leu Leu Leu Ala Arg Glu Gly Ile Asp Ser Glu Cys Gly
705                 710                 715                 720

Pro Phe Ile Lys Leu Ser Asp Pro Gly Ile Pro Ile Thr Val Leu Ser
                725                 730                 735

Arg Gln Glu Cys Ile Glu Arg Ile Pro Trp Ile Ala Pro Glu Cys Val
                740                 745                 750

Glu Asp Ser Lys Asn Leu Ser Val Ala Ala Asp Lys Trp Ser Phe Gly
            755                 760                 765

Thr Thr Leu Trp Glu Ile Cys Tyr Asn Gly Glu Ile Pro Leu Lys Asp
770                 775                 780

Lys Thr Leu Ile Glu Lys Glu Arg Phe Tyr Glu Ser Arg Cys Arg Pro
785                 790                 795                 800

Val Thr Pro Ser Cys Lys Glu Leu Ala Asp Leu Met Thr Arg Cys Met
                805                 810                 815

Asn Tyr Asp Pro Asn Gln Arg Pro Phe Phe Arg Ala Ile Met Arg Asp
            820                 825                 830

Ile Asn Lys Leu Glu Glu Gln Asn Pro Asp Ile Val Ser Arg Lys Lys
        835                 840                 845

Asn Gln Pro Thr Glu Val Asp Pro Thr His Phe Glu Lys Arg Phe Leu
850                 855                 860

Lys Arg Ile Arg Asp Leu Gly Glu Gly His Phe Gly Lys Val Glu Leu
865                 870                 875                 880

Cys Arg Tyr Asp Pro Glu Asp Asn Thr Gly Glu Gln Val Ala Val Lys
                885                 890                 895

Ser Leu Lys Pro Glu Ser Gly Gly Asn His Ile Ala Asp Leu Lys Lys
            900                 905                 910

Glu Ile Glu Ile Leu Arg Asn Leu Tyr His Glu Asn Ile Val Lys Tyr
        915                 920                 925

Lys Gly Ile Cys Thr Glu Asp Gly Gly Asn Gly Ile Lys Leu Ile Met
    930                 935                 940

Glu Phe Leu Pro Ser Gly Ser Leu Lys Glu Tyr Leu Pro Lys Asn Lys
945                 950                 955                 960

Asn Lys Ile Asn Leu Lys Gln Gln Leu Lys Tyr Ala Val Gln Ile Cys
                965                 970                 975

Lys Gly Met Asp Tyr Leu Gly Ser Arg Gln Tyr Val His Arg Asp Leu
            980                 985                 990

Ala Ala Arg Asn Val Leu Val Glu  Ser Glu His Gln Val  Lys Ile Asp
        995                 1000                1005

Phe Gly Leu Thr Lys Ala Ile  Glu Thr Asp Lys Glu  Tyr Tyr Thr
    1010                1015                1020

Val Lys Asp Asp Arg Asp Ser  Pro Val Phe Trp Tyr  Ala Pro Glu
    1025                1030                1035

Cys Leu Met Gln Ser Lys Phe  Tyr Ile Ala Ser Asp  Val Trp Ser
    1040                1045                1050

Phe Gly Val Thr Leu His Glu  Leu Leu Thr Tyr Cys  Asp Ser Asp
    1055                1060                1065

Ser Ser Pro Met Ala Leu Phe  Leu Lys Met Ile Gly  Pro Thr His
    1070                1075                1080

Gly Gln Met Thr Val Thr Arg  Leu Val Asn Thr Leu  Lys Glu Gly
    1085                1090                1095
```

Lys Arg Leu Pro Cys Pro Pro Asn Cys Pro Asp Glu Val Tyr Gln
    1100            1105                1110

Leu Met Arg Lys Cys Trp Glu Phe Gln Pro Ser Asn Arg Thr Ser
    1115            1120                1125

Phe Gln Asn Leu Ile Glu Gly Phe Glu Ala Leu Leu Lys
    1130            1135                1140

<210> SEQ ID NO 69
<211> LENGTH: 666
<212> TYPE: PRT
<213> ORGANISM: Homo sapiens

<400> SEQUENCE: 69

Met Ala Cys Leu Met Ala Ala Phe Ser Val Gly Thr Ala Met Asn Ala
1               5                   10                  15

Ser Ser Tyr Ser Ala Glu Met Thr Glu Pro Lys Ser Val Cys Val Ser
            20                  25                  30

Val Asp Glu Val Val Ser Ser Asn Met Glu Ala Thr Glu Thr Asp Leu
        35                  40                  45

Leu Asn Gly His Leu Lys Lys Val Asp Asn Leu Thr Glu Ala Gln
50                  55                  60

Arg Phe Ser Ser Leu Pro Arg Arg Ala Val Asn Ile Glu Phe Arg
65              70                  75                  80

Asp Leu Ser Tyr Ser Val Pro Glu Gly Pro Trp Trp Arg Lys Lys Gly
                85                  90                  95

Tyr Lys Thr Leu Leu Lys Gly Ile Ser Gly Lys Phe Asn Ser Gly Glu
            100                 105                 110

Leu Val Ala Ile Met Gly Pro Ser Gly Ala Gly Lys Ser Thr Leu Met
        115                 120                 125

Asn Ile Leu Ala Gly Tyr Arg Glu Thr Gly Met Lys Gly Ala Val Leu
    130                 135                 140

Ile Asn Gly Leu Pro Arg Asp Leu Arg Cys Phe Arg Lys Val Ser Cys
145                 150                 155                 160

Tyr Ile Met Gln Asp Asp Met Leu Leu Pro His Leu Thr Val Gln Glu
                165                 170                 175

Ala Met Met Val Ser Ala His Leu Lys Leu Gln Glu Lys Asp Glu Gly
            180                 185                 190

Arg Arg Glu Met Val Lys Glu Ile Leu Thr Ala Leu Gly Leu Leu Ser
        195                 200                 205

Cys Ala Asn Thr Arg Thr Gly Ser Leu Ser Gly Gly Gln Arg Lys Arg
    210                 215                 220

Leu Ala Ile Ala Leu Glu Leu Val Asn Asn Pro Pro Val Met Phe Phe
225                 230                 235                 240

Asp Glu Pro Thr Ser Gly Leu Asp Ser Ala Ser Cys Phe Gln Val Val
                245                 250                 255

Ser Leu Met Lys Gly Leu Ala Gln Gly Gly Arg Ser Ile Ile Cys Thr
            260                 265                 270

Ile His Gln Pro Ser Ala Lys Leu Phe Glu Leu Phe Asp Gln Leu Tyr
        275                 280                 285

Val Leu Ser Gln Gly Gln Cys Val Tyr Arg Gly Lys Val Cys Asn Leu
    290                 295                 300

Val Pro Tyr Leu Arg Asp Leu Gly Leu Asn Cys Pro Thr Tyr His Asn
305                 310                 315                 320

Pro Ala Asp Phe Val Met Glu Val Ala Ser Gly Glu Tyr Gly Asp Gln
                325                 330                 335

Asn Ser Arg Leu Val Arg Ala Val Arg Glu Gly Met Cys Asp Ser Asp
            340                 345                 350

His Lys Arg Asp Leu Gly Gly Asp Ala Glu Val Asn Pro Phe Leu Trp
        355                 360                 365

His Arg Pro Ser Glu Glu Asp Ser Ser Ser Met Glu Gly Cys His Ser
370                 375                 380

Phe Ser Ala Ser Cys Leu Thr Gln Phe Cys Ile Leu Phe Lys Arg Thr
385                 390                 395                 400

Phe Leu Ser Ile Met Arg Asp Ser Val Leu Thr His Leu Arg Ile Thr
                405                 410                 415

Ser His Ile Gly Ile Gly Leu Leu Ile Gly Leu Leu Tyr Leu Gly Ile
            420                 425                 430

Gly Asn Glu Ala Lys Lys Val Leu Ser Asn Ser Gly Phe Leu Phe Phe
        435                 440                 445

Ser Met Leu Phe Leu Met Phe Ala Ala Leu Met Pro Thr Val Leu Thr
450                 455                 460

Phe Pro Leu Glu Met Gly Val Phe Leu Arg Glu His Leu Asn Tyr Trp
465                 470                 475                 480

Tyr Ser Leu Lys Ala Tyr Tyr Leu Ala Lys Thr Met Ala Asp Val Pro
                485                 490                 495

Phe Gln Ile Met Phe Pro Val Ala Tyr Cys Ser Ile Val Tyr Trp Met
            500                 505                 510

Thr Ser Gln Pro Ser Asp Ala Val Arg Phe Val Leu Phe Ala Ala Leu
        515                 520                 525

Gly Thr Met Thr Ser Leu Val Ala Gln Ser Leu Gly Leu Leu Ile Gly
530                 535                 540

Ala Ala Ser Thr Ser Leu Gln Val Ala Thr Phe Val Gly Pro Val Thr
545                 550                 555                 560

Ala Ile Pro Val Leu Leu Phe Ser Gly Phe Phe Val Ser Phe Asp Thr
                565                 570                 575

Ile Pro Thr Tyr Leu Gln Trp Met Ser Tyr Ile Ser Tyr Val Arg Tyr
            580                 585                 590

Gly Phe Glu Gly Val Ile Leu Ser Ile Tyr Gly Leu Asp Arg Glu Asp
        595                 600                 605

Leu His Cys Asp Ile Asp Glu Thr Cys His Phe Gln Lys Ser Glu Ala
610                 615                 620

Ile Leu Arg Glu Leu Asp Val Glu Asn Ala Lys Leu Tyr Leu Asp Phe
625                 630                 635                 640

Ile Val Leu Gly Ile Phe Phe Ile Ser Leu Arg Leu Ile Ala Tyr Phe
                645                 650                 655

Val Leu Arg Tyr Lys Ile Arg Ala Glu Arg
            660                 665

<210> SEQ ID NO 70
<211> LENGTH: 678
<212> TYPE: PRT
<213> ORGANISM: Homo sapiens

<400> SEQUENCE: 70

Met Ala Cys Leu Met Ala Ala Phe Ser Val Gly Thr Ala Met Asn Ala
1               5                   10                  15

Ser Ser Tyr Ser Ala Glu Met Thr Glu Pro Lys Ser Val Cys Val Ser
            20                  25                  30

Val Asp Glu Val Val Ser Ser Asn Met Glu Ala Thr Gly Thr Asp Leu
        35                  40                  45

-continued

Leu Asn Gly His Leu Lys Lys Val Asp Asn Leu Thr Glu Ala Gln
        50                  55                  60

Arg Phe Ser Ser Leu Pro Arg Arg Ala Ala Val Asn Ile Glu Phe Arg
65                  70                  75                  80

Asp Leu Ser Tyr Ser Val Pro Glu Gly Pro Trp Trp Arg Lys Lys Gly
                85                  90                  95

Tyr Lys Thr Leu Leu Lys Gly Ile Ser Gly Lys Phe Asn Ser Gly Glu
            100                 105                 110

Leu Val Ala Ile Met Gly Pro Ser Gly Ala Gly Lys Ser Thr Leu Met
            115                 120                 125

Asn Ile Leu Ala Gly Tyr Arg Glu Thr Gly Met Lys Gly Ala Val Leu
        130                 135                 140

Ile Asn Gly Leu Pro Arg Asp Leu Arg Cys Phe Arg Lys Val Ser Cys
145                 150                 155                 160

Tyr Ile Met Gln Asp Asp Met Leu Leu Pro His Leu Thr Val Gln Glu
                165                 170                 175

Ala Met Met Val Ser Ala His Leu Lys Leu Gln Glu Lys Asp Glu Gly
            180                 185                 190

Arg Arg Glu Met Val Lys Glu Ile Leu Thr Ala Leu Gly Leu Leu Ser
            195                 200                 205

Cys Ala Asn Thr Arg Thr Gly Ser Leu Ser Gly Gly Gln Arg Lys Arg
210                 215                 220

Leu Ala Ile Ala Leu Glu Leu Val Asn Asn Pro Pro Val Met Phe Phe
225                 230                 235                 240

Asp Glu Pro Thr Ser Gly Leu Asp Ser Ala Ser Cys Phe Gln Val Val
                245                 250                 255

Ser Leu Met Lys Gly Leu Ala Gln Gly Gly Arg Ser Ile Ile Cys Thr
            260                 265                 270

Ile His Gln Pro Ser Ala Lys Leu Phe Glu Leu Phe Asp Gln Leu Tyr
        275                 280                 285

Val Leu Ser Gln Gly Gln Cys Val Tyr Arg Gly Lys Val Cys Asn Leu
290                 295                 300

Val Pro Tyr Leu Arg Asp Leu Gly Leu Asn Cys Pro Thr Tyr His Asn
305                 310                 315                 320

Pro Ala Asp Phe Val Met Glu Val Ala Ser Gly Glu Tyr Gly Asp Gln
                325                 330                 335

Asn Ser Arg Leu Val Arg Ala Val Arg Glu Gly Met Cys Asp Ser Asp
            340                 345                 350

His Lys Arg Asp Leu Gly Gly Asp Ala Glu Val Asn Pro Phe Leu Trp
        355                 360                 365

His Arg Pro Ser Glu Glu Val Lys Gln Thr Lys Arg Leu Lys Gly Leu
        370                 375                 380

Arg Lys Asp Ser Ser Ser Met Glu Gly Cys His Ser Phe Ser Ala Ser
385                 390                 395                 400

Cys Leu Thr Gln Phe Cys Ile Leu Phe Lys Arg Thr Phe Leu Ser Ile
                405                 410                 415

Met Arg Asp Ser Val Leu Thr His Leu Arg Ile Thr Ser His Ile Gly
            420                 425                 430

Ile Gly Leu Leu Ile Gly Leu Leu Tyr Leu Gly Ile Gly Asn Glu Ala
        435                 440                 445

Lys Lys Val Leu Ser Asn Ser Gly Phe Leu Phe Phe Ser Met Leu Phe
450                 455                 460

Leu Met Phe Ala Ala Leu Met Pro Thr Val Leu Thr Phe Pro Leu Glu

```
                465                 470                 475                 480
Met Gly Val Phe Leu Arg Glu His Leu Asn Tyr Trp Tyr Ser Leu Lys
                    485                 490                 495

Ala Tyr Tyr Leu Ala Lys Thr Met Ala Asp Val Pro Phe Gln Ile Met
                500                 505                 510

Phe Pro Val Ala Tyr Cys Ser Ile Val Tyr Trp Met Thr Ser Gln Pro
            515                 520                 525

Ser Asp Ala Val Arg Phe Val Leu Phe Ala Ala Leu Gly Thr Met Thr
        530                 535                 540

Ser Leu Val Ala Gln Ser Leu Gly Leu Leu Ile Gly Ala Ala Ser Thr
545                 550                 555                 560

Ser Leu Gln Val Ala Thr Phe Val Gly Pro Val Thr Ala Ile Pro Val
                565                 570                 575

Leu Leu Phe Ser Gly Phe Phe Val Ser Phe Asp Thr Ile Pro Thr Tyr
                580                 585                 590

Leu Gln Trp Met Ser Tyr Ile Ser Tyr Val Arg Tyr Gly Phe Glu Gly
                595                 600                 605

Val Ile Leu Ser Ile Tyr Gly Leu Asp Arg Glu Asp Leu His Cys Asp
            610                 615                 620

Ile Asp Glu Thr Cys His Phe Gln Lys Ser Glu Ala Ile Leu Arg Glu
625                 630                 635                 640

Leu Asp Val Glu Asn Ala Lys Leu Tyr Leu Asp Phe Ile Val Leu Gly
                645                 650                 655

Ile Phe Phe Ile Ser Leu Arg Leu Ile Ala Tyr Phe Val Leu Arg Tyr
                660                 665                 670

Lys Ile Arg Ala Glu Arg
            675

<210> SEQ ID NO 71
<211> LENGTH: 677
<212> TYPE: PRT
<213> ORGANISM: Homo sapiens

<400> SEQUENCE: 71

Met Arg Ile Ser Leu Pro Arg Ala Pro Glu Arg Asp Gly Gly Val Ser
1               5                   10                  15

Ala Ser Ser Leu Leu Asp Thr Val Thr Asn Ala Ser Ser Tyr Ser Ala
                20                  25                  30

Glu Met Thr Glu Pro Lys Ser Val Cys Val Ser Val Asp Glu Val Val
            35                  40                  45

Ser Ser Asn Met Glu Ala Thr Glu Thr Asp Leu Leu Asn Gly His Leu
50                  55                  60

Lys Lys Val Asp Asn Asn Leu Thr Glu Ala Gln Arg Phe Ser Ser Leu
65                  70                  75                  80

Pro Arg Arg Ala Ala Val Asn Ile Glu Phe Arg Asp Leu Ser Tyr Ser
                85                  90                  95

Val Pro Glu Gly Pro Trp Trp Arg Lys Lys Gly Tyr Lys Thr Leu Leu
                100                 105                 110

Lys Gly Ile Ser Gly Lys Phe Asn Ser Gly Glu Leu Val Ala Ile Met
            115                 120                 125

Gly Pro Ser Gly Ala Gly Lys Ser Thr Leu Met Asn Ile Leu Ala Gly
        130                 135                 140

Tyr Arg Glu Thr Gly Met Lys Gly Ala Val Leu Ile Asn Gly Leu Pro
145                 150                 155                 160

Arg Asp Leu Arg Cys Phe Arg Lys Val Ser Cys Tyr Ile Met Gln Asp
```

-continued

```
                165                 170                 175
Asp Met Leu Leu Pro His Leu Thr Val Gln Glu Ala Met Met Val Ser
            180                 185                 190
Ala His Leu Lys Leu Gln Glu Lys Asp Glu Gly Arg Arg Glu Met Val
            195                 200                 205
Lys Glu Ile Leu Thr Ala Leu Gly Leu Leu Ser Cys Ala Asn Thr Arg
            210                 215                 220
Thr Gly Ser Leu Ser Gly Gly Gln Arg Lys Arg Leu Ala Ile Ala Leu
225                 230                 235                 240
Glu Leu Val Asn Asn Pro Pro Val Met Phe Phe Asp Glu Pro Thr Ser
            245                 250                 255
Gly Leu Asp Ser Ala Ser Cys Phe Gln Val Val Ser Leu Met Lys Gly
            260                 265                 270
Leu Ala Gln Gly Gly Arg Ser Ile Ile Cys Thr Ile His Gln Pro Ser
            275                 280                 285
Ala Lys Leu Phe Glu Leu Phe Asp Gln Leu Tyr Val Leu Ser Gln Gly
            290                 295                 300
Gln Cys Val Tyr Arg Gly Lys Val Cys Asn Leu Val Pro Tyr Leu Arg
305                 310                 315                 320
Asp Leu Gly Leu Asn Cys Pro Thr Tyr His Asn Pro Ala Asp Phe Val
            325                 330                 335
Met Glu Val Ala Ser Gly Glu Tyr Gly Asp Gln Asn Ser Arg Leu Val
            340                 345                 350
Arg Ala Val Arg Glu Gly Met Cys Asp Ser Asp His Lys Arg Asp Leu
            355                 360                 365
Gly Gly Asp Ala Glu Val Asn Pro Phe Leu Trp His Arg Pro Ser Glu
            370                 375                 380
Glu Asp Ser Ser Ser Met Glu Gly Cys His Ser Phe Ser Ala Ser Cys
385                 390                 395                 400
Leu Thr Gln Phe Cys Ile Leu Phe Lys Arg Thr Phe Leu Ser Ile Met
            405                 410                 415
Arg Asp Ser Val Leu Thr His Leu Arg Ile Thr Ser His Ile Gly Ile
            420                 425                 430
Gly Leu Leu Ile Gly Leu Leu Tyr Leu Gly Ile Gly Asn Glu Ala Lys
            435                 440                 445
Lys Val Leu Ser Asn Ser Gly Phe Leu Phe Phe Ser Met Leu Phe Leu
            450                 455                 460
Met Phe Ala Ala Leu Met Pro Thr Val Leu Thr Phe Pro Leu Glu Met
465                 470                 475                 480
Gly Val Phe Leu Arg Glu His Leu Asn Tyr Trp Tyr Ser Leu Lys Ala
            485                 490                 495
Tyr Tyr Leu Ala Lys Thr Met Ala Asp Val Pro Phe Gln Ile Met Phe
            500                 505                 510
Pro Val Ala Tyr Cys Ser Ile Val Tyr Trp Met Thr Ser Gln Pro Ser
            515                 520                 525
Asp Ala Val Arg Phe Val Leu Phe Ala Ala Leu Gly Thr Met Thr Ser
            530                 535                 540
Leu Val Ala Gln Ser Leu Gly Leu Leu Ile Gly Ala Ala Ser Thr Ser
545                 550                 555                 560
Leu Gln Val Ala Thr Phe Val Gly Pro Val Thr Ala Ile Pro Val Leu
            565                 570                 575
Leu Phe Ser Gly Phe Phe Val Ser Phe Asp Thr Ile Pro Thr Tyr Leu
            580                 585                 590
```

-continued

```
Gln Trp Met Ser Tyr Ile Ser Tyr Val Arg Tyr Gly Phe Glu Gly Val
            595                 600                 605

Ile Leu Ser Ile Tyr Gly Leu Asp Arg Glu Asp Leu His Cys Asp Ile
            610                 615                 620

Asp Glu Thr Cys His Phe Gln Lys Ser Glu Ala Ile Leu Arg Glu Leu
625                 630                 635                 640

Asp Val Glu Asn Ala Lys Leu Tyr Leu Asp Phe Ile Val Leu Gly Ile
                645                 650                 655

Phe Phe Ile Ser Leu Arg Leu Ile Ala Tyr Phe Val Leu Arg Tyr Lys
            660                 665                 670

Ile Arg Ala Glu Arg
            675

<210> SEQ ID NO 72
<211> LENGTH: 668
<212> TYPE: PRT
<213> ORGANISM: Homo sapiens

<400> SEQUENCE: 72

Met Leu Gly Thr Gln Gly Trp Thr Lys Gln Arg Lys Pro Cys Pro Gln
1               5                   10                  15

Asn Ala Ser Ser Tyr Ser Ala Glu Met Thr Glu Pro Lys Ser Val Cys
                20                  25                  30

Val Ser Val Asp Glu Val Val Ser Asn Met Glu Ala Thr Glu Thr
            35                  40                  45

Asp Leu Leu Asn Gly His Leu Lys Lys Val Asp Asn Asn Leu Thr Glu
    50                  55                  60

Ala Gln Arg Phe Ser Ser Leu Pro Arg Ala Ala Val Asn Ile Glu
65                  70                  75                  80

Phe Arg Asp Leu Ser Tyr Ser Val Pro Glu Gly Pro Trp Trp Arg Lys
                85                  90                  95

Lys Gly Tyr Lys Thr Leu Leu Lys Gly Ile Ser Gly Lys Phe Asn Ser
            100                 105                 110

Gly Glu Leu Val Ala Ile Met Gly Pro Ser Gly Ala Gly Lys Ser Thr
        115                 120                 125

Leu Met Asn Ile Leu Ala Gly Tyr Arg Glu Thr Gly Met Lys Gly Ala
    130                 135                 140

Val Leu Ile Asn Gly Leu Pro Arg Asp Leu Arg Cys Phe Arg Lys Val
145                 150                 155                 160

Ser Cys Tyr Ile Met Gln Asp Asp Met Leu Leu Pro His Leu Thr Val
                165                 170                 175

Gln Glu Ala Met Met Val Ser Ala His Leu Lys Leu Gln Glu Lys Asp
            180                 185                 190

Glu Gly Arg Arg Glu Met Val Lys Glu Ile Leu Thr Ala Leu Gly Leu
        195                 200                 205

Leu Ser Cys Ala Asn Thr Arg Thr Gly Ser Leu Ser Gly Gly Gln Arg
    210                 215                 220

Lys Arg Leu Ala Ile Ala Leu Glu Leu Val Asn Asn Pro Pro Val Met
225                 230                 235                 240

Phe Phe Asp Glu Pro Thr Ser Gly Leu Asp Ser Ala Ser Cys Phe Gln
                245                 250                 255

Val Val Ser Leu Met Lys Gly Leu Ala Gln Gly Gly Arg Ser Ile Ile
            260                 265                 270

Cys Thr Ile His Gln Pro Ser Ala Lys Leu Phe Glu Leu Phe Asp Gln
        275                 280                 285
```

Leu Tyr Val Leu Ser Gln Gly Gln Cys Val Tyr Arg Gly Lys Val Cys
            290                 295                 300

Asn Leu Val Pro Tyr Leu Arg Asp Leu Gly Leu Asn Cys Pro Thr Tyr
305                 310                 315                 320

His Asn Pro Ala Asp Phe Val Met Glu Val Ala Ser Gly Glu Tyr Gly
                325                 330                 335

Asp Gln Asn Ser Arg Leu Val Arg Ala Val Arg Glu Gly Met Cys Asp
            340                 345                 350

Ser Asp His Lys Arg Asp Leu Gly Gly Asp Ala Glu Val Asn Pro Phe
        355                 360                 365

Leu Trp His Arg Pro Ser Glu Glu Asp Ser Ser Met Glu Gly Cys
370                 375                 380

His Ser Phe Ser Ala Ser Cys Leu Thr Gln Phe Cys Ile Leu Phe Lys
385                 390                 395                 400

Arg Thr Phe Leu Ser Ile Met Arg Asp Ser Val Leu Thr His Leu Arg
                405                 410                 415

Ile Thr Ser His Ile Gly Ile Gly Leu Ile Gly Leu Leu Tyr Leu
            420                 425                 430

Gly Ile Gly Asn Glu Ala Lys Lys Val Leu Ser Asn Ser Gly Phe Leu
            435                 440                 445

Phe Phe Ser Met Leu Phe Leu Met Phe Ala Ala Leu Met Pro Thr Val
450                 455                 460

Leu Thr Phe Pro Leu Glu Met Gly Val Phe Leu Arg Glu His Leu Asn
465                 470                 475                 480

Tyr Trp Tyr Ser Leu Lys Ala Tyr Tyr Leu Ala Lys Thr Met Ala Asp
                485                 490                 495

Val Pro Phe Gln Ile Met Phe Pro Val Ala Tyr Cys Ser Ile Val Tyr
            500                 505                 510

Trp Met Thr Ser Gln Pro Ser Asp Ala Val Arg Phe Val Leu Phe Ala
        515                 520                 525

Ala Leu Gly Thr Met Thr Ser Leu Val Ala Gln Ser Leu Gly Leu Leu
530                 535                 540

Ile Gly Ala Ala Ser Thr Ser Leu Gln Val Ala Thr Phe Val Gly Pro
545                 550                 555                 560

Val Thr Ala Ile Pro Val Leu Leu Phe Ser Gly Phe Phe Val Ser Phe
                565                 570                 575

Asp Thr Ile Pro Thr Tyr Leu Gln Trp Met Ser Tyr Ile Ser Tyr Val
            580                 585                 590

Arg Tyr Gly Phe Glu Gly Val Ile Leu Ser Ile Tyr Gly Leu Asp Arg
        595                 600                 605

Glu Asp Leu His Cys Asp Ile Asp Glu Thr Cys His Phe Gln Lys Ser
610                 615                 620

Glu Ala Ile Leu Arg Glu Leu Asp Val Glu Asn Ala Lys Leu Tyr Leu
625                 630                 635                 640

Asp Phe Ile Val Leu Gly Ile Phe Phe Ile Ser Leu Arg Leu Ile Ala
                645                 650                 655

Tyr Phe Val Leu Arg Tyr Lys Ile Arg Ala Glu Arg
            660                 665

<210> SEQ ID NO 73
<211> LENGTH: 644
<212> TYPE: PRT
<213> ORGANISM: Homo sapiens

<400> SEQUENCE: 73

Met Thr Glu Pro Lys Ser Val Cys Val Ser Val Asp Glu Val Val Ser
1               5                   10                  15

Ser Asn Met Glu Ala Thr Glu Thr Asp Leu Leu Asn Gly His Leu Lys
            20                  25                  30

Lys Val Asp Asn Asn Leu Thr Glu Ala Gln Arg Phe Ser Ser Leu Pro
        35                  40                  45

Arg Arg Ala Ala Val Asn Ile Glu Phe Arg Asp Leu Ser Tyr Ser Val
    50                  55                  60

Pro Glu Gly Pro Trp Trp Arg Lys Lys Gly Tyr Lys Thr Leu Leu Lys
65              70                  75                  80

Gly Ile Ser Gly Lys Phe Asn Ser Gly Glu Leu Val Ala Ile Met Gly
                85                  90                  95

Pro Ser Gly Ala Gly Lys Ser Thr Leu Met Asn Ile Leu Ala Gly Tyr
            100                 105                 110

Arg Glu Thr Gly Met Lys Gly Ala Val Leu Ile Asn Gly Leu Pro Arg
        115                 120                 125

Asp Leu Arg Cys Phe Arg Lys Val Ser Cys Tyr Ile Met Gln Asp Asp
    130                 135                 140

Met Leu Leu Pro His Leu Thr Val Gln Glu Ala Met Met Val Ser Ala
145                 150                 155                 160

His Leu Lys Leu Gln Glu Lys Asp Glu Gly Arg Arg Glu Met Val Lys
                165                 170                 175

Glu Ile Leu Thr Ala Leu Gly Leu Leu Ser Cys Ala Asn Thr Arg Thr
            180                 185                 190

Gly Ser Leu Ser Gly Gly Gln Arg Lys Arg Leu Ala Ile Ala Leu Glu
        195                 200                 205

Leu Val Asn Asn Pro Pro Val Met Phe Phe Asp Glu Pro Thr Ser Gly
    210                 215                 220

Leu Asp Ser Ala Ser Cys Phe Gln Val Val Ser Leu Met Lys Gly Leu
225                 230                 235                 240

Ala Gln Gly Gly Arg Ser Ile Ile Cys Thr Ile His Gln Pro Ser Ala
                245                 250                 255

Lys Leu Phe Glu Leu Phe Asp Gln Leu Tyr Val Leu Ser Gln Gly Gln
            260                 265                 270

Cys Val Tyr Arg Gly Lys Val Cys Asn Leu Val Pro Tyr Leu Arg Asp
        275                 280                 285

Leu Gly Leu Asn Cys Pro Thr Tyr His Asn Pro Ala Asp Phe Val Met
    290                 295                 300

Glu Val Ala Ser Gly Glu Tyr Gly Asp Gln Asn Ser Arg Leu Val Arg
305                 310                 315                 320

Ala Val Arg Glu Gly Met Cys Asp Ser Asp His Lys Arg Asp Leu Gly
                325                 330                 335

Gly Asp Ala Glu Val Asn Pro Phe Leu Trp His Arg Pro Ser Glu Glu
            340                 345                 350

Asp Ser Ser Ser Met Glu Gly Cys His Ser Phe Ser Ala Ser Cys Leu
        355                 360                 365

Thr Gln Phe Cys Ile Leu Phe Lys Arg Thr Phe Leu Ser Ile Met Arg
    370                 375                 380

Asp Ser Val Leu Thr His Leu Arg Ile Thr Ser His Ile Gly Ile Gly
385                 390                 395                 400

Leu Leu Ile Gly Leu Leu Tyr Leu Gly Ile Gly Asn Glu Ala Lys Lys
                405                 410                 415

Val Leu Ser Asn Ser Gly Phe Leu Phe Phe Ser Met Leu Phe Leu Met
            420                 425                 430

```
Phe Ala Ala Leu Met Pro Thr Val Leu Thr Phe Pro Leu Glu Met Gly
            435                 440                 445

Val Phe Leu Arg Glu His Leu Asn Tyr Trp Tyr Ser Leu Lys Ala Tyr
    450                 455                 460

Tyr Leu Ala Lys Thr Met Ala Asp Val Pro Phe Gln Ile Met Phe Pro
465                 470                 475                 480

Val Ala Tyr Cys Ser Ile Val Tyr Trp Met Thr Ser Gln Pro Ser Asp
                485                 490                 495

Ala Val Arg Phe Val Leu Phe Ala Ala Leu Gly Thr Met Thr Ser Leu
            500                 505                 510

Val Ala Gln Ser Leu Gly Leu Leu Ile Gly Ala Ala Ser Thr Ser Leu
        515                 520                 525

Gln Val Ala Thr Phe Val Gly Pro Val Thr Ala Ile Pro Val Leu Leu
        530                 535                 540

Phe Ser Gly Phe Phe Val Ser Phe Asp Thr Ile Pro Thr Tyr Leu Gln
545                 550                 555                 560

Trp Met Ser Tyr Ile Ser Tyr Val Arg Tyr Gly Phe Glu Gly Val Ile
                565                 570                 575

Leu Ser Ile Tyr Gly Leu Asp Arg Glu Asp Leu His Cys Asp Ile Asp
                580                 585                 590

Glu Thr Cys His Phe Gln Lys Ser Glu Ala Ile Leu Arg Glu Leu Asp
                595                 600                 605

Val Glu Asn Ala Lys Leu Tyr Leu Asp Phe Ile Val Leu Gly Ile Phe
            610                 615                 620

Phe Ile Ser Leu Arg Leu Ile Ala Tyr Phe Val Leu Arg Tyr Lys Ile
625                 630                 635                 640

Arg Ala Glu Arg

<210> SEQ ID NO 74
<211> LENGTH: 663
<212> TYPE: PRT
<213> ORGANISM: Homo sapiens

<400> SEQUENCE: 74

Met Ile Met Arg Leu Pro Gln Pro His Gly Thr Asn Ala Ser Ser Tyr
1               5                   10                  15

Ser Ala Glu Met Thr Glu Pro Lys Ser Val Cys Val Ser Val Asp Glu
                20                  25                  30

Val Val Ser Ser Asn Met Glu Ala Thr Glu Thr Asp Leu Leu Asn Gly
            35                  40                  45

His Leu Lys Lys Val Asp Asn Asn Leu Thr Glu Ala Gln Arg Phe Ser
    50                  55                  60

Ser Leu Pro Arg Arg Ala Ala Val Asn Ile Glu Phe Arg Asp Leu Ser
65                  70                  75                  80

Tyr Ser Val Pro Glu Gly Pro Trp Trp Arg Lys Lys Gly Tyr Lys Thr
                85                  90                  95

Leu Leu Lys Gly Ile Ser Gly Lys Phe Asn Ser Gly Glu Leu Val Ala
                100                 105                 110

Ile Met Gly Pro Ser Gly Ala Gly Lys Ser Thr Leu Met Asn Ile Leu
            115                 120                 125

Ala Gly Tyr Arg Glu Thr Gly Met Lys Gly Ala Val Leu Ile Asn Gly
    130                 135                 140

Leu Pro Arg Asp Leu Arg Cys Phe Arg Lys Val Ser Cys Tyr Ile Met
145                 150                 155                 160
```

```
Gln Asp Asp Met Leu Leu Pro His Leu Thr Val Gln Glu Ala Met Met
                165                 170                 175

Val Ser Ala His Leu Lys Leu Gln Glu Lys Asp Glu Gly Arg Arg Glu
            180                 185                 190

Met Val Lys Glu Ile Leu Thr Ala Leu Gly Leu Leu Ser Cys Ala Asn
        195                 200                 205

Thr Arg Thr Gly Ser Leu Ser Gly Gly Gln Arg Lys Arg Leu Ala Ile
    210                 215                 220

Ala Leu Glu Leu Val Asn Asn Pro Val Met Phe Phe Asp Glu Pro
225                 230                 235                 240

Thr Ser Gly Leu Asp Ser Ala Ser Cys Phe Gln Val Val Ser Leu Met
            245                 250                 255

Lys Gly Leu Ala Gln Gly Gly Arg Ser Ile Ile Cys Thr Ile His Gln
        260                 265                 270

Pro Ser Ala Lys Leu Phe Glu Leu Phe Asp Gln Leu Tyr Val Leu Ser
    275                 280                 285

Gln Gly Gln Cys Val Tyr Arg Gly Lys Val Cys Asn Leu Val Pro Tyr
    290                 295                 300

Leu Arg Asp Leu Gly Leu Asn Cys Pro Thr Tyr His Asn Pro Ala Asp
305                 310                 315                 320

Phe Val Met Glu Val Ala Ser Gly Glu Tyr Gly Asp Gln Asn Ser Arg
            325                 330                 335

Leu Val Arg Ala Val Arg Glu Gly Met Cys Asp Ser Asp His Lys Arg
        340                 345                 350

Asp Leu Gly Gly Asp Ala Glu Val Asn Pro Phe Leu Trp His Arg Pro
    355                 360                 365

Ser Glu Glu Asp Ser Ser Ser Met Glu Gly Cys His Ser Phe Ser Ala
370                 375                 380

Ser Cys Leu Thr Gln Phe Cys Ile Leu Phe Lys Arg Thr Phe Leu Ser
385                 390                 395                 400

Ile Met Arg Asp Ser Val Leu Thr His Leu Arg Ile Thr Ser His Ile
            405                 410                 415

Gly Ile Gly Leu Leu Ile Gly Leu Leu Tyr Leu Gly Ile Gly Asn Glu
        420                 425                 430

Ala Lys Lys Val Leu Ser Asn Ser Gly Phe Leu Phe Phe Ser Met Leu
    435                 440                 445

Phe Leu Met Phe Ala Ala Leu Met Pro Thr Val Leu Thr Phe Pro Leu
450                 455                 460

Glu Met Gly Val Phe Leu Arg Glu His Leu Asn Tyr Trp Tyr Ser Leu
465                 470                 475                 480

Lys Ala Tyr Tyr Leu Ala Lys Thr Met Ala Asp Val Pro Phe Gln Ile
            485                 490                 495

Met Phe Pro Val Ala Tyr Cys Ser Ile Val Tyr Trp Met Thr Ser Gln
        500                 505                 510

Pro Ser Asp Ala Val Arg Phe Val Leu Phe Ala Ala Leu Gly Thr Met
    515                 520                 525

Thr Ser Leu Val Ala Gln Ser Leu Gly Leu Leu Ile Gly Ala Ala Ser
530                 535                 540

Thr Ser Leu Gln Val Ala Thr Phe Val Gly Pro Val Thr Ala Ile Pro
545                 550                 555                 560

Val Leu Leu Phe Ser Gly Phe Phe Val Ser Phe Asp Thr Ile Pro Thr
            565                 570                 575

Tyr Leu Gln Trp Met Ser Tyr Ile Ser Tyr Val Arg Tyr Gly Phe Glu
        580                 585                 590
```

```
Gly Val Ile Leu Ser Ile Tyr Gly Leu Asp Arg Glu Asp Leu His Cys
            595                 600                 605

Asp Ile Asp Glu Thr Cys His Phe Gln Lys Ser Glu Ala Ile Leu Arg
            610                 615                 620

Glu Leu Asp Val Glu Asn Ala Lys Leu Tyr Leu Asp Phe Ile Val Leu
625                 630                 635                 640

Gly Ile Phe Phe Ile Ser Leu Arg Leu Ile Ala Tyr Phe Val Leu Arg
                645                 650                 655

Tyr Lys Ile Arg Ala Glu Arg
            660

<210> SEQ ID NO 75
<211> LENGTH: 824
<212> TYPE: PRT
<213> ORGANISM: Homo sapiens

<400> SEQUENCE: 75

Met Leu Ala Val Gln Gln Thr Glu His Leu Pro Ala Cys Pro Pro Ala
1               5                   10                  15

Arg Arg Trp Ser Ser Asn Phe Cys Pro Glu Ser Thr Glu Gly Gly Pro
            20                  25                  30

Ser Leu Leu Gly Leu Arg Asp Met Val Arg Arg Gly Trp Ser Val Cys
        35                  40                  45

Thr Ala Ile Leu Leu Ala Arg Leu Trp Cys Leu Val Pro Thr His Thr
    50                  55                  60

Phe Leu Ser Glu Tyr Pro Glu Ala Ala Glu Tyr Pro His Pro Gly Trp
65              70                  75                  80

Val Tyr Trp Leu Gln Met Ala Val Ala Pro Gly His Leu Arg Ala Trp
                85                  90                  95

Val Met Arg Asn Asn Val Thr Thr Asn Ile Pro Ser Ala Phe Ser Gly
            100                 105                 110

Thr Leu Thr His Glu Glu Lys Ala Val Leu Thr Val Phe Thr Gly Thr
        115                 120                 125

Ala Thr Ala Val His Val Gln Val Ala Ala Leu Ala Ser Ala Lys Leu
    130                 135                 140

Glu Ser Ser Val Phe Val Thr Asp Cys Val Ser Cys Lys Ile Glu Asn
145                 150                 155                 160

Val Cys Asp Ser Ala Leu Gln Gly Lys Arg Val Pro Met Ser Gly Leu
                165                 170                 175

Gln Gly Ser Ser Ile Val Ile Met Pro Pro Ser Asn Arg Pro Leu Ala
            180                 185                 190

Ser Ala Ala Ser Cys Thr Trp Ser Val Gln Val Gln Gly Gly Pro His
        195                 200                 205

His Leu Gly Val Val Ala Ile Ser Gly Lys Val Leu Ser Ala Ala His
    210                 215                 220

Gly Ala Gly Arg Ala Tyr Gly Trp Gly Phe Pro Gly Asp Pro Met Glu
225                 230                 235                 240

Glu Gly Tyr Lys Thr Leu Leu Lys Gly Ile Ser Gly Lys Phe Asn Ser
                245                 250                 255

Gly Glu Leu Val Ala Ile Met Gly Pro Ser Gly Ala Gly Lys Ser Thr
            260                 265                 270

Leu Met Asn Ile Leu Ala Gly Tyr Arg Glu Thr Gly Met Lys Gly Ala
        275                 280                 285

Val Leu Ile Asn Gly Leu Pro Arg Asp Leu Arg Cys Phe Arg Lys Val
    290                 295                 300
```

-continued

```
Ser Cys Tyr Ile Met Gln Asp Asp Met Leu Leu Pro His Leu Thr Val
305                 310                 315                 320

Gln Glu Ala Met Met Val Ser Ala His Leu Lys Leu Gln Glu Lys Asp
            325                 330                 335

Glu Gly Arg Arg Glu Met Val Lys Glu Ile Leu Thr Ala Leu Gly Leu
        340                 345                 350

Leu Ser Cys Ala Asn Thr Arg Thr Gly Ser Leu Ser Gly Gly Gln Arg
    355                 360                 365

Lys Arg Leu Ala Ile Ala Leu Glu Leu Val Asn Asn Pro Pro Val Met
370                 375                 380

Phe Phe Asp Glu Pro Thr Ser Gly Leu Asp Ser Ala Ser Cys Phe Gln
385                 390                 395                 400

Val Val Ser Leu Met Lys Gly Leu Ala Gln Gly Gly Arg Ser Ile Ile
                405                 410                 415

Cys Thr Ile His Gln Pro Ser Ala Lys Leu Phe Glu Leu Phe Asp Gln
                420                 425                 430

Leu Tyr Val Leu Ser Gln Gly Gln Cys Val Tyr Arg Gly Lys Val Cys
            435                 440                 445

Asn Leu Val Pro Tyr Leu Arg Asp Leu Gly Leu Asn Cys Pro Thr Tyr
450                 455                 460

His Asn Pro Ala Asp Phe Val Met Glu Val Ala Ser Gly Glu Tyr Gly
465                 470                 475                 480

Asp Gln Asn Ser Arg Leu Val Arg Ala Val Arg Glu Gly Met Cys Asp
                485                 490                 495

Ser Asp His Lys Arg Asp Leu Gly Gly Asp Ala Glu Val Asn Pro Phe
            500                 505                 510

Leu Trp His Arg Pro Ser Glu Glu Val Lys Gln Thr Lys Arg Leu Lys
        515                 520                 525

Gly Leu Arg Lys Asp Ser Ser Met Glu Gly Cys His Ser Phe Ser
530                 535                 540

Ala Ser Cys Leu Thr Gln Phe Cys Ile Leu Phe Lys Arg Thr Phe Leu
545                 550                 555                 560

Ser Ile Met Arg Asp Ser Val Leu Thr His Leu Arg Ile Thr Ser His
                565                 570                 575

Ile Gly Ile Gly Leu Leu Ile Gly Leu Leu Tyr Leu Gly Ile Gly Asn
                580                 585                 590

Glu Ala Lys Lys Val Leu Ser Asn Ser Gly Phe Leu Phe Phe Ser Met
            595                 600                 605

Leu Phe Leu Met Phe Ala Ala Leu Met Pro Thr Val Leu Thr Phe Pro
610                 615                 620

Leu Glu Met Gly Val Phe Leu Arg Glu His Leu Asn Tyr Trp Tyr Ser
625                 630                 635                 640

Leu Lys Ala Tyr Tyr Leu Ala Lys Thr Met Ala Asp Val Pro Phe Gln
                645                 650                 655

Ile Met Phe Pro Val Ala Tyr Cys Ser Ile Val Tyr Trp Met Thr Ser
            660                 665                 670

Gln Pro Ser Asp Ala Val Arg Phe Val Leu Phe Ala Ala Leu Gly Thr
        675                 680                 685

Met Thr Ser Leu Val Ala Gln Ser Leu Gly Leu Leu Ile Gly Ala Ala
    690                 695                 700

Ser Thr Ser Leu Gln Val Ala Thr Phe Val Gly Pro Val Thr Ala Ile
705                 710                 715                 720

Pro Val Leu Leu Phe Ser Gly Phe Phe Val Ser Phe Asp Thr Ile Pro
```

```
                          725                 730                 735
Thr Tyr Leu Gln Trp Met Ser Tyr Ile Ser Tyr Val Arg Tyr Gly Phe
            740                 745                 750
Glu Gly Val Ile Leu Ser Ile Tyr Gly Leu Asp Arg Glu Asp Leu His
            755                 760                 765
Cys Asp Ile Asp Glu Thr Cys His Phe Gln Lys Ser Glu Ala Ile Leu
            770                 775                 780
Arg Glu Leu Asp Val Glu Asn Ala Lys Leu Tyr Leu Asp Phe Ile Val
785                 790                 795                 800
Leu Gly Ile Phe Phe Ile Ser Leu Arg Leu Ile Ala Tyr Phe Val Leu
                805                 810                 815
Arg Tyr Lys Ile Arg Ala Glu Arg
            820

<210> SEQ ID NO 76
<211> LENGTH: 970
<212> TYPE: PRT
<213> ORGANISM: Homo sapiens

<400> SEQUENCE: 76

Met Ala Gln Leu Glu Arg Ser Ala Ile Ser Gly Phe Ser Ser Lys Ser
1               5                   10                  15
Arg Arg Asn Ser Phe Ala Tyr Asp Val Lys Arg Glu Val Tyr Asn Glu
                20                  25                  30
Glu Thr Phe Gln Gln Glu His Lys Arg Lys Ala Ser Ser Ser Gly Asn
            35                  40                  45
Met Asn Ile Asn Ile Thr Thr Phe Arg His His Val Gln Cys Arg Cys
    50                  55                  60
Ser Trp His Arg Phe Leu Arg Cys Val Leu Thr Ile Phe Pro Phe Leu
65                  70                  75                  80
Glu Trp Met Cys Met Tyr Arg Leu Lys Asp Trp Leu Leu Gly Asp Leu
                85                  90                  95
Leu Ala Gly Ile Ser Val Gly Leu Val Gln Val Pro Gln Gly Leu Thr
            100                 105                 110
Leu Ser Leu Leu Ala Arg Gln Leu Ile Pro Pro Leu Asn Ile Ala Tyr
            115                 120                 125
Ala Ala Phe Cys Ser Ser Val Ile Tyr Val Ile Phe Gly Ser Cys His
        130                 135                 140
Gln Met Ser Ile Gly Ser Phe Phe Leu Val Ser Ala Leu Leu Ile Asn
145                 150                 155                 160
Val Leu Lys Val Ser Pro Phe Asn Asn Gly Gln Leu Val Met Gly Ser
                165                 170                 175
Phe Val Lys Asn Glu Phe Ser Ala Pro Ser Tyr Leu Met Gly Tyr Asn
            180                 185                 190
Lys Ser Leu Ser Val Val Ala Thr Thr Thr Phe Leu Thr Gly Ile Ile
        195                 200                 205
Gln Leu Ile Met Gly Val Leu Gly Leu Gly Phe Ile Ala Thr Tyr Leu
    210                 215                 220
Pro Glu Ser Ala Met Ser Ala Tyr Leu Ala Ala Val Ala Leu His Ile
225                 230                 235                 240
Met Leu Ser Gln Leu Thr Phe Ile Phe Gly Ile Met Ile Ser Phe His
                245                 250                 255
Ala Gly Pro Ile Ser Phe Phe Tyr Asp Ile Ile Asn Tyr Cys Val Ala
            260                 265                 270
Leu Pro Lys Ala Asn Ser Thr Ser Ile Leu Val Phe Leu Thr Val Val
```

```
                    275                 280                 285
Val Ala Leu Arg Ile Asn Lys Cys Ile Arg Ile Ser Phe Asn Gln Tyr
290                 295                 300

Pro Ile Glu Phe Pro Met Glu Leu Phe Leu Ile Ile Gly Phe Thr Val
305                 310                 315                 320

Ile Ala Asn Lys Ile Ser Met Ala Thr Glu Thr Ser Gln Thr Leu Ile
                325                 330                 335

Asp Met Ile Pro Tyr Ser Phe Leu Leu Pro Val Thr Pro Asp Phe Ser
                340                 345                 350

Leu Leu Pro Lys Ile Ile Leu Gln Ala Phe Ser Leu Ser Leu Val Ser
                355                 360                 365

Ser Phe Leu Leu Ile Phe Leu Gly Lys Lys Ile Ala Ser Leu His Asn
                370                 375                 380

Tyr Ser Val Asn Ser Asn Gln Asp Leu Ile Ala Ile Gly Leu Cys Asn
385                 390                 395                 400

Val Val Ser Ser Phe Phe Arg Ser Cys Val Phe Thr Gly Ala Ile Ala
                405                 410                 415

Arg Thr Ile Ile Gln Asp Lys Ser Gly Gly Arg Gln Gln Phe Ala Ser
                420                 425                 430

Leu Val Gly Ala Gly Val Met Leu Leu Leu Met Val Lys Met Gly His
                435                 440                 445

Phe Phe Tyr Thr Leu Pro Asn Ala Val Leu Ala Gly Ile Ile Leu Ser
                450                 455                 460

Asn Val Ile Pro Tyr Leu Glu Thr Ile Ser Asn Leu Pro Ser Leu Trp
465                 470                 475                 480

Arg Gln Asp Gln Tyr Asp Cys Ala Leu Trp Met Met Thr Phe Ser Ser
                485                 490                 495

Ser Ile Phe Leu Gly Leu Asp Ile Gly Leu Ile Ile Ser Val Val Ser
                500                 505                 510

Ala Phe Phe Ile Thr Thr Val Arg Ser His Arg Ala Lys Ile Leu Leu
                515                 520                 525

Leu Gly Gln Ile Pro Asn Thr Asn Ile Tyr Arg Ser Ile Asn Asp Tyr
                530                 535                 540

Arg Glu Ile Ile Thr Ile Pro Gly Val Lys Ile Phe Gln Cys Cys Ser
545                 550                 555                 560

Ser Ile Thr Phe Val Asn Val Tyr Tyr Leu Lys His Lys Leu Leu Lys
                565                 570                 575

Glu Val Asp Met Val Lys Val Pro Leu Lys Glu Glu Ile Phe Ser
                580                 585                 590

Leu Phe Asn Ser Ser Asp Thr Asn Leu Gln Gly Gly Lys Ile Cys Arg
                595                 600                 605

Cys Phe Cys Asn Cys Asp Asp Leu Glu Pro Leu Pro Arg Ile Leu Tyr
                610                 615                 620

Thr Glu Arg Phe Glu Asn Lys Leu Asp Pro Ala Ser Ser Ile Asn
625                 630                 635                 640

Leu Ile His Cys Ser His Phe Glu Ser Met Asn Thr Ser Gln Thr Ala
                645                 650                 655

Ser Glu Asp Gln Val Pro Tyr Thr Val Ser Ser Val Ser Gln Lys Asn
                660                 665                 670

Gln Gly Gln Gln Tyr Glu Glu Val Glu Val Trp Leu Pro Asn Asn
                675                 680                 685

Ser Ser Arg Asn Ser Ser Pro Gly Leu Pro Asp Val Ala Glu Ser Gln
                690                 695                 700
```

```
Gly Arg Arg Ser Leu Ile Pro Tyr Ser Asp Ala Ser Leu Leu Pro Ser
705                 710                 715                 720

Val His Thr Ile Ile Leu Asp Phe Ser Met Val His Tyr Val Asp Ser
                725                 730                 735

Arg Gly Leu Val Val Leu Arg Gln Ile Cys Asn Ala Phe Gln Asn Ala
            740                 745                 750

Asn Ile Leu Ile Leu Ile Ala Gly Cys His Ser Ser Ile Val Arg Ala
        755                 760                 765

Phe Glu Arg Asn Asp Phe Phe Asp Ala Gly Ile Thr Lys Thr Gln Leu
    770                 775                 780

Phe Leu Ser Val His Asp Ala Val Leu Phe Ala Leu Ser Arg Lys Val
785                 790                 795                 800

Ile Gly Ser Ser Glu Leu Ser Ile Asp Glu Ser Glu Thr Val Ile Arg
                805                 810                 815

Glu Thr Tyr Ser Glu Thr Asp Lys Asn Asp Asn Ser Arg Tyr Lys Met
            820                 825                 830

Ser Ser Ser Phe Leu Gly Ser Gln Lys Asn Val Ser Pro Gly Phe Ile
        835                 840                 845

Lys Ile Gln Gln Pro Val Glu Glu Ser Glu Leu Asp Leu Glu Leu
    850                 855                 860

Glu Ser Glu Gln Glu Ala Gly Leu Gly Leu Asp Leu Asp Leu Asp Arg
865                 870                 875                 880

Glu Leu Glu Pro Glu Met Glu Pro Lys Ala Glu Thr Glu Thr Lys Thr
                885                 890                 895

Gln Thr Glu Met Glu Pro Gln Pro Glu Thr Pro Glu Met Glu Pro
            900                 905                 910

Asn Pro Lys Ser Arg Pro Arg Ala His Thr Phe Pro Gln Gln Arg Tyr
        915                 920                 925

Trp Pro Met Tyr His Pro Ser Met Ala Ser Thr Gln Ser Gln Thr Gln
    930                 935                 940

Thr Arg Thr Trp Ser Val Glu Arg Arg Arg His Pro Met Asp Ser Tyr
945                 950                 955                 960

Ser Pro Glu Gly Asn Ser Asn Glu Asp Val
                965                 970

<210> SEQ ID NO 77
<211> LENGTH: 225
<212> TYPE: PRT
<213> ORGANISM: Homo sapiens

<400> SEQUENCE: 77

Met Thr Ser Glu Phe Phe Ser Ala Gln Leu Arg Ala Gln Ile Ser Asp
1               5                   10                  15

Asp Thr His Pro Ile Ser Tyr Tyr Lys Pro Glu Phe Tyr Met Pro
            20                  25                  30

Asp Asp Gly Gly Thr Ala His Leu Ser Val Val Ala Glu Asp Gly Ser
        35                  40                  45

Ala Val Ser Ala Thr Ser Thr Ile Asn Leu Tyr Phe Gly Ser Lys Val
    50                  55                  60

Arg Ser Pro Val Ser Gly Ile Leu Leu Asn Asn Glu Met Asp Asp Phe
65                  70                  75                  80

Ser Ser Thr Ser Ile Thr Asn Glu Phe Gly Val Pro Ser Pro Ala
        85                  90                  95

Asn Phe Ile Gln Pro Gly Lys Gln Pro Leu Ser Ser Met Cys Pro Thr
    100                 105                 110
```

```
Ile Met Val Gly Gln Asp Gly Gln Val Arg Met Val Gly Ala Ala
        115                 120                 125

Gly Gly Thr Gln Ile Thr Met Ala Thr Ala Leu Ala Ile Ile Tyr Asn
        130                 135                 140

Leu Trp Phe Gly Tyr Asp Val Lys Trp Ala Val Glu Glu Pro Arg Leu
145                 150                 155                 160

His Asn Gln Leu Leu Pro Asn Val Thr Val Glu Arg Asn Ile Asp
                165                 170                 175

Gln Glu Val Thr Ala Ala Leu Glu Thr Arg His His Thr Gln Ile
                180                 185                 190

Thr Ser Thr Phe Ile Ala Val Val Gln Ala Ile Val Arg Met Ala Gly
                195                 200                 205

Gly Trp Ala Ala Ala Ser Asp Ser Arg Lys Gly Gly Glu Pro Ala Gly
    210                 215                 220

Tyr
225

<210> SEQ ID NO 78
<211> LENGTH: 225
<212> TYPE: PRT
<213> ORGANISM: Homo sapiens

<400> SEQUENCE: 78

Met Thr Ser Glu Phe Phe Ser Ala Gln Leu Arg Ala Gln Ile Ser Asp
1               5                   10                  15

Asp Thr Thr His Pro Ile Ser Tyr Tyr Lys Pro Glu Phe Tyr Met Pro
                20                  25                  30

Asp Asp Gly Gly Thr Ala His Leu Ser Val Val Ala Glu Asp Gly Ser
            35                  40                  45

Ala Val Ser Ala Thr Ser Thr Ile Asn Leu Tyr Phe Gly Ser Lys Val
        50                  55                  60

Arg Ser Pro Val Ser Gly Ile Leu Leu Asn Asn Glu Met Asp Asp Phe
65                  70                  75                  80

Ser Ser Thr Ser Ile Thr Asn Glu Phe Gly Val Pro Pro Ser Pro Ala
                85                  90                  95

Asn Phe Ile Gln Pro Gly Lys Gln Pro Leu Ser Ser Met Cys Pro Thr
            100                 105                 110

Ile Met Val Gly Gln Asp Gly Gln Val Arg Met Val Gly Ala Ala
        115                 120                 125

Gly Gly Thr Gln Ile Thr Met Ala Thr Ala Leu Ala Ile Ile Tyr Asn
        130                 135                 140

Leu Trp Phe Gly Tyr Asp Val Lys Trp Ala Val Glu Glu Pro Arg Leu
145                 150                 155                 160

His Asn Gln Leu Leu Pro Asn Val Thr Val Glu Arg Asn Ile Asp
                165                 170                 175

Gln Glu Val Thr Ala Ala Leu Glu Thr Arg His His Thr Gln Ile
                180                 185                 190

Thr Ser Thr Phe Ile Ala Val Val Gln Ala Ile Val Arg Met Ala Gly
                195                 200                 205

Gly Trp Ala Ala Ala Ser Asp Ser Arg Lys Gly Gly Glu Pro Ala Gly
    210                 215                 220

Tyr
225

<210> SEQ ID NO 79
<211> LENGTH: 225
```

```
<212> TYPE: PRT
<213> ORGANISM: Homo sapiens

<400> SEQUENCE: 79

Met Thr Ser Glu Phe Ser Ala Gln Leu Arg Ala Gln Ile Ser Asp
1               5                   10                  15

Asp Thr Thr His Pro Ile Ser Tyr Tyr Lys Pro Glu Phe Tyr Met Pro
                20                  25                  30

Asp Asp Gly Gly Thr Ala His Leu Ser Val Val Ala Glu Asp Gly Ser
            35                  40                  45

Ala Val Ser Ala Thr Ser Thr Ile Asn Leu Tyr Phe Gly Ser Lys Val
    50                  55                  60

Arg Ser Pro Val Ser Gly Ile Leu Leu Asn Asn Glu Met Asp Asp Phe
65                  70                  75                  80

Ser Ser Thr Ser Ile Thr Asn Glu Phe Gly Val Pro Pro Ser Pro Ala
                85                  90                  95

Asn Phe Ile Gln Pro Gly Lys Gln Pro Leu Ser Ser Met Cys Pro Thr
                100                 105                 110

Ile Met Val Gly Gln Asp Gly Gln Val Arg Met Val Val Gly Ala Ala
            115                 120                 125

Gly Gly Thr Gln Ile Thr Met Ala Thr Ala Leu Ala Ile Ile Tyr Asn
130                 135                 140

Leu Trp Phe Gly Tyr Asp Val Lys Trp Ala Val Glu Glu Pro Arg Leu
145                 150                 155                 160

His Asn Gln Leu Leu Pro Asn Val Thr Thr Val Glu Arg Asn Ile Asp
                165                 170                 175

Gln Glu Val Thr Ala Ala Leu Glu Thr Arg His His His Thr Gln Ile
            180                 185                 190

Thr Ser Thr Phe Ile Ala Val Val Gln Ala Ile Val Arg Met Ala Gly
        195                 200                 205

Gly Trp Ala Ala Ala Ser Asp Ser Arg Lys Gly Gly Glu Pro Ala Gly
    210                 215                 220

Tyr
225

<210> SEQ ID NO 80
<211> LENGTH: 545
<212> TYPE: PRT
<213> ORGANISM: Homo sapiens

<400> SEQUENCE: 80

Met Gly Ser Ser Ala Thr Glu Ile Glu Glu Leu Glu Asn Thr Thr Phe
1               5                   10                  15

Lys Tyr Leu Thr Gly Glu Gln Thr Glu Lys Met Trp Gln Arg Leu Lys
                20                  25                  30

Gly Ile Leu Arg Cys Leu Val Lys Gln Leu Glu Arg Gly Asp Val Asn
            35                  40                  45

Val Val Asp Leu Lys Lys Asn Ile Glu Tyr Ala Ala Ser Val Leu Glu
    50                  55                  60

Ala Val Tyr Ile Asp Glu Thr Arg Arg Leu Leu Asp Thr Glu Asp Glu
65                  70                  75                  80

Leu Ser Asp Ile Gln Thr Asp Ser Val Pro Ser Glu Val Arg Asp Trp
                85                  90                  95

Leu Ala Ser Thr Phe Thr Arg Lys Met Gly Met Thr Lys Lys Lys Pro
                100                 105                 110

Glu Glu Lys Pro Lys Phe Arg Ser Ile Val His Ala Val Gln Ala Gly
```

```
            115                 120                 125
Ile Phe Val Glu Arg Met Tyr Arg Lys Thr Tyr His Met Val Gly Leu
130                 135                 140
Ala Tyr Pro Ala Ala Val Ile Val Thr Leu Lys Asp Val Asp Lys Trp
145                 150                 155                 160
Ser Phe Asp Val Phe Ala Leu Asn Glu Ala Ser Gly Glu His Ser Leu
                165                 170                 175
Lys Phe Met Ile Tyr Glu Leu Phe Thr Arg Tyr Asp Leu Ile Asn Arg
                180                 185                 190
Phe Lys Ile Pro Val Ser Cys Leu Ile Thr Phe Ala Glu Ala Leu Glu
                195                 200                 205
Val Gly Tyr Ser Lys Tyr Lys Asn Pro Tyr His Asn Leu Ile His Ala
210                 215                 220
Ala Asp Val Thr Gln Thr Val His Tyr Ile Met Leu His Thr Gly Ile
225                 230                 235                 240
Met His Trp Leu Thr Glu Leu Glu Ile Leu Ala Met Val Phe Ala Ala
                245                 250                 255
Ala Ile His Asp Tyr Glu His Thr Gly Thr Thr Asn Asn Phe His Ile
                260                 265                 270
Gln Thr Arg Ser Asp Val Ala Ile Leu Tyr Asn Asp Arg Ser Val Leu
                275                 280                 285
Glu Asn His His Val Ser Ala Ala Tyr Arg Leu Met Gln Glu Glu Glu
                290                 295                 300
Met Asn Ile Leu Ile Asn Leu Ser Lys Asp Asp Trp Arg Asp Leu Arg
305                 310                 315                 320
Asn Leu Val Ile Glu Met Val Leu Ser Thr Asp Met Ser Gly His Phe
                325                 330                 335
Gln Gln Ile Lys Asn Ile Arg Asn Ser Leu Gln Gln Pro Glu Gly Ile
                340                 345                 350
Asp Arg Ala Lys Thr Met Ser Leu Ile Leu His Ala Ala Asp Ile Ser
                355                 360                 365
His Pro Ala Lys Ser Trp Lys Leu His Tyr Arg Trp Thr Met Ala Leu
                370                 375                 380
Met Glu Glu Phe Phe Leu Gln Gly Asp Lys Glu Ala Glu Leu Gly Leu
385                 390                 395                 400
Pro Phe Ser Pro Leu Cys Asp Arg Lys Ser Thr Met Val Ala Gln Ser
                405                 410                 415
Gln Ile Gly Phe Ile Asp Phe Ile Val Glu Pro Thr Phe Ser Leu Leu
                420                 425                 430
Thr Asp Ser Thr Glu Lys Ile Val Ile Pro Leu Ile Glu Glu Ala Ser
                435                 440                 445
Lys Ala Glu Thr Ser Ser Tyr Val Ala Ser Ser Thr Thr Ile Val
450                 455                 460
Gly Leu His Ile Ala Asp Ala Leu Arg Arg Ser Asn Thr Lys Gly Ser
465                 470                 475                 480
Met Ser Asp Gly Ser Tyr Ser Pro Asp Tyr Ser Leu Ala Ala Val Asp
                485                 490                 495
Leu Lys Ser Phe Lys Asn Asn Leu Val Asp Ile Ile Gln Gln Asn Lys
                500                 505                 510
Glu Arg Trp Lys Glu Leu Ala Ala Gln Gly Glu Ser Asp Leu His Lys
                515                 520                 525
Asn Ser Glu Asp Leu Val Asn Ala Glu Glu Lys His Asp Glu Thr His
530                 535                 540
```

Ser
545

<210> SEQ ID NO 81
<211> LENGTH: 535
<212> TYPE: PRT
<213> ORGANISM: Homo sapiens

<400> SEQUENCE: 81

| | | | | | | | | | | | | | | |
|---|---|---|---|---|---|---|---|---|---|---|---|---|---|---|
| Met | Gly | Ser | Ser | Ala | Thr | Glu | Ile | Glu | Glu | Leu | Glu | Asn | Thr | Thr | Phe |
| 1 | | | | 5 | | | | | 10 | | | | | 15 | |
| Lys | Tyr | Leu | Thr | Gly | Glu | Gln | Thr | Glu | Lys | Met | Trp | Gln | Arg | Leu | Lys |
| | | | 20 | | | | | 25 | | | | | 30 | | |
| Gly | Ile | Leu | Arg | Cys | Leu | Val | Lys | Gln | Leu | Glu | Arg | Gly | Asp | Val | Asn |
| | | | 35 | | | | | 40 | | | | | 45 | | |
| Val | Val | Asp | Leu | Lys | Lys | Asn | Ile | Glu | Tyr | Ala | Ala | Ser | Val | Leu | Glu |
| | 50 | | | | | 55 | | | | | 60 | | | | |
| Ala | Val | Tyr | Ile | Asp | Glu | Thr | Arg | Arg | Leu | Leu | Asp | Thr | Glu | Asp | Glu |
| 65 | | | | | 70 | | | | | 75 | | | | | 80 |
| Leu | Ser | Asp | Ile | Gln | Thr | Asp | Ser | Val | Pro | Ser | Glu | Val | Arg | Asp | Trp |
| | | | | 85 | | | | | 90 | | | | | 95 | |
| Leu | Ala | Ser | Thr | Phe | Thr | Arg | Lys | Met | Gly | Met | Thr | Lys | Lys | Lys | Pro |
| | | | 100 | | | | | 105 | | | | | 110 | | |
| Glu | Glu | Lys | Pro | Lys | Phe | Arg | Ser | Ile | Val | His | Ala | Val | Gln | Ala | Gly |
| | | | 115 | | | | | 120 | | | | | 125 | | |
| Ile | Phe | Val | Glu | Arg | Met | Tyr | Arg | Lys | Thr | Tyr | His | Met | Val | Gly | Leu |
| | 130 | | | | | 135 | | | | | 140 | | | | |
| Ala | Tyr | Pro | Ala | Ala | Val | Ile | Val | Thr | Leu | Lys | Asp | Val | Asp | Lys | Trp |
| 145 | | | | | 150 | | | | | 155 | | | | | 160 |
| Ser | Phe | Asp | Val | Phe | Ala | Leu | Asn | Glu | Ala | Ser | Gly | Glu | His | Ser | Leu |
| | | | | 165 | | | | | 170 | | | | | 175 | |
| Lys | Phe | Met | Ile | Tyr | Glu | Leu | Phe | Thr | Arg | Tyr | Asp | Leu | Ile | Asn | Arg |
| | | | 180 | | | | | 185 | | | | | 190 | | |
| Phe | Lys | Ile | Pro | Val | Ser | Cys | Leu | Ile | Thr | Phe | Ala | Glu | Ala | Leu | Glu |
| | | | 195 | | | | | 200 | | | | | 205 | | |
| Val | Gly | Tyr | Ser | Lys | Tyr | Lys | Asn | Pro | Tyr | His | Asn | Leu | Ile | His | Ala |
| | 210 | | | | | 215 | | | | | 220 | | | | |
| Ala | Asp | Val | Thr | Gln | Thr | Val | His | Tyr | Ile | Met | Leu | His | Thr | Gly | Ile |
| 225 | | | | | 230 | | | | | 235 | | | | | 240 |
| Met | His | Trp | Leu | Thr | Glu | Leu | Glu | Ile | Leu | Ala | Met | Val | Phe | Ala | Ala |
| | | | | 245 | | | | | 250 | | | | | 255 | |
| Ala | Ile | His | Asp | Tyr | Glu | His | Thr | Gly | Thr | Thr | Asn | Asn | Phe | His | Ile |
| | | | 260 | | | | | 265 | | | | | 270 | | |
| Gln | Thr | Arg | Ser | Asp | Val | Ala | Ile | Leu | Tyr | Asn | Asp | Arg | Ser | Val | Leu |
| | | | 275 | | | | | 280 | | | | | 285 | | |
| Glu | Asn | His | His | Val | Ser | Ala | Ala | Tyr | Arg | Leu | Met | Gln | Glu | Glu | Glu |
| | 290 | | | | | 295 | | | | | 300 | | | | |
| Met | Asn | Ile | Leu | Ile | Asn | Leu | Ser | Lys | Asp | Asp | Trp | Arg | Asp | Leu | Arg |
| 305 | | | | | 310 | | | | | 315 | | | | | 320 |
| Asn | Leu | Val | Ile | Glu | Met | Val | Leu | Ser | Thr | Asp | Met | Ser | Gly | His | Phe |
| | | | | 325 | | | | | 330 | | | | | 335 | |
| Gln | Gln | Ile | Lys | Asn | Ile | Arg | Asn | Ser | Leu | Gln | Gln | Pro | Glu | Gly | Ile |
| | | | 340 | | | | | 345 | | | | | 350 | | |
| Asp | Arg | Ala | Lys | Thr | Met | Ser | Leu | Ile | Leu | His | Ala | Ala | Asp | Ile | Ser |
| | | | 355 | | | | | 360 | | | | | 365 | | |

```
His Pro Ala Lys Ser Trp Lys Leu His Tyr Arg Trp Thr Met Ala Leu
    370                 375                 380

Met Glu Glu Phe Phe Leu Gln Gly Asp Lys Glu Ala Glu Leu Gly Leu
385                 390                 395                 400

Pro Phe Ser Pro Leu Cys Asp Arg Lys Ser Thr Met Val Ala Gln Ser
                405                 410                 415

Gln Ile Gly Phe Ile Asp Phe Ile Val Glu Pro Thr Phe Ser Leu Leu
            420                 425                 430

Thr Asp Ser Thr Glu Lys Ile Val Ile Pro Leu Ile Glu Glu Ala Ser
        435                 440                 445

Lys Ala Glu Thr Ser Ser Tyr Val Ala Ser Ser Thr Thr Ile Val
    450                 455                 460

Gly Leu His Ile Ala Asp Ala Leu Arg Arg Ser Asn Thr Lys Gly Ser
465                 470                 475                 480

Met Ser Asp Gly Ser Tyr Ser Pro Asp Tyr Ser Leu Ala Ala Val Asp
                485                 490                 495

Leu Lys Ser Phe Lys Asn Asn Leu Val Asp Ile Ile Gln Gln Asn Lys
            500                 505                 510

Glu Arg Trp Lys Glu Leu Ala Ala Gln Glu Ala Arg Thr Ser Ser Gln
    515                 520                 525

Lys Cys Glu Phe Ile His Gln
    530                 535

<210> SEQ ID NO 82
<211> LENGTH: 729
<212> TYPE: PRT
<213> ORGANISM: Homo sapiens

<400> SEQUENCE: 82

Met Asn Pro Phe Gln Lys Asn Glu Ser Lys Glu Thr Leu Phe Ser Pro
1               5                   10                  15

Val Ser Ile Glu Glu Val Pro Pro Arg Pro Ser Pro Lys Lys
            20                  25                  30

Pro Ser Pro Thr Ile Cys Gly Ser Asn Tyr Pro Leu Ser Ile Ala Phe
            35                  40                  45

Ile Val Val Asn Glu Phe Cys Glu Arg Phe Ser Tyr Tyr Gly Met Lys
    50                  55                  60

Ala Val Leu Ile Leu Tyr Phe Leu Tyr Phe Leu His Trp Asn Glu Asp
65                  70                  75                  80

Thr Ser Thr Ser Ile Tyr His Ala Phe Ser Ser Leu Cys Tyr Phe Thr
                85                  90                  95

Pro Ile Leu Gly Ala Ala Ile Ala Asp Ser Trp Leu Gly Lys Phe Lys
            100                 105                 110

Thr Ile Ile Tyr Leu Ser Leu Val Tyr Val Leu Gly His Val Ile Lys
        115                 120                 125

Ser Leu Gly Ala Leu Pro Ile Leu Gly Gly Gln Val Val His Thr Val
    130                 135                 140

Leu Ser Leu Ile Gly Leu Ser Leu Ile Ala Leu Gly Thr Gly Gly Ile
145                 150                 155                 160

Lys Pro Cys Val Ala Ala Phe Gly Gly Asp Gln Phe Glu Glu Lys His
                165                 170                 175

Ala Glu Glu Arg Thr Arg Tyr Phe Ser Val Phe Tyr Leu Ser Ile Asn
            180                 185                 190

Ala Gly Ser Leu Ile Ser Thr Phe Ile Thr Pro Met Leu Arg Gly Asp
        195                 200                 205
```

-continued

Val Gln Cys Phe Gly Glu Asp Cys Tyr Ala Leu Ala Phe Gly Val Pro
    210                 215                 220

Gly Leu Leu Met Val Ile Ala Leu Val Val Phe Ala Met Gly Ser Lys
225                 230                 235                 240

Ile Tyr Asn Lys Pro Pro Glu Gly Asn Ile Val Ala Gln Val Phe
                245                 250                 255

Lys Cys Ile Trp Phe Ala Ile Ser Asn Arg Phe Lys Asn Arg Ser Gly
        260                 265                 270

Asp Ile Pro Lys Arg Gln His Trp Leu Asp Trp Ala Ala Glu Lys Tyr
            275                 280                 285

Pro Lys Gln Leu Ile Met Asp Val Lys Ala Leu Thr Arg Val Leu Phe
        290                 295                 300

Leu Tyr Ile Pro Leu Pro Met Phe Trp Ala Leu Leu Asp Gln Gln Gly
305                 310                 315                 320

Ser Arg Trp Thr Leu Gln Ala Ile Arg Met Asn Arg Asn Leu Gly Phe
                325                 330                 335

Phe Val Leu Gln Pro Asp Gln Met Gln Val Leu Asn Pro Leu Leu Val
                340                 345                 350

Leu Ile Phe Ile Pro Leu Phe Asp Phe Val Ile Tyr Arg Leu Val Ser
            355                 360                 365

Lys Cys Gly Ile Asn Phe Ser Ser Leu Arg Lys Met Ala Val Gly Met
        370                 375                 380

Ile Leu Ala Cys Leu Ala Phe Ala Val Ala Ala Val Glu Ile Lys
385                 390                 395                 400

Ile Asn Glu Met Ala Pro Ala Gln Pro Gly Pro Gln Glu Val Phe Leu
                405                 410                 415

Gln Val Leu Asn Leu Ala Asp Asp Glu Val Lys Val Thr Val Val Gly
            420                 425                 430

Asn Glu Asn Asn Ser Leu Leu Ile Glu Ser Ile Lys Ser Phe Gln Lys
            435                 440                 445

Thr Pro His Tyr Ser Lys Leu His Leu Lys Thr Lys Ser Gln Asp Phe
        450                 455                 460

His Phe His Leu Lys Tyr His Asn Leu Ser Leu Tyr Thr Glu His Ser
465                 470                 475                 480

Val Gln Glu Lys Asn Trp Tyr Ser Leu Val Ile Arg Glu Asp Gly Asn
                485                 490                 495

Ser Ile Ser Ser Met Met Val Lys Asp Thr Glu Ser Arg Thr Thr Asn
            500                 505                 510

Gly Met Thr Thr Val Arg Phe Val Asn Thr Leu His Lys Asp Val Asn
        515                 520                 525

Ile Ser Leu Ser Thr Asp Thr Ser Leu Asn Val Gly Glu Asp Tyr Gly
        530                 535                 540

Val Ser Ala Tyr Arg Thr Val Gln Arg Gly Glu Tyr Pro Ala Val His
545                 550                 555                 560

Cys Arg Thr Glu Asp Lys Asn Phe Ser Leu Asn Leu Gly Leu Leu Asp
                565                 570                 575

Phe Gly Ala Ala Tyr Leu Phe Val Ile Thr Asn Asn Thr Asn Gln Gly
            580                 585                 590

Leu Gln Ala Trp Lys Ile Glu Asp Ile Pro Ala Asn Lys Met Ser Ile
        595                 600                 605

Ala Trp Gln Leu Pro Gln Tyr Ala Leu Val Thr Ala Gly Glu Val Met
        610                 615                 620

Phe Ser Val Thr Gly Leu Glu Phe Ser Tyr Ser Gln Ala Pro Ser Gly
625                 630                 635                 640

```
Met Lys Ser Val Leu Gln Ala Ala Trp Leu Leu Thr Ile Ala Val Gly
            645                 650                 655

Asn Ile Ile Val Leu Val Val Ala Gln Phe Ser Gly Leu Val Gln Trp
            660                 665                 670

Ala Glu Phe Ile Leu Phe Ser Cys Leu Leu Val Ile Cys Leu Ile
    675                 680                 685

Phe Ser Ile Met Gly Tyr Tyr Tyr Val Pro Val Lys Thr Glu Asp Met
    690                 695                 700

Arg Gly Pro Ala Asp Lys His Ile Pro His Ile Gln Gly Asn Met Ile
705                 710                 715                 720

Lys Leu Glu Thr Lys Lys Thr Lys Leu
                725
```

<210> SEQ ID NO 83
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 83 uugcuaua                                                              8

<210> SEQ ID NO 84
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 84
ttccatggta atggtgtgc                                                 19

<210> SEQ ID NO 85
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 85
ccgaagcaag gaataatcc                                                 19

<210> SEQ ID NO 86
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 86
tatgtttcgc ctttatgac                                                 19

<210> SEQ ID NO 87
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 87
ggattcaagg aggaatgac                                                 19

```
<210> SEQ ID NO 88
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 88
ctccctcttg catcaagac                                                19

<210> SEQ ID NO 89
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 89
aaatcctcgt caggtttac                                                19

<210> SEQ ID NO 90
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 90
agtgccttac agtatcatc                                                19

<210> SEQ ID NO 91
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 91
cctgaatgtg actgtggac                                                19

<210> SEQ ID NO 92
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 92
gactgactgg cctgaaggc                                                19

<210> SEQ ID NO 93
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 93
gcagcactat ttgaagcac                                                19

<210> SEQ ID NO 94
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 94
```
gcctgagaac ctcctctgc                                            19

<210> SEQ ID NO 95
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 95
acagctagtc aggcacttc                                            19

<210> SEQ ID NO 96
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 96
tataagaaat ggcatactc                                            19

<210> SEQ ID NO 97
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 97
ctaatccatg gtctagttc                                            19

<210> SEQ ID NO 98
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 98
gtctgctata aggaatatc                                            19

<210> SEQ ID NO 99
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 99
aagtactcct gaggtctac                                            19

<210> SEQ ID NO 100
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 100
aggcaccagg gacttgtgc                                            19

<210> SEQ ID NO 101
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 101
gatctacacc accttcatc                                                19

<210> SEQ ID NO 102
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 102
tggtgttcta cgtggtgac                                                19

<210> SEQ ID NO 103
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 103
tgttaggcgc ctgcattgc                                                19

<210> SEQ ID NO 104
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 104
caacatcttt atctgctcc                                                19

<210> SEQ ID NO 105
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 105
cgaagggctt tcacaatgc                                                19

<210> SEQ ID NO 106
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 106
gtactacgtt gtagcccac                                                19

<210> SEQ ID NO 107
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 107
tgcaggcgct taacattac                                                19

```
<210> SEQ ID NO 108
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 108
ggtgtatggg ctcatgtac                                               19

<210> SEQ ID NO 109
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 109
catcgtcatc gcctgctac                                               19

<210> SEQ ID NO 110
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 110
gctcatggtg cgcattggc                                               19

<210> SEQ ID NO 111
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 111
gtaccttatg acgctgatc                                               19

<210> SEQ ID NO 112
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 112
acctggtatg ggtttggcc                                               19

<210> SEQ ID NO 113
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 113
atgtgtgcag gtctactgc                                               19

<210> SEQ ID NO 114
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 114
```

```
ttatttaggg cggttttaac                                              19

<210> SEQ ID NO 115
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 115
taatgtcatc gcctccaac                                               19

<210> SEQ ID NO 116
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 116
agaactgggt gatgacagc                                               19

<210> SEQ ID NO 117
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 117
caacagtccc tgctacatc                                               19

<210> SEQ ID NO 118
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 118
gatcgtggtg catccatac                                               19

<210> SEQ ID NO 119
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 119
gcgtggatta ccagaagac                                               19

<210> SEQ ID NO 120
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 120
taacaacagt ccctgctac                                               19

<210> SEQ ID NO 121
<211> LENGTH: 19
<212> TYPE: DNA
<213> ORGANISM: Artificial Sequence
```

```
<220> FEATURE:
<223> OTHER INFORMATION: Synthetic oligonucleotide

<400> SEQUENCE: 121
ccattgcttg gtgaatggc                                                19

<210> SEQ ID NO 122
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 122
attctctcca tggagtgac                                                19

<210> SEQ ID NO 123
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 123
atgaactctg tgatccagc                                                19

<210> SEQ ID NO 124
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 124
aggttggcta gtggatctc                                                19

<210> SEQ ID NO 125
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 125
aagtgggtaa ttcctgctc                                                19

<210> SEQ ID NO 126
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 126
cgaatggcag aatggatac                                                19

<210> SEQ ID NO 127
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 127
tctggcaggt tgcatattc                                                19
```

```
<210> SEQ ID NO 128
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 128
ctgcaagttt catatctac                                                  19

<210> SEQ ID NO 129
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 129
atagcatcag attgtatgc                                                  19

<210> SEQ ID NO 130
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 130
tttacacgat gatatgttc                                                  19

<210> SEQ ID NO 131
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 131
cagaggattt gccagaaac                                                  19

<210> SEQ ID NO 132
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 132
ttggaattcc agtgtaccc                                                  19

<210> SEQ ID NO 133
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 133
cagagacacc atctccctc                                                  19

<210> SEQ ID NO 134
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 134
```
acccagaccc aaagtttgc                                          19

<210> SEQ ID NO 135
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 135
aaggtggaaa gactatctc                                          19

<210> SEQ ID NO 136
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 136
tataaaccag aggatttgc                                          19

<210> SEQ ID NO 137
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 137
gtataatcta catcagatc                                          19

<210> SEQ ID NO 138
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 138
ccacatgttt accagagac                                          19

<210> SEQ ID NO 139
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 139
gctagttatc gcctacctc                                          19

<210> SEQ ID NO 140
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 140
gacacacagg agttcaacc                                          19

<210> SEQ ID NO 141
<211> LENGTH: 19
<212> TYPE: DNA
<213> ORGANISM: Artificial Sequence

```
<220> FEATURE:
<223> OTHER INFORMATION: Synthetic oligonucleotide

<400> SEQUENCE: 141
gctgcagaaa ctaggcatc                                               19

<210> SEQ ID NO 142
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 142
tgccaacttc tacaaggac                                               19

<210> SEQ ID NO 143
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 143
cgacacacag gagttcaac                                               19

<210> SEQ ID NO 144
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 144
gatggacgtc aagtctgcc                                               19

<210> SEQ ID NO 145
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 145
acaggagttc aacctcagc                                               19

<210> SEQ ID NO 146
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 146
ttggcatgga accaacgac                                               19

<210> SEQ ID NO 147
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 147
cctctttgcc ctgtatgac                                               19
```

```
<210> SEQ ID NO 148
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 148
agattccaga tgcaacccc                                              19

<210> SEQ ID NO 149
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 149
catgagccag ctgagtttc                                              19

<210> SEQ ID NO 150
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 150
gtggaagtga tcttctatc                                              19

<210> SEQ ID NO 151
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 151
tggctgtcat ggtccaatc                                              19

<210> SEQ ID NO 152
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 152
ccgctgcatg aactatgac                                              19

<210> SEQ ID NO 153
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 153
ttggagactt cggtttaac                                              19

<210> SEQ ID NO 154
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 154
```
tgtgattcag attctagtc                                                19

<210> SEQ ID NO 155
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 155
agtggatgtc ctacatctc                                                19

<210> SEQ ID NO 156
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 156
atcatgcagg atgacatgc                                                19

<210> SEQ ID NO 157
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 157
ctgaactact ggtacagcc                                                19

<210> SEQ ID NO 158
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 158
cagctttacg tcctgagtc                                                19

<210> SEQ ID NO 159
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 159
tcagaccaca agagagacc                                                19

<210> SEQ ID NO 160
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 160
gtacctacag tggatgtcc                                                19

<210> SEQ ID NO 161
<211> LENGTH: 19
<212> TYPE: DNA
<213> ORGANISM: Artificial Sequence

```
<220> FEATURE:
<223> OTHER INFORMATION: Synthetic oligonucleotide

<400> SEQUENCE: 161
tggtcaagga gatactgac                                              19

<210> SEQ ID NO 162
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 162
ccctccagtc atgttcttc                                              19

<210> SEQ ID NO 163
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 163
ttctgcaact gtgatgatc                                              19

<210> SEQ ID NO 164
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 164
gtacactacg tggattcac                                              19

<210> SEQ ID NO 165
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 165
gcgaattcca ccagcattc                                              19

<210> SEQ ID NO 166
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 166
tcttccagtg ctgcagctc                                              19

<210> SEQ ID NO 167
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 167
tcagaacaag aggctgggc                                              19
```

-continued

```
<210> SEQ ID NO 168
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 168
gaagattgcc agtcttcac                                                   19

<210> SEQ ID NO 169
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 169
gattcctcct ctcaacatc                                                   19

<210> SEQ ID NO 170
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 170
gcattctagt atttctaac                                                   19

<210> SEQ ID NO 171
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 171
ttacagtgtc aattccaac                                                   19

<210> SEQ ID NO 172
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 172
tgattatcgg gagatcatc                                                   19

<210> SEQ ID NO 173
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 173
gaatggatgt gtatgtatc                                                   19

<210> SEQ ID NO 174
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 174
```
tgacatgatt ccttatagc                                              19

<210> SEQ ID NO 175
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 175
tctacacact gccaaatgc                                              19

<210> SEQ ID NO 176
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 176
actggccatc atctacaac                                              19

<210> SEQ ID NO 177
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 177
tgctcacctg tctgtggtc                                              19

<210> SEQ ID NO 178
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 178
acattgacca ggaagtgac                                              19

<210> SEQ ID NO 179
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 179
tggatgactt cagctctac                                              19

<210> SEQ ID NO 180
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 180
ctacaacctc tggttcggc                                              19

<210> SEQ ID NO 181
<211> LENGTH: 19
<212> TYPE: DNA
<213> ORGANISM: Artificial Sequence

```
<220> FEATURE:
<223> OTHER INFORMATION: Synthetic oligonucleotide

<400> SEQUENCE: 181
cacgacagtg gagagaaac                                               19

<210> SEQ ID NO 182
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 182
gttctacatg ccggatgac                                               19

<210> SEQ ID NO 183
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 183
aggtatcatg cactggctc                                               19

<210> SEQ ID NO 184
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 184
gaagctgaat tagggcttc                                               19

<210> SEQ ID NO 185
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 185
ctggtggaca tcattcagc                                               19

<210> SEQ ID NO 186
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 186
tttgtgatcg gaagtcaac                                               19

<210> SEQ ID NO 187
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 187
attgctgatg cactaagac                                               19
```

<210> SEQ ID NO 188
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 188
cagatatgat cttatcaac                                              19

<210> SEQ ID NO 189
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 189
actgtgcatt acataatgc                                              19

<210> SEQ ID NO 190
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 190
cacgtgagtg cagcttatc                                              19

<210> SEQ ID NO 191
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 191
agtcctatca ttgatcggc                                              19

<210> SEQ ID NO 192
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 192
gaagccatct ccgacaatc                                              19

<210> SEQ ID NO 193
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 193
atggctgttg gtatgatcc                                              19

<210> SEQ ID NO 194
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 194

```
ccgtgaggtt tgttaacac                                                    19
```

<210> SEQ ID NO 195
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 195

```
ttgggtgcct taccaatac                                                    19
```

<210> SEQ ID NO 196
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 196

```
ctccaagtgt ggaattaac                                                    19
```

<210> SEQ ID NO 197
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 197

```
gcatgatggt aaaggatac                                                    19
```

<210> SEQ ID NO 198
<211> LENGTH: 109
<212> TYPE: PRT
<213> ORGANISM: Homo sapiens

<400> SEQUENCE: 198

Met Ile Cys Cys Ser Ala Leu Ser Pro Arg Ile His Leu Ser Phe His
1               5                   10                  15

Arg Ser Leu Thr Gly Ile Val Leu Ala Asn Ser Ser Leu Asp Ile Val
            20                  25                  30

Leu His Asp Thr Tyr Tyr Val Ala His Cys Gly Gly Asn Val Arg
        35                  40                  45

Arg Leu His Cys Gly Gly Pro Ala Ser Arg Glu Arg Thr Ala Met Gln
    50                  55                  60

Ala Leu Asn Ile Thr Pro Glu Gln Phe Ser Arg Leu Leu Arg Asp His
65                  70                  75                  80

Asn Leu Thr Arg Glu Gln Phe Ile Ala Leu Tyr Arg Leu Arg Pro Leu
                85                  90                  95

Val Tyr Thr Pro Glu Leu Pro Gly Arg Ala Lys Leu Ala
            100                 105

<210> SEQ ID NO 199
<211> LENGTH: 23
<212> TYPE: PRT
<213> ORGANISM: Homo sapiens

<400> SEQUENCE: 199

Leu Val Leu Thr Gly Val Leu Ile Phe Ala Leu Ala Leu Phe Gly Asn
1               5                   10                  15

Ala Leu Val Phe Tyr Val Val

20

<210> SEQ ID NO 200
<211> LENGTH: 11
<212> TYPE: PRT
<213> ORGANISM: Homo sapiens

<400> SEQUENCE: 200

Thr Arg Ser Lys Ala Met Arg Thr Val Thr Asn
1               5                   10

<210> SEQ ID NO 201
<211> LENGTH: 23
<212> TYPE: PRT
<213> ORGANISM: Homo sapiens

<400> SEQUENCE: 201

Ile Phe Ile Cys Ser Leu Ala Leu Ser Asp Leu Leu Ile Thr Phe Phe
1               5                   10                  15

Cys Ile Pro Val Thr Met Leu
            20

<210> SEQ ID NO 202
<211> LENGTH: 14
<212> TYPE: PRT
<213> ORGANISM: Homo sapiens

<400> SEQUENCE: 202

Gln Asn Ile Ser Asp Asn Trp Leu Gly Gly Ala Phe Ile Cys
1               5                   10

<210> SEQ ID NO 203
<211> LENGTH: 23
<212> TYPE: PRT
<213> ORGANISM: Homo sapiens

<400> SEQUENCE: 203

Lys Met Val Pro Phe Val Gln Ser Thr Ala Val Val Thr Glu Ile Leu
1               5                   10                  15

Thr Met Thr Cys Ile Ala Val
            20

<210> SEQ ID NO 204
<211> LENGTH: 20
<212> TYPE: PRT
<213> ORGANISM: Homo sapiens

<400> SEQUENCE: 204

Glu Arg His Gln Gly Leu Val His Pro Phe Lys Met Lys Trp Gln Tyr
1               5                   10                  15

Thr Asn Arg Arg
            20

<210> SEQ ID NO 205
<211> LENGTH: 23
<212> TYPE: PRT
<213> ORGANISM: Homo sapiens

<400> SEQUENCE: 205

Ala Phe Thr Met Leu Gly Val Val Trp Leu Val Ala Val Ile Val Gly
1               5                   10                  15

Ser Pro Met Trp His Val Gln
            20

<210> SEQ ID NO 206
<211> LENGTH: 48
<212> TYPE: PRT
<213> ORGANISM: Homo sapiens

<400> SEQUENCE: 206

Gln Leu Glu Ile Lys Tyr Asp Phe Leu Tyr Glu Lys Glu His Ile Cys
1               5                   10                  15

Cys Leu Glu Glu Trp Thr Ser Pro Val His Gln Lys Ile Tyr Thr Thr
            20                  25                  30

Phe Ile Leu Ser Ser Ser Ser Cys Leu Leu Trp Lys Lys Lys Arg
        35                  40                  45

<210> SEQ ID NO 207
<211> LENGTH: 23
<212> TYPE: PRT
<213> ORGANISM: Homo sapiens

<400> SEQUENCE: 207

Ala Val Ile Met Met Val Thr Val Val Ala Leu Phe Ala Val Cys Trp
1               5                   10                  15

Ala Pro Phe His Val Val His
            20

<210> SEQ ID NO 208
<211> LENGTH: 19
<212> TYPE: PRT
<213> ORGANISM: Homo sapiens

<400> SEQUENCE: 208

Met Met Ile Glu Tyr Ser Asn Phe Glu Lys Glu Tyr Asp Asp Val Thr
1               5                   10                  15

Ile Lys Met

<210> SEQ ID NO 209
<211> LENGTH: 23
<212> TYPE: PRT
<213> ORGANISM: Homo sapiens

<400> SEQUENCE: 209

Ile Phe Ala Ile Val Gln Ile Ile Gly Phe Ser Asn Ser Ile Cys Asn
1               5                   10                  15

Pro Ile Val Tyr Ala Phe Met
            20

<210> SEQ ID NO 210
<211> LENGTH: 96
<212> TYPE: PRT
<213> ORGANISM: Homo sapiens

<400> SEQUENCE: 210

Asn Glu Asn Phe Lys Lys Asn Val Leu Ser Ala Val Cys Tyr Cys Ile
1               5                   10                  15

Val Asn Lys Thr Phe Ser Pro Ala Gln Arg His Gly Asn Ser Gly Ile
            20                  25                  30

Thr Met Met Arg Lys Lys Ala Lys Phe Ser Leu Arg Glu Asn Pro Val
        35                  40                  45

Glu Glu Thr Lys Gly Glu Ala Phe Ser Asp Gly Asn Ile Glu Val Lys
    50                  55                  60

Leu Cys Glu Gln Thr Glu Glu Lys Lys Leu Lys Arg His Leu Ala
65                  70                  75                  80

```
Leu Phe Arg Ser Glu Leu Ala Glu Asn Ser Pro Leu Asp Ser Gly His
                85                  90                  95

<210> SEQ ID NO 211
<211> LENGTH: 47
<212> TYPE: PRT
<213> ORGANISM: Homo sapiens

<400> SEQUENCE: 211

Met Gln Ala Leu Asn Ile Thr Pro Glu Gln Phe Ser Arg Leu Leu Arg
1               5                   10                  15

Asp His Asn Leu Thr Arg Glu Gln Phe Ile Ala Val His Arg Leu Arg
                20                  25                  30

Pro Leu Val Tyr Thr Pro Glu Leu Pro Gly Arg Ala Lys Leu Ala
            35                  40                  45

<210> SEQ ID NO 212
<211> LENGTH: 23
<212> TYPE: PRT
<213> ORGANISM: Homo sapiens

<400> SEQUENCE: 212

Leu Val Leu Thr Gly Val Leu Ile Phe Ala Leu Ala Leu Phe Gly Asn
1               5                   10                  15

Ala Leu Val Phe Tyr Val Val
            20

<210> SEQ ID NO 213
<211> LENGTH: 11
<212> TYPE: PRT
<213> ORGANISM: Homo sapiens

<400> SEQUENCE: 213

Thr Arg Ser Lys Ala Met Arg Thr Val Thr Asn
1               5                   10

<210> SEQ ID NO 214
<211> LENGTH: 23
<212> TYPE: PRT
<213> ORGANISM: Homo sapiens

<400> SEQUENCE: 214

Ile Phe Ile Cys Ser Leu Ala Leu Ser Asp Leu Leu Ile Thr Phe Phe
1               5                   10                  15

Cys Ile Pro Val Thr Met Leu
            20

<210> SEQ ID NO 215
<211> LENGTH: 14
<212> TYPE: PRT
<213> ORGANISM: Homo sapiens

<400> SEQUENCE: 215

Gln Asn Ile Ser Asp Asn Trp Leu Gly Gly Ala Phe Ile Cys
1               5                   10

<210> SEQ ID NO 216
<211> LENGTH: 23
<212> TYPE: PRT
<213> ORGANISM: Homo sapiens

<400> SEQUENCE: 216

Lys Met Val Pro Phe Val Gln Ser Thr Ala Val Val Thr Glu Ile Leu
```

```
                1               5                  10                  15
Thr Met Thr Cys Ile Ala Val
                20

<210> SEQ ID NO 217
<211> LENGTH: 20
<212> TYPE: PRT
<213> ORGANISM: Homo sapiens

<400> SEQUENCE: 217

Glu Arg His Gln Gly Leu Val His Pro Phe Lys Met Lys Trp Gln Tyr
1               5                   10                  15

Thr Asn Arg Arg
            20

<210> SEQ ID NO 218
<211> LENGTH: 23
<212> TYPE: PRT
<213> ORGANISM: Homo sapiens

<400> SEQUENCE: 218

Ala Phe Thr Met Leu Gly Val Val Trp Leu Val Ala Val Ile Val Gly
1               5                   10                  15

Ser Pro Met Trp His Val Gln
            20

<210> SEQ ID NO 219
<211> LENGTH: 28
<212> TYPE: PRT
<213> ORGANISM: Homo sapiens

<400> SEQUENCE: 219

Gln Leu Glu Ile Lys Tyr Asp Phe Leu Tyr Glu Lys Glu His Ile Cys
1               5                   10                  15

Cys Leu Glu Glu Trp Thr Ser Pro Val His Gln Lys
            20                  25

<210> SEQ ID NO 220
<211> LENGTH: 23
<212> TYPE: PRT
<213> ORGANISM: Homo sapiens

<400> SEQUENCE: 220

Ile Tyr Thr Thr Phe Ile Leu Val Ile Leu Phe Leu Leu Pro Leu Met
1               5                   10                  15

Val Met Leu Ile Leu Tyr Ser
            20

<210> SEQ ID NO 221
<211> LENGTH: 34
<212> TYPE: PRT
<213> ORGANISM: Homo sapiens

<400> SEQUENCE: 221

Lys Ile Gly Tyr Glu Leu Trp Ile Lys Lys Arg Val Gly Asp Gly Ser
1               5                   10                  15

Val Leu Arg Thr Ile His Gly Lys Glu Met Ser Lys Ile Ala Arg Lys
            20                  25                  30

Lys Lys

<210> SEQ ID NO 222
<211> LENGTH: 23
```

```
<212> TYPE: PRT
<213> ORGANISM: Homo sapiens

<400> SEQUENCE: 222

Arg Ala Val Ile Met Met Val Thr Val Val Ala Leu Phe Ala Val Cys
1               5                   10                  15

Trp Ala Pro Phe His Val Val
            20

<210> SEQ ID NO 223
<211> LENGTH: 19
<212> TYPE: PRT
<213> ORGANISM: Homo sapiens

<400> SEQUENCE: 223

His Met Met Ile Glu Tyr Ser Asn Phe Glu Lys Glu Tyr Asp Asp Val
1               5                   10                  15

Thr Ile Lys

<210> SEQ ID NO 224
<211> LENGTH: 23
<212> TYPE: PRT
<213> ORGANISM: Homo sapiens

<400> SEQUENCE: 224

Met Ile Phe Ala Ile Val Gln Ile Ile Gly Phe Ser Asn Ser Ile Cys
1               5                   10                  15

Asn Pro Ile Val Tyr Ala Phe
            20

<210> SEQ ID NO 225
<211> LENGTH: 97
<212> TYPE: PRT
<213> ORGANISM: Homo sapiens

<400> SEQUENCE: 225

Met Asn Glu Asn Phe Lys Lys Asn Val Leu Ser Ala Val Cys Tyr Cys
1               5                   10                  15

Ile Val Asn Lys Thr Phe Ser Pro Ala Gln Arg His Gly Asn Ser Gly
                20                  25                  30

Ile Thr Met Met Arg Lys Lys Ala Lys Phe Ser Leu Arg Glu Asn Pro
            35                  40                  45

Val Glu Glu Thr Lys Gly Glu Ala Phe Ser Asp Gly Asn Ile Glu Val
        50                  55                  60

Lys Leu Cys Glu Gln Thr Glu Lys Lys Lys Leu Lys Arg His Leu
65                  70                  75                  80

Ala Leu Phe Arg Ser Glu Leu Ala Glu Asn Ser Pro Leu Asp Ser Gly
                85                  90                  95

His

<210> SEQ ID NO 226
<211> LENGTH: 320
<212> TYPE: PRT
<213> ORGANISM: Homo sapiens

<400> SEQUENCE: 226

Met Ala Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
            20                  25                  30
```

```
Glu Gly Ser Gly Asp Ala Gly Gly Arg Arg Arg Pro Pro Val Asp Pro
            35                  40                  45

Arg Arg Leu Ala Arg Gln Leu Leu Leu Leu Trp Leu Leu Glu Ala
 50                  55                  60

Pro Leu Leu Gly Val Arg Ala Gln Ala Gly Gln Gly Pro Gly
 65                  70                  75                  80

Gln Gly Pro Gly Pro Gly Gln Gln Pro Pro Pro Gln Gln Gln
             85                  90                  95

Gln Ser Gly Gln Gln Tyr Asn Gly Glu Arg Gly Ile Ser Val Pro Asp
            100                 105                 110

His Gly Tyr Cys Gln Pro Ile Ser Ile Pro Leu Cys Thr Asp Ile Ala
            115                 120                 125

Tyr Asn Gln Thr Ile Met Pro Asn Leu Leu Gly His Thr Asn Gln Glu
130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
                165                 170                 175

Cys Thr Val Leu Glu Gln Ala Leu Pro Pro Cys Arg Ser Leu Cys Glu
            180                 185                 190

Arg Ala Arg Gln Gly Cys Glu Ala Leu Met Asn Lys Phe Gly Phe Gln
            195                 200                 205

Trp Pro Asp Thr Leu Lys Cys Glu Lys Phe Pro Val His Gly Ala Gly
210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
                245                 250                 255

Gly His Arg Gly Gly Phe Pro Gly Gly Ala Gly Ala Ser Glu Arg Gly
            260                 265                 270

Lys Phe Ser Cys Pro Arg Ala Leu Lys Val Pro Ser Tyr Leu Asn Tyr
            275                 280                 285

His Phe Leu Gly Glu Lys Asp Cys Gly Ala Pro Cys Glu Pro Thr Lys
290                 295                 300

Val Tyr Gly Leu Met Tyr Phe Gly Pro Glu Glu Leu Arg Phe Ser Arg
305                 310                 315                 320

<210> SEQ ID NO 227
<211> LENGTH: 23
<212> TYPE: PRT
<213> ORGANISM: Homo sapiens

<400> SEQUENCE: 227

Thr Trp Ile Gly Ile Trp Ser Val Leu Cys Cys Ala Ser Thr Leu Phe
1               5                   10                  15

Thr Val Leu Thr Tyr Leu Val
            20

<210> SEQ ID NO 228
<211> LENGTH: 12
<212> TYPE: PRT
<213> ORGANISM: Homo sapiens

<400> SEQUENCE: 228

Asp Met Arg Arg Phe Ser Tyr Pro Glu Arg Pro Ile
1               5                   10
```

```
<210> SEQ ID NO 229
<211> LENGTH: 20
<212> TYPE: PRT
<213> ORGANISM: Homo sapiens

<400> SEQUENCE: 229

Ile Phe Leu Ser Gly Cys Tyr Thr Ala Val Ala Val Ala Tyr Ile Ala
1               5                   10                  15

Gly Phe Leu Leu
            20

<210> SEQ ID NO 230
<211> LENGTH: 27
<212> TYPE: PRT
<213> ORGANISM: Homo sapiens

<400> SEQUENCE: 230

Glu Asp Arg Val Val Cys Asn Asp Lys Phe Ala Glu Asp Gly Ala Arg
1               5                   10                  15

Thr Val Ala Gln Gly Thr Lys Lys Glu Gly Cys
            20                  25

<210> SEQ ID NO 231
<211> LENGTH: 23
<212> TYPE: PRT
<213> ORGANISM: Homo sapiens

<400> SEQUENCE: 231

Thr Ile Leu Phe Met Met Leu Tyr Phe Phe Ser Met Ala Ser Ser Ile
1               5                   10                  15

Trp Trp Val Ile Leu Ser Leu
            20

<210> SEQ ID NO 232
<211> LENGTH: 20
<212> TYPE: PRT
<213> ORGANISM: Homo sapiens

<400> SEQUENCE: 232

Thr Trp Phe Leu Ala Ala Gly Met Lys Trp Gly His Glu Ala Ile Glu
1               5                   10                  15

Ala Asn Ser Gln
            20

<210> SEQ ID NO 233
<211> LENGTH: 23
<212> TYPE: PRT
<213> ORGANISM: Homo sapiens

<400> SEQUENCE: 233

Tyr Phe His Leu Ala Ala Trp Ala Val Pro Ala Ile Lys Thr Ile Thr
1               5                   10                  15

Ile Leu Ala Leu Gly Gln Val
            20

<210> SEQ ID NO 234
<211> LENGTH: 23
<212> TYPE: PRT
<213> ORGANISM: Homo sapiens

<400> SEQUENCE: 234

Asp Gly Asp Val Leu Ser Gly Val Cys Phe Val Gly Leu Asn Asn Val
1               5                   10                  15
```

Asp Ala Leu Arg Gly Phe Val
            20

<210> SEQ ID NO 235
<211> LENGTH: 23
<212> TYPE: PRT
<213> ORGANISM: Homo sapiens

<400> SEQUENCE: 235

Leu Ala Pro Leu Phe Val Tyr Leu Phe Ile Gly Thr Ser Phe Leu Leu
1               5                   10                  15

Ala Gly Phe Val Ser Leu Phe
            20

<210> SEQ ID NO 236
<211> LENGTH: 20
<212> TYPE: PRT
<213> ORGANISM: Homo sapiens

<400> SEQUENCE: 236

Arg Ile Arg Thr Ile Met Lys His Asp Gly Thr Lys Thr Glu Lys Leu
1               5                   10                  15

Glu Lys Leu Met
            20

<210> SEQ ID NO 237
<211> LENGTH: 23
<212> TYPE: PRT
<213> ORGANISM: Homo sapiens

<400> SEQUENCE: 237

Val Arg Ile Gly Val Phe Ser Val Leu Tyr Thr Val Pro Ala Thr Ile
1               5                   10                  15

Val Ile Ala Cys Tyr Phe Tyr
            20

<210> SEQ ID NO 238
<211> LENGTH: 42
<212> TYPE: PRT
<213> ORGANISM: Homo sapiens

<400> SEQUENCE: 238

Glu Gln Ala Phe Arg Asp Gln Trp Glu Arg Ser Trp Val Ala Gln Ser
1               5                   10                  15

Cys Lys Ser Tyr Ala Ile Pro Cys Pro His Leu Gln Ala Gly Gly Gly
            20                  25                  30

Ala Pro Pro His Pro Pro Met Ser Pro Asp
        35                  40

<210> SEQ ID NO 239
<211> LENGTH: 23
<212> TYPE: PRT
<213> ORGANISM: Homo sapiens

<400> SEQUENCE: 239

Phe Thr Val Phe Met Ile Lys Tyr Leu Met Thr Leu Ile Val Gly Ile
1               5                   10                  15

Thr Ser Gly Phe Trp Ile Trp
            20

<210> SEQ ID NO 240
<211> LENGTH: 25
<212> TYPE: PRT

<213> ORGANISM: Homo sapiens

<400> SEQUENCE: 240

```
Ser Gly Lys Thr Leu Asn Ser Trp Arg Lys Phe Tyr Thr Arg Leu Thr
1               5                   10                  15

Asn Ser Lys Gln Gly Glu Thr Thr Val
            20                  25
```

<210> SEQ ID NO 241
<211> LENGTH: 409
<212> TYPE: PRT
<213> ORGANISM: Homo sapiens

<400> SEQUENCE: 241

```
Met Ala Cys Leu Met Ala Ala Phe Ser Val Gly Thr Ala Met Asn Ala
1               5                   10                  15

Ser Ser Tyr Ser Ala Glu Met Thr Glu Pro Lys Ser Val Cys Val Ser
            20                  25                  30

Val Asp Glu Val Val Ser Ser Met Glu Ala Thr Glu Thr Asp Leu
        35                  40                  45

Leu Asn Gly His Leu Lys Lys Val Asp Asn Leu Thr Glu Ala Gln
    50                  55                  60

Arg Phe Ser Ser Leu Pro Arg Arg Ala Val Asn Ile Glu Phe Arg
65                  70                  75                  80

Asp Leu Ser Tyr Ser Val Pro Glu Gly Pro Trp Trp Arg Lys Lys Gly
                85                  90                  95

Tyr Lys Thr Leu Leu Lys Gly Ile Ser Gly Lys Phe Asn Ser Gly Glu
            100                 105                 110

Leu Val Ala Ile Met Gly Pro Ser Gly Ala Gly Lys Ser Thr Leu Met
        115                 120                 125

Asn Ile Leu Ala Gly Tyr Arg Glu Thr Gly Met Lys Gly Ala Val Leu
    130                 135                 140

Ile Asn Gly Leu Pro Arg Asp Leu Arg Cys Phe Arg Lys Val Ser Cys
145                 150                 155                 160

Tyr Ile Met Gln Asp Asp Met Leu Leu Pro His Leu Thr Val Gln Glu
                165                 170                 175

Ala Met Met Val Ser Ala His Leu Lys Leu Gln Glu Lys Asp Glu Gly
            180                 185                 190

Arg Arg Glu Met Val Lys Glu Ile Leu Thr Ala Leu Gly Leu Leu Ser
        195                 200                 205

Cys Ala Asn Thr Arg Thr Gly Ser Leu Ser Gly Gly Gln Arg Lys Arg
    210                 215                 220

Leu Ala Ile Ala Leu Glu Leu Val Asn Asn Pro Pro Val Met Phe Phe
225                 230                 235                 240

Asp Glu Pro Thr Ser Gly Leu Asp Ser Ala Ser Cys Phe Gln Val Val
                245                 250                 255

Ser Leu Met Lys Gly Leu Ala Gln Gly Gly Arg Ser Ile Ile Cys Thr
            260                 265                 270

Ile His Gln Pro Ser Ala Lys Leu Phe Glu Leu Phe Asp Gln Leu Tyr
        275                 280                 285

Val Leu Ser Gln Gly Gln Cys Val Tyr Arg Gly Lys Val Cys Asn Leu
    290                 295                 300

Val Pro Tyr Leu Arg Asp Leu Gly Leu Asn Cys Pro Thr Tyr His Asn
305                 310                 315                 320

Pro Ala Asp Phe Val Met Glu Val Ala Ser Gly Glu Tyr Gly Asp Gln
                325                 330                 335
```

```
Asn Ser Arg Leu Val Arg Ala Val Arg Glu Gly Met Cys Asp Ser Asp
        340                 345                 350

His Lys Arg Asp Leu Gly Gly Asp Ala Glu Val Asn Pro Phe Leu Trp
        355                 360                 365

His Arg Pro Ser Glu Glu Asp Ser Ser Ser Met Glu Gly Cys His Ser
    370                 375                 380

Phe Ser Ala Ser Cys Leu Thr Gln Phe Cys Ile Leu Phe Lys Arg Thr
385                 390                 395                 400

Phe Leu Ser Ile Met Arg Asp Ser Val
                405

<210> SEQ ID NO 242
<211> LENGTH: 23
<212> TYPE: PRT
<213> ORGANISM: Homo sapiens

<400> SEQUENCE: 242

Leu Thr His Leu Arg Ile Thr Ser His Ile Gly Ile Gly Leu Leu Ile
1               5                   10                  15

Gly Leu Leu Tyr Leu Gly Ile
            20

<210> SEQ ID NO 243
<211> LENGTH: 12
<212> TYPE: PRT
<213> ORGANISM: Homo sapiens

<400> SEQUENCE: 243

Gly Asn Glu Ala Lys Lys Val Leu Ser Asn Ser Gly
1               5                   10

<210> SEQ ID NO 244
<211> LENGTH: 23
<212> TYPE: PRT
<213> ORGANISM: Homo sapiens

<400> SEQUENCE: 244

Phe Leu Phe Phe Ser Met Leu Phe Leu Met Phe Ala Ala Leu Met Pro
1               5                   10                  15

Thr Val Leu Thr Phe Pro Leu
            20

<210> SEQ ID NO 245
<211> LENGTH: 23
<212> TYPE: PRT
<213> ORGANISM: Homo sapiens

<400> SEQUENCE: 245

Glu Met Gly Val Phe Leu Arg Glu His Leu Asn Tyr Trp Tyr Ser Leu
1               5                   10                  15

Lys Ala Tyr Tyr Leu Ala Lys
            20

<210> SEQ ID NO 246
<211> LENGTH: 23
<212> TYPE: PRT
<213> ORGANISM: Homo sapiens

<400> SEQUENCE: 246

Thr Met Ala Asp Val Pro Phe Gln Ile Met Phe Pro Val Ala Tyr Cys
1               5                   10                  15
```

```
Ser Ile Val Tyr Trp Met Thr
            20

<210> SEQ ID NO 247
<211> LENGTH: 6
<212> TYPE: PRT
<213> ORGANISM: Homo sapiens

<400> SEQUENCE: 247

Ser Gln Pro Ser Asp Ala
1               5

<210> SEQ ID NO 248
<211> LENGTH: 23
<212> TYPE: PRT
<213> ORGANISM: Homo sapiens

<400> SEQUENCE: 248

Val Arg Phe Val Leu Phe Ala Ala Leu Gly Thr Met Thr Ser Leu Val
1               5                   10                  15

Ala Gln Ser Leu Gly Leu Leu
            20

<210> SEQ ID NO 249
<211> LENGTH: 9
<212> TYPE: PRT
<213> ORGANISM: Homo sapiens

<400> SEQUENCE: 249

Ile Gly Ala Ala Ser Thr Ser Leu Gln
1               5

<210> SEQ ID NO 250
<211> LENGTH: 23
<212> TYPE: PRT
<213> ORGANISM: Homo sapiens

<400> SEQUENCE: 250

Val Ala Thr Phe Val Gly Pro Val Thr Ala Ile Pro Val Leu Leu Phe
1               5                   10                  15

Ser Gly Phe Phe Val Ser Phe
            20

<210> SEQ ID NO 251
<211> LENGTH: 12
<212> TYPE: PRT
<213> ORGANISM: Homo sapiens

<400> SEQUENCE: 251

Asp Thr Ile Pro Thr Tyr Leu Gln Trp Met Ser Tyr
1               5                   10

<210> SEQ ID NO 252
<211> LENGTH: 18
<212> TYPE: PRT
<213> ORGANISM: Homo sapiens

<400> SEQUENCE: 252

Ile Ser Tyr Val Arg Tyr Gly Phe Glu Gly Val Ile Leu Ser Ile Tyr
1               5                   10                  15

Gly Leu

<210> SEQ ID NO 253
<211> LENGTH: 31
```

```
<212> TYPE: PRT
<213> ORGANISM: Homo sapiens

<400> SEQUENCE: 253

Asp Arg Glu Asp Leu His Cys Asp Ile Asp Glu Thr Cys His Phe Gln
1               5                   10                  15

Lys Ser Glu Ala Ile Leu Arg Glu Leu Asp Val Glu Asn Ala Lys
            20                  25                  30

<210> SEQ ID NO 254
<211> LENGTH: 23
<212> TYPE: PRT
<213> ORGANISM: Homo sapiens

<400> SEQUENCE: 254

Leu Tyr Leu Asp Phe Ile Val Leu Gly Ile Phe Phe Ile Ser Leu Arg
1               5                   10                  15

Leu Ile Ala Tyr Phe Val Leu
            20

<210> SEQ ID NO 255
<211> LENGTH: 8
<212> TYPE: PRT
<213> ORGANISM: Homo sapiens

<400> SEQUENCE: 255

Arg Tyr Lys Ile Arg Ala Glu Arg
1               5

<210> SEQ ID NO 256
<211> LENGTH: 421
<212> TYPE: PRT
<213> ORGANISM: Homo sapiens

<400> SEQUENCE: 256

Met Ala Cys Leu Met Ala Ala Phe Ser Val Gly Thr Ala Met Asn Ala
1               5                   10                  15

Ser Ser Tyr Ser Ala Glu Met Thr Glu Pro Lys Ser Val Cys Val Ser
            20                  25                  30

Val Asp Glu Val Val Ser Ser Asn Met Glu Ala Thr Glu Thr Asp Leu
        35                  40                  45

Leu Asn Gly His Leu Lys Lys Val Asp Asn Asn Leu Thr Glu Ala Gln
    50                  55                  60

Arg Phe Ser Ser Leu Pro Arg Arg Ala Ala Val Asn Ile Glu Phe Arg
65                  70                  75                  80

Asp Leu Ser Tyr Ser Val Pro Glu Gly Pro Trp Trp Arg Lys Lys Gly
                85                  90                  95

Tyr Lys Thr Leu Leu Lys Gly Ile Ser Gly Lys Phe Asn Ser Gly Glu
            100                 105                 110

Leu Val Ala Ile Met Gly Pro Ser Gly Ala Gly Lys Ser Thr Leu Met
        115                 120                 125

Asn Ile Leu Ala Gly Tyr Arg Glu Thr Gly Met Lys Gly Ala Val Leu
    130                 135                 140

Ile Asn Gly Leu Pro Arg Asp Leu Arg Cys Phe Arg Lys Val Ser Cys
145                 150                 155                 160

Tyr Ile Met Gln Asp Asp Met Leu Leu Pro His Leu Thr Val Gln Glu
                165                 170                 175

Ala Met Val Ser Ala His Leu Lys Leu Gln Glu Lys Asp Glu Gly
            180                 185                 190
```

```
Arg Arg Glu Met Val Lys Glu Ile Leu Thr Ala Leu Gly Leu Leu Ser
        195                 200                 205

Cys Ala Asn Thr Arg Thr Gly Ser Leu Ser Gly Gly Gln Arg Lys Arg
    210                 215                 220

Leu Ala Ile Ala Leu Glu Leu Val Asn Asn Pro Pro Val Met Phe Phe
225                 230                 235                 240

Asp Glu Pro Thr Ser Gly Leu Asp Ser Ala Ser Cys Phe Gln Val Val
                245                 250                 255

Ser Leu Met Lys Gly Leu Ala Gln Gly Gly Arg Ser Ile Ile Cys Thr
                260                 265                 270

Ile His Gln Pro Ser Ala Lys Leu Phe Glu Leu Phe Asp Gln Leu Tyr
                275                 280                 285

Val Leu Ser Gln Gly Gln Cys Val Tyr Arg Gly Lys Val Cys Asn Leu
290                 295                 300

Val Pro Tyr Leu Arg Asp Leu Gly Leu Asn Cys Pro Thr Tyr His Asn
305                 310                 315                 320

Pro Ala Asp Phe Val Met Glu Val Ala Ser Gly Glu Tyr Gly Asp Gln
                    325                 330                 335

Asn Ser Arg Leu Val Arg Ala Val Arg Glu Gly Met Cys Asp Ser Asp
                340                 345                 350

His Lys Arg Asp Leu Gly Gly Asp Ala Glu Val Asn Pro Phe Leu Trp
            355                 360                 365

His Arg Pro Ser Glu Glu Val Lys Gln Thr Lys Arg Leu Lys Gly Leu
        370                 375                 380

Arg Lys Asp Ser Ser Ser Met Glu Gly Cys His Ser Phe Ser Ala Ser
385                 390                 395                 400

Cys Leu Thr Gln Phe Cys Ile Leu Phe Lys Arg Thr Phe Leu Ser Ile
                405                 410                 415

Met Arg Asp Ser Val
                420

<210> SEQ ID NO 257
<211> LENGTH: 23
<212> TYPE: PRT
<213> ORGANISM: Homo sapiens

<400> SEQUENCE: 257

Leu Thr His Leu Arg Ile Thr Ser His Ile Gly Ile Gly Leu Leu Ile
1               5                   10                  15

Gly Leu Leu Tyr Leu Gly Ile
            20

<210> SEQ ID NO 258
<211> LENGTH: 12
<212> TYPE: PRT
<213> ORGANISM: Homo sapiens

<400> SEQUENCE: 258

Gly Asn Glu Ala Lys Lys Val Leu Ser Asn Ser Gly
1               5                   10

<210> SEQ ID NO 259
<211> LENGTH: 23
<212> TYPE: PRT
<213> ORGANISM: Homo sapiens

<400> SEQUENCE: 259

Phe Leu Phe Phe Ser Met Leu Phe Leu Met Phe Ala Ala Leu Met Pro
1               5                   10                  15
```

Thr Val Leu Thr Phe Pro Leu
            20

<210> SEQ ID NO 260
<211> LENGTH: 23
<212> TYPE: PRT
<213> ORGANISM: Homo sapiens

<400> SEQUENCE: 260

Glu Met Gly Val Phe Leu Arg Glu His Leu Asn Tyr Trp Tyr Ser Leu
1               5                   10                  15

Lys Ala Tyr Tyr Leu Ala Lys
            20

<210> SEQ ID NO 261
<211> LENGTH: 23
<212> TYPE: PRT
<213> ORGANISM: Homo sapiens

<400> SEQUENCE: 261

Thr Met Ala Asp Val Pro Phe Gln Ile Met Phe Pro Val Ala Tyr Cys
1               5                   10                  15

Ser Ile Val Tyr Trp Met Thr
            20

<210> SEQ ID NO 262
<211> LENGTH: 6
<212> TYPE: PRT
<213> ORGANISM: Homo sapiens

<400> SEQUENCE: 262

Ser Gln Pro Ser Asp Ala
1               5

<210> SEQ ID NO 263
<211> LENGTH: 23
<212> TYPE: PRT
<213> ORGANISM: Homo sapiens

<400> SEQUENCE: 263

Val Arg Phe Val Leu Phe Ala Ala Leu Gly Thr Met Thr Ser Leu Val
1               5                   10                  15

Ala Gln Ser Leu Gly Leu Leu
            20

<210> SEQ ID NO 264
<211> LENGTH: 9
<212> TYPE: PRT
<213> ORGANISM: Homo sapiens

<400> SEQUENCE: 264

Ile Gly Ala Ala Ser Thr Ser Leu Gln
1               5

<210> SEQ ID NO 265
<211> LENGTH: 23
<212> TYPE: PRT
<213> ORGANISM: Homo sapiens

<400> SEQUENCE: 265

Val Ala Thr Phe Val Gly Pro Val Thr Ala Ile Pro Val Leu Leu Phe
1               5                   10                  15

Ser Gly Phe Phe Val Ser Phe

```
                   20

<210> SEQ ID NO 266
<211> LENGTH: 12
<212> TYPE: PRT
<213> ORGANISM: Homo sapiens

<400> SEQUENCE: 266

Asp Thr Ile Pro Thr Tyr Leu Gln Trp Met Ser Tyr
1               5                   10

<210> SEQ ID NO 267
<211> LENGTH: 18
<212> TYPE: PRT
<213> ORGANISM: Homo sapiens

<400> SEQUENCE: 267

Ile Ser Tyr Val Arg Tyr Gly Phe Glu Gly Val Ile Leu Ser Ile Tyr
1               5                   10                  15

Gly Leu

<210> SEQ ID NO 268
<211> LENGTH: 31
<212> TYPE: PRT
<213> ORGANISM: Homo sapiens

<400> SEQUENCE: 268

Asp Arg Glu Asp Leu His Cys Asp Ile Asp Glu Thr Cys His Phe Gln
1               5                   10                  15

Lys Ser Glu Ala Ile Leu Arg Glu Leu Asp Val Glu Asn Ala Lys
            20                  25                  30

<210> SEQ ID NO 269
<211> LENGTH: 23
<212> TYPE: PRT
<213> ORGANISM: Homo sapiens

<400> SEQUENCE: 269

Leu Tyr Leu Asp Phe Ile Val Leu Gly Ile Phe Phe Ile Ser Leu Arg
1               5                   10                  15

Leu Ile Ala Tyr Phe Val Leu
            20

<210> SEQ ID NO 270
<211> LENGTH: 8
<212> TYPE: PRT
<213> ORGANISM: Homo sapiens

<400> SEQUENCE: 270

Arg Tyr Lys Ile Arg Ala Glu Arg
1               5

<210> SEQ ID NO 271
<211> LENGTH: 420
<212> TYPE: PRT
<213> ORGANISM: Homo sapiens

<400> SEQUENCE: 271

Met Arg Ile Ser Leu Pro Arg Ala Pro Glu Arg Asp Gly Gly Val Ser
1               5                   10                  15

Ala Ser Ser Leu Leu Asp Thr Val Thr Asn Ala Ser Ser Tyr Ser Ala
            20                  25                  30

Glu Met Thr Glu Pro Lys Ser Val Cys Val Ser Val Asp Glu Val Val
```

-continued

```
                 35                  40                  45
Ser Ser Asn Met Glu Ala Thr Glu Thr Asp Leu Leu Asn Gly His Leu
 50                  55                  60
Lys Lys Val Asp Asn Asn Leu Thr Glu Ala Gln Arg Phe Ser Ser Leu
 65                  70                  75                  80
Pro Arg Arg Ala Ala Val Asn Ile Glu Phe Arg Asp Leu Ser Tyr Ser
                 85                  90                  95
Val Pro Glu Gly Pro Trp Trp Arg Lys Lys Gly Tyr Lys Thr Leu Leu
                100                 105                 110
Lys Gly Ile Ser Gly Lys Phe Asn Ser Gly Glu Leu Val Ala Ile Met
            115                 120                 125
Gly Pro Ser Gly Ala Gly Lys Ser Thr Leu Met Asn Ile Leu Ala Gly
        130                 135                 140
Tyr Arg Glu Thr Gly Met Lys Gly Ala Val Leu Ile Asn Gly Leu Pro
145                 150                 155                 160
Arg Asp Leu Arg Cys Phe Arg Lys Val Ser Cys Tyr Ile Met Gln Asp
                165                 170                 175
Asp Met Leu Leu Pro His Leu Thr Val Gln Glu Ala Met Met Val Ser
            180                 185                 190
Ala His Leu Lys Leu Gln Glu Lys Asp Glu Gly Arg Arg Glu Met Val
        195                 200                 205
Lys Glu Ile Leu Thr Ala Leu Gly Leu Leu Ser Cys Ala Asn Thr Arg
210                 215                 220
Thr Gly Ser Leu Ser Gly Gly Gln Arg Lys Arg Leu Ala Ile Ala Leu
225                 230                 235                 240
Glu Leu Val Asn Asn Pro Pro Val Met Phe Phe Asp Glu Pro Thr Ser
                245                 250                 255
Gly Leu Asp Ser Ala Ser Cys Phe Gln Val Val Ser Leu Met Lys Gly
            260                 265                 270
Leu Ala Gln Gly Gly Arg Ser Ile Ile Cys Thr Ile His Gln Pro Ser
        275                 280                 285
Ala Lys Leu Phe Glu Leu Phe Asp Gln Leu Tyr Val Leu Ser Gln Gly
290                 295                 300
Gln Cys Val Tyr Arg Gly Lys Val Cys Asn Leu Val Pro Tyr Leu Arg
305                 310                 315                 320
Asp Leu Gly Leu Asn Cys Pro Thr Tyr His Asn Pro Ala Asp Phe Val
                325                 330                 335
Met Glu Val Ala Ser Gly Glu Tyr Gly Asp Gln Asn Ser Arg Leu Val
            340                 345                 350
Arg Ala Val Arg Glu Gly Met Cys Asp Ser Asp His Lys Arg Asp Leu
        355                 360                 365
Gly Gly Asp Ala Glu Val Asn Pro Phe Leu Trp His Arg Pro Ser Glu
370                 375                 380
Glu Asp Ser Ser Ser Met Glu Gly Cys His Ser Phe Ser Ala Ser Cys
385                 390                 395                 400
Leu Thr Gln Phe Cys Ile Leu Phe Lys Arg Thr Phe Leu Ser Ile Met
                405                 410                 415
Arg Asp Ser Val
            420

<210> SEQ ID NO 272
<211> LENGTH: 23
<212> TYPE: PRT
<213> ORGANISM: Homo sapiens
```

-continued

```
<400> SEQUENCE: 272

Leu Thr His Leu Arg Ile Thr Ser His Ile Gly Ile Gly Leu Leu Ile
1               5                   10                  15

Gly Leu Leu Tyr Leu Gly Ile
            20

<210> SEQ ID NO 273
<211> LENGTH: 12
<212> TYPE: PRT
<213> ORGANISM: Homo sapiens

<400> SEQUENCE: 273

Gly Asn Glu Ala Lys Lys Val Leu Ser Asn Ser Gly
1               5                   10

<210> SEQ ID NO 274
<211> LENGTH: 23
<212> TYPE: PRT
<213> ORGANISM: Homo sapiens

<400> SEQUENCE: 274

Phe Leu Phe Phe Ser Met Leu Phe Leu Met Phe Ala Ala Leu Met Pro
1               5                   10                  15

Thr Val Leu Thr Phe Pro Leu
            20

<210> SEQ ID NO 275
<211> LENGTH: 23
<212> TYPE: PRT
<213> ORGANISM: Homo sapiens

<400> SEQUENCE: 275

Glu Met Gly Val Phe Leu Arg Glu His Leu Asn Tyr Trp Tyr Ser Leu
1               5                   10                  15

Lys Ala Tyr Tyr Leu Ala Lys
            20

<210> SEQ ID NO 276
<211> LENGTH: 23
<212> TYPE: PRT
<213> ORGANISM: Homo sapiens

<400> SEQUENCE: 276

Thr Met Ala Asp Val Pro Phe Gln Ile Met Phe Pro Val Ala Tyr Cys
1               5                   10                  15

Ser Ile Val Tyr Trp Met Thr
            20

<210> SEQ ID NO 277
<211> LENGTH: 6
<212> TYPE: PRT
<213> ORGANISM: Homo sapiens

<400> SEQUENCE: 277

Ser Gln Pro Ser Asp Ala
1               5

<210> SEQ ID NO 278
<211> LENGTH: 23
<212> TYPE: PRT
<213> ORGANISM: Homo sapiens

<400> SEQUENCE: 278
```

-continued

Val Arg Phe Val Leu Phe Ala Ala Leu Gly Thr Met Thr Ser Leu Val
1               5                   10                  15

Ala Gln Ser Leu Gly Leu Leu
            20

<210> SEQ ID NO 279
<211> LENGTH: 9
<212> TYPE: PRT
<213> ORGANISM: Homo sapiens

<400> SEQUENCE: 279

Ile Gly Ala Ala Ser Thr Ser Leu Gln
1               5

<210> SEQ ID NO 280
<211> LENGTH: 23
<212> TYPE: PRT
<213> ORGANISM: Homo sapiens

<400> SEQUENCE: 280

Val Ala Thr Phe Val Gly Pro Val Thr Ala Ile Pro Val Leu Leu Phe
1               5                   10                  15

Ser Gly Phe Phe Val Ser Phe
            20

<210> SEQ ID NO 281
<211> LENGTH: 12
<212> TYPE: PRT
<213> ORGANISM: Homo sapiens

<400> SEQUENCE: 281

Asp Thr Ile Pro Thr Tyr Leu Gln Trp Met Ser Tyr
1               5                   10

<210> SEQ ID NO 282
<211> LENGTH: 18
<212> TYPE: PRT
<213> ORGANISM: Homo sapiens

<400> SEQUENCE: 282

Ile Ser Tyr Val Arg Tyr Gly Phe Glu Gly Val Ile Leu Ser Ile Tyr
1               5                   10                  15

Gly Leu

<210> SEQ ID NO 283
<211> LENGTH: 31
<212> TYPE: PRT
<213> ORGANISM: Homo sapiens

<400> SEQUENCE: 283

Asp Arg Glu Asp Leu His Cys Asp Ile Asp Glu Thr Cys His Phe Gln
1               5                   10                  15

Lys Ser Glu Ala Ile Leu Arg Glu Leu Asp Val Glu Asn Ala Lys
            20                  25                  30

<210> SEQ ID NO 284
<211> LENGTH: 23
<212> TYPE: PRT
<213> ORGANISM: Homo sapiens

<400> SEQUENCE: 284

Leu Tyr Leu Asp Phe Ile Val Leu Gly Ile Phe Phe Ile Ser Leu Arg
1               5                   10                  15

Leu Ile Ala Tyr Phe Val Leu
            20

<210> SEQ ID NO 285
<211> LENGTH: 8
<212> TYPE: PRT
<213> ORGANISM: Homo sapiens

<400> SEQUENCE: 285

Arg Tyr Lys Ile Arg Ala Glu Arg
1               5

<210> SEQ ID NO 286
<211> LENGTH: 411
<212> TYPE: PRT
<213> ORGANISM: Homo sapiens

<400> SEQUENCE: 286

Met Leu Gly Thr Gln Gly Trp Thr Lys Gln Arg Lys Pro Cys Pro Gln
1               5                   10                  15

Asn Ala Ser Ser Tyr Ser Ala Glu Met Thr Glu Pro Lys Ser Val Cys
            20                  25                  30

Val Ser Val Asp Glu Val Val Ser Asn Met Glu Ala Thr Glu Thr
        35                  40                  45

Asp Leu Leu Asn Gly His Leu Lys Lys Val Asp Asn Asn Leu Thr Glu
    50                  55                  60

Ala Gln Arg Phe Ser Ser Leu Pro Arg Ala Ala Val Asn Ile Glu
65                  70                  75                  80

Phe Arg Asp Leu Ser Tyr Ser Val Pro Glu Gly Pro Trp Trp Arg Lys
                85                  90                  95

Lys Gly Tyr Lys Thr Leu Leu Lys Gly Ile Ser Gly Lys Phe Asn Ser
            100                 105                 110

Gly Glu Leu Val Ala Ile Met Gly Pro Ser Gly Ala Gly Lys Ser Thr
        115                 120                 125

Leu Met Asn Ile Leu Ala Gly Tyr Arg Glu Thr Gly Met Lys Gly Ala
    130                 135                 140

Val Leu Ile Asn Gly Leu Pro Arg Asp Leu Arg Cys Phe Arg Lys Val
145                 150                 155                 160

Ser Cys Tyr Ile Met Gln Asp Asp Met Leu Leu Pro His Leu Thr Val
                165                 170                 175

Gln Glu Ala Met Met Val Ser Ala His Leu Lys Leu Gln Glu Lys Asp
            180                 185                 190

Glu Gly Arg Arg Glu Met Val Lys Glu Ile Leu Thr Ala Leu Gly Leu
        195                 200                 205

Leu Ser Cys Ala Asn Thr Arg Thr Gly Ser Leu Ser Gly Gly Gln Arg
    210                 215                 220

Lys Arg Leu Ala Ile Ala Leu Glu Leu Val Asn Asn Pro Pro Val Met
225                 230                 235                 240

Phe Phe Asp Glu Pro Thr Ser Gly Leu Asp Ser Ala Ser Cys Phe Gln
                245                 250                 255

Val Val Ser Leu Met Lys Gly Leu Ala Gln Gly Gly Arg Ser Ile Ile
            260                 265                 270

Cys Thr Ile His Gln Pro Ser Ala Lys Leu Phe Glu Leu Phe Asp Gln
        275                 280                 285

Leu Tyr Val Leu Ser Gln Gly Gln Cys Val Tyr Arg Gly Lys Val Cys
    290                 295                 300

Asn Leu Val Pro Tyr Leu Arg Asp Leu Gly Leu Asn Cys Pro Thr Tyr

```
              305                 310                 315                 320
His Asn Pro Ala Asp Phe Val Met Glu Val Ala Ser Gly Glu Tyr Gly
                325                 330                 335

Asp Gln Asn Ser Arg Leu Val Arg Ala Val Arg Glu Gly Met Cys Asp
                340                 345                 350

Ser Asp His Lys Arg Asp Leu Gly Gly Asp Ala Glu Val Asn Pro Phe
                355                 360                 365

Leu Trp His Arg Pro Ser Glu Glu Asp Ser Ser Ser Met Glu Gly Cys
            370                 375                 380

His Ser Phe Ser Ala Ser Cys Leu Thr Gln Phe Cys Ile Leu Phe Lys
385                 390                 395                 400

Arg Thr Phe Leu Ser Ile Met Arg Asp Ser Val
                405                 410

<210> SEQ ID NO 287
<211> LENGTH: 23
<212> TYPE: PRT
<213> ORGANISM: Homo sapiens

<400> SEQUENCE: 287

Leu Thr His Leu Arg Ile Thr Ser His Ile Gly Ile Gly Leu Leu Ile
1               5                   10                  15

Gly Leu Leu Tyr Leu Gly Ile
            20

<210> SEQ ID NO 288
<211> LENGTH: 12
<212> TYPE: PRT
<213> ORGANISM: Homo sapiens

<400> SEQUENCE: 288

Gly Asn Glu Ala Lys Lys Val Leu Ser Asn Ser Gly
1               5                   10

<210> SEQ ID NO 289
<211> LENGTH: 23
<212> TYPE: PRT
<213> ORGANISM: Homo sapiens

<400> SEQUENCE: 289

Phe Leu Phe Phe Ser Met Leu Phe Leu Met Phe Ala Ala Leu Met Pro
1               5                   10                  15

Thr Val Leu Thr Phe Pro Leu
            20

<210> SEQ ID NO 290
<211> LENGTH: 23
<212> TYPE: PRT
<213> ORGANISM: Homo sapiens

<400> SEQUENCE: 290

Glu Met Gly Val Phe Leu Arg Glu His Leu Asn Tyr Trp Tyr Ser Leu
1               5                   10                  15

Lys Ala Tyr Tyr Leu Ala Lys
            20

<210> SEQ ID NO 291
<211> LENGTH: 23
<212> TYPE: PRT
<213> ORGANISM: Homo sapiens

<400> SEQUENCE: 291
```

Thr Met Ala Asp Val Pro Phe Gln Ile Met Phe Pro Val Ala Tyr Cys
1               5                   10                  15

Ser Ile Val Tyr Trp Met Thr
            20

<210> SEQ ID NO 292
<211> LENGTH: 6
<212> TYPE: PRT
<213> ORGANISM: Homo sapiens

<400> SEQUENCE: 292

Ser Gln Pro Ser Asp Ala
1               5

<210> SEQ ID NO 293
<211> LENGTH: 23
<212> TYPE: PRT
<213> ORGANISM: Homo sapiens

<400> SEQUENCE: 293

Val Arg Phe Val Leu Phe Ala Ala Leu Gly Thr Met Thr Ser Leu Val
1               5                   10                  15

Ala Gln Ser Leu Gly Leu Leu
            20

<210> SEQ ID NO 294
<211> LENGTH: 9
<212> TYPE: PRT
<213> ORGANISM: Homo sapiens

<400> SEQUENCE: 294

Ile Gly Ala Ala Ser Thr Ser Leu Gln
1               5

<210> SEQ ID NO 295
<211> LENGTH: 23
<212> TYPE: PRT
<213> ORGANISM: Homo sapiens

<400> SEQUENCE: 295

Val Ala Thr Phe Val Gly Pro Val Thr Ala Ile Pro Val Leu Leu Phe
1               5                   10                  15

Ser Gly Phe Phe Val Ser Phe
            20

<210> SEQ ID NO 296
<211> LENGTH: 12
<212> TYPE: PRT
<213> ORGANISM: Homo sapiens

<400> SEQUENCE: 296

Asp Thr Ile Pro Thr Tyr Leu Gln Trp Met Ser Tyr
1               5                   10

<210> SEQ ID NO 297
<211> LENGTH: 18
<212> TYPE: PRT
<213> ORGANISM: Homo sapiens

<400> SEQUENCE: 297

Ile Ser Tyr Val Arg Tyr Gly Phe Glu Gly Val Ile Leu Ser Ile Tyr
1               5                   10                  15

Gly Leu

<210> SEQ ID NO 298
<211> LENGTH: 31
<212> TYPE: PRT
<213> ORGANISM: Homo sapiens

<400> SEQUENCE: 298

Asp Arg Glu Asp Leu His Cys Asp Ile Asp Glu Thr Cys His Phe Gln
1               5                   10                  15

Lys Ser Glu Ala Ile Leu Arg Glu Leu Asp Val Glu Asn Ala Lys
            20                  25                  30

<210> SEQ ID NO 299
<211> LENGTH: 23
<212> TYPE: PRT
<213> ORGANISM: Homo sapiens

<400> SEQUENCE: 299

Leu Tyr Leu Asp Phe Ile Val Leu Gly Ile Phe Phe Ile Ser Leu Arg
1               5                   10                  15

Leu Ile Ala Tyr Phe Val Leu
            20

<210> SEQ ID NO 300
<211> LENGTH: 8
<212> TYPE: PRT
<213> ORGANISM: Homo sapiens

<400> SEQUENCE: 300

Arg Tyr Lys Ile Arg Ala Glu Arg
1               5

<210> SEQ ID NO 301
<211> LENGTH: 387
<212> TYPE: PRT
<213> ORGANISM: Homo sapiens

<400> SEQUENCE: 301

Met Thr Glu Pro Lys Ser Val Cys Val Ser Val Asp Glu Val Val Ser
1               5                   10                  15

Ser Asn Met Glu Ala Thr Glu Thr Asp Leu Leu Asn Gly His Leu Lys
            20                  25                  30

Lys Val Asp Asn Asn Leu Thr Glu Ala Gln Arg Phe Ser Ser Leu Pro
        35                  40                  45

Arg Arg Ala Ala Val Asn Ile Glu Phe Arg Asp Leu Ser Tyr Ser Val
    50                  55                  60

Pro Glu Gly Pro Trp Trp Arg Lys Lys Gly Tyr Lys Thr Leu Leu Lys
65                  70                  75                  80

Gly Ile Ser Gly Lys Phe Asn Ser Gly Glu Leu Val Ala Ile Met Gly
                85                  90                  95

Pro Ser Gly Ala Gly Lys Ser Thr Leu Met Asn Ile Leu Ala Gly Tyr
            100                 105                 110

Arg Glu Thr Gly Met Lys Gly Ala Val Leu Ile Asn Gly Leu Pro Arg
        115                 120                 125

Asp Leu Arg Cys Phe Arg Lys Val Ser Cys Tyr Ile Met Gln Asp Asp
    130                 135                 140

Met Leu Leu Pro His Leu Thr Val Gln Glu Ala Met Met Val Ser Ala
145                 150                 155                 160

His Leu Lys Leu Gln Glu Lys Asp Glu Gly Arg Arg Glu Met Val Lys
                165                 170                 175

```
Glu Ile Leu Thr Ala Leu Gly Leu Leu Ser Cys Ala Asn Thr Arg Thr
            180                 185                 190

Gly Ser Leu Ser Gly Gly Gln Arg Lys Arg Leu Ala Ile Ala Leu Glu
            195                 200                 205

Leu Val Asn Asn Pro Pro Val Met Phe Phe Asp Glu Pro Thr Ser Gly
210                 215                 220

Leu Asp Ser Ala Ser Cys Phe Gln Val Val Ser Leu Met Lys Gly Leu
225                 230                 235                 240

Ala Gln Gly Gly Arg Ser Ile Ile Cys Thr Ile His Gln Pro Ser Ala
            245                 250                 255

Lys Leu Phe Glu Leu Phe Asp Gln Leu Tyr Val Leu Ser Gln Gly Gln
            260                 265                 270

Cys Val Tyr Arg Gly Lys Val Cys Asn Leu Val Pro Tyr Leu Arg Asp
            275                 280                 285

Leu Gly Leu Asn Cys Pro Thr Tyr His Asn Pro Ala Asp Phe Val Met
            290                 295                 300

Glu Val Ala Ser Gly Glu Tyr Gly Asp Gln Asn Ser Arg Leu Val Arg
305                 310                 315                 320

Ala Val Arg Glu Gly Met Cys Asp Ser Asp His Lys Arg Asp Leu Gly
            325                 330                 335

Gly Asp Ala Glu Val Asn Pro Phe Leu Trp His Arg Pro Ser Glu Glu
            340                 345                 350

Asp Ser Ser Ser Met Glu Gly Cys His Ser Phe Ser Ala Ser Cys Leu
            355                 360                 365

Thr Gln Phe Cys Ile Leu Phe Lys Arg Thr Phe Leu Ser Ile Met Arg
            370                 375                 380

Asp Ser Val
385

<210> SEQ ID NO 302
<211> LENGTH: 23
<212> TYPE: PRT
<213> ORGANISM: Homo sapiens

<400> SEQUENCE: 302

Leu Thr His Leu Arg Ile Thr Ser His Ile Gly Ile Gly Leu Leu Ile
1               5                   10                  15

Gly Leu Leu Tyr Leu Gly Ile
            20

<210> SEQ ID NO 303
<211> LENGTH: 12
<212> TYPE: PRT
<213> ORGANISM: Homo sapiens

<400> SEQUENCE: 303

Gly Asn Glu Ala Lys Lys Val Leu Ser Asn Ser Gly
1               5                   10

<210> SEQ ID NO 304
<211> LENGTH: 23
<212> TYPE: PRT
<213> ORGANISM: Homo sapiens

<400> SEQUENCE: 304

Phe Leu Phe Phe Ser Met Leu Phe Leu Met Phe Ala Ala Leu Met Pro
1               5                   10                  15

Thr Val Leu Thr Phe Pro Leu
```

```
<210> SEQ ID NO 305
<211> LENGTH: 23
<212> TYPE: PRT
<213> ORGANISM: Homo sapiens

<400> SEQUENCE: 305

Glu Met Gly Val Phe Leu Arg Glu His Leu Asn Tyr Trp Tyr Ser Leu
1               5                   10                  15

Lys Ala Tyr Tyr Leu Ala Lys
            20

<210> SEQ ID NO 306
<211> LENGTH: 23
<212> TYPE: PRT
<213> ORGANISM: Homo sapiens

<400> SEQUENCE: 306

Thr Met Ala Asp Val Pro Phe Gln Ile Met Phe Pro Val Ala Tyr Cys
1               5                   10                  15

Ser Ile Val Tyr Trp Met Thr
            20

<210> SEQ ID NO 307
<211> LENGTH: 6
<212> TYPE: PRT
<213> ORGANISM: Homo sapiens

<400> SEQUENCE: 307

Ser Gln Pro Ser Asp Ala
1               5

<210> SEQ ID NO 308
<211> LENGTH: 23
<212> TYPE: PRT
<213> ORGANISM: Homo sapiens

<400> SEQUENCE: 308

Val Arg Phe Val Leu Phe Ala Ala Leu Gly Thr Met Thr Ser Leu Val
1               5                   10                  15

Ala Gln Ser Leu Gly Leu Leu
            20

<210> SEQ ID NO 309
<211> LENGTH: 9
<212> TYPE: PRT
<213> ORGANISM: Homo sapiens

<400> SEQUENCE: 309

Ile Gly Ala Ala Ser Thr Ser Leu Gln
1               5

<210> SEQ ID NO 310
<211> LENGTH: 23
<212> TYPE: PRT
<213> ORGANISM: Homo sapiens

<400> SEQUENCE: 310

Val Ala Thr Phe Val Gly Pro Val Thr Ala Ile Pro Val Leu Leu Phe
1               5                   10                  15

Ser Gly Phe Phe Val Ser Phe
            20
```

-continued

```
<210> SEQ ID NO 311
<211> LENGTH: 12
<212> TYPE: PRT
<213> ORGANISM: Homo sapiens

<400> SEQUENCE: 311

Asp Thr Ile Pro Thr Tyr Leu Gln Trp Met Ser Tyr
1               5                   10

<210> SEQ ID NO 312
<211> LENGTH: 18
<212> TYPE: PRT
<213> ORGANISM: Homo sapiens

<400> SEQUENCE: 312

Ile Ser Tyr Val Arg Tyr Gly Phe Glu Gly Val Ile Leu Ser Ile Tyr
1               5                   10                  15

Gly Leu

<210> SEQ ID NO 313
<211> LENGTH: 31
<212> TYPE: PRT
<213> ORGANISM: Homo sapiens

<400> SEQUENCE: 313

Asp Arg Glu Asp Leu His Cys Asp Ile Asp Glu Thr Cys His Phe Gln
1               5                   10                  15

Lys Ser Glu Ala Ile Leu Arg Glu Leu Asp Val Glu Asn Ala Lys
            20                  25                  30

<210> SEQ ID NO 314
<211> LENGTH: 23
<212> TYPE: PRT
<213> ORGANISM: Homo sapiens

<400> SEQUENCE: 314

Leu Tyr Leu Asp Phe Ile Val Leu Gly Ile Phe Phe Ile Ser Leu Arg
1               5                   10                  15

Leu Ile Ala Tyr Phe Val Leu
            20

<210> SEQ ID NO 315
<211> LENGTH: 8
<212> TYPE: PRT
<213> ORGANISM: Homo sapiens

<400> SEQUENCE: 315

Arg Tyr Lys Ile Arg Ala Glu Arg
1               5

<210> SEQ ID NO 316
<211> LENGTH: 406
<212> TYPE: PRT
<213> ORGANISM: Homo sapiens

<400> SEQUENCE: 316

Met Ile Met Arg Leu Pro Gln Pro His Gly Thr Asn Ala Ser Ser Tyr
1               5                   10                  15

Ser Ala Glu Met Thr Glu Pro Lys Ser Val Cys Val Ser Val Asp Glu
            20                  25                  30

Val Val Ser Ser Asn Met Glu Ala Thr Glu Thr Asp Leu Leu Asn Gly
        35                  40                  45
```

His Leu Lys Lys Val Asp Asn Asn Leu Thr Glu Ala Gln Arg Phe Ser
                50                   55                    60

Ser Leu Pro Arg Arg Ala Val Asn Ile Glu Phe Arg Asp Leu Ser
 65                 70                   75                    80

Tyr Ser Val Pro Glu Gly Pro Trp Trp Arg Lys Gly Tyr Lys Thr
                    85                   90                   95

Leu Leu Lys Gly Ile Ser Gly Lys Phe Asn Ser Gly Glu Leu Val Ala
                100                 105                 110

Ile Met Gly Pro Ser Gly Ala Gly Lys Ser Thr Leu Met Asn Ile Leu
                115                 120                 125

Ala Gly Tyr Arg Glu Thr Gly Met Lys Gly Ala Val Leu Ile Asn Gly
                130                 135                 140

Leu Pro Arg Asp Leu Arg Cys Phe Arg Lys Val Ser Cys Tyr Ile Met
145                 150                 155                 160

Gln Asp Asp Met Leu Leu Pro His Leu Thr Val Gln Glu Ala Met Met
                165                 170                 175

Val Ser Ala His Leu Lys Leu Gln Glu Lys Asp Glu Gly Arg Arg Glu
                180                 185                 190

Met Val Lys Glu Ile Leu Thr Ala Leu Gly Leu Leu Ser Cys Ala Asn
                195                 200                 205

Thr Arg Thr Gly Ser Leu Ser Gly Gly Gln Arg Lys Arg Leu Ala Ile
210                 215                 220

Ala Leu Glu Leu Val Asn Asn Pro Pro Val Met Phe Phe Asp Glu Pro
225                 230                 235                 240

Thr Ser Gly Leu Asp Ser Ala Ser Cys Phe Gln Val Val Ser Leu Met
                245                 250                 255

Lys Gly Leu Ala Gln Gly Gly Arg Ser Ile Ile Cys Thr Ile His Gln
                260                 265                 270

Pro Ser Ala Lys Leu Phe Glu Leu Phe Asp Gln Leu Tyr Val Leu Ser
                275                 280                 285

Gln Gly Gln Cys Val Tyr Arg Gly Lys Val Cys Asn Leu Val Pro Tyr
                290                 295                 300

Leu Arg Asp Leu Gly Leu Asn Cys Pro Thr Tyr His Asn Pro Ala Asp
305                 310                 315                 320

Phe Val Met Glu Val Ala Ser Gly Glu Tyr Gly Asp Gln Asn Ser Arg
                325                 330                 335

Leu Val Arg Ala Val Arg Glu Gly Met Cys Asp Ser Asp His Lys Arg
                340                 345                 350

Asp Leu Gly Gly Asp Ala Glu Val Asn Pro Phe Leu Trp His Arg Pro
                355                 360                 365

Ser Glu Glu Asp Ser Ser Met Glu Gly Cys His Ser Phe Ser Ala
                370                 375                 380

Ser Cys Leu Thr Gln Phe Cys Ile Leu Phe Lys Arg Thr Phe Leu Ser
385                 390                 395                 400

Ile Met Arg Asp Ser Val
                405

<210> SEQ ID NO 317
<211> LENGTH: 23
<212> TYPE: PRT
<213> ORGANISM: Homo sapiens

<400> SEQUENCE: 317

Leu Thr His Leu Arg Ile Thr Ser His Ile Gly Ile Gly Leu Leu Ile
1                   5                   10                  15

```
Gly Leu Leu Tyr Leu Gly Ile
                20

<210> SEQ ID NO 318
<211> LENGTH: 12
<212> TYPE: PRT
<213> ORGANISM: Homo sapiens

<400> SEQUENCE: 318

Gly Asn Glu Ala Lys Lys Val Leu Ser Asn Ser Gly
1               5                   10

<210> SEQ ID NO 319
<211> LENGTH: 23
<212> TYPE: PRT
<213> ORGANISM: Homo sapiens

<400> SEQUENCE: 319

Phe Leu Phe Phe Ser Met Leu Phe Leu Met Phe Ala Ala Leu Met Pro
1               5                   10                  15

Thr Val Leu Thr Phe Pro Leu
                20

<210> SEQ ID NO 320
<211> LENGTH: 23
<212> TYPE: PRT
<213> ORGANISM: Homo sapiens

<400> SEQUENCE: 320

Glu Met Gly Val Phe Leu Arg Glu His Leu Asn Tyr Trp Tyr Ser Leu
1               5                   10                  15

Lys Ala Tyr Tyr Leu Ala Lys
                20

<210> SEQ ID NO 321
<211> LENGTH: 23
<212> TYPE: PRT
<213> ORGANISM: Homo sapiens

<400> SEQUENCE: 321

Thr Met Ala Asp Val Pro Phe Gln Ile Met Phe Pro Val Ala Tyr Cys
1               5                   10                  15

Ser Ile Val Tyr Trp Met Thr
                20

<210> SEQ ID NO 322
<211> LENGTH: 6
<212> TYPE: PRT
<213> ORGANISM: Homo sapiens

<400> SEQUENCE: 322

Ser Gln Pro Ser Asp Ala
1               5

<210> SEQ ID NO 323
<211> LENGTH: 23
<212> TYPE: PRT
<213> ORGANISM: Homo sapiens

<400> SEQUENCE: 323

Val Arg Phe Val Leu Phe Ala Ala Leu Gly Thr Met Thr Ser Leu Val
1               5                   10                  15

Ala Gln Ser Leu Gly Leu Leu
                20
```

```
<210> SEQ ID NO 324
<211> LENGTH: 9
<212> TYPE: PRT
<213> ORGANISM: Homo sapiens

<400> SEQUENCE: 324

Ile Gly Ala Ala Ser Thr Ser Leu Gln
1               5

<210> SEQ ID NO 325
<211> LENGTH: 23
<212> TYPE: PRT
<213> ORGANISM: Homo sapiens

<400> SEQUENCE: 325

Val Ala Thr Phe Val Gly Pro Val Thr Ala Ile Pro Val Leu Leu Phe
1               5                   10                  15

Ser Gly Phe Phe Val Ser Phe
            20

<210> SEQ ID NO 326
<211> LENGTH: 12
<212> TYPE: PRT
<213> ORGANISM: Homo sapiens

<400> SEQUENCE: 326

Asp Thr Ile Pro Thr Tyr Leu Gln Trp Met Ser Tyr
1               5                   10

<210> SEQ ID NO 327
<211> LENGTH: 18
<212> TYPE: PRT
<213> ORGANISM: Homo sapiens

<400> SEQUENCE: 327

Ile Ser Tyr Val Arg Tyr Gly Phe Glu Gly Val Ile Leu Ser Ile Tyr
1               5                   10                  15

Gly Leu

<210> SEQ ID NO 328
<211> LENGTH: 31
<212> TYPE: PRT
<213> ORGANISM: Homo sapiens

<400> SEQUENCE: 328

Asp Arg Glu Asp Leu His Cys Asp Ile Asp Glu Thr Cys His Phe Gln
1               5                   10                  15

Lys Ser Glu Ala Ile Leu Arg Glu Leu Asp Val Glu Asn Ala Lys
            20                  25                  30

<210> SEQ ID NO 329
<211> LENGTH: 23
<212> TYPE: PRT
<213> ORGANISM: Homo sapiens

<400> SEQUENCE: 329

Leu Tyr Leu Asp Phe Ile Val Leu Gly Ile Phe Phe Ile Ser Leu Arg
1               5                   10                  15

Leu Ile Ala Tyr Phe Val Leu
            20

<210> SEQ ID NO 330
```

```
<211> LENGTH: 8
<212> TYPE: PRT
<213> ORGANISM: Homo sapiens

<400> SEQUENCE: 330

Arg Tyr Lys Ile Arg Ala Glu Arg
1               5

<210> SEQ ID NO 331
<211> LENGTH: 567
<212> TYPE: PRT
<213> ORGANISM: Homo sapiens

<400> SEQUENCE: 331

Met Leu Ala Val Gln Gln Thr Glu His Leu Pro Ala Cys Pro Pro Ala
1               5                   10                  15

Arg Arg Trp Ser Ser Asn Phe Cys Pro Glu Ser Thr Glu Gly Gly Pro
                20                  25                  30

Ser Leu Leu Gly Leu Arg Asp Met Val Arg Arg Gly Trp Ser Val Cys
            35                  40                  45

Thr Ala Ile Leu Leu Ala Arg Leu Trp Cys Leu Val Pro Thr His Thr
        50                  55                  60

Phe Leu Ser Glu Tyr Pro Glu Ala Ala Glu Tyr Pro His Pro Gly Trp
65                  70                  75                  80

Val Tyr Trp Leu Gln Met Ala Val Ala Pro Gly His Leu Arg Ala Trp
                85                  90                  95

Val Met Arg Asn Asn Val Thr Thr Asn Ile Pro Ser Ala Phe Ser Gly
                100                 105                 110

Thr Leu Thr His Glu Glu Lys Ala Val Leu Thr Val Phe Thr Gly Thr
            115                 120                 125

Ala Thr Ala Val His Val Gln Val Ala Leu Ala Ser Ala Lys Leu
        130                 135                 140

Glu Ser Ser Val Phe Val Thr Asp Cys Val Ser Cys Lys Ile Glu Asn
145                 150                 155                 160

Val Cys Asp Ser Ala Leu Gln Gly Lys Arg Val Pro Met Ser Gly Leu
                165                 170                 175

Gln Gly Ser Ser Ile Val Ile Met Pro Pro Ser Asn Arg Pro Leu Ala
            180                 185                 190

Ser Ala Ala Ser Cys Thr Trp Ser Val Gln Val Gln Gly Gly Pro His
        195                 200                 205

His Leu Gly Val Val Ala Ile Ser Gly Lys Val Leu Ser Ala Ala His
    210                 215                 220

Gly Ala Gly Arg Ala Tyr Gly Trp Gly Phe Pro Gly Asp Pro Met Glu
225                 230                 235                 240

Glu Gly Tyr Lys Thr Leu Leu Lys Gly Ile Ser Gly Lys Phe Asn Ser
                245                 250                 255

Gly Glu Leu Val Ala Ile Met Gly Pro Ser Gly Ala Gly Lys Ser Thr
            260                 265                 270

Leu Met Asn Ile Leu Ala Gly Tyr Arg Glu Thr Gly Met Lys Gly Ala
        275                 280                 285

Val Leu Ile Asn Gly Leu Pro Arg Asp Leu Arg Cys Phe Arg Lys Val
    290                 295                 300

Ser Cys Tyr Ile Met Gln Asp Asp Met Leu Pro His Leu Thr Val
305                 310                 315                 320

Gln Glu Ala Met Met Val Ser Ala His Leu Lys Leu Gln Glu Lys Asp
                325                 330                 335
```

```
Glu Gly Arg Arg Glu Met Val Lys Glu Ile Leu Thr Ala Leu Gly Leu
                340                 345                 350

Leu Ser Cys Ala Asn Thr Arg Thr Gly Ser Leu Ser Gly Gly Gln Arg
            355                 360                 365

Lys Arg Leu Ala Ile Ala Leu Glu Leu Val Asn Asn Pro Pro Val Met
        370                 375                 380

Phe Phe Asp Glu Pro Thr Ser Gly Leu Asp Ser Ala Ser Cys Phe Gln
385                 390                 395                 400

Val Val Ser Leu Met Lys Gly Leu Ala Gln Gly Gly Arg Ser Ile Ile
                405                 410                 415

Cys Thr Ile His Gln Pro Ser Ala Lys Leu Phe Glu Leu Phe Asp Gln
                420                 425                 430

Leu Tyr Val Leu Ser Gln Gly Gln Cys Val Tyr Arg Gly Lys Val Cys
            435                 440                 445

Asn Leu Val Pro Tyr Leu Arg Asp Leu Gly Leu Asn Cys Pro Thr Tyr
        450                 455                 460

His Asn Pro Ala Asp Phe Val Met Glu Val Ala Ser Gly Glu Tyr Gly
465                 470                 475                 480

Asp Gln Asn Ser Arg Leu Val Arg Ala Val Arg Glu Gly Met Cys Asp
                485                 490                 495

Ser Asp His Lys Arg Asp Leu Gly Gly Asp Ala Glu Val Asn Pro Phe
            500                 505                 510

Leu Trp His Arg Pro Ser Glu Glu Val Lys Gln Thr Lys Arg Leu Lys
        515                 520                 525

Gly Leu Arg Lys Asp Ser Ser Ser Met Glu Gly Cys His Ser Phe Ser
530                 535                 540

Ala Ser Cys Leu Thr Gln Phe Cys Ile Leu Phe Lys Arg Thr Phe Leu
545                 550                 555                 560

Ser Ile Met Arg Asp Ser Val
                565

<210> SEQ ID NO 332
<211> LENGTH: 23
<212> TYPE: PRT
<213> ORGANISM: Homo sapiens

<400> SEQUENCE: 332

Leu Thr His Leu Arg Ile Thr Ser His Ile Gly Ile Gly Leu Leu Ile
1               5                   10                  15

Gly Leu Leu Tyr Leu Gly Ile
            20

<210> SEQ ID NO 333
<211> LENGTH: 12
<212> TYPE: PRT
<213> ORGANISM: Homo sapiens

<400> SEQUENCE: 333

Gly Asn Glu Ala Lys Lys Val Leu Ser Asn Ser Gly
1               5                   10

<210> SEQ ID NO 334
<211> LENGTH: 23
<212> TYPE: PRT
<213> ORGANISM: Homo sapiens

<400> SEQUENCE: 334

Phe Leu Phe Phe Ser Met Leu Phe Leu Met Phe Ala Ala Leu Met Pro
1               5                   10                  15
```

Thr Val Leu Thr Phe Pro Leu
            20

<210> SEQ ID NO 335
<211> LENGTH: 23
<212> TYPE: PRT
<213> ORGANISM: Homo sapiens

<400> SEQUENCE: 335

Glu Met Gly Val Phe Leu Arg Glu His Leu Asn Tyr Trp Tyr Ser Leu
1               5                   10                  15

Lys Ala Tyr Tyr Leu Ala Lys
            20

<210> SEQ ID NO 336
<211> LENGTH: 23
<212> TYPE: PRT
<213> ORGANISM: Homo sapiens

<400> SEQUENCE: 336

Thr Met Ala Asp Val Pro Phe Gln Ile Met Phe Pro Val Ala Tyr Cys
1               5                   10                  15

Ser Ile Val Tyr Trp Met Thr
            20

<210> SEQ ID NO 337
<211> LENGTH: 6
<212> TYPE: PRT
<213> ORGANISM: Homo sapiens

<400> SEQUENCE: 337

Ser Gln Pro Ser Asp Ala
1               5

<210> SEQ ID NO 338
<211> LENGTH: 23
<212> TYPE: PRT
<213> ORGANISM: Homo sapiens

<400> SEQUENCE: 338

Val Arg Phe Val Leu Phe Ala Ala Leu Gly Thr Met Thr Ser Leu Val
1               5                   10                  15

Ala Gln Ser Leu Gly Leu Leu
            20

<210> SEQ ID NO 339
<211> LENGTH: 9
<212> TYPE: PRT
<213> ORGANISM: Homo sapiens

<400> SEQUENCE: 339

Ile Gly Ala Ala Ser Thr Ser Leu Gln
1               5

<210> SEQ ID NO 340
<211> LENGTH: 23
<212> TYPE: PRT
<213> ORGANISM: Homo sapiens

<400> SEQUENCE: 340

Val Ala Thr Phe Val Gly Pro Val Thr Ala Ile Pro Val Leu Leu Phe
1               5                   10                  15

Ser Gly Phe Phe Val Ser Phe

-continued

20

<210> SEQ ID NO 341
<211> LENGTH: 12
<212> TYPE: PRT
<213> ORGANISM: Homo sapiens

<400> SEQUENCE: 341

Asp Thr Ile Pro Thr Tyr Leu Gln Trp Met Ser Tyr
1               5                   10

<210> SEQ ID NO 342
<211> LENGTH: 18
<212> TYPE: PRT
<213> ORGANISM: Homo sapiens

<400> SEQUENCE: 342

Ile Ser Tyr Val Arg Tyr Gly Phe Glu Gly Val Ile Leu Ser Ile Tyr
1               5                   10                  15

Gly Leu

<210> SEQ ID NO 343
<211> LENGTH: 31
<212> TYPE: PRT
<213> ORGANISM: Homo sapiens

<400> SEQUENCE: 343

Asp Arg Glu Asp Leu His Cys Asp Ile Asp Glu Thr Cys His Phe Gln
1               5                   10                  15

Lys Ser Glu Ala Ile Leu Arg Glu Leu Asp Val Glu Asn Ala Lys
            20                  25                  30

<210> SEQ ID NO 344
<211> LENGTH: 23
<212> TYPE: PRT
<213> ORGANISM: Homo sapiens

<400> SEQUENCE: 344

Leu Tyr Leu Asp Phe Ile Val Leu Gly Ile Phe Phe Ile Ser Leu Arg
1               5                   10                  15

Leu Ile Ala Tyr Phe Val Leu
            20

<210> SEQ ID NO 345
<211> LENGTH: 8
<212> TYPE: PRT
<213> ORGANISM: Homo sapiens

<400> SEQUENCE: 345

Arg Tyr Lys Ile Arg Ala Glu Arg
1               5

<210> SEQ ID NO 346
<211> LENGTH: 90
<212> TYPE: PRT
<213> ORGANISM: Homo sapiens

<400> SEQUENCE: 346

Met Ala Gln Leu Glu Arg Ser Ala Ile Ser Gly Phe Ser Lys Ser
1               5                   10                  15

Arg Arg Asn Ser Phe Ala Tyr Asp Val Lys Arg Glu Val Tyr Asn Glu
            20                  25                  30

Glu Thr Phe Gln Gln Glu His Lys Arg Lys Ala Ser Ser Ser Gly Asn

```
                35                  40                  45
Met Asn Ile Asn Ile Thr Thr Phe Arg His His Val Gln Cys Arg Cys
            50                  55                  60

Ser Trp His Arg Phe Leu Arg Cys Val Leu Thr Ile Phe Pro Phe Leu
65                  70                  75                  80

Glu Trp Met Cys Met Tyr Arg Leu Lys Asp
                85                  90

<210> SEQ ID NO 347
<211> LENGTH: 23
<212> TYPE: PRT
<213> ORGANISM: Homo sapiens

<400> SEQUENCE: 347

Trp Leu Leu Gly Asp Leu Leu Ala Gly Ile Ser Val Gly Leu Val Gln
1               5                   10                  15

Val Pro Gln Gly Leu Thr Leu
            20

<210> SEQ ID NO 348
<211> LENGTH: 5
<212> TYPE: PRT
<213> ORGANISM: Homo sapiens

<400> SEQUENCE: 348

Ser Leu Leu Ala Arg
1               5

<210> SEQ ID NO 349
<211> LENGTH: 23
<212> TYPE: PRT
<213> ORGANISM: Homo sapiens

<400> SEQUENCE: 349

Gln Leu Ile Pro Pro Leu Asn Ile Ala Tyr Ala Ala Phe Cys Ser Ser
1               5                   10                  15

Val Ile Tyr Val Ile Phe Gly
            20

<210> SEQ ID NO 350
<211> LENGTH: 6
<212> TYPE: PRT
<213> ORGANISM: Homo sapiens

<400> SEQUENCE: 350

Ser Cys His Gln Met Ser
1               5

<210> SEQ ID NO 351
<211> LENGTH: 20
<212> TYPE: PRT
<213> ORGANISM: Homo sapiens

<400> SEQUENCE: 351

Ile Gly Ser Phe Phe Leu Val Ser Ala Leu Leu Ile Asn Val Leu Lys
1               5                   10                  15

Val Ser Pro Phe
            20

<210> SEQ ID NO 352
<211> LENGTH: 29
<212> TYPE: PRT
<213> ORGANISM: Homo sapiens
```

<400> SEQUENCE: 352

Asn Asn Gly Gln Leu Val Met Gly Ser Phe Val Lys Asn Glu Phe Ser
1               5                   10                  15

Ala Pro Ser Tyr Leu Met Gly Tyr Asn Lys Ser Leu Ser
            20                  25

<210> SEQ ID NO 353
<211> LENGTH: 23
<212> TYPE: PRT
<213> ORGANISM: Homo sapiens

<400> SEQUENCE: 353

Val Val Ala Thr Thr Thr Phe Leu Thr Gly Ile Ile Gln Leu Ile Met
1               5                   10                  15

Gly Val Leu Gly Leu Gly Phe
            20

<210> SEQ ID NO 354
<211> LENGTH: 12
<212> TYPE: PRT
<213> ORGANISM: Homo sapiens

<400> SEQUENCE: 354

Ile Ala Thr Tyr Leu Pro Glu Ser Ala Met Ser Ala
1               5                   10

<210> SEQ ID NO 355
<211> LENGTH: 23
<212> TYPE: PRT
<213> ORGANISM: Homo sapiens

<400> SEQUENCE: 355

Tyr Leu Ala Ala Val Ala Leu His Ile Met Leu Ser Gln Leu Thr Phe
1               5                   10                  15

Ile Phe Gly Ile Met Ile Ser
            20

<210> SEQ ID NO 356
<211> LENGTH: 14
<212> TYPE: PRT
<213> ORGANISM: Homo sapiens

<400> SEQUENCE: 356

Phe His Ala Gly Pro Ile Ser Phe Phe Tyr Asp Ile Ile Asn
1               5                   10

<210> SEQ ID NO 357
<211> LENGTH: 23
<212> TYPE: PRT
<213> ORGANISM: Homo sapiens

<400> SEQUENCE: 357

Tyr Cys Val Ala Leu Pro Lys Ala Asn Ser Thr Ser Ile Leu Val Phe
1               5                   10                  15

Leu Thr Val Val Val Ala Leu
            20

<210> SEQ ID NO 358
<211> LENGTH: 20
<212> TYPE: PRT
<213> ORGANISM: Homo sapiens

<400> SEQUENCE: 358

-continued

```
Arg Ile Asn Lys Cys Ile Arg Ile Ser Phe Asn Gln Tyr Pro Ile Glu
1               5                   10                  15

Phe Pro Met Glu
            20

<210> SEQ ID NO 359
<211> LENGTH: 18
<212> TYPE: PRT
<213> ORGANISM: Homo sapiens

<400> SEQUENCE: 359

Leu Phe Leu Ile Ile Gly Phe Thr Val Ile Ala Asn Lys Ile Ser Met
1               5                   10                  15

Ala Thr

<210> SEQ ID NO 360
<211> LENGTH: 27
<212> TYPE: PRT
<213> ORGANISM: Homo sapiens

<400> SEQUENCE: 360

Glu Thr Ser Gln Thr Leu Ile Asp Met Ile Pro Tyr Ser Phe Leu Leu
1               5                   10                  15

Pro Val Thr Pro Asp Phe Ser Leu Leu Pro Lys
            20                  25

<210> SEQ ID NO 361
<211> LENGTH: 20
<212> TYPE: PRT
<213> ORGANISM: Homo sapiens

<400> SEQUENCE: 361

Ile Ile Leu Gln Ala Phe Ser Leu Ser Leu Val Ser Ser Phe Leu Leu
1               5                   10                  15

Ile Phe Leu Gly
            20

<210> SEQ ID NO 362
<211> LENGTH: 53
<212> TYPE: PRT
<213> ORGANISM: Homo sapiens

<400> SEQUENCE: 362

Lys Lys Ile Ala Ser Leu His Asn Tyr Ser Val Asn Ser Asn Gln Asp
1               5                   10                  15

Leu Ile Ala Ile Gly Leu Cys Asn Val Val Ser Ser Phe Phe Arg Ser
            20                  25                  30

Cys Val Phe Thr Gly Ala Ile Ala Arg Thr Ile Ile Gln Asp Lys Ser
        35                  40                  45

Gly Gly Arg Gln Gln
        50

<210> SEQ ID NO 363
<211> LENGTH: 23
<212> TYPE: PRT
<213> ORGANISM: Homo sapiens

<400> SEQUENCE: 363

Phe Ala Ser Leu Val Gly Ala Gly Val Met Leu Leu Leu Met Val Lys
1               5                   10                  15

Met Gly His Phe Phe Tyr Thr
```

-continued

<210> SEQ ID NO 364
<211> LENGTH: 4
<212> TYPE: PRT
<213> ORGANISM: Homo sapiens

<400> SEQUENCE: 364

Leu Pro Asn Ala
1

<210> SEQ ID NO 365
<211> LENGTH: 20
<212> TYPE: PRT
<213> ORGANISM: Homo sapiens

<400> SEQUENCE: 365

Val Leu Ala Gly Ile Ile Leu Ser Asn Val Ile Pro Tyr Leu Glu Thr
1               5                   10                  15

Ile Ser Asn Leu
            20

<210> SEQ ID NO 366
<211> LENGTH: 20
<212> TYPE: PRT
<213> ORGANISM: Homo sapiens

<400> SEQUENCE: 366

Pro Ser Leu Trp Arg Gln Asp Gln Tyr Asp Cys Ala Leu Trp Met Met
1               5                   10                  15

Thr Phe Ser Ser
            20

<210> SEQ ID NO 367
<211> LENGTH: 23
<212> TYPE: PRT
<213> ORGANISM: Homo sapiens

<400> SEQUENCE: 367

Ser Ile Phe Leu Gly Leu Asp Ile Gly Leu Ile Ile Ser Val Val Ser
1               5                   10                  15

Ala Phe Phe Ile Thr Thr Val
            20

<210> SEQ ID NO 368
<211> LENGTH: 451
<212> TYPE: PRT
<213> ORGANISM: Homo sapiens

<400> SEQUENCE: 368

Arg Ser His Arg Ala Lys Ile Leu Leu Leu Gly Gln Ile Pro Asn Thr
1               5                   10                  15

Asn Ile Tyr Arg Ser Ile Asn Asp Tyr Arg Glu Ile Ile Thr Ile Pro
                20                  25                  30

Gly Val Lys Ile Phe Gln Cys Cys Ser Ser Ile Thr Phe Val Asn Val
            35                  40                  45

Tyr Tyr Leu Lys His Lys Leu Leu Lys Glu Val Asp Met Val Lys Val
        50                  55                  60

Pro Leu Lys Glu Glu Glu Ile Phe Ser Leu Phe Asn Ser Ser Asp Thr
65                  70                  75                  80

Asn Leu Gln Gly Gly Lys Ile Cys Arg Cys Phe Cys Asn Cys Asp Asp
                85                  90                  95

```
Leu Glu Pro Leu Pro Arg Ile Leu Tyr Thr Glu Arg Phe Glu Asn Lys
            100                 105                 110

Leu Asp Pro Glu Ala Ser Ser Ile Asn Leu Ile His Cys Ser His Phe
        115                 120                 125

Glu Ser Met Asn Thr Ser Gln Thr Ala Ser Glu Asp Gln Val Pro Tyr
    130                 135                 140

Thr Val Ser Ser Val Ser Gln Lys Asn Gln Gly Gln Gln Tyr Glu Glu
145                 150                 155                 160

Val Glu Glu Val Trp Leu Pro Asn Asn Ser Arg Asn Ser Ser Arg Pro
                165                 170                 175

Gly Leu Pro Asp Val Ala Glu Ser Gln Gly Arg Arg Ser Leu Ile Pro
            180                 185                 190

Tyr Ser Asp Ala Ser Leu Leu Pro Ser Val His Thr Ile Ile Leu Asp
        195                 200                 205

Phe Ser Met Val His Tyr Val Asp Ser Arg Gly Leu Val Val Leu Arg
    210                 215                 220

Gln Ile Cys Asn Ala Phe Gln Asn Ala Asn Ile Leu Ile Leu Ile Ala
225                 230                 235                 240

Gly Cys His Ser Ser Ile Val Arg Ala Phe Glu Arg Asn Asp Phe Phe
                245                 250                 255

Asp Ala Gly Ile Thr Lys Thr Gln Leu Phe Leu Ser Val His Asp Ala
            260                 265                 270

Val Leu Phe Ala Leu Ser Arg Lys Val Ile Gly Ser Ser Glu Leu Ser
        275                 280                 285

Ile Asp Glu Ser Glu Thr Val Ile Arg Glu Thr Tyr Ser Glu Thr Asp
    290                 295                 300

Lys Asn Asp Asn Ser Arg Tyr Lys Met Ser Ser Ser Phe Leu Gly Ser
305                 310                 315                 320

Gln Lys Asn Val Ser Pro Gly Phe Ile Lys Ile Gln Gln Pro Val Glu
                325                 330                 335

Glu Glu Ser Glu Leu Asp Leu Glu Leu Glu Ser Glu Gln Glu Ala Gly
            340                 345                 350

Leu Gly Leu Asp Leu Asp Leu Asp Arg Glu Leu Glu Pro Glu Met Glu
        355                 360                 365

Pro Lys Ala Glu Thr Glu Thr Lys Thr Gln Thr Glu Met Glu Pro Gln
    370                 375                 380

Pro Glu Thr Glu Pro Glu Met Glu Pro Asn Pro Lys Ser Arg Pro Arg
385                 390                 395                 400

Ala His Thr Phe Pro Gln Gln Arg Tyr Trp Pro Met Tyr His Pro Ser
                405                 410                 415

Met Ala Ser Thr Gln Ser Gln Thr Gln Thr Arg Thr Trp Ser Val Glu
            420                 425                 430

Arg Arg Arg His Pro Met Asp Ser Tyr Ser Pro Glu Gly Asn Ser Asn
        435                 440                 445

Glu Asp Val
    450

<210> SEQ ID NO 369
<211> LENGTH: 57
<212> TYPE: PRT
<213> ORGANISM: Homo sapiens

<400> SEQUENCE: 369

Met Asn Pro Phe Gln Lys Asn Glu Ser Lys Glu Thr Leu Phe Ser Pro
1               5                   10                  15
```

Val Ser Ile Glu Glu Val Pro Pro Arg Pro Ser Pro Pro Lys Lys
            20                  25                  30

Pro Ser Pro Thr Ile Cys Gly Ser Asn Tyr Pro Leu Ser Ile Ala Phe
        35                  40                  45

Ile Val Val Asn Glu Phe Cys Glu Arg
        50                  55

<210> SEQ ID NO 370
<211> LENGTH: 18
<212> TYPE: PRT
<213> ORGANISM: Homo sapiens

<400> SEQUENCE: 370

Phe Ser Tyr Tyr Gly Met Lys Ala Val Leu Ile Leu Tyr Phe Leu Tyr
1               5                   10                  15

Phe Leu

<210> SEQ ID NO 371
<211> LENGTH: 9
<212> TYPE: PRT
<213> ORGANISM: Homo sapiens

<400> SEQUENCE: 371

His Trp Asn Glu Asp Thr Ser Thr Ser
1               5

<210> SEQ ID NO 372
<211> LENGTH: 23
<212> TYPE: PRT
<213> ORGANISM: Homo sapiens

<400> SEQUENCE: 372

Ile Tyr His Ala Phe Ser Ser Leu Cys Tyr Phe Thr Pro Ile Leu Gly
1               5                   10                  15

Ala Ala Ile Ala Asp Ser Trp
            20

<210> SEQ ID NO 373
<211> LENGTH: 6
<212> TYPE: PRT
<213> ORGANISM: Homo sapiens

<400> SEQUENCE: 373

Leu Gly Lys Phe Lys Thr
1               5

<210> SEQ ID NO 374
<211> LENGTH: 23
<212> TYPE: PRT
<213> ORGANISM: Homo sapiens

<400> SEQUENCE: 374

Ile Ile Tyr Leu Ser Leu Val Tyr Val Leu Gly His Val Ile Lys Ser
1               5                   10                  15

Leu Gly Ala Leu Pro Ile Leu
            20

<210> SEQ ID NO 375
<211> LENGTH: 3
<212> TYPE: PRT
<213> ORGANISM: Homo sapiens

<400> SEQUENCE: 375

Gly Gly Gln
1

<210> SEQ ID NO 376
<211> LENGTH: 23
<212> TYPE: PRT
<213> ORGANISM: Homo sapiens

<400> SEQUENCE: 376

Val Val His Thr Val Leu Ser Leu Ile Gly Leu Ser Leu Ile Ala Leu
1               5                   10                  15

Gly Thr Gly Gly Ile Lys Pro
            20

<210> SEQ ID NO 377
<211> LENGTH: 20
<212> TYPE: PRT
<213> ORGANISM: Homo sapiens

<400> SEQUENCE: 377

Cys Val Ala Ala Phe Gly Gly Asp Gln Phe Glu Glu Lys His Ala Glu
1               5                   10                  15

Glu Arg Thr Arg
            20

<210> SEQ ID NO 378
<211> LENGTH: 20
<212> TYPE: PRT
<213> ORGANISM: Homo sapiens

<400> SEQUENCE: 378

Tyr Phe Ser Val Phe Tyr Leu Ser Ile Asn Ala Gly Ser Leu Ile Ser
1               5                   10                  15

Thr Phe Ile Thr
            20

<210> SEQ ID NO 379
<211> LENGTH: 14
<212> TYPE: PRT
<213> ORGANISM: Homo sapiens

<400> SEQUENCE: 379

Pro Met Leu Arg Gly Asp Val Gln Cys Phe Gly Glu Asp Cys
1               5                   10

<210> SEQ ID NO 380
<211> LENGTH: 20
<212> TYPE: PRT
<213> ORGANISM: Homo sapiens

<400> SEQUENCE: 380

Tyr Ala Leu Ala Phe Gly Val Pro Gly Leu Leu Met Val Ile Ala Leu
1               5                   10                  15

Val Val Phe Ala
            20

<210> SEQ ID NO 381
<211> LENGTH: 61
<212> TYPE: PRT
<213> ORGANISM: Homo sapiens

<400> SEQUENCE: 381

Met Gly Ser Lys Ile Tyr Asn Lys Pro Pro Pro Glu Gly Asn Ile Val

```
                1               5                  10                 15
Ala Gln Val Phe Lys Cys Ile Trp Phe Ala Ile Ser Asn Arg Phe Lys
                    20                 25                 30

Asn Arg Ser Gly Asp Ile Pro Lys Arg Gln His Trp Leu Asp Trp Ala
        35                 40                 45

Ala Glu Lys Tyr Pro Lys Gln Leu Ile Met Asp Val Lys
    50                 55                 60
```

<210> SEQ ID NO 382
<211> LENGTH: 19
<212> TYPE: PRT
<213> ORGANISM: Homo sapiens

<400> SEQUENCE: 382

```
Ala Leu Thr Arg Val Leu Phe Leu Tyr Ile Pro Leu Pro Met Phe Trp
1               5                   10                  15

Ala Leu Leu
```

<210> SEQ ID NO 383
<211> LENGTH: 29
<212> TYPE: PRT
<213> ORGANISM: Homo sapiens

<400> SEQUENCE: 383

```
Asp Gln Gln Gly Ser Arg Trp Thr Leu Gln Ala Ile Arg Met Asn Arg
1               5                   10                  15

Asn Leu Gly Phe Phe Val Leu Gln Pro Asp Gln Met Gln
            20                  25
```

<210> SEQ ID NO 384
<211> LENGTH: 23
<212> TYPE: PRT
<213> ORGANISM: Homo sapiens

<400> SEQUENCE: 384

```
Val Leu Asn Pro Leu Leu Val Leu Ile Phe Ile Pro Leu Phe Asp Phe
1               5                   10                  15

Val Ile Tyr Arg Leu Val Ser
            20
```

<210> SEQ ID NO 385
<211> LENGTH: 11
<212> TYPE: PRT
<213> ORGANISM: Homo sapiens

<400> SEQUENCE: 385

```
Lys Cys Gly Ile Asn Phe Ser Ser Leu Arg Lys
1               5                   10
```

<210> SEQ ID NO 386
<211> LENGTH: 18
<212> TYPE: PRT
<213> ORGANISM: Homo sapiens

<400> SEQUENCE: 386

```
Met Ala Val Gly Met Ile Leu Ala Cys Leu Ala Phe Ala Val Ala Ala
1               5                   10                  15

Ala Val
```

<210> SEQ ID NO 387
<211> LENGTH: 250
<212> TYPE: PRT

<213> ORGANISM: Homo sapiens

<400> SEQUENCE: 387

```
Glu Ile Lys Ile Asn Glu Met Ala Pro Ala Gln Pro Gly Pro Gln Glu
1               5                   10                  15
Val Phe Leu Gln Val Leu Asn Leu Ala Asp Asp Glu Val Lys Val Thr
            20                  25                  30
Val Val Gly Asn Glu Asn Asn Ser Leu Leu Ile Glu Ser Ile Lys Ser
        35                  40                  45
Phe Gln Lys Thr Pro His Tyr Ser Lys Leu His Leu Lys Thr Lys Ser
    50                  55                  60
Gln Asp Phe His Phe His Leu Lys Tyr His Asn Leu Ser Leu Tyr Thr
65                  70                  75                  80
Glu His Ser Val Gln Lys Asn Trp Tyr Ser Leu Val Ile Arg Glu
                85                  90                  95
Asp Gly Asn Ser Ile Ser Ser Met Met Val Lys Asp Thr Glu Ser Arg
            100                 105                 110
Thr Thr Asn Gly Met Thr Thr Val Arg Phe Val Asn Thr Leu His Lys
        115                 120                 125
Asp Val Asn Ile Ser Leu Ser Thr Asp Thr Ser Leu Asn Val Gly Glu
    130                 135                 140
Asp Tyr Gly Val Ser Ala Tyr Arg Thr Val Gln Arg Gly Glu Tyr Pro
145                 150                 155                 160
Ala Val His Cys Arg Thr Glu Asp Lys Asn Phe Ser Leu Asn Leu Gly
                165                 170                 175
Leu Leu Asp Phe Gly Ala Ala Tyr Leu Phe Val Ile Thr Asn Asn Thr
            180                 185                 190
Asn Gln Gly Leu Gln Ala Trp Lys Ile Glu Asp Ile Pro Ala Asn Lys
        195                 200                 205
Met Ser Ile Ala Trp Gln Leu Pro Gln Tyr Ala Leu Val Thr Ala Gly
    210                 215                 220
Glu Val Met Phe Ser Val Thr Gly Leu Glu Phe Ser Tyr Ser Gln Ala
225                 230                 235                 240
Pro Ser Gly Met Lys Ser Val Leu Gln Ala
                245                 250
```

<210> SEQ ID NO 388
<211> LENGTH: 23
<212> TYPE: PRT
<213> ORGANISM: Homo sapiens

<400> SEQUENCE: 388

```
Ala Trp Leu Leu Thr Ile Ala Val Gly Asn Ile Ile Val Leu Val Val
1               5                   10                  15
Ala Gln Phe Ser Gly Leu Val
            20
```

<210> SEQ ID NO 389
<211> LENGTH: 4
<212> TYPE: PRT
<213> ORGANISM: Homo sapiens

<400> SEQUENCE: 389

```
Gln Trp Ala Glu
1
```

<210> SEQ ID NO 390
<211> LENGTH: 23

```
<212> TYPE: PRT
<213> ORGANISM: Homo sapiens

<400> SEQUENCE: 390

Phe Ile Leu Phe Ser Cys Leu Leu Leu Val Ile Cys Leu Ile Phe Ser
1               5                   10                  15

Ile Met Gly Tyr Tyr Tyr Val
            20

<210> SEQ ID NO 391
<211> LENGTH: 32
<212> TYPE: PRT
<213> ORGANISM: Homo sapiens

<400> SEQUENCE: 391

Pro Val Lys Thr Glu Asp Met Arg Gly Pro Ala Asp Lys His Ile Pro
1               5                   10                  15

His Ile Gln Gly Asn Met Ile Lys Leu Glu Thr Lys Lys Thr Lys Leu
            20                  25                  30

<210> SEQ ID NO 392
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 392
ataagcggtt atcactgcc                                               19

<210> SEQ ID NO 393
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 393
gctgggattc caagtggac                                               19

<210> SEQ ID NO 394
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 394
aactgtgcag ggcctctcc                                               19

<210> SEQ ID NO 395
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 395
gctgctggat gtcattcac                                               19

<210> SEQ ID NO 396
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 396
agagacacag tgcccatcc                                               19

<210> SEQ ID NO 397
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 397
actgaacctc cgaaatgcc                                               19

<210> SEQ ID NO 398
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 398
gtgctggagt gcttccatc                                               19

<210> SEQ ID NO 399
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 399
ttcagaccta ccttcagtc                                               19

<210> SEQ ID NO 400
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 400
gagtcacaca gagatgagc                                               19

<210> SEQ ID NO 401
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 401
cgatgtgcct tcaagattc                                               19

<210> SEQ ID NO 402
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 402
cagtggtttg ggaatctgc                                               19

<210> SEQ ID NO 403
<211> LENGTH: 19
```

```
<212> TYPE: DNA
<213> ORGANISM: Artificial Sequence
<220> FEATURE:
<223> OTHER INFORMATION: Synthetic oligonucleotide

<400> SEQUENCE: 403
gtgactacac aaggactcc                                          19

<210> SEQ ID NO 404
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 404
gactgattcg ctctttgcc                                          19

<210> SEQ ID NO 405
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 405
agtgcagcct tgtgggttc                                          19

<210> SEQ ID NO 406
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 406
taacactcac tgcacctgc                                          19

<210> SEQ ID NO 407
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 407
taactgaaac tcagctagc                                          19

<210> SEQ ID NO 408
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 408
actgaagtag ccctccttc                                          19

<210> SEQ ID NO 409
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 409
agtgcagtac agcgatgac                                          19
```

<210> SEQ ID NO 410
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 410
ttcacatcgc tgagcaccc                                                19

<210> SEQ ID NO 411
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 411
agccagcaac gacatgtac                                                19

<210> SEQ ID NO 412
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 412
gctgctgggc atgtccttc                                                19

<210> SEQ ID NO 413
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 413
tgtgatcgtc atcacagtc                                                19

<210> SEQ ID NO 414
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 414
aacatgatat gtgctggac                                                19

<210> SEQ ID NO 415
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 415
ctgagaaggc ttccactgc                                                19

<210> SEQ ID NO 416
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 416
tgatacgtgg atccaggcc					19

<210> SEQ ID NO 417
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 417
ctacagtgac aaggctaac					19

<210> SEQ ID NO 418
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 418
gaactggata gccctcatc					19

<210> SEQ ID NO 419
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 419
ccctggtaaa gctgcattc					19

<210> SEQ ID NO 420
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 420
gatgaaggct tcgggcttc					19

<210> SEQ ID NO 421
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 421
tgtaaagctg gaaagggac					19

<210> SEQ ID NO 422
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 422
ctgaagaagc tggagttgc					19

<210> SEQ ID NO 423
<211> LENGTH: 19

```
<212> TYPE: DNA
<213> ORGANISM: Artificial Sequence
<220> FEATURE:
<223> OTHER INFORMATION: Synthetic oligonucleotide

<400> SEQUENCE: 423
tccttgcagc aggcacatc                                                19

<210> SEQ ID NO 424
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 424
tctgtgcgtg gactggaac                                                19

<210> SEQ ID NO 425
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 425
ctttgctcgg aagacgttc                                                19

<210> SEQ ID NO 426
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 426
gaaggctttg gaaagtgtc                                                19

<210> SEQ ID NO 427
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 427
gtgaactctg ctgcgactc                                                19

<210> SEQ ID NO 428
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 428
gacaaggcta tgatgctgc                                                19

<210> SEQ ID NO 429
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 429
ggatgtgtgg tgctgtcac                                                19
```

-continued

<210> SEQ ID NO 430
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 430
ctctgtgttc cacttcggc                                               19

<210> SEQ ID NO 431
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 431
cagcaatgca gagtgtgac                                               19

<210> SEQ ID NO 432
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 432
caaagctggc tactactac                                               19

<210> SEQ ID NO 433
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 433
cagtgcaaag agcccaaac                                               19

<210> SEQ ID NO 434
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 434
gtattctgta caccctggc                                               19

<210> SEQ ID NO 435
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 435
gtgatcgaca ggattgctc                                               19

<210> SEQ ID NO 436
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 436
cacagtgaaa ccttcctgc                                              19

<210> SEQ ID NO 437
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 437
atctgtgaca ctggatcgc                                              19

<210> SEQ ID NO 438
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 438
agagactgga gttgtcagc                                              19

<210> SEQ ID NO 439
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 439
cctgagttga atgtcatac                                              19

<210> SEQ ID NO 440
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 440
ctgaactagt gactatccc                                              19

<210> SEQ ID NO 441
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 441
ataagcaccg tgagcgacc                                              19

<210> SEQ ID NO 442
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 442
cattgggcca cagacctac                                              19

<210> SEQ ID NO 443
<211> LENGTH: 19

```
<212> TYPE: DNA
<213> ORGANISM: Artificial Sequence
<220> FEATURE:
<223> OTHER INFORMATION: Synthetic oligonucleotide

<400> SEQUENCE: 443
gatgaagaca gcaaccaac                                               19

<210> SEQ ID NO 444
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 444
agcatatgat gaccttggc                                               19

<210> SEQ ID NO 445
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 445
attccactac tacagctgc                                               19

<210> SEQ ID NO 446
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 446
gaaactgtgg caggctaac                                               19

<210> SEQ ID NO 447
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 447
ctgatgaagg ccttcgacc                                               19

<210> SEQ ID NO 448
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 448
ttgaaacaag aggaagtcc                                               19

<210> SEQ ID NO 449
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 449
tgaacttgct ctgagctgc                                               19
```

<210> SEQ ID NO 450
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 450
atctgtaacc tcagcacac                                                19

<210> SEQ ID NO 451
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 451
gaagctaagc ctcggttac                                                19

<210> SEQ ID NO 452
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 452
taaccgtggc atctacctc                                                19

<210> SEQ ID NO 453
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 453
tgaccacctg gagtatcac                                                19

<210> SEQ ID NO 454
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 454
gtggacatct ttgagcttc                                                19

<210> SEQ ID NO 455
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 455
gctgagaagt acttccacc                                                19

<210> SEQ ID NO 456
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 456
agactactgc aagggcggc					19

<210> SEQ ID NO 457
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 457
gagtatttgc tggcattcc					19

<210> SEQ ID NO 458
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 458
ggagacacgg aataaactc					19

<210> SEQ ID NO 459
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 459
ccgagaccac ctcaatgtc					19

<210> SEQ ID NO 460
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 460
atggacatct ccacgggac					19

<210> SEQ ID NO 461
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 461
tatcctgacc ttcctgcgc					19

<210> SEQ ID NO 462
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 462
cacatgatca agctaggtc					19

<210> SEQ ID NO 463
<211> LENGTH: 19

```
<212> TYPE: DNA
<213> ORGANISM: Artificial Sequence
<220> FEATURE:
<223> OTHER INFORMATION: Synthetic oligonucleotide

<400> SEQUENCE: 463
gaagccaggc atcttcatc                                                19

<210> SEQ ID NO 464
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 464
gctgaagtta tccagtctc                                                19

<210> SEQ ID NO 465
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 465
agcattggac cagttgatc                                                19

<210> SEQ ID NO 466
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 466
gtgatctacg tgaactggc                                                19

<210> SEQ ID NO 467
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 467
gccgacagtg gtgcactac                                                19

<210> SEQ ID NO 468
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 468
aacatgatgg ctcagaacc                                                19

<210> SEQ ID NO 469
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 469
tacagtgatg gatcatagc                                                19
```

```
<210> SEQ ID NO 470
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 470
accaatatgc ctaccttcc                                               19

<210> SEQ ID NO 471
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 471
actgtatccc agcagtccc                                               19

<210> SEQ ID NO 472
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 472
aagctgaaca taaccttgc                                               19

<210> SEQ ID NO 473
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 473
ttgaatagct cggtgtccc                                               19

<210> SEQ ID NO 474
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 474
gtggaaggca agatcttcc                                               19

<210> SEQ ID NO 475
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 475
tgtatggctg gtcgatcac                                               19

<210> SEQ ID NO 476
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 476
gctgcgacaa cttctgttc                                                   19

<210> SEQ ID NO 477
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 477
gcccacggtc ttccactac                                                   19

<210> SEQ ID NO 478
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 478
gactgaatca ggccttccc                                                   19

<210> SEQ ID NO 479
<211> LENGTH: 2196
<212> TYPE: DNA
<213> ORGANISM: homo sapiens

<400> SEQUENCE: 479
ccggcatttg cgtttggggc gccctccctg cgccggggc gggagcccag cgagcgcaga         60
gccccggccc cgcgcggccc gagtgccaca tcactgcgct ggccgtccaa ggtccgccgc       120
cccaccatgc cgccccgcc gccgctgctg ctccttacag tcctggtcgt cgccgctgcc       180
cggccggggt gcgagtttga gcggaacccc gccgccacct cgtgtgacct gcagctcagg       240
acctgcagcg atgccgccta caaccacacc accttcccca acctgcttca gcaccggtcg       300
tgggaggtgg tggaggccag ctccgagtac atcctgctga gcgttctaca ccagctcctg       360
gaaggccagt gcaacccgga cctgcggctg ctgggctgtg ctgtgctggc ccccggtgt        420 gagggcggct gggtgcgcag accctgccgg cacatctgcg agggcctgcg ggaggtctgc       480
cagcccgcct tcgacgccat tgacatggcc tggccctact ccttgactg ccaccgctac       540 ttcacgagag aggacgaggg ctgctatgac ccgctggaga agcttcgggg aggcctggag       600
gctgacgagg cactgcccctc agggctgccg cccaccttca tccgcttcag ccaccactcc       660
tacgcccaga tggtgcgtgt gctgaggcgg acggcctccc gctgcgccca cgtggccagg       720
acctacagca tcgggcgcag cttcgacggc agggagctgc tggtcatcga gttctccagc       780
cgccccggcc agcacgagct gatggagccc gaggtgaagc tcatcggcaa cattcatggc       840
aacgaggtgg cgggccggga gatgctcatc tacctagccc agtacctgtg ctctgagtac       900
ctgcttggta ccccccgcat ccagcgcctg ctcaacacca cccgcatcca cctgctgccc       960
tccatgaacc ctgacggcta tgaggtggca gctgccgagg tgccggcta caacgggtgg      1020 acgagcggga ggcagaacgc gcagaacctg gatctgaacc gaaatttccc ggacctgacg      1080
tccgagtact accggctggc ggagaccgcg ggcgcacgca gcgaccacat ccccatcccc      1140
cagcactact ggtggggtaa ggtggcccg gagacaaagg caatcatgaa gtggatgcag      1200
accataccct ttgtgctctc agccagcctt catggggcg acctggtggt gtcctacccc      1260
ttcgacttct ccaagcaccc ccaggaggag aagatgtttt ctcccacgcc cgacgagaag      1320
```

```
atgttcaagc tgctgtccag agcctacgct gacgtccacc ccatgatgat ggacaggtcg    1380
gagaataggt gtggaggcaa tttcctgaag aggggagca tcatcaacgg ggcggactgg    1440
tacagcttca cgggaggcat gtccgatttc aactacctgc acaccaactg ctttgagatc    1500
acggtagagc tgggctgtgt gaagttcccc cccgaggagg ccctgtacac actctggcag    1560
cacaacaagg agtcactcct gaatttcgtg agacggtgc accggggcat caaaggtgtg    1620
gtgacagata aattcggcaa gccagtcaaa aacgcccgga tctcagtcaa aggcattcgc    1680
cacgacatca ccacagcccc agatggtgac tactggagac tgctgccccc aggtatccac    1740
attgtcattg cccaagcccc tggctacgcc aaagtcatca gaaagtcat catccccgcc    1800 cggatgaaga gggctggccg tgtggacttc attctgcaac ctctggggat gggacccaag    1860
aactttattc atgggctgcg gaggactggg ccccacgacc cgctgggagg tgccagctct    1920 ttggggagg ccacggagcc cgacccgctc cgggcgcgca ggcagccctc ggccgacggg    1980
agtaagccct ggtggtggtc ctacttcaca tcgctgagca cccacaggcc acgctggctg    2040
ctcaagtact agccccggcc ccagcacccg ccaggatgtg gagaccgagg cccatctccg    2100
catcccgggc tcctggctct tgattttgtc tgccacagac atcccacaaa gccgctgcca    2160
ttttattaaa gtgttttgat ccactttcca ctggaa                              2196
```

<210> SEQ ID NO 480
<211> LENGTH: 641
<212> TYPE: PRT
<213> ORGANISM: homo sapiens

<400> SEQUENCE: 480

```
Met Pro Pro Pro Pro Leu Leu Leu Thr Val Leu Val Ala
1               5                   10                  15

Ala Ala Arg Pro Gly Cys Glu Phe Glu Arg Asn Pro Ala Ala Thr Cys
            20                  25                  30

Val Asp Leu Gln Leu Arg Thr Cys Ser Asp Ala Ala Tyr Asn His Thr
        35                  40                  45

Thr Phe Pro Asn Leu Leu Gln His Arg Ser Trp Glu Val Val Glu Ala
    50                  55                  60

Ser Ser Glu Tyr Ile Leu Leu Ser Val Leu His Gln Leu Leu Glu Gly
65                  70                  75                  80

Gln Cys Asn Pro Asp Leu Arg Leu Leu Gly Cys Ala Val Leu Ala Pro
                85                  90                  95

Arg Cys Glu Gly Gly Trp Val Arg Arg Pro Cys Arg His Ile Cys Glu
            100                 105                 110

Gly Leu Arg Glu Val Cys Gln Pro Ala Phe Asp Ala Ile Asp Met Ala
        115                 120                 125

Trp Pro Tyr Phe Leu Asp Cys His Arg Tyr Phe Thr Arg Glu Asp Glu
    130                 135                 140

Gly Cys Tyr Asp Pro Leu Glu Lys Leu Arg Gly Gly Leu Glu Ala Asp
145                 150                 155                 160

Glu Ala Leu Pro Ser Gly Leu Pro Pro Thr Phe Ile Arg Phe Ser His
                165                 170                 175

His Ser Tyr Ala Gln Met Val Arg Val Leu Arg Arg Thr Ala Ser Arg
            180                 185                 190
```

-continued

Cys Ala His Val Ala Arg Thr Tyr Ser Ile Gly Arg Ser Phe Asp Gly
              195                 200                 205

Arg Glu Leu Leu Val Ile Glu Phe Ser Ser Arg Pro Gly Gln His Glu
    210                 215                 220

Leu Met Glu Pro Glu Val Lys Leu Ile Gly Asn Ile His Gly Asn Glu
225                 230                 235                 240

Val Ala Gly Arg Glu Met Leu Ile Tyr Leu Ala Gln Tyr Leu Cys Ser
                245                 250                 255

Glu Tyr Leu Leu Gly Asn Pro Arg Ile Gln Arg Leu Leu Asn Thr Thr
            260                 265                 270

Arg Ile His Leu Leu Pro Ser Met Asn Pro Asp Gly Tyr Glu Val Ala
        275                 280                 285

Ala Ala Glu Gly Ala Gly Tyr Asn Gly Trp Thr Ser Gly Arg Gln Asn
    290                 295                 300

Ala Gln Asn Leu Asp Leu Asn Arg Asn Phe Pro Asp Leu Thr Ser Glu
305                 310                 315                 320

Tyr Tyr Arg Leu Ala Glu Thr Arg Gly Ala Arg Ser Asp His Ile Pro
                325                 330                 335

Ile Pro Gln His Tyr Trp Trp Gly Lys Val Ala Pro Gly Thr Lys Ala
            340                 345                 350

Ile Met Lys Trp Met Gln Thr Ile Pro Phe Val Leu Ser Ala Ser Leu
        355                 360                 365

His Gly Gly Asp Leu Val Val Ser Tyr Pro Phe Asp Phe Ser Lys His
    370                 375                 380

Pro Gln Glu Glu Lys Met Phe Ser Pro Thr Pro Asp Glu Lys Met Phe
385                 390                 395                 400

Lys Leu Leu Ser Arg Ala Tyr Ala Asp Val His Pro Met Met Met Asp
                405                 410                 415

Arg Ser Glu Asn Arg Cys Gly Gly Asn Phe Leu Lys Arg Gly Ser Ile
            420                 425                 430

Ile Asn Gly Ala Asp Trp Tyr Ser Phe Thr Gly Gly Met Ser Asp Phe
        435                 440                 445

Asn Tyr Leu His Thr Asn Cys Phe Glu Ile Thr Val Glu Leu Gly Cys
    450                 455                 460

Val Lys Phe Pro Pro Glu Glu Ala Leu Tyr Thr Leu Trp Gln His Asn
465                 470                 475                 480

Lys Glu Ser Leu Leu Asn Phe Val Glu Thr Val His Arg Gly Ile Lys
                485                 490                 495

Gly Val Val Thr Asp Lys Phe Gly Lys Pro Val Lys Asn Ala Arg Ile
            500                 505                 510

Ser Val Lys Gly Ile Arg His Asp Ile Thr Thr Ala Pro Asp Gly Asp
        515                 520                 525

Tyr Trp Arg Leu Leu Pro Pro Gly Ile His Ile Val Ile Ala Gln Ala
    530                 535                 540

Pro Gly Tyr Ala Lys Val Ile Lys Lys Val Ile Ile Pro Ala Arg Met
545                 550                 555                 560

Lys Arg Ala Gly Arg Val Asp Phe Ile Leu Gln Pro Leu Gly Met Gly
                565                 570                 575

Pro Lys Asn Phe Ile His Gly Leu Arg Arg Thr Gly Pro His Asp Pro
            580                 585                 590

Leu Gly Gly Ala Ser Ser Leu Gly Glu Ala Thr Glu Pro Asp Pro Leu
        595                 600                 605

Arg Ala Arg Arg Gln Pro Ser Ala Asp Gly Ser Lys Pro Trp Trp Trp
    610                 615                 620

```
Ser Tyr Phe Thr Ser Leu Ser Thr His Arg Pro Arg Trp Leu Leu Lys
625                 630                 635                 640
Tyr
```